(12) United States Patent
Kadoma et al.

(10) Patent No.: US 8,815,412 B2
(45) Date of Patent: *Aug. 26, 2014

(54) QUINOXALINE DERIVATIVE, AND LIGHT-EMITTING ELEMENT, LIGHT-EMITTING DEVICE, AND ELECTRONIC APPLIANCE USING THE QUINOXALINE DERIVATIVE

(75) Inventors: Hiroshi Kadoma, Kanagawa (JP);
Sachiko Kawakami, Kanagawa (JP);
Satoko Shitagaki, Kanagawa (JP);
Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 400 days.

This patent is subject to a terminal disclaimer.

(21) Appl. No.: 12/337,297

(22) Filed: Dec. 17, 2008

(65) Prior Publication Data
US 2009/0184633 A1   Jul. 23, 2009

(30) Foreign Application Priority Data
Dec. 21, 2007   (JP) .................................. 2007-330084

(51) Int. Cl.
*H01J 1/63* (2006.01)
*C07D 403/10* (2006.01)

(52) U.S. Cl.
USPC ........... 428/690; 313/504; 544/356; 544/230; 544/353

(58) Field of Classification Search
None
See application file for complete search history.

(56) References Cited

U.S. PATENT DOCUMENTS

| | | |
|---|---|---|
| 5,077,142 A | 12/1991 | Sakon et al. |
| 7,227,313 B2 | 6/2007 | Huiberts et al. |
| 7,238,806 B2 | 7/2007 | Inoue et al. |
| 7,245,073 B2 | 7/2007 | Shitagaki et al. |
| 7,355,340 B2 | 4/2008 | Shitagaki et al. |
| 7,601,435 B2 | 10/2009 | Shitagaki et al. |
| 7,771,844 B2 | 8/2010 | Inoue et al. |
| 7,795,429 B2 | 9/2010 | Inoue et al. |
| 7,867,629 B2 | 1/2011 | Yamamoto et al. |
| 7,915,409 B2 | 3/2011 | Inoue et al. |

(Continued)

FOREIGN PATENT DOCUMENTS

| | | |
|---|---|---|
| EP | 1 582 516 A1 | 10/2005 |
| EP | 1 616 864 A1 | 1/2006 |

(Continued)

OTHER PUBLICATIONS

Tao, Y.T. et al, "Sharp Green Electroluminescence from 1*H*-Pyrazolo[3,4-b]Quinoline-Based Light-Emitting Diodes," Applied Physics Letters, vol. 77, No. 11, Sep. 11, 2000, pp. 1575-1577.

(Continued)

*Primary Examiner* — J. L. Yang
(74) *Attorney, Agent, or Firm* — Husch Blackwell LLP

(57) ABSTRACT

An object is to provide a novel quinoxaline derivative, a light-emitting element with low driving voltage, and a light-emitting element which consumes low power. Another object is to provide a light-emitting device and an electronic appliance which consume low power by using the above light-emitting element. A quinoxaline derivative represented by a general formula (G11) is provided, in which at least one of carbon at a 2-position and carbon at a 3-position of quinoxaline, and carbon at a 2-position of a 1H-benzimidazole ring are bonded to each other via an arylene group.

20 Claims, 30 Drawing Sheets

(56) References Cited

U.S. PATENT DOCUMENTS

| | | | |
|---|---|---|---|
| 8,119,259 B2 * | 2/2012 | Kadoma et al. | 428/690 |
| 8,231,984 B2 | 7/2012 | Shitagaki et al. | |
| 8,278,444 B2 | 10/2012 | Inoue et al. | |
| 8,314,101 B2 * | 11/2012 | Kadoma et al. | 514/249 |
| 2005/0118454 A1 | 6/2005 | Nakaya et al. | |
| 2005/0186446 A1 | 8/2005 | Shitagaki et al. | |
| 2006/0051613 A1 * | 3/2006 | Tomita et al. | 428/690 |
| 2006/0194076 A1 * | 8/2006 | Nariyuki | 428/690 |
| 2008/0036369 A1 | 2/2008 | Tokuda et al. | |
| 2008/0091012 A1 | 4/2008 | Egawa et al. | |
| 2009/0140641 A1 | 6/2009 | Nomura et al. | |
| 2009/0140642 A1 * | 6/2009 | Kadoma et al. | 313/504 |
| 2009/0203704 A1 * | 8/2009 | Kadoma et al. | 514/249 |
| 2011/0001133 A1 | 1/2011 | Inoue et al. | |
| 2012/0286257 A1 | 11/2012 | Shitagaki et al. | |
| 2013/0001473 A1 | 1/2013 | Inoue et al. | |

FOREIGN PATENT DOCUMENTS

| | | |
|---|---|---|
| EP | 1 690 866 A1 | 8/2006 |
| EP | 2 336 143 A1 | 6/2011 |
| JP | 07-142169 | 6/1995 |
| JP | 7-142169 | 6/1995 |
| JP | 2003-40873 | 2/2003 |
| JP | 2004-2297 | 1/2004 |
| JP | 2004-200162 | 7/2004 |
| JP | 2006-16384 | 1/2006 |
| JP | 2004-043937 | 3/2006 |
| JP | 2006-89728 | 4/2006 |
| JP | 2006-151887 | 6/2006 |
| JP | 2004-094389 | 7/2006 |
| JP | 2006-182772 | 7/2006 |
| JP | 2006-182775 | 7/2006 |
| JP | 2005-009979 | 9/2006 |
| JP | 2005-054261 | 12/2009 |
| WO | WO 2004/094389 A1 | 11/2004 |
| WO | WO 2006/022193 A1 | 3/2006 |
| WO | WO 2006/059802 A1 | 6/2006 |

OTHER PUBLICATIONS

Thomas, K.R.J. et al, "Quinoxalines Incorporating Triarylamines: Potential Electroluminescent Materials with Tunable Emission Characteristics," Chemistry of Materials, vol. 14, No. 6, Jun. 1, 2002, pp. 2796-2802.

Tsuji, T. et al, "23.3: Distinguished Paper: Red-Phosphorescent OLEDs Employing Bis(8-Quinolinolato)-Phenolato-Aluminum(III) Complexes as Emission-Layer Hosts," SID Digest 04: SID International Symposium Digest of Technical Papers, vol. 35, book 2, May 2004, pp. 900-903.

Thomas, K.R.J. et al, "Chromophore-Labeled Quinoxaline Derivatives as Efficient Electroluminescent Materials," Chemistry of Materials, vol. 17, No. 7, Apr. 5, 2005, pp. 1860-1866.

Dorwald, F.Z., *Side Reactions in Organic Synthesis, A Guide to Successful Synthesis Design*, Wiley-VCH Verlag GmbH & Co. KGaA, 2005, preface, p. IX.

Chen, S. et al, "New Organic Light-Emitting Materials: Synthesis, Thermal, Photophysical, Electrochemical and Electroluminescent Properties," Database Caplus on STN, AN 2006:1296274, DN 146:260905, Journal of Physical Chemistry, vol. 111, No. 2, 2007, pp. 1029-1034.

Xiao, L. et al, "Highly Efficient Electron-Transporting Phenanthroline Derivatives for Electroluminescent Devices," Chemistry Letters, vol. 36, No. 6, Jun. 1, 2007, pp. 802-803.

Krueger, H. et al, "Some New Electron-Affine Polymers for Organic Photovoltaics," Proceedings of SPIE, vol. 5215, 2004, pp. 141-152.

* cited by examiner

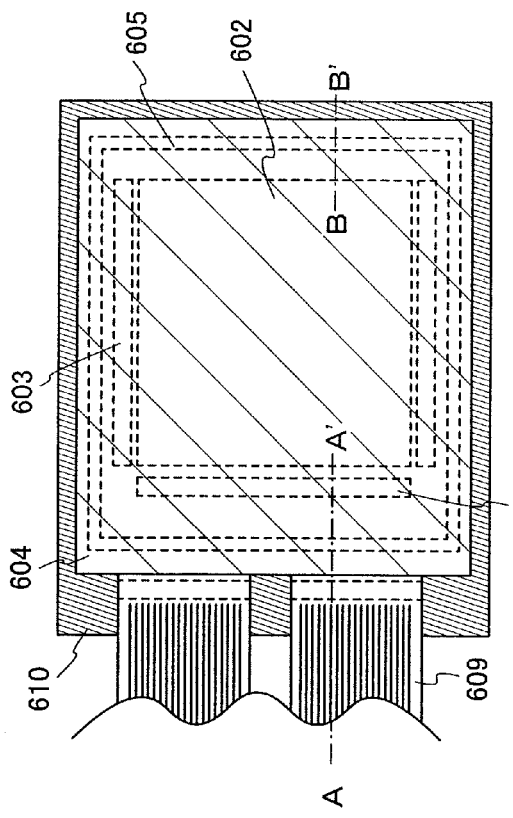
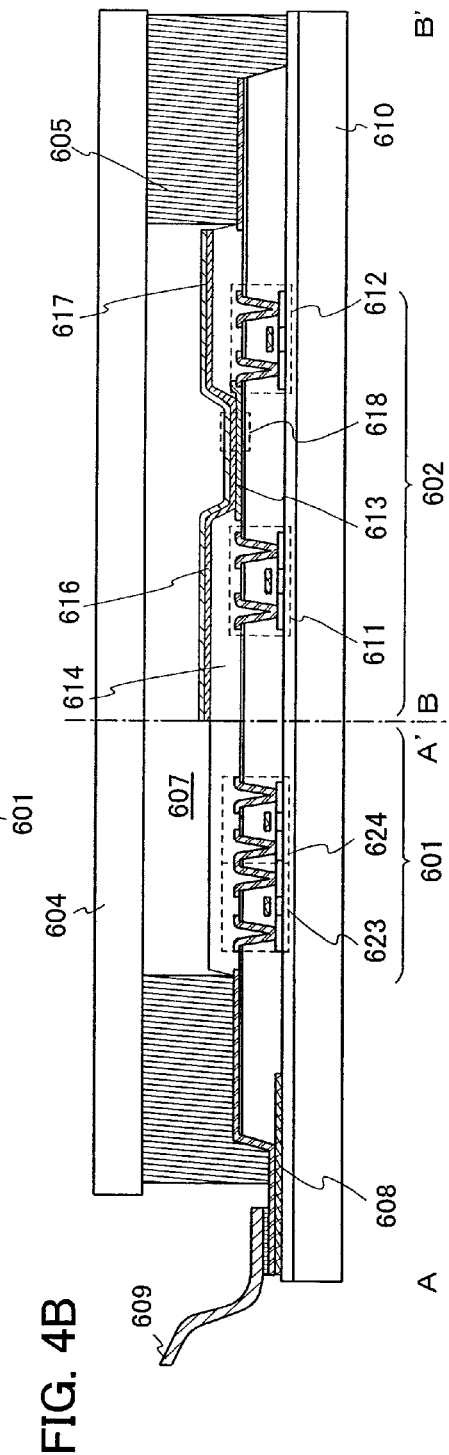
FIG. 4A
FIG. 4B

QUINOXALINE DERIVATIVE, AND LIGHT-EMITTING ELEMENT, LIGHT-EMITTING DEVICE, AND ELECTRONIC APPLIANCE USING THE QUINOXALINE DERIVATIVE

BACKGROUND OF THE INVENTION

1. Field of the Invention

The present invention relates to a quinoxaline derivative, and a light-emitting element, a light-emitting device, and an electronic appliance each of which uses the quinoxaline derivative.

2. Description of the Related Art

An organic compound can take various structures compared with an inorganic compound, and it is possible to synthesize a material having various functions by appropriate molecular-design of an organic compound. Owing to these advantages, photo electronics and electronics which use a functional organic material have been attracting attention in recent years.

For example, a solar cell, a light-emitting element, an organic transistor, and the like are exemplified as an electronics device utilizing an organic compound as a functional material. These are devices taking advantage of electric properties and optical properties of the organic compound. Among them, in particular, a light-emitting element has been making remarkable development.

It is considered that the light emission mechanism of a light-emitting element is as follows: by applying a voltage between a pair of electrodes which interpose a light-emitting layer, electrons injected from a cathode and holes injected from an anode are recombined in a luminescent center of the light-emitting layer to form a molecular exciton, and energy is released to emit light when the molecular exciton relaxes to the ground state. A singlet excited state and a triplet excited state are known as excited states, and it is thought that light emission can be obtained through either of the excitation states.

In improving the element characteristics of such a light-emitting element, there are many problems which depend on the material, and in order to solve such problems, an improvement of the element structure, a development of materials, and the like have been carried out.

For example, 2,2',2"-(1,3,5-benzenetriyl)-tris(1-phenyl-1H-benzimidazole) (abbreviation: TPBI) or the like is widely used as an electron-transporting material of the light-emitting element (see Non-Patent Document 1: X. T. TAO et al., Applied Physics Letters, vol. 77, No. 11, p. 1575 (2000)). However, a development of a material with more excellent characteristics such as further higher mobility has been demanded. In particular, in view of commercialization, reduction in power consumption is an important object, and a development of a material and a light-emitting element with more excellent characteristics has been desired.

SUMMARY OF THE INVENTION

The present inventors succeeded in the development of the present invention by making efforts to overcome the foregoing problem. In other words, it is an object of the present invention to provide a novel quinoxaline derivative which solves the foregoing problem.

Further, it is another object of the present invention to reduce driving voltage of a light-emitting element.

Furthermore, it is another object of the present invention to reduce power consumption of a light-emitting element, a light-emitting device, and an electronic appliance.

As a result of diligent studies, the present inventors have synthesized a quinoxaline derivative in which at least one of carbon at a 2-position and carbon at a 3-position of quinoxaline, and carbon at a 2-position of a benzimidazole ring are bonded to each other via an arylene group, and have found that the quinoxaline derivative can be suitably used for a light-emitting element.

Therefore, one aspect of the present invention is a quinoxaline derivative represented by a general formula (G11).

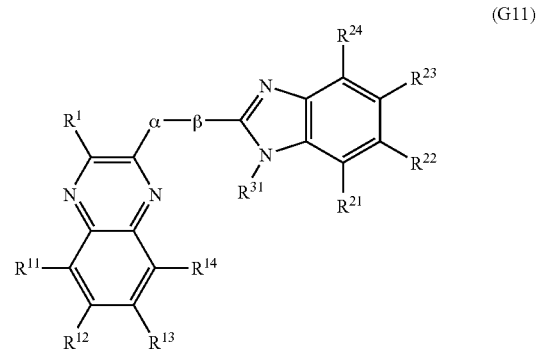

(G11)

In the formula, α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, $R^1$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, or an aryl group having 6 to 13 carbon atoms.

Another aspect of the present invention is a quinoxaline derivative represented by a general formula (G12).

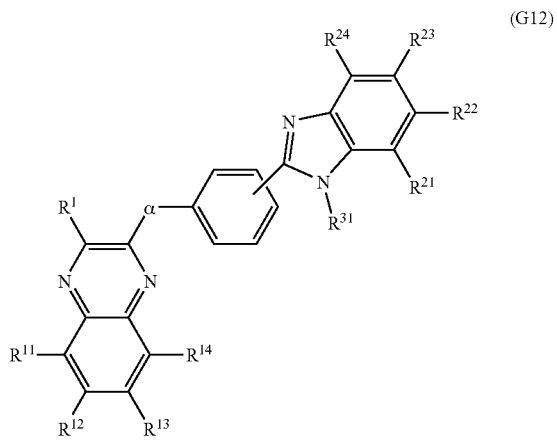

(G12)

In the formula, α represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, $R^1$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, or an aryl group having 6 to 13 carbon atoms.

Another aspect of the present invention is a quinoxaline derivative represented by a general formula (G13).

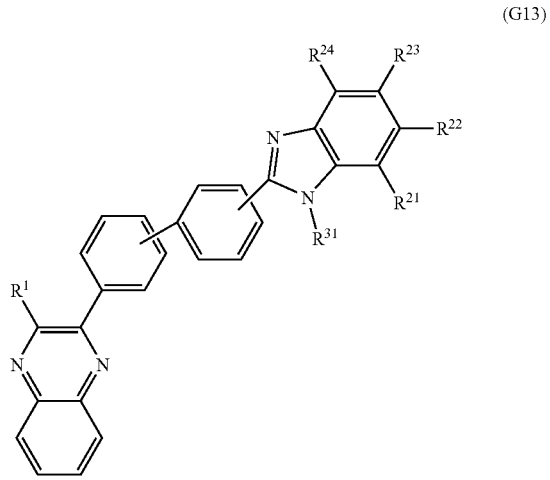

(G13)

In the formula, $R^{31}$ represents either an alkyl group having 1 to 4 carbon atoms or a substituted or unsubstituted aryl group having 6 to 13 carbon atoms, $R^{21}$ to $R^{24}$ individually represent hydrogen or an alkyl group having 1 to 4 carbon atoms, and $R^1$ represents either an alkyl group having 1 to 4 carbon atoms or a substituted or unsubstituted aryl group having 6 to 13 carbon atoms.

Another feature of the present invention is a quinoxaline derivative represented by a general formula (G14).

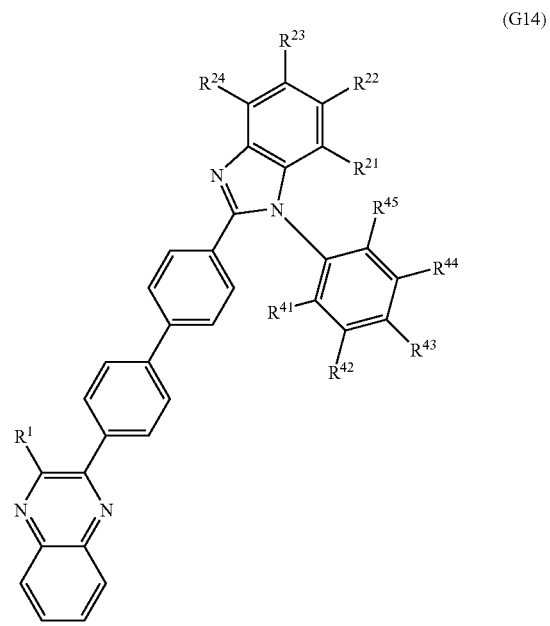

(G14)

In the formula, $R^{21}$ to $R^{24}$ individually represent hydrogen or an alkyl group having 1 to 4 carbon atoms, $R^{41}$ to $R^{45}$ individually represent hydrogen or an alkyl group having 1 to 4 carbon atoms, and $R^1$ represents either an alkyl group having 1 to 4 carbon atoms or a substituted or unsubstituted aryl group having 6 to 13 carbon atoms.

In each of the above structures, $R^1$ is preferably a phenyl group or a biphenyl group.

Another aspect of the present invention is a quinoxaline derivative represented by a general formula (G21).

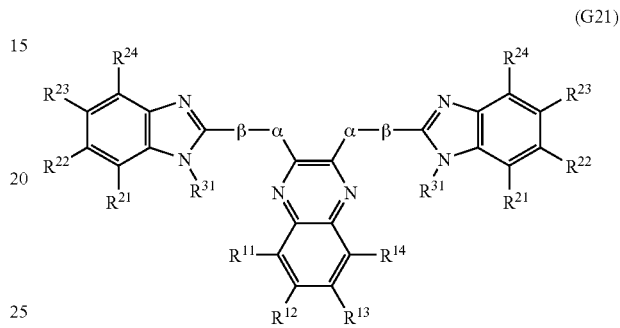

(G21)

In the formula, α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, or an aryl group having 6 to 13 carbon atoms.

Another aspect of the present invention is a quinoxaline derivative represented by a general formula (G22).

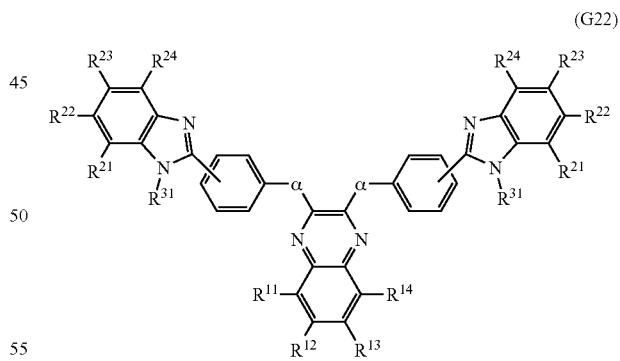

(G22)

In the formula, α represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, or an aryl group having 6 to 13 carbon atoms.

Another aspect of the present invention is a quinoxaline derivative represented by a general formula (G23).

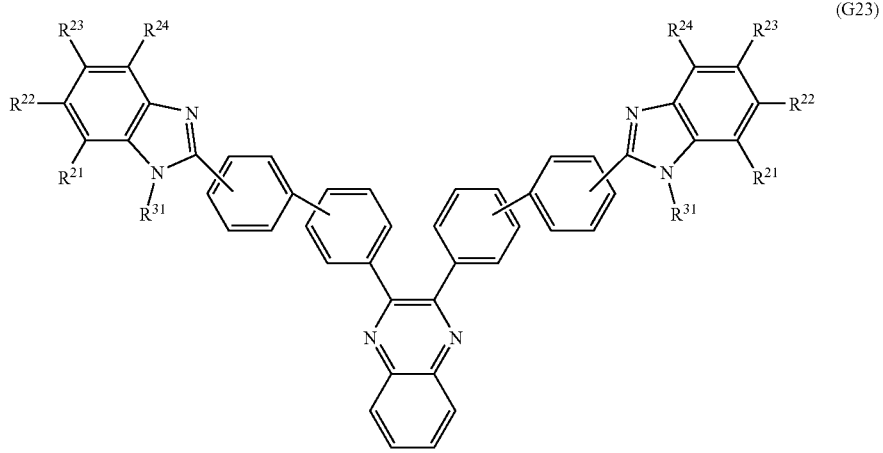

(G23)

In the formula, $R^{21}$ to $R^{24}$ individually represent hydrogen or an alkyl group having 1 to 4 carbon atoms, and $R^{31}$ represents either an alkyl group having 1 to 4 carbon atoms or a substituted or unsubstituted aryl group having 6 to 13 carbon atoms.

Another aspect of the present invention is a quinoxaline derivative represented by a general formula (G24).

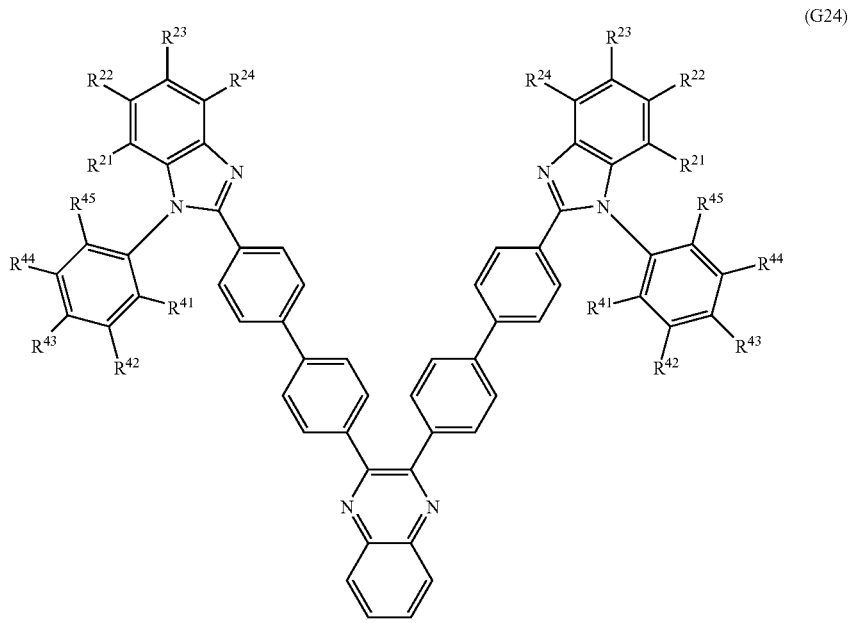

(G24)

In the formula, $R^{21}$ to $R^{24}$ individually represent hydrogen or an alkyl group having 1 to 4 carbon atoms, and $R^{41}$ to $R^{45}$ individually represent hydrogen or an alkyl group having 1 to 4 carbon atoms.

In addition, the above-described quinoxaline derivative can be used preferably for a light-emitting element.

Therefore, another aspect of the present invention is a light-emitting element including any of the above-described quinoxaline derivatives between a pair of electrodes.

In particular, the above-described quinoxaline derivatives are excellent in an electron-transporting property; thus, it is preferable that the quinoxaline derivative be used in an electron-transporting layer.

Therefore, another aspect of the present invention is a light-emitting element having a light-emitting layer and a layer including any of the above-described quinoxaline derivatives between an anode and a cathode, in which the layer including the quinoxaline derivative is provided between the light-emitting layer and the cathode.

Further, the present invention also includes in its scope a light-emitting device having the above-described light-emitting element.

Therefore, another aspect of the present invention is a light-emitting element including any of the above-described quinoxaline derivatives and a control circuit which controls light emission from the light-emitting element.

The light-emitting device in this specification includes an image display device, a light-emitting device, and a light source (including a lighting apparatus). Further, the following are all included in a light-emitting device: a module in which a connector, for example, an FPC (flexible printed circuit), a TAB (tape automated bonding) tape, or a TCP (tape carrier package) is attached to a panel provided with a light-emitting element; a module provided with a printed wiring board at the end of the TAB tape or the TCP; and a module in which an IC (integrated circuit) is directly mounted to a light-emitting element by a COG (chip on glass) method.

Further, an electronic appliance using the light-emitting element of the present invention in a display portion is also included in the scope of the present invention. Accordingly, an electronic appliance of the present invention includes a display portion, in which the display portion includes the above-described light-emitting element and control circuit which controls light emission of the light-emitting element.

The above-described quinoxaline derivatives of the present invention are excellent in an electron-transporting property. Therefore, they can be favorably used in a light-emitting element.

In addition, by using any of the above-described quinoxaline derivatives of the present invention for a light-emitting element, a light-emitting element with low driving voltage can be obtained. Therefore, a light-emitting element consuming low power can be obtained.

Further, the light-emitting element of the present invention is applied to a light-emitting device and an electronic appliance, whereby a light-emitting device and an electronic appliance consuming low power can be obtained.

BRIEF DESCRIPTION OF THE DRAWINGS

FIGS. 4A and 4B are drawings illustrating a light-emitting device according to an aspect of the present invention.

DETAILED DESCRIPTION OF THE INVENTION

[Embodiment Mode]

Figure 1:
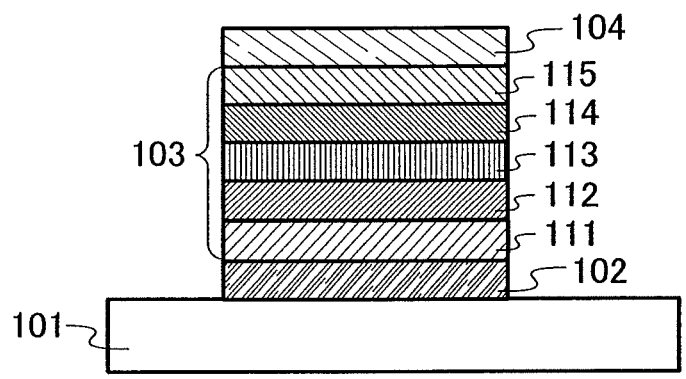
FIG. 1 is a drawing illustrating a light-emitting element according to an aspect of the present invention.

Hereinafter, various embodiment modes including a best mode of the present invention will be described in detail with reference to the accompanying drawings. However, the present invention is not limited to the description given below, and it will be readily apparent to those skilled in the art that various changes and modifications in modes and details thereof can be made without departing from the purpose and scope of the present invention. Therefore, the present invention should not be interpreted as being limited to the description of the embodiment modes given below.

[Embodiment Mode 1]

In this embodiment mode, a quinoxaline derivative of the present invention will be described.

The quinoxaline derivative of the present invention has a structure in which at least one of carbon at a 2-position and carbon at a 3-position of quinoxaline, and carbon at a 2-position of a benzimidazole ring are bonded to each other via an arylene group. In other words, a quinoxaline derivative of the present invention can be broadly divided into two modes, i.e., a case of having a structure in which one of carbon at a 2-position and carbon at a 3-position of quinoxaline, and carbon at a 2-position of a benzimidazole ring are bonded to each other via an arylene group, and a case of having a structure in which both carbon at a 2-position and carbon at a 3-position of quinoxaline, and a carbon at a 2-position of a benzimidazole ring are bonded to each other via an arylene group. As described above, one of carbon at a 2-position and carbon at a 3-position of quinoxaline, and carbon at a 2-position of a benzimidazole ring are bonded to each other via an arylene group, whereby a quinoxaline derivative having a high an electron-transporting property can be obtained.

More specifically, a quinoxaline derivative of the present invention is a quinoxaline derivative represented by a general formula (G11).

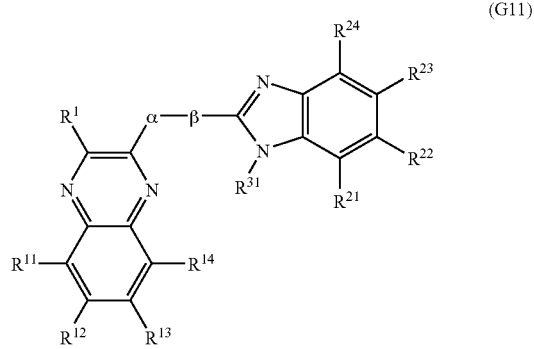

(G11)

In the formula, α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, $R^1$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, or an aryl group having 6 to 13 carbon atoms.

Further, a quinoxaline derivative of the present invention is a quinoxaline derivative represented by a general formula (G21).

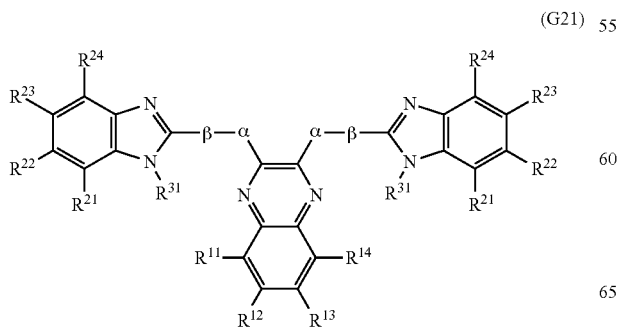

(G21)

In the formula, α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, or a substituted or unsubstituted aryl group having 6 to 13 carbon atoms.

The quinoxaline derivative represented by the general formula (G21) has a structure in which carbon at a 2-position and carbon at a 3-position (that is, both carbon at a 2-position and carbon at a 3-position) of quinoxaline, and carbon at a 2-position of a benzimidazole ring are bonded to each other via an arylene group. Thus, the molecular weight of the quinoxaline derivative represented by the general formula (G21) is larger than that of the quinoxaline derivative represented by the general formula (G11), and the thermophysical property of the quinoxaline derivative represented by the general formula (G21) is improved. In addition, by the improvement in the thermophysical property, an improvement in the stability of film quality (crystallization can be suppressed) can be expected.

Further, in the general formulae (G11) and (G21), as a substituent represented by α, an arylene group represented by any of structural formulae (12-1) to (12-10) can be given, for example. As shown in the structural formulae (12-4), (12-8) to (12-10), and the like, an arylene group represented by α may include a substituent. Note that the carbon atoms of an aryl group or an arylene group which is described in this specification represent carbon atoms which form a ring of the main skeleton, and carbon atoms of a substituent bonded thereto are not included therein. For example, the arylene group represented by the structural formula (12-4) has 6 carbon atoms, and the arylene group represented by the structural formula (12-5) has 10 carbon atoms. Further, in the case where the arylene group has two or more substituents, substituents may be bonded to each other to form a ring, and a spiro structure is included as a ring structure. For example, the arylene group represented by the structural formula (12-9) has 13 carbon atoms.

(12-1)

(12-2)

(12-3)

(12-4)

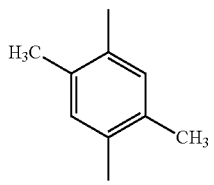

(12-5)

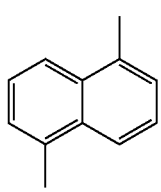

(12-6)

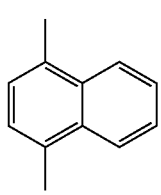

(12-7)

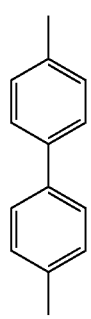

(12-8)

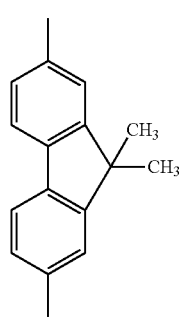

(12-9)

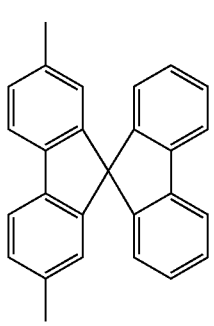

(12-10)

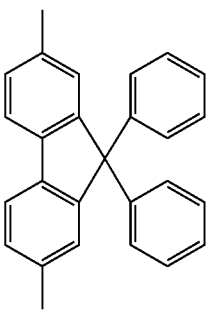

Further, in the general formulae (G11) and (G21), as a substituent represented by β, an arylene group represented by structural formulae (13-1) to (13-10) can be given, for example. As shown in the structural formulae (13-4), (13-8) to (13-10), and the like, an arylene group represented by β may include a substituent. Further, in the case where the arylene group has two or more substituents, substituents may be bonded to each other to form a ring, and a spiro structure is included as a ring structure.

(13-1)

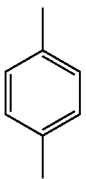

(13-2)

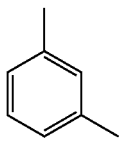

(13-3)

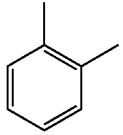

(13-4)

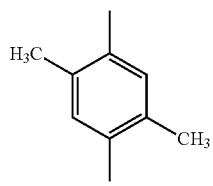

(13-5)

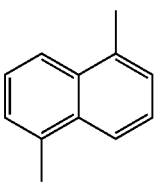

-continued

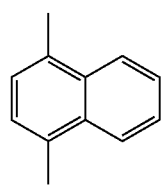 (13-6)

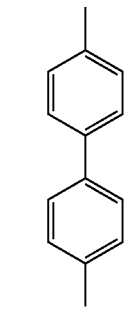 (13-7)

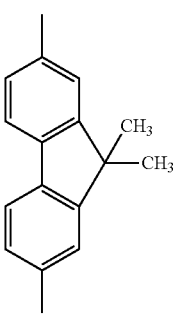 (13-8)

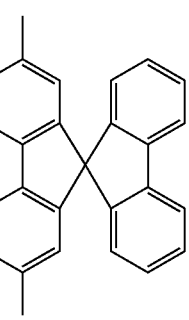 (13-9)

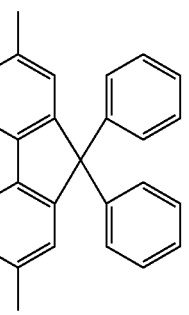 (13-10)

Further, in the general formulae (G11) and (G21), as substituents represented by $R^{11}$ to $R^{14}$, hydrogen, an alkyl group, and an aryl group which are represented by structural formulae (14-1) to (14-22) and the like can be given, for example. As shown in the structural formulae (14-11) to (14-14) and the like, aryl groups represented by $R^{11}$ to $R^{14}$ may each include a substituent. Further, in the case where the arylene group has two or more substituents, substituents may be bonded to each other to form a ring, and a spiro structure is included as a ring structure.

 (14-1)

 (14-2)

 (14-3)

 (14-4)

 (14-5)

 (14-6)

 (14-7)

 (14-8)

 (14-9)

 (14-10)

 (14-11)

 (14-12)

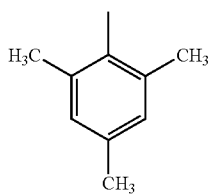 (14-13)
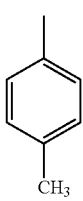 (14-14)
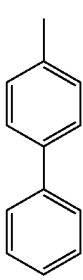 (14-15)
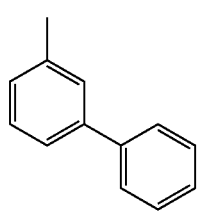 (14-16)
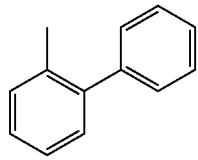 (14-17)
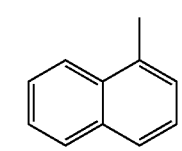 (14-18)
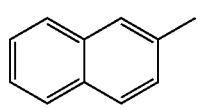 (14-19)
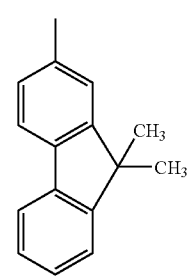 (14-20)
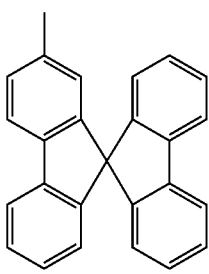 (14-21)
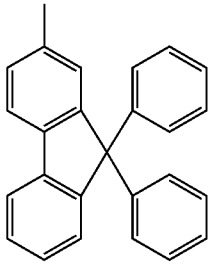 (14-22)
Further, in the general formulae (G11) and (G21), as substituents represented by $R^{21}$ to $R^{24}$, hydrogen and an alkyl group which are represented by structural formulae (15-1) to (15-9) can be given, for example.
 (15-1)
 (15-2)
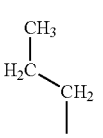 (15-3)
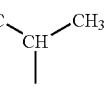 (15-4)
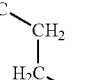 (15-5)
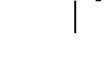 (15-6)
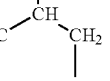 (15-7)
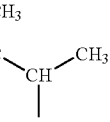 (15-8)

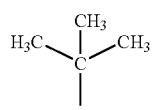
(15-9)

Further, in the general formulae (G11) and (G21), as a substituent represented by $R^{31}$, for example, an alkyl group and an aryl group which are represented by structural formulae (16-1) to (16-21) can be given. As shown in structural formulae (16-10) to (16-21) and the like, an alkyl group or an aryl group which is represented by $R^{31}$ may include a substituent. Further, in the case where the arylene group has two or more substituents, substituents may be bonded to each other to form a ring, and a spiro structure is included as a ring structure.

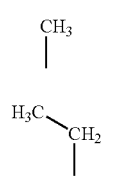
(16-1)

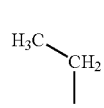
(16-2)

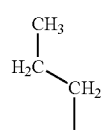
(16-3)

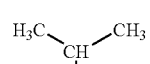
(16-4)

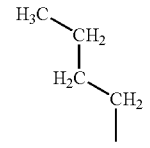
(16-5)

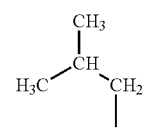
(16-6)

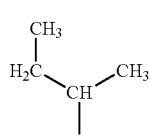
(16-7)

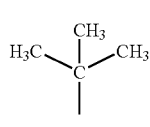
(16-8)

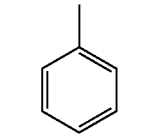
(16-9)

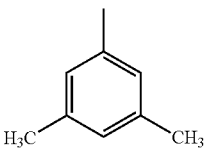
(16-10)

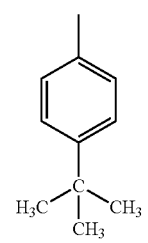
(16-11)

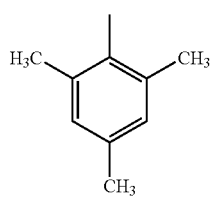
(16-12)

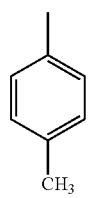
(16-13)

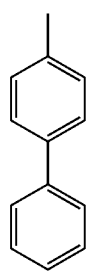
(16-14)

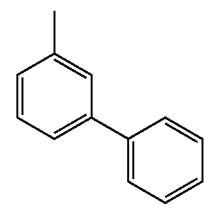
(16-15)

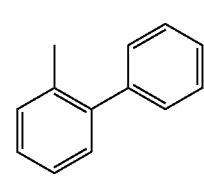
(16-16)

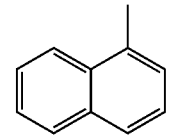
(16-17)

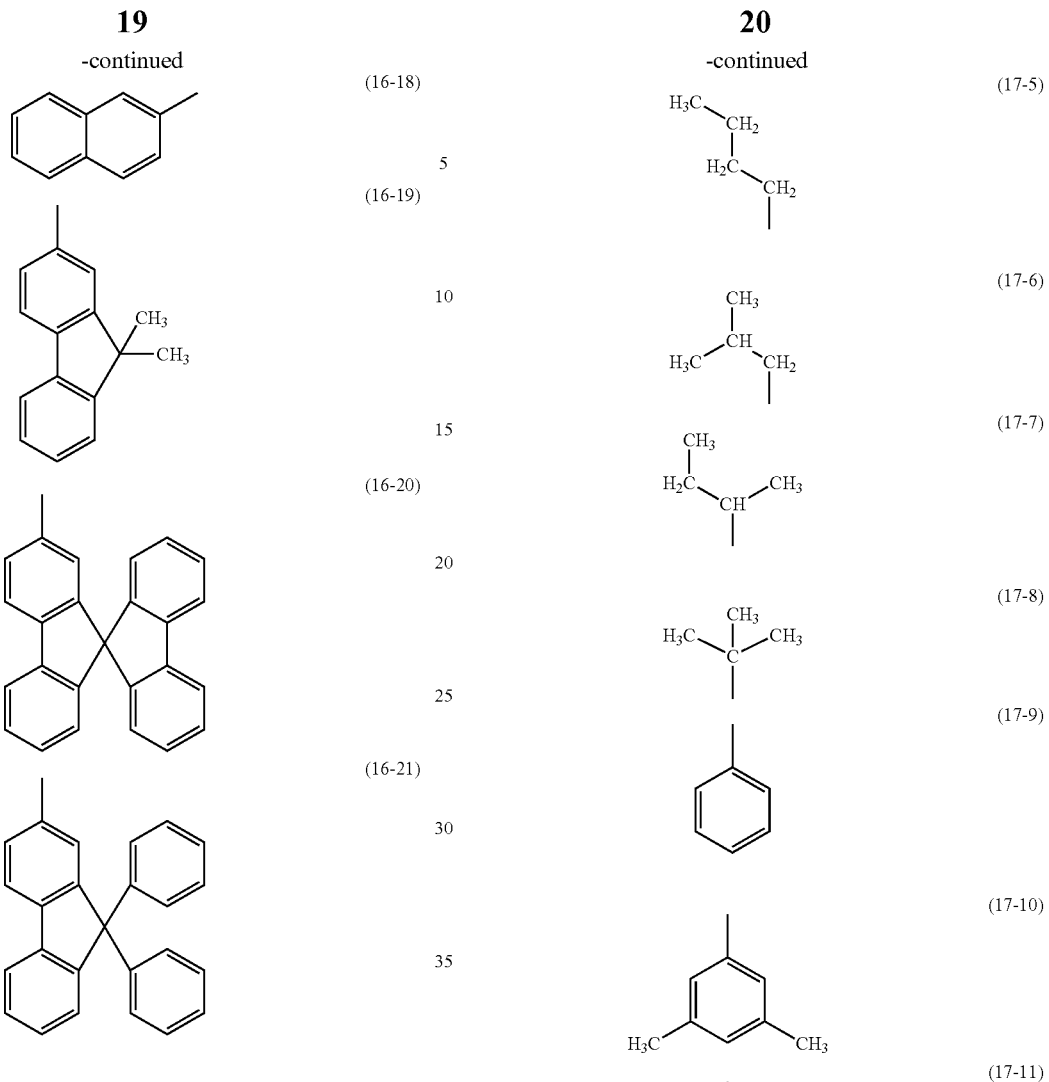

In addition, in the general formula (G11), as a substituent represented by $R^1$, an alkyl group and an aryl group which are represented by structural formulae (17-1) to (17-21) can be given, for example. As shown in the structural formulae (17-10) to (17-13) and the like, an alkyl group or an aryl group which is represented by $R^1$ may include a substituent. Further, in the case where the arylene group has two or more substituents, substituents may be bonded to each other to form a ring, and a spiro structure is included as a ring structure.

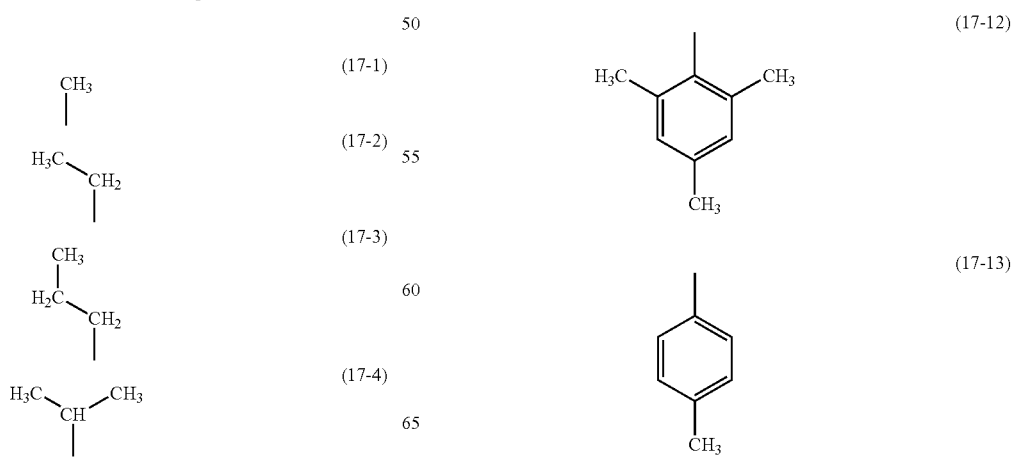

-continued (17-14)
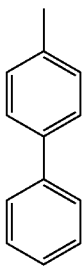

(17-15)
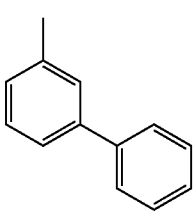

(17-16)
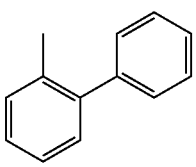

(17-17)
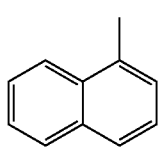

(17-18)
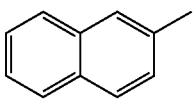

(17-19)
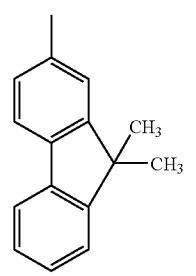

(17-20)
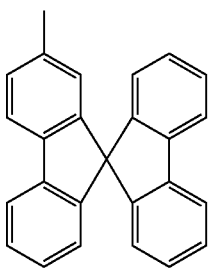

-continued (17-21)
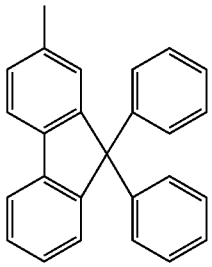

In the quinoxaline derivative represented by the general formula (G11), β is preferably a phenylene group for ease of synthesis. That is, a quinoxaline derivative represented by the general formula (G12) is preferable.

(G12)
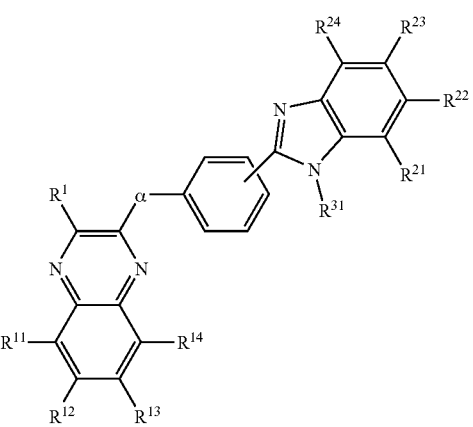

In the formula, α represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, $R^1$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, or an aryl group having 6 to 13 carbon atoms.

Similarly, in the quinoxaline derivative represented by the general formula (G21), β is preferably a phenylene group for ease of synthesis. That is, a quinoxaline derivative represented by the general formula (G22) is preferable.

(G22)

In the formula, α represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, or a substituted or unsubstituted aryl group having 6 to 13 carbon atoms.

More preferably, in the quinoxaline derivative represented by the general formula (G11), α is preferably a phenylene group for ease of synthesis and purification (purity improvement). Further, $R^{11}$ to $R^{14}$ are preferably hydrogen for ease of synthesis and purification (purity improvement). That is, a quinoxaline derivative represented by a general formula (G13) is preferably used.

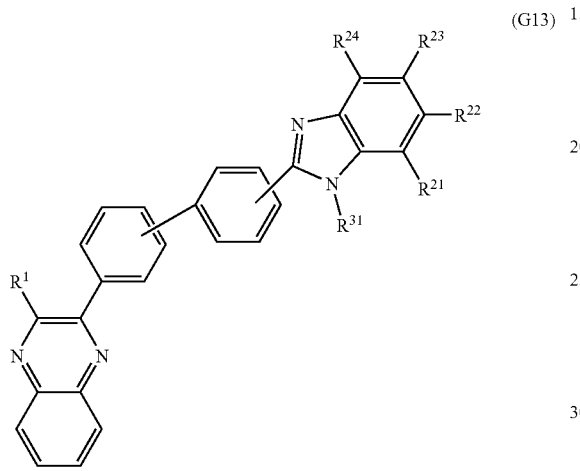

(G13)

In the formula, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, and $R^1$ represents either an alkyl group having 1 to 4 carbon atoms or a substituted or unsubstituted aryl group having 6 to 13 carbon atoms.

Similarly, in the quinoxaline derivative represented by the general formula (G21), α is preferably a phenylene group for ease of synthesis and purification (improvement in purity). Further, each of $R^{11}$ to $R^{14}$ is preferably hydrogen for ease of synthesis and purification (improvement in purity). That is, a quinoxaline derivative represented by a general formula (G23) is preferable.

In the formula, $R^{21}$ to $R^{24}$ individually represent hydrogen or an alkyl group having 1 to 4 carbon atoms, and $R^{31}$ represents either an alkyl group having 1 to 4 carbon atoms or a substituted or unsubstituted aryl group having 6 to 13 carbon atoms.

Further, in the quinoxaline derivative represented by the general formula (G11), when both α and β are phenylene groups, they are preferable to be bonded to each other at a para position. With such a structure, steric hindrance is further reduced, and synthesis becomes easier. That is, a quinoxaline derivative represented by a general formula (G14) is preferable.

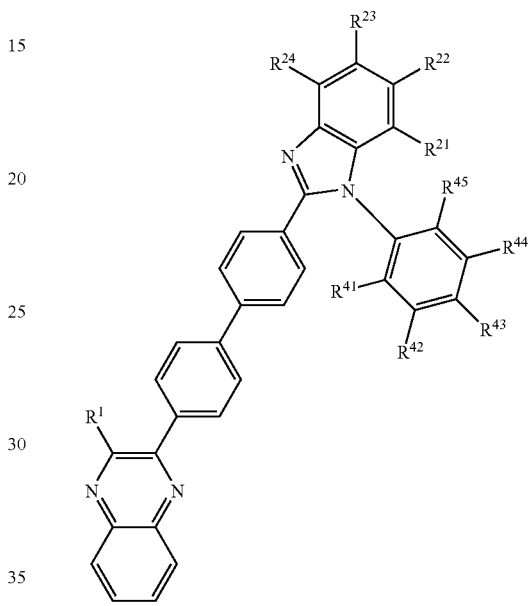

(G14)

In the formula, $R^{21}$ to $R^{24}$ individually represent hydrogen or an alkyl group having 1 to 4 carbon atoms, $R^{41}$ to $R^{45}$ individually represent hydrogen or an alkyl group having 1 to 4 carbon atoms, and $R^1$ represents either an alkyl group having 1 to 4 carbon atoms or a substituted or unsubstituted aryl group having 6 to 13 carbon atoms.

Similarly, in the quinoxaline derivative represented by the general formula (G21), when both α and β are phenylene groups, they are preferable to be bonded to each other at a para position. With such a structure, steric hindrance is further

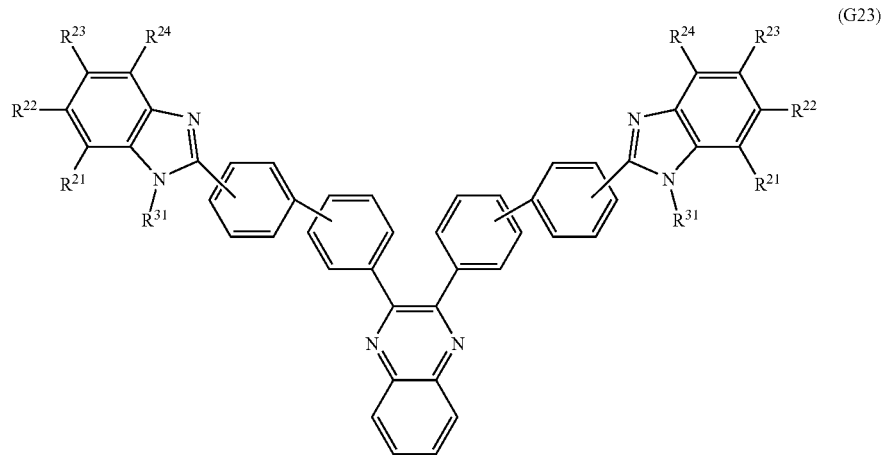

(G23)

reduced, and synthesis becomes easier. That is, the quinoxaline derivative represented by a general formula (G24) is preferable.

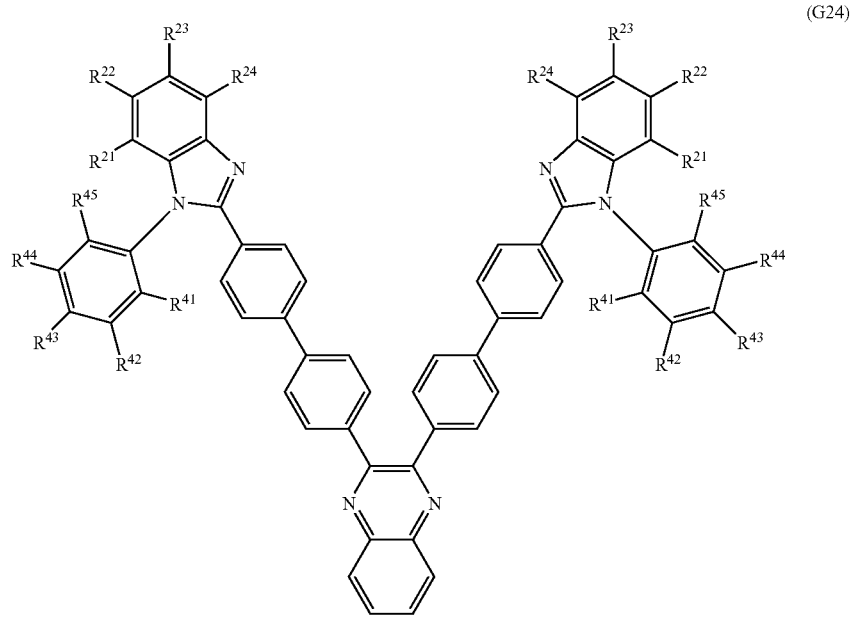

(G24)

In the formula, $R^{21}$ to $R^{24}$ individually represent hydrogen or an alkyl group having 1 to 4 carbon atoms, and $R^{41}$ to $R^{45}$ individually represent hydrogen or an alkyl group having 1 to 4 carbon atoms.

Further, in the general formulae (G14) and (G24), as the substituents represented by $R^{41}$ to $R^{45}$, hydrogen and an alkyl group which are represented by structural formulae (18-1) to (18-9), and the like are given, for example.

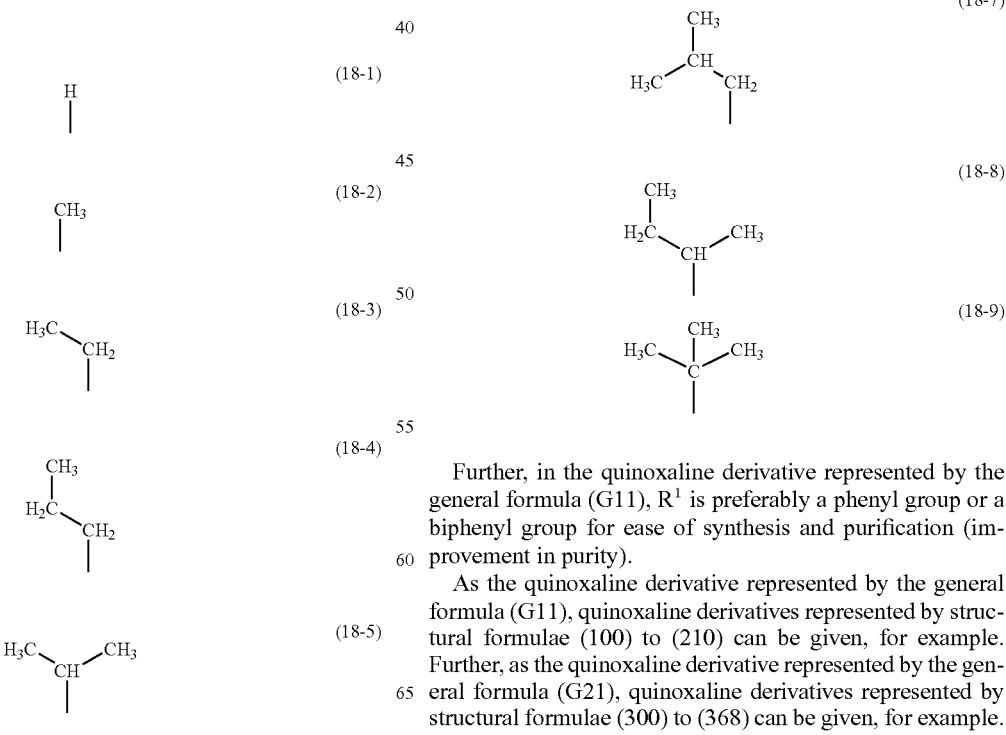

Further, in the quinoxaline derivative represented by the general formula (G11), $R^1$ is preferably a phenyl group or a biphenyl group for ease of synthesis and purification (improvement in purity).

As the quinoxaline derivative represented by the general formula (G11), quinoxaline derivatives represented by structural formulae (100) to (210) can be given, for example. Further, as the quinoxaline derivative represented by the general formula (G21), quinoxaline derivatives represented by structural formulae (300) to (368) can be given, for example. However, the present invention is not limited to these.

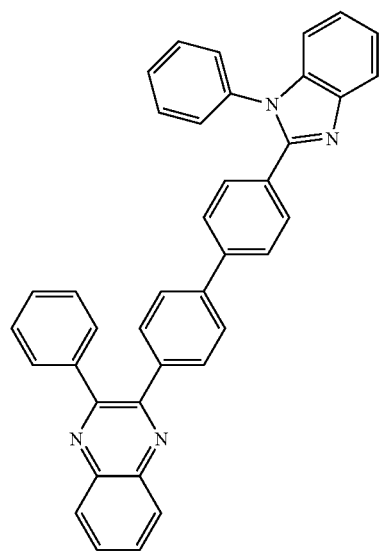
(100)
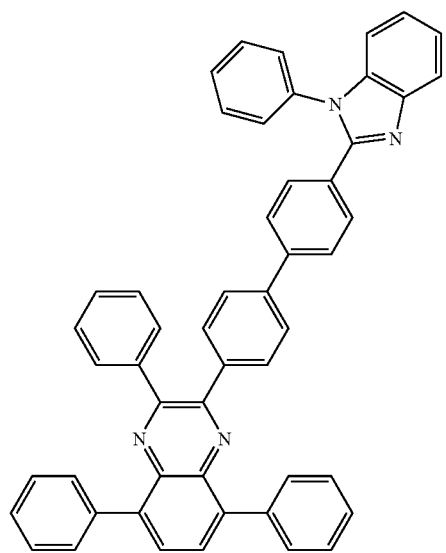
(101)
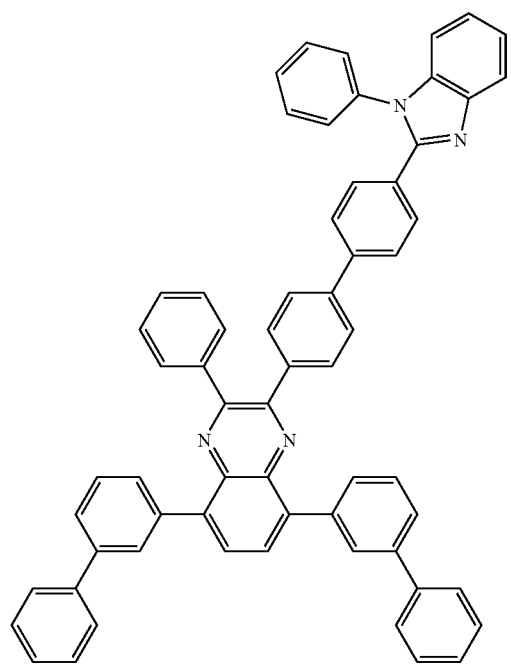
(102)
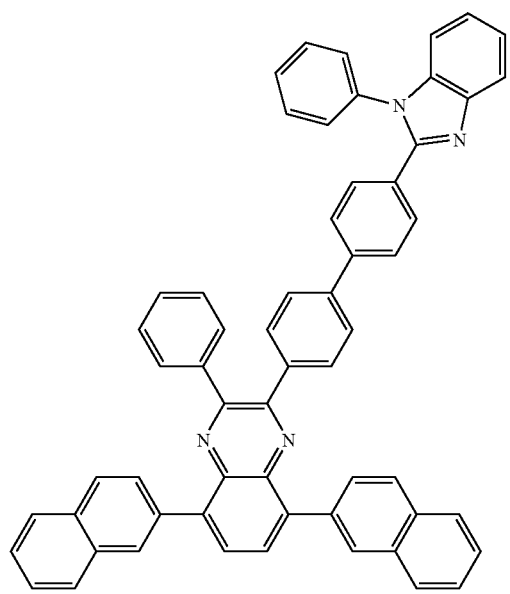
(103)

-continued
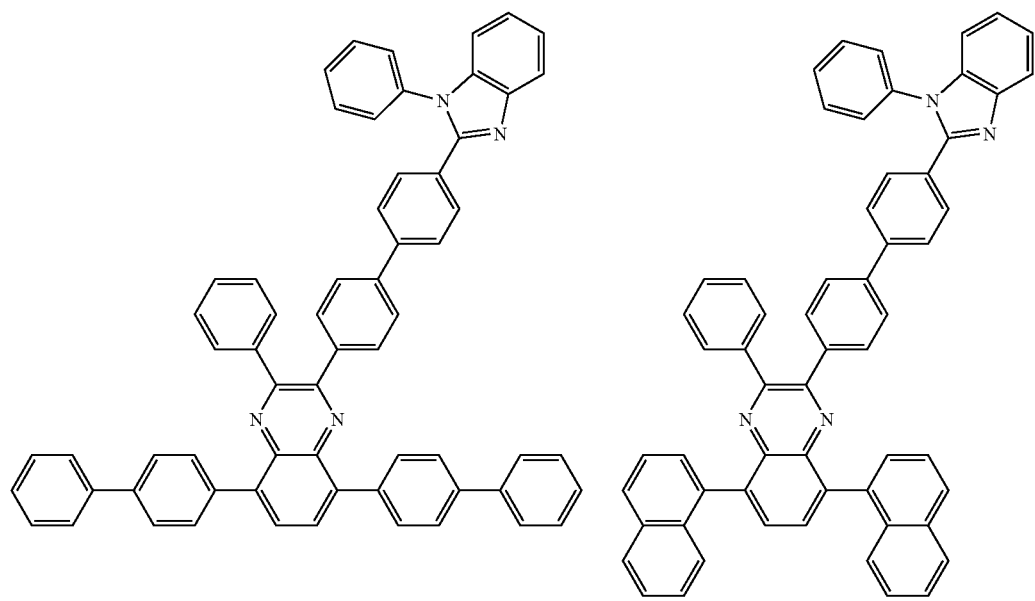
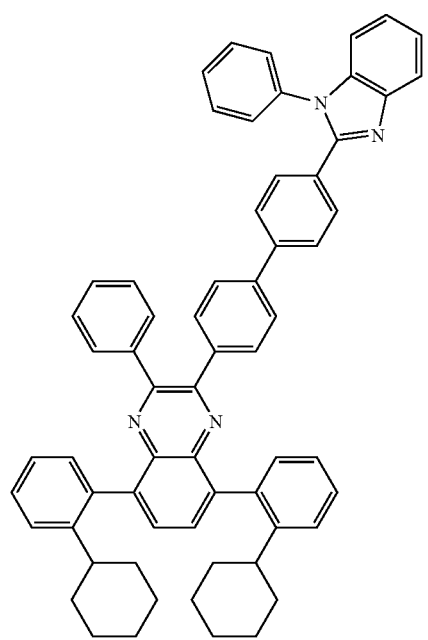

-continued
(107)
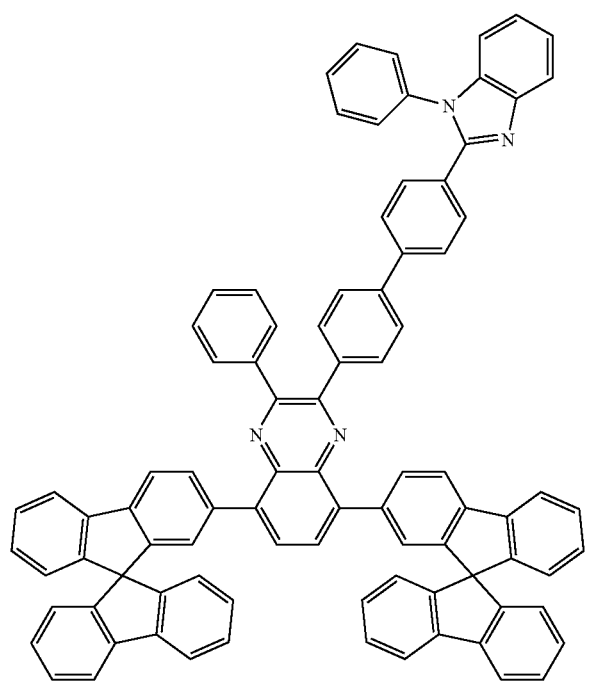
(108)
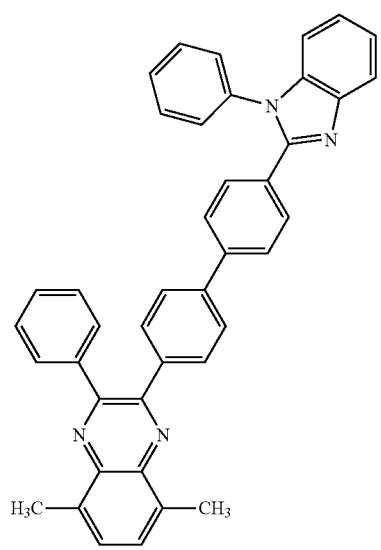
(109)
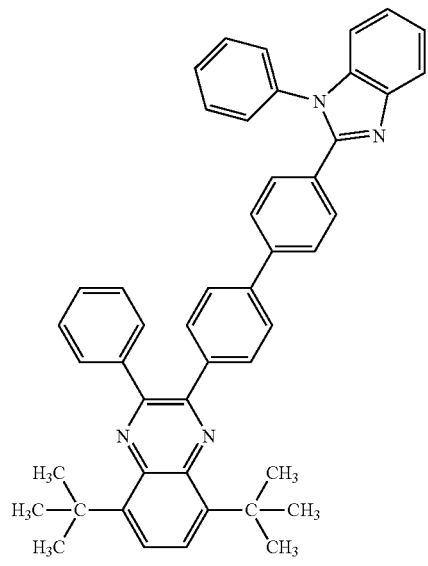
(110)
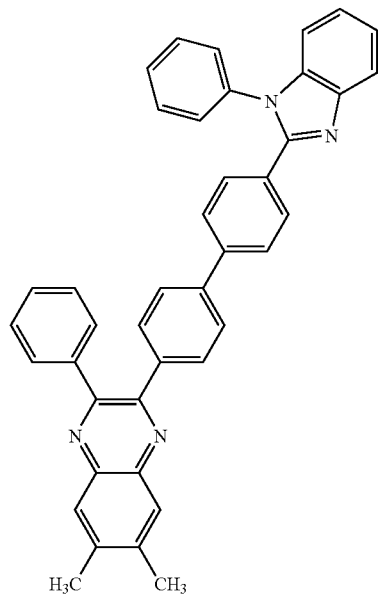

-continued
(111)
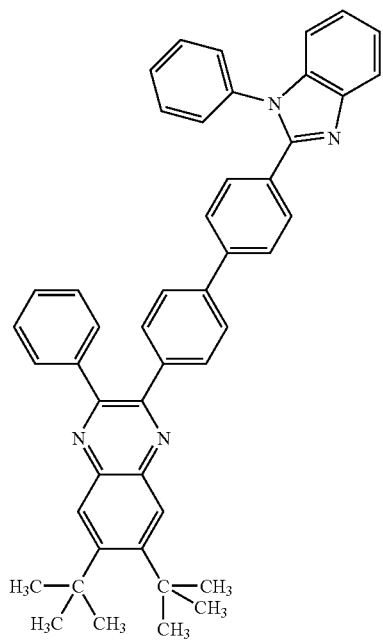
(112)
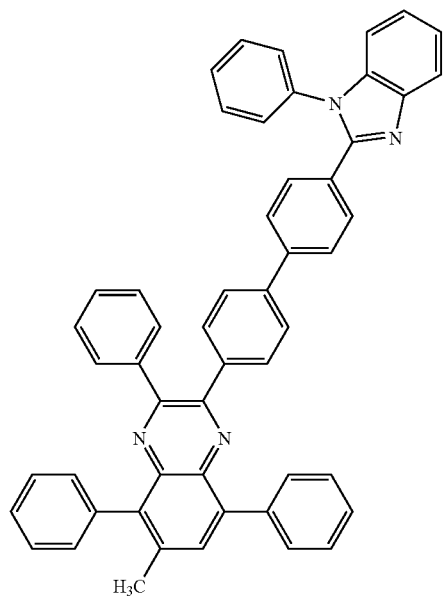
(113)
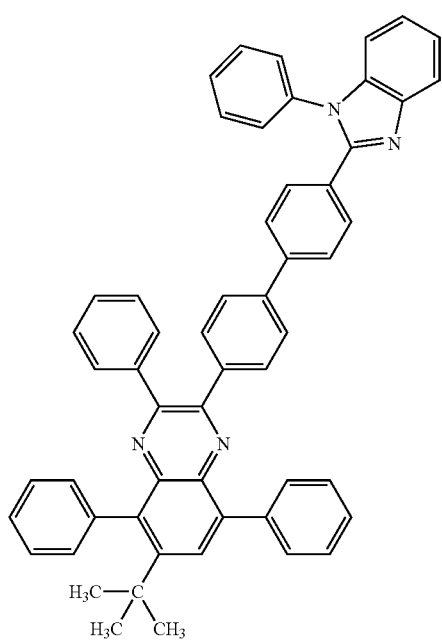
(114)
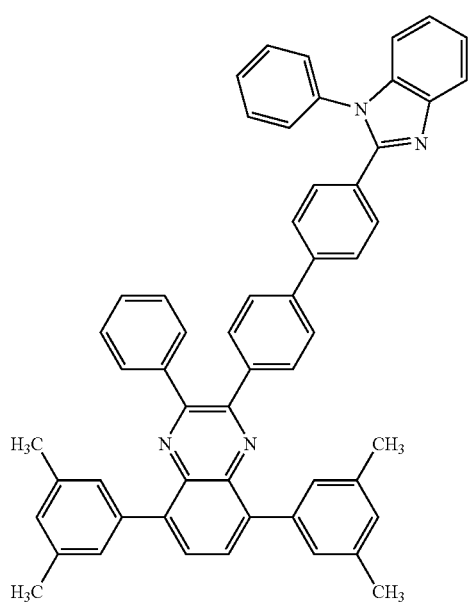

(115)
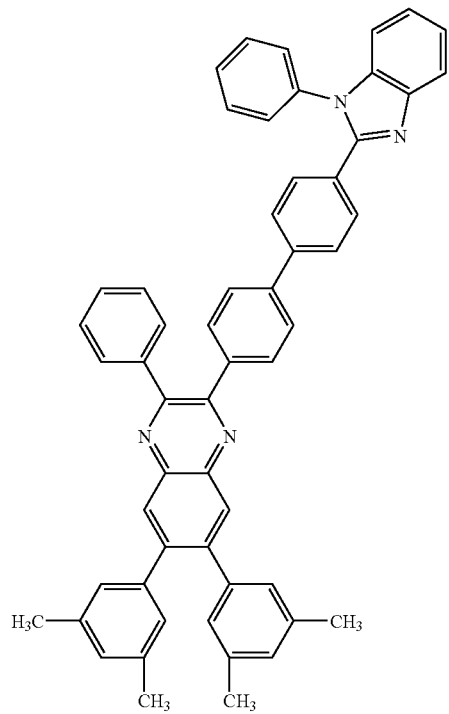
(116)
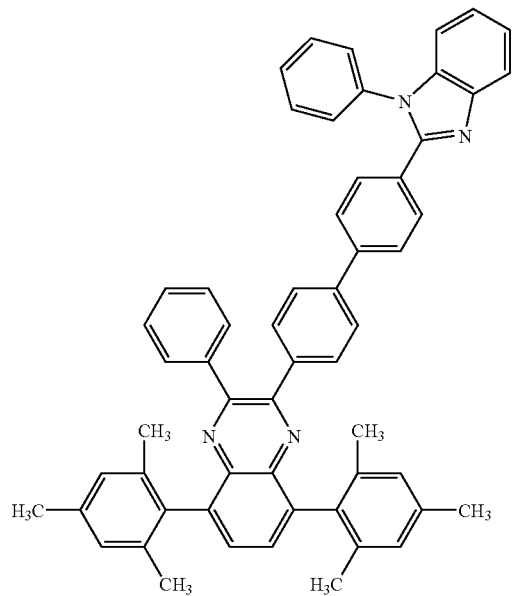
(117)
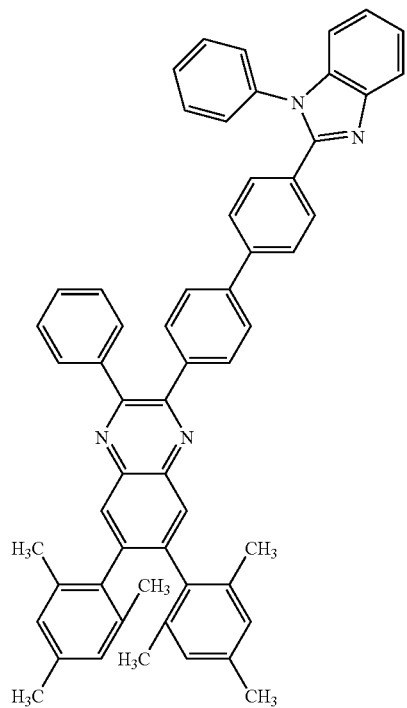
(118)
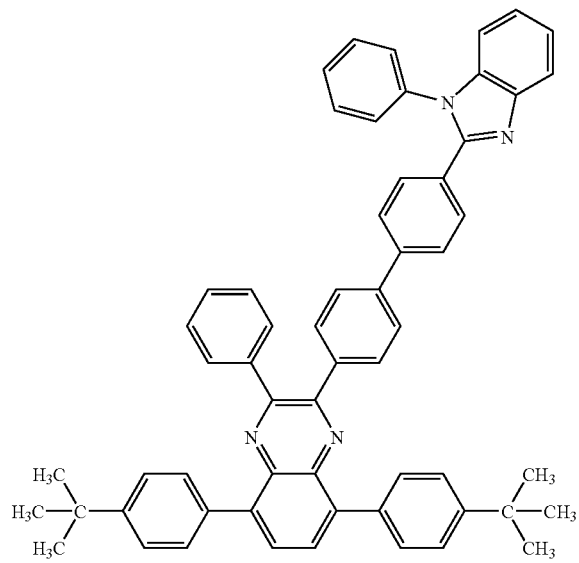

-continued
(119)
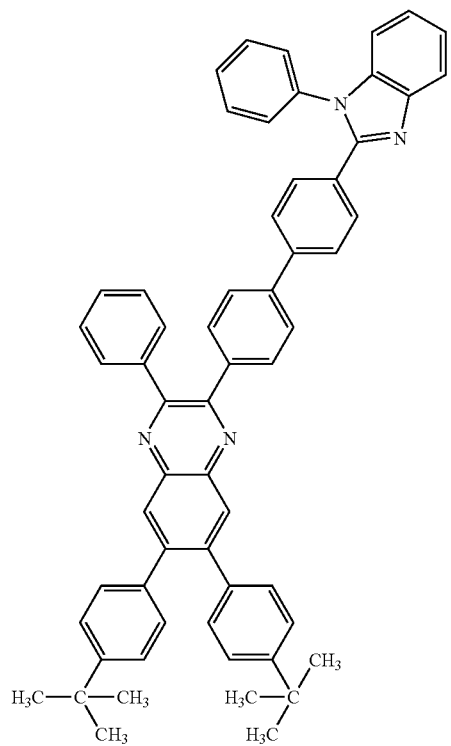
(120)
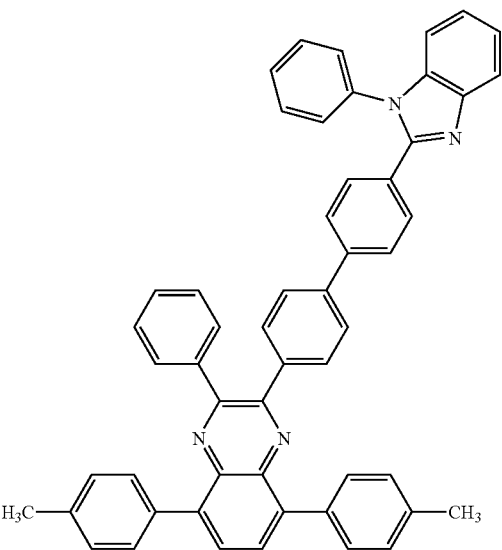
(121)
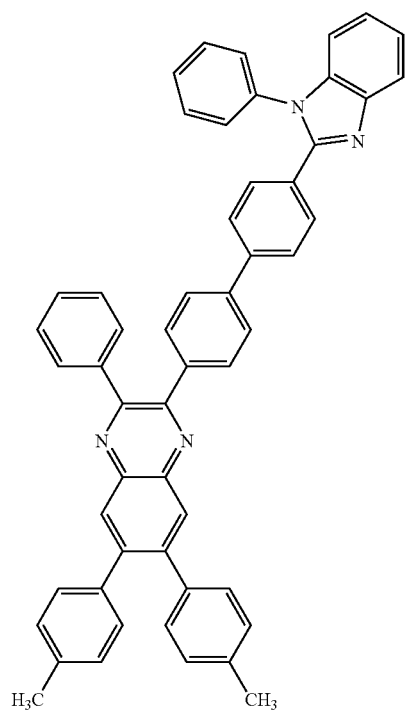
(122)

-continued
(123)
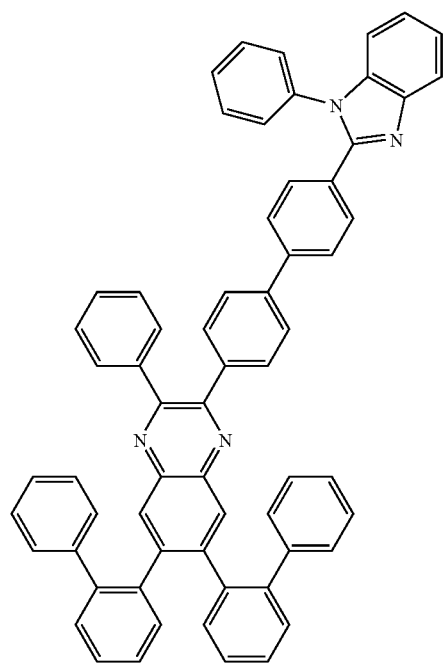
(124)
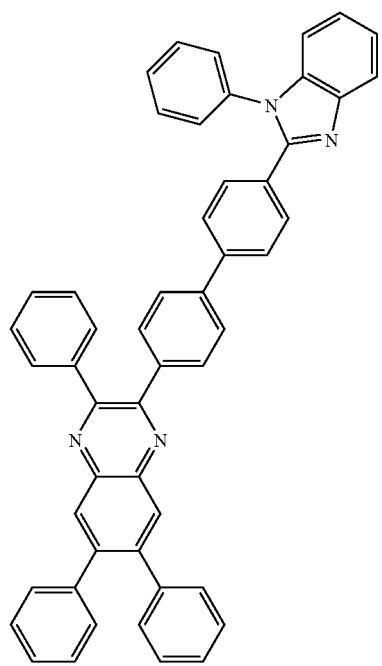
(125)
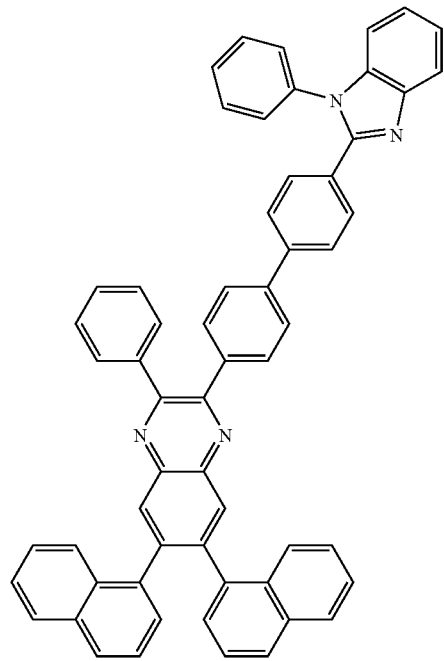
(126)
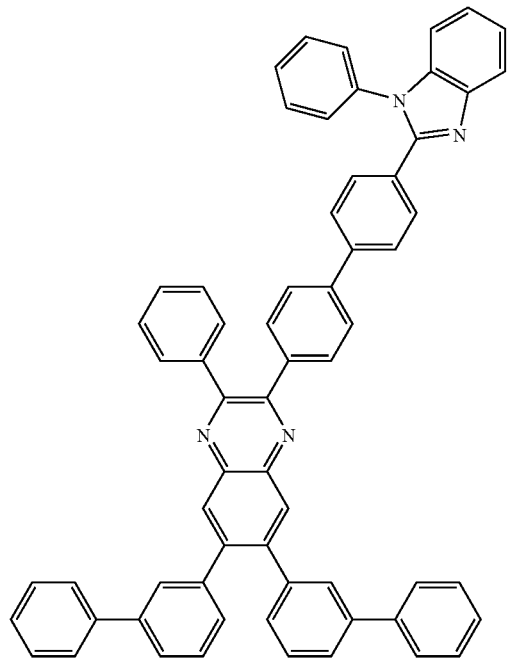

(127)
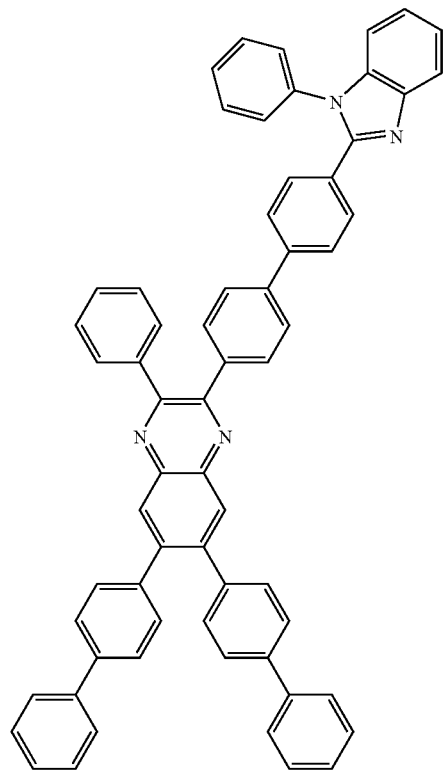
(128)
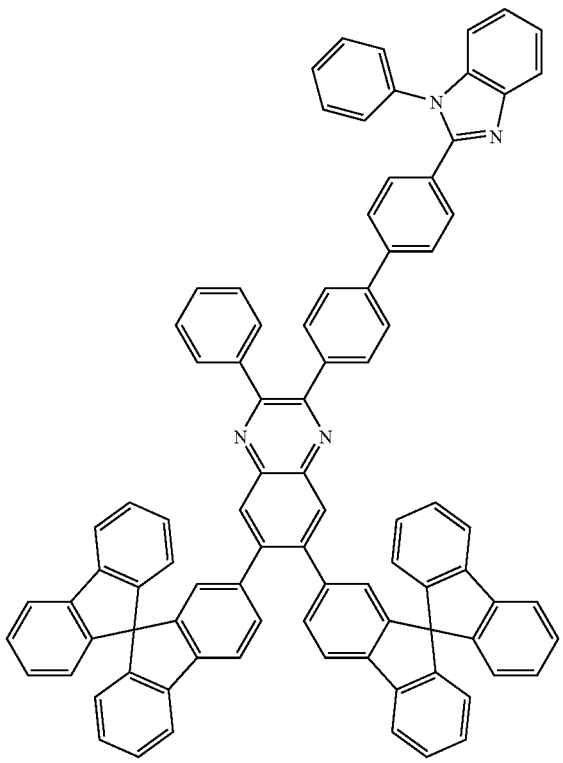
(129)
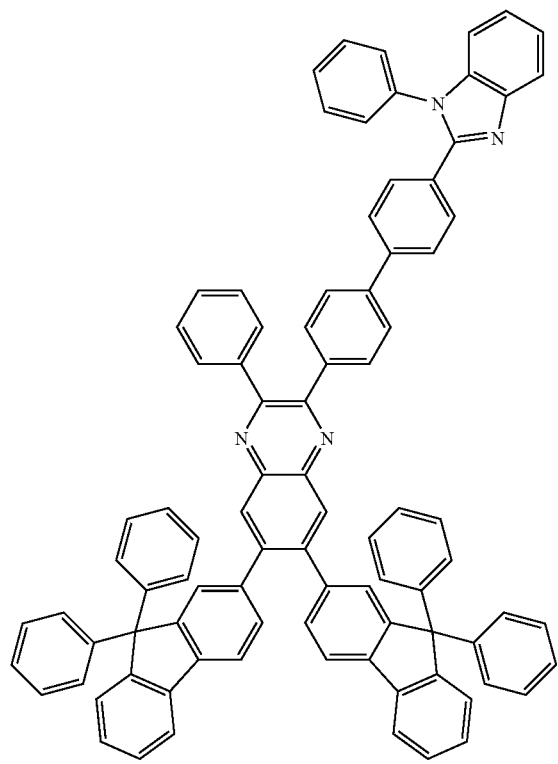
(130)
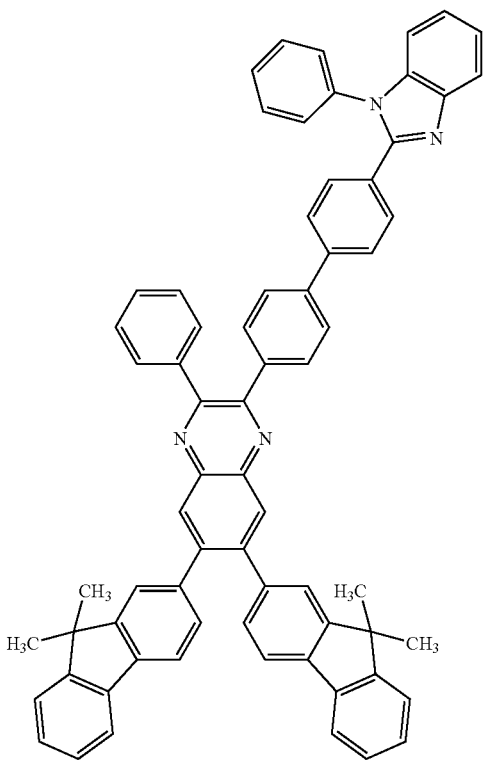

-continued
(131)
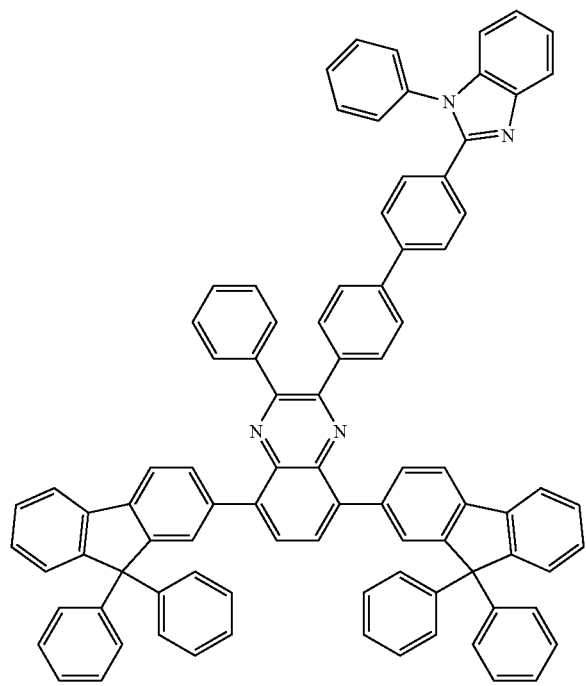
(132)
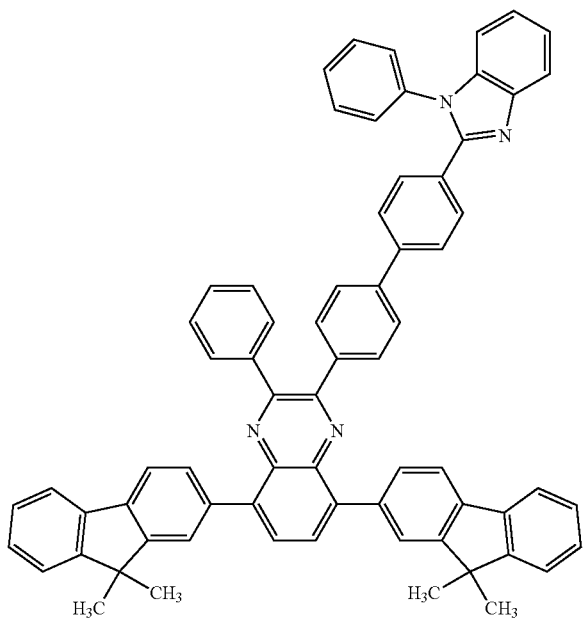
(133)
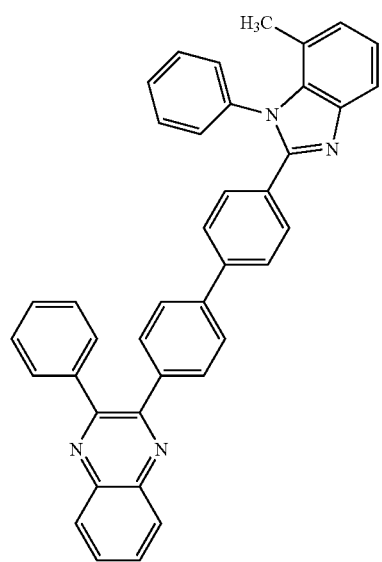
(134)
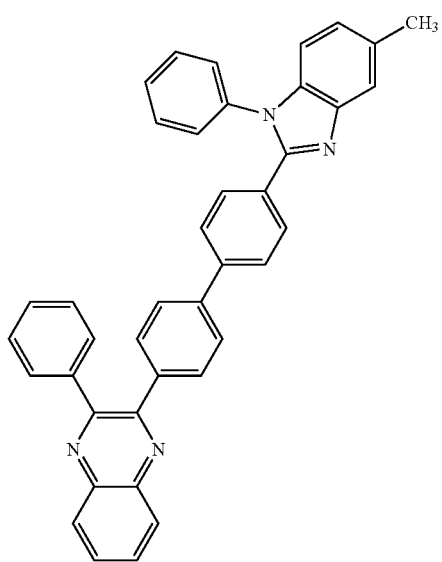

-continued
(135)
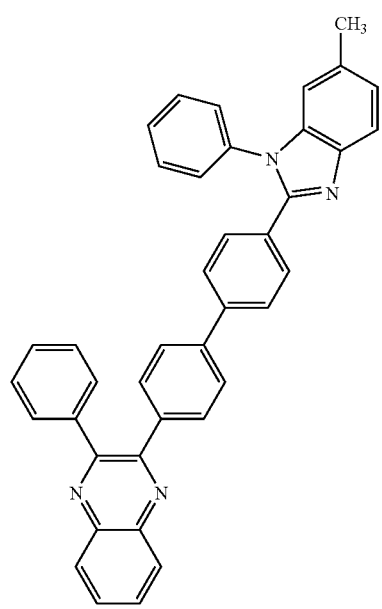
(136)
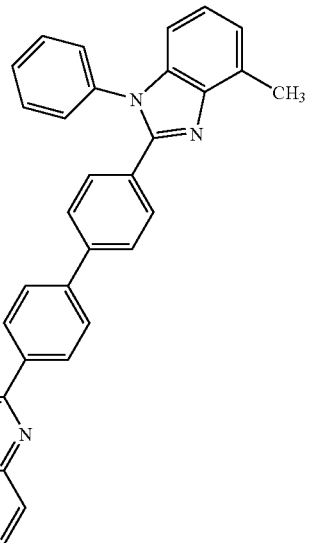
(137)
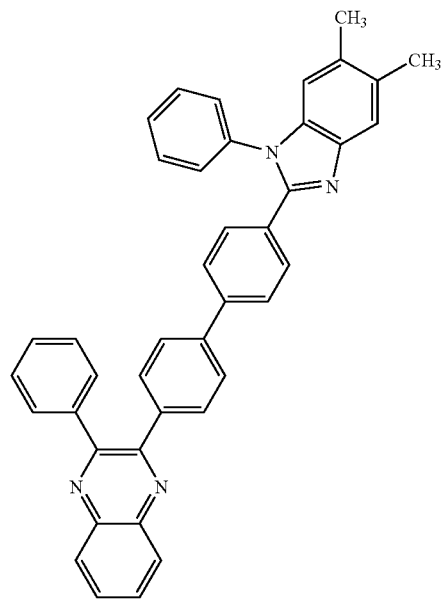
(138)
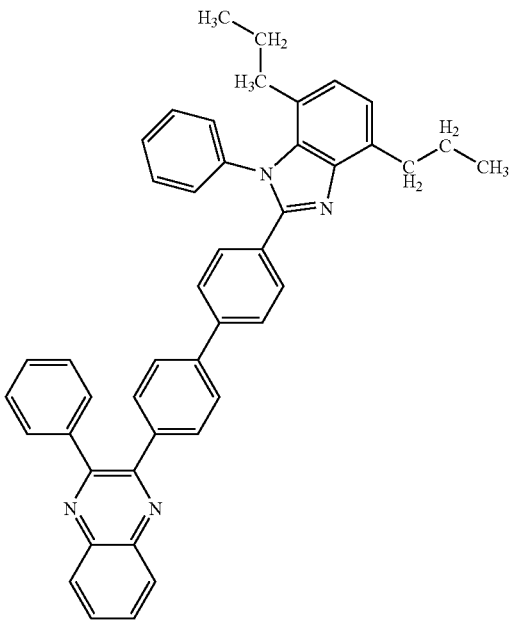

-continued
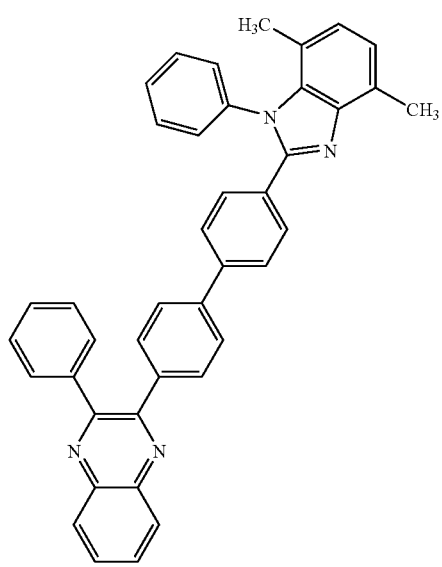
(139)
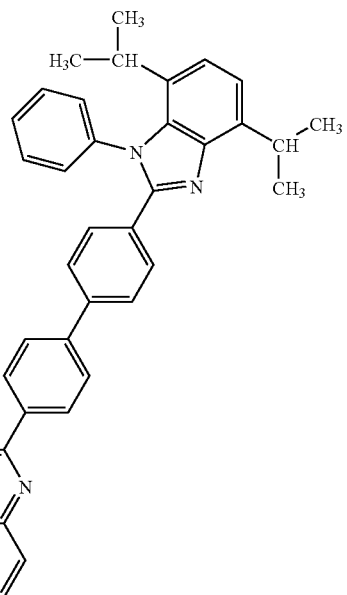
(140)
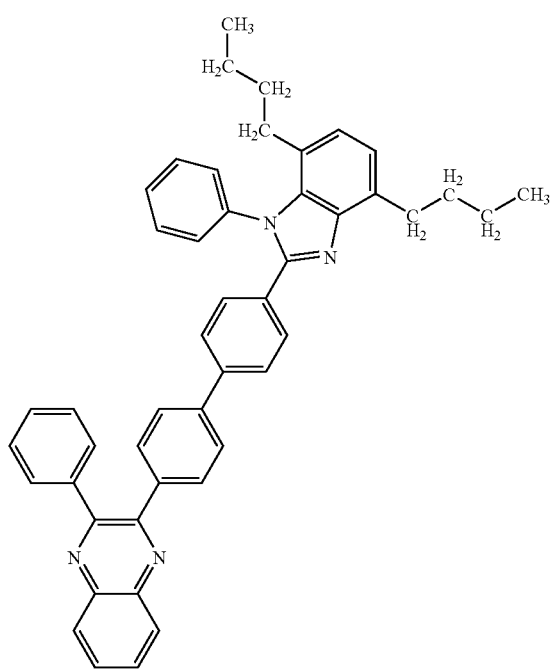
(141)
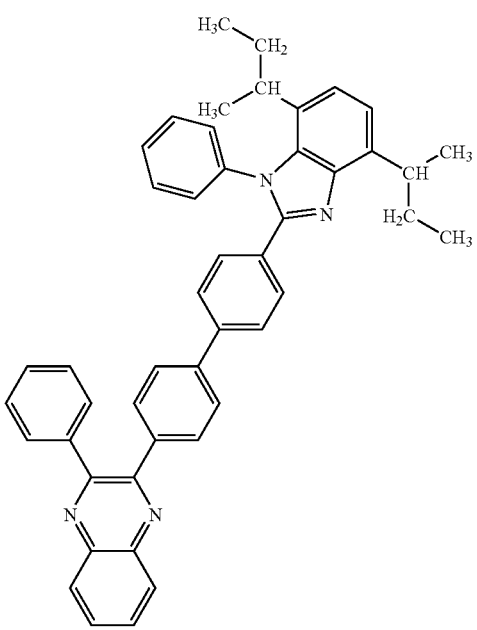
(142)

-continued
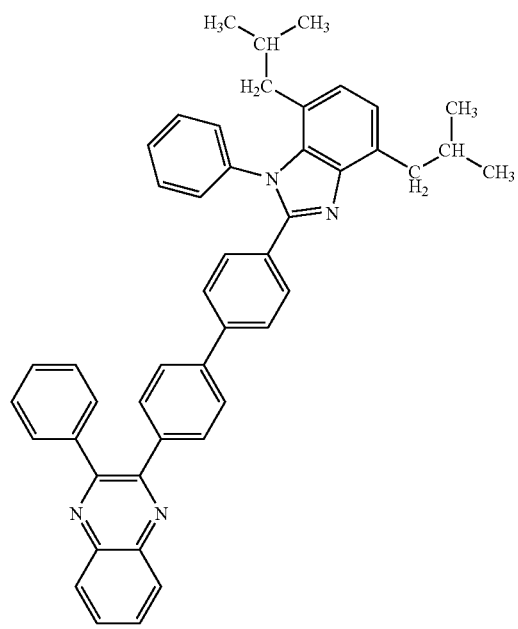
(143)
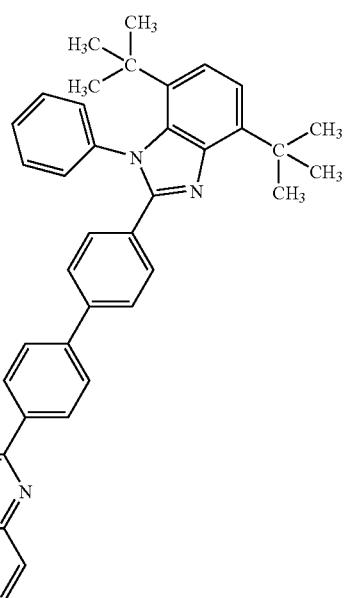
(144)
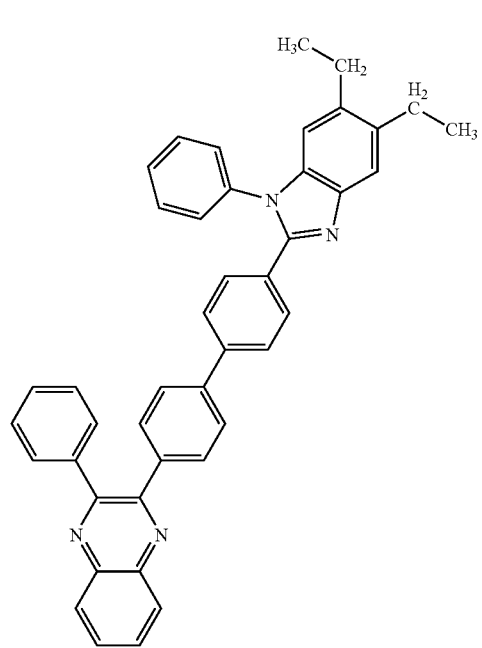
(145)
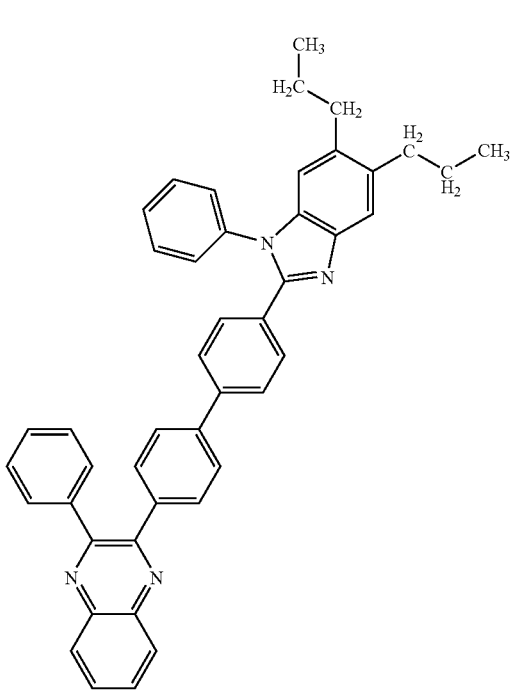
(146)

-continued
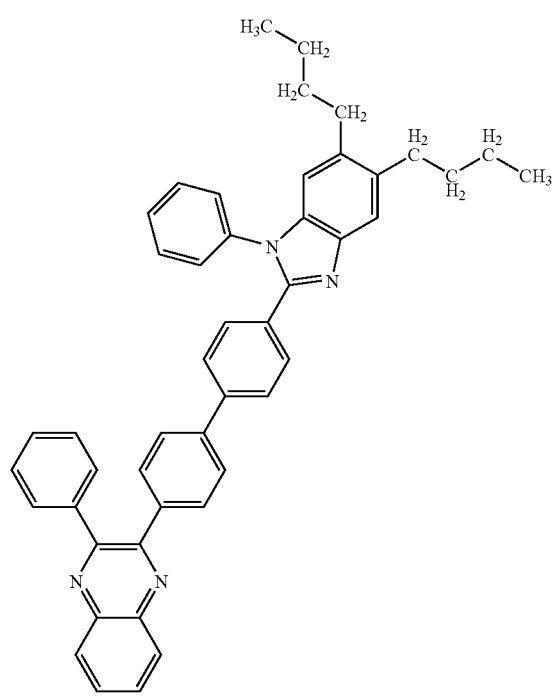
(147)
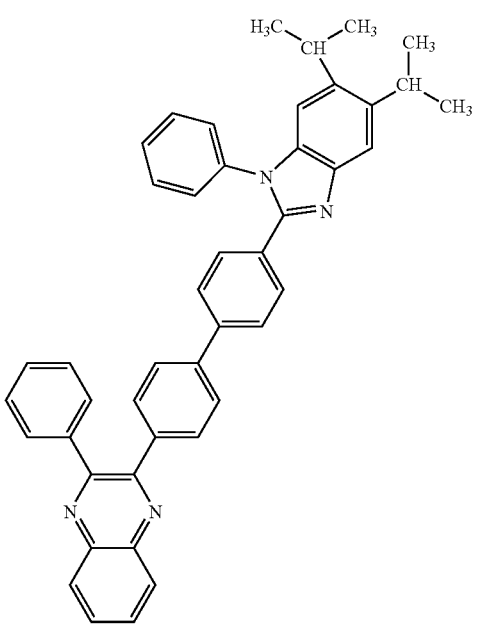
(148)
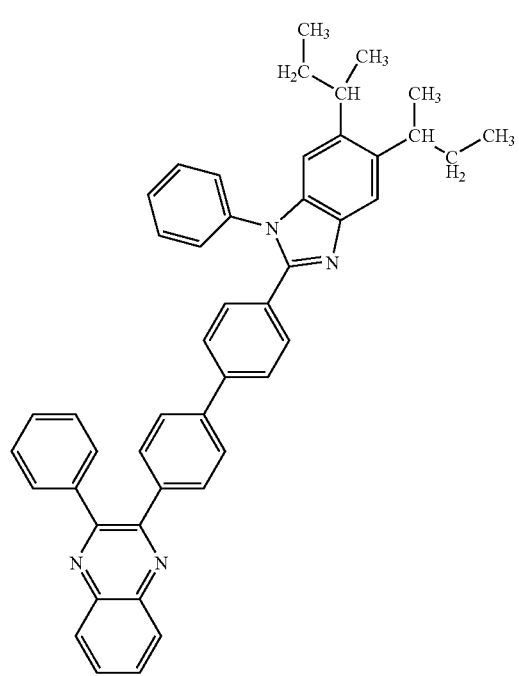
(149)
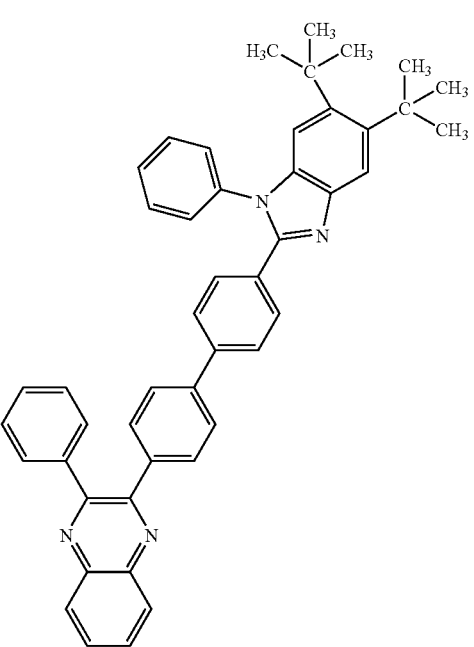
(150)

-continued
(151)
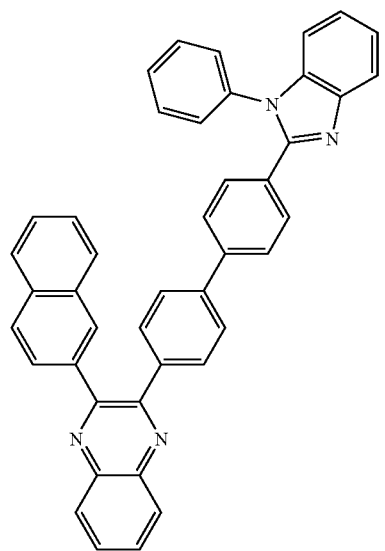
(152)
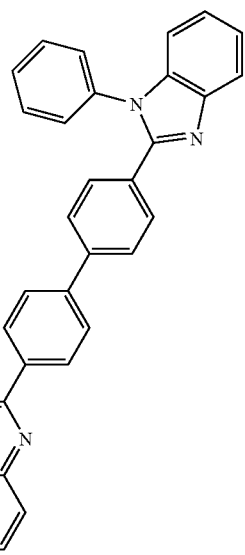
(153)
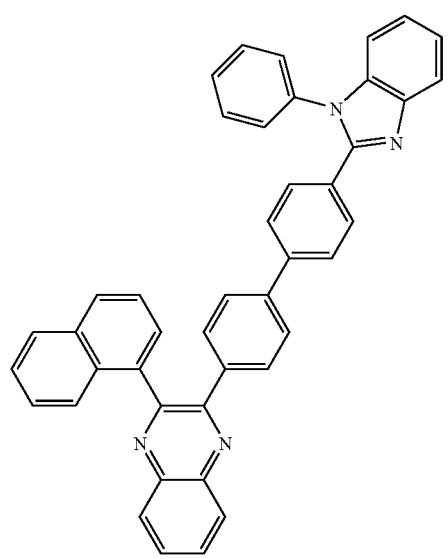
(154)
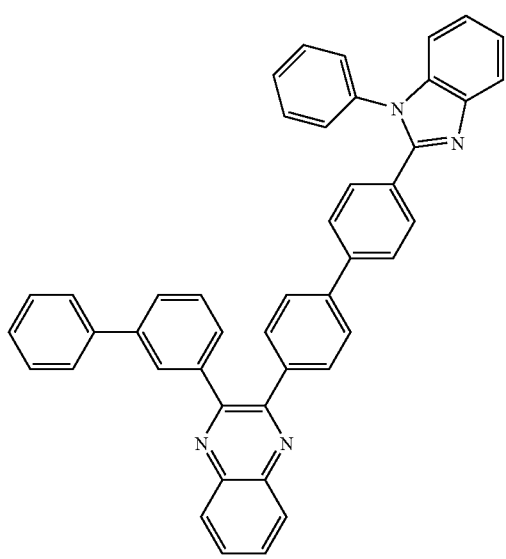
(155)
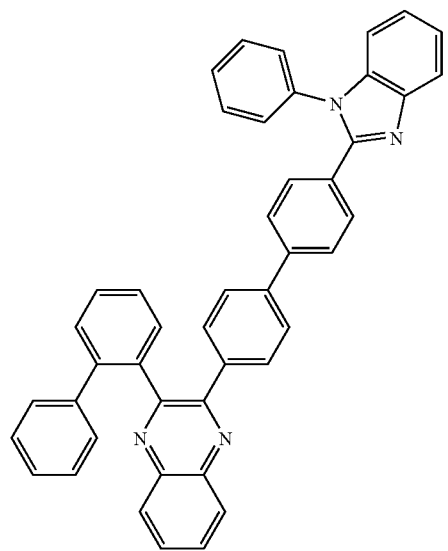
(156)
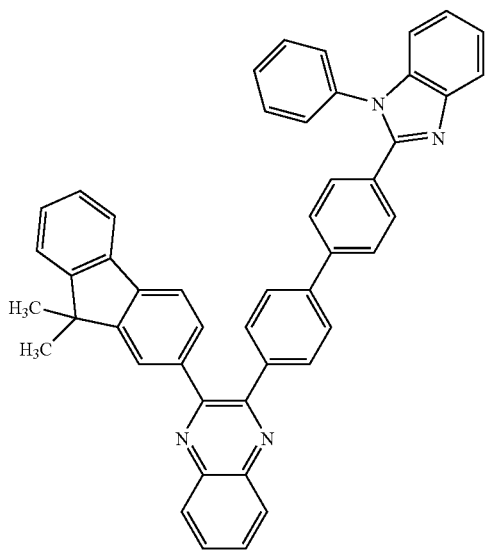

-continued
(157)
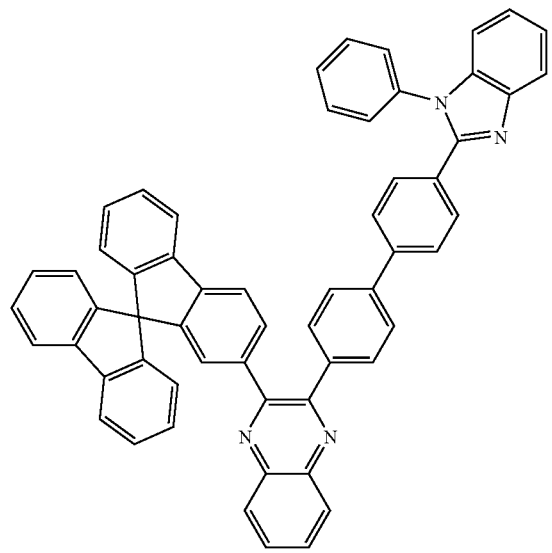
(158)
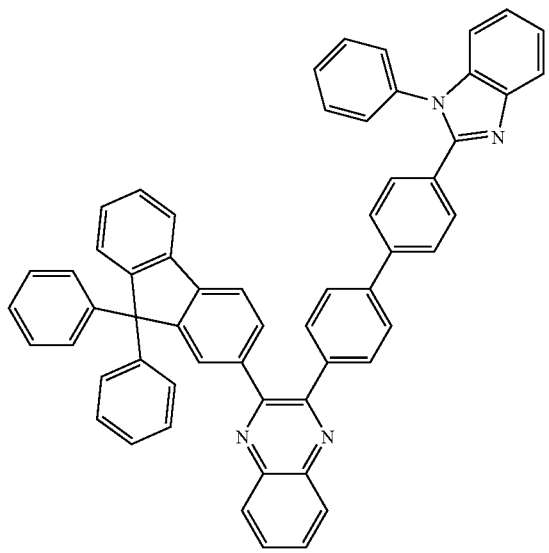
(159)
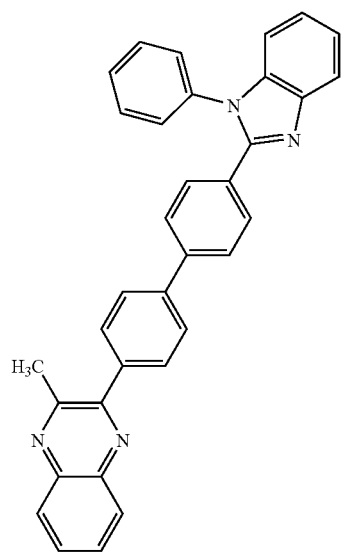
(160)
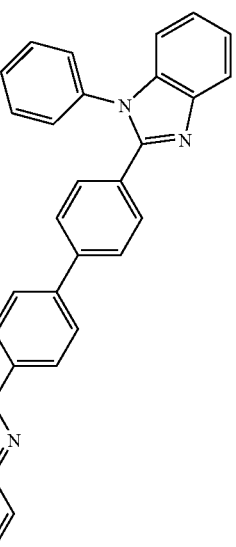
(161)
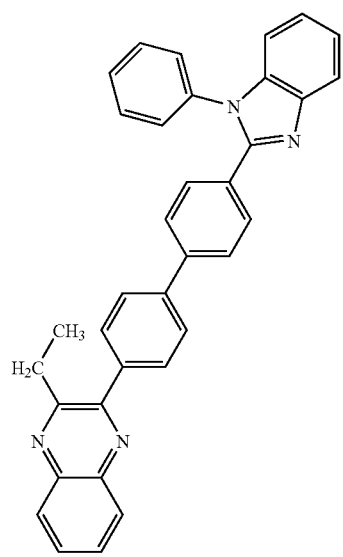
(162)
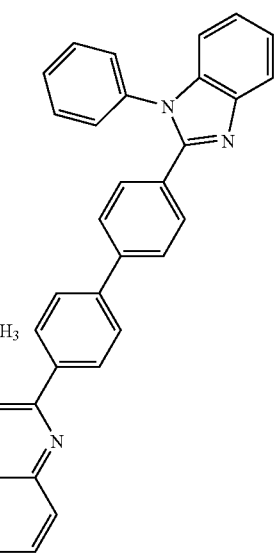

-continued
(163)
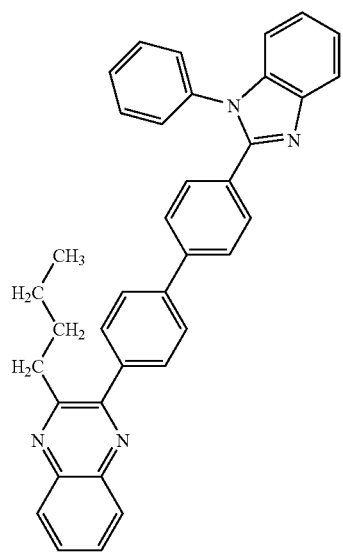
(164)
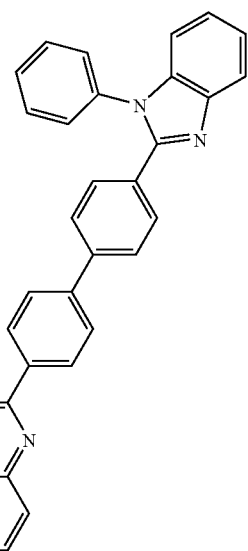
(165)
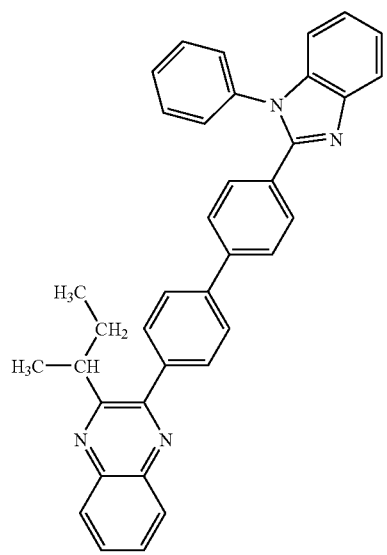
(166)
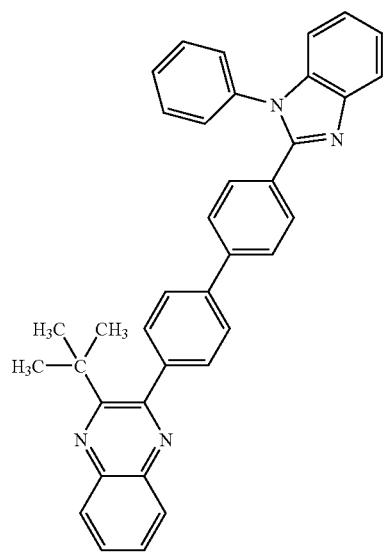
(167)
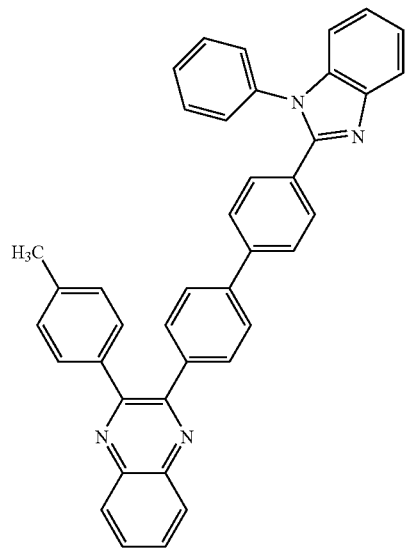
(168)
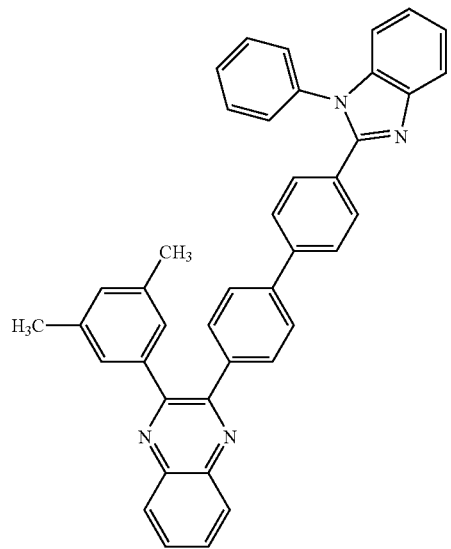

-continued
(169)
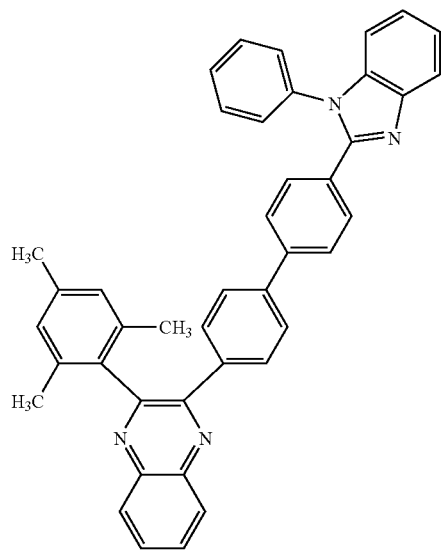
(170)
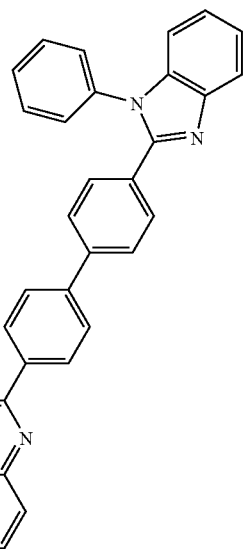
(171)
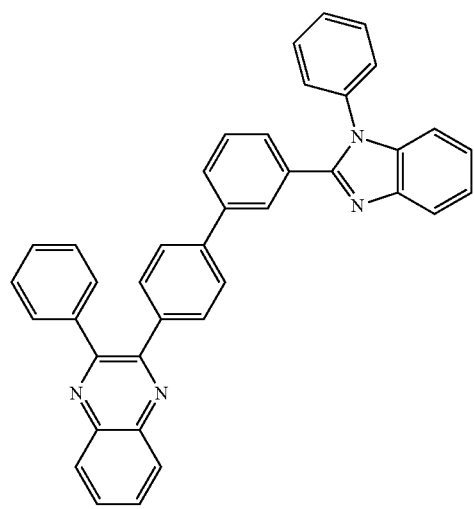
(172)
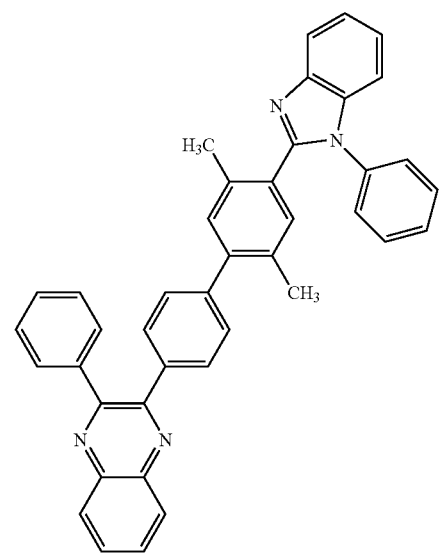
(173)
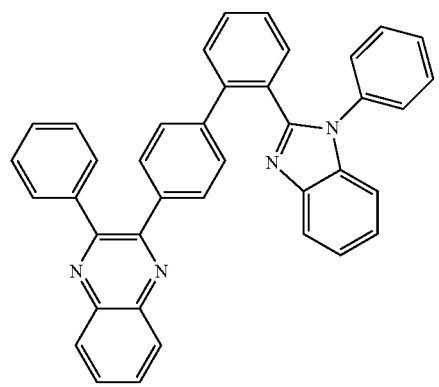
(174)
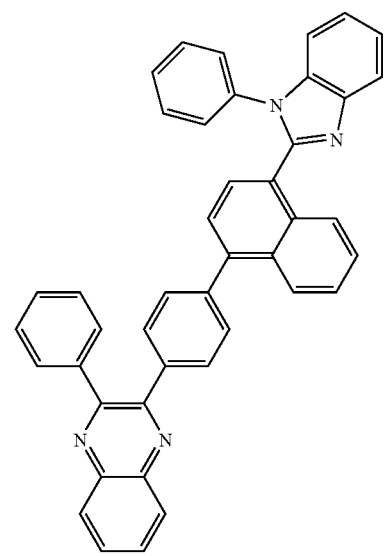

-continued
(175)
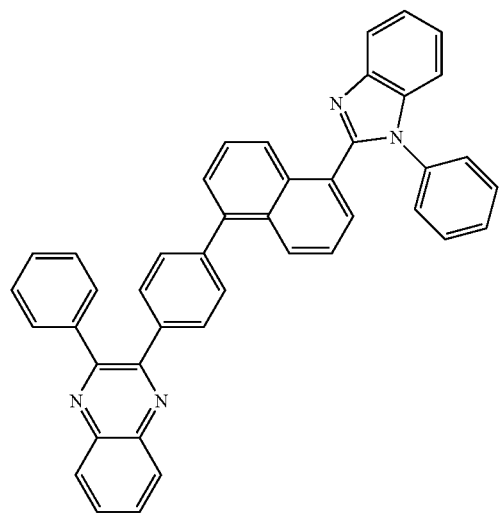
(176)
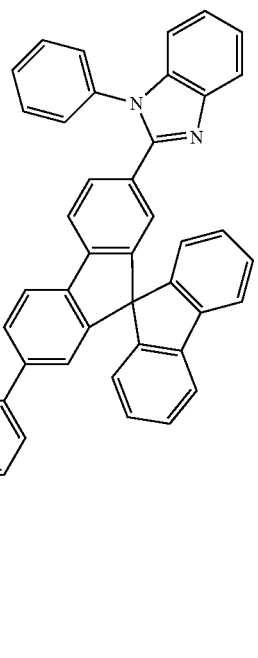
(177)
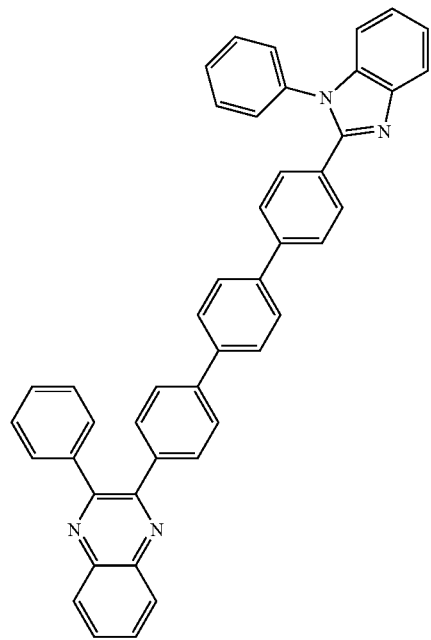
(178)
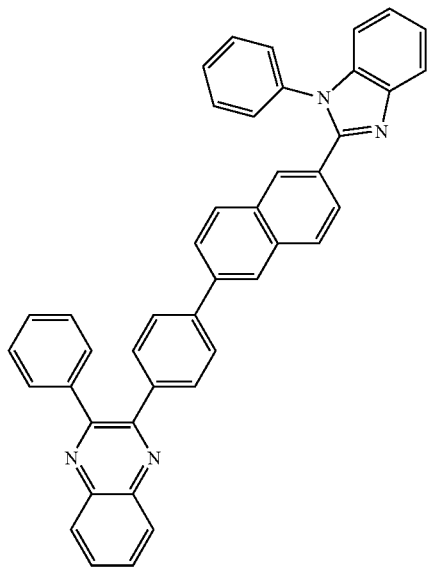

-continued
(179)
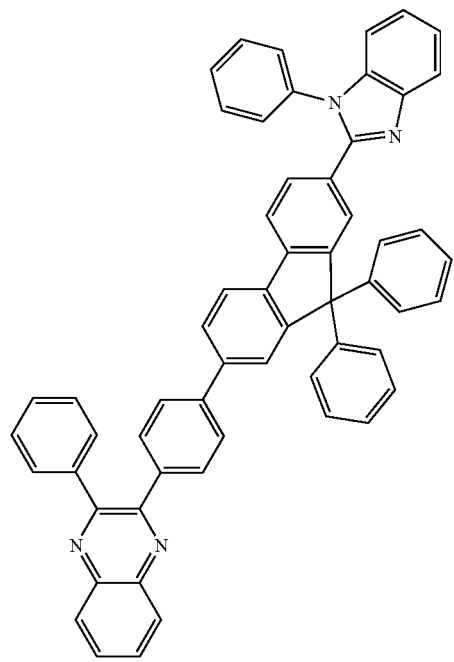
(180)
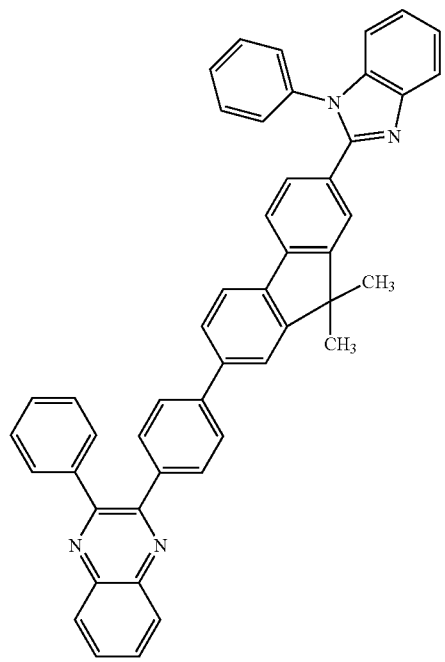
(181)
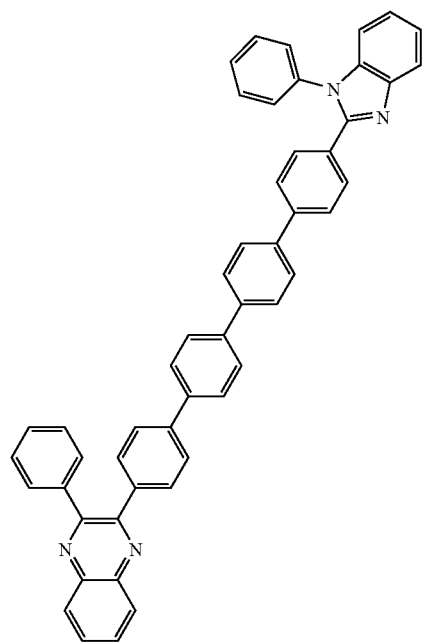
(182)
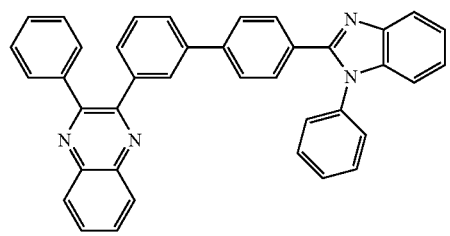

-continued
(183)
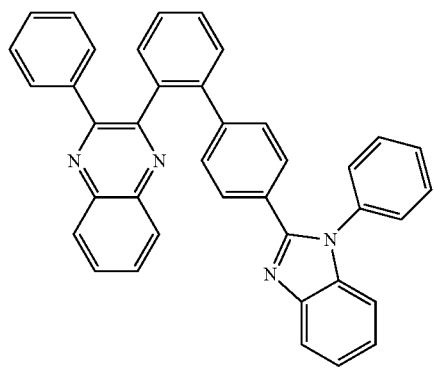
(184)
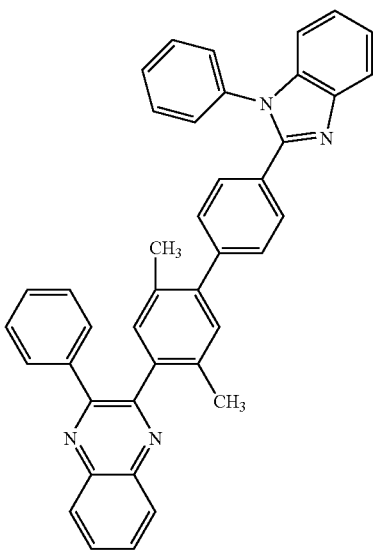
(185)
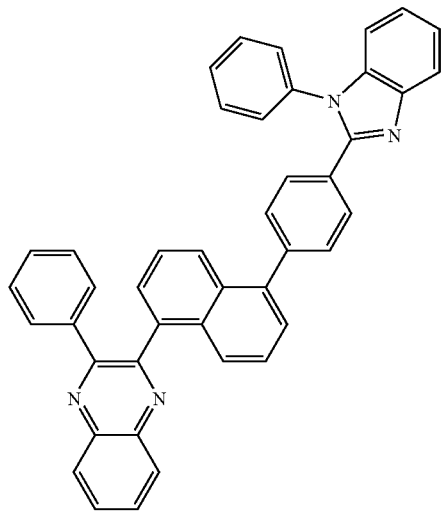
(186)
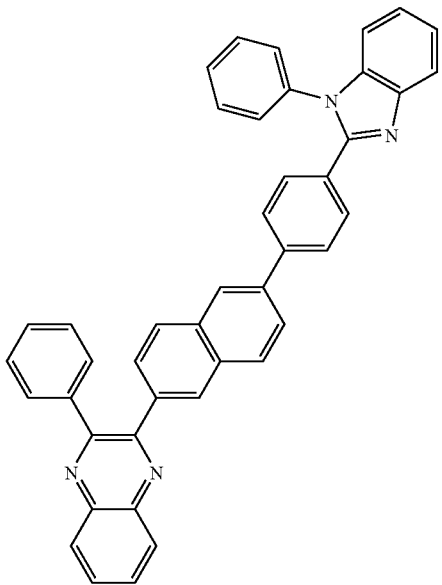

-continued
(187)
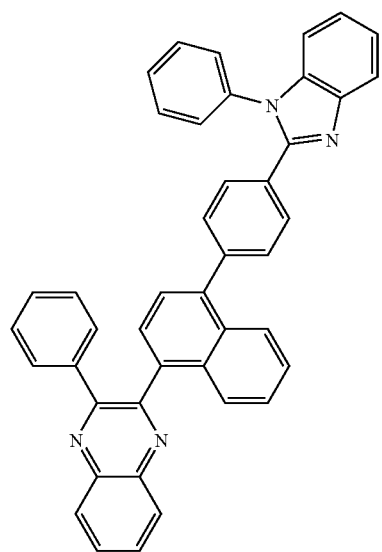
(188)
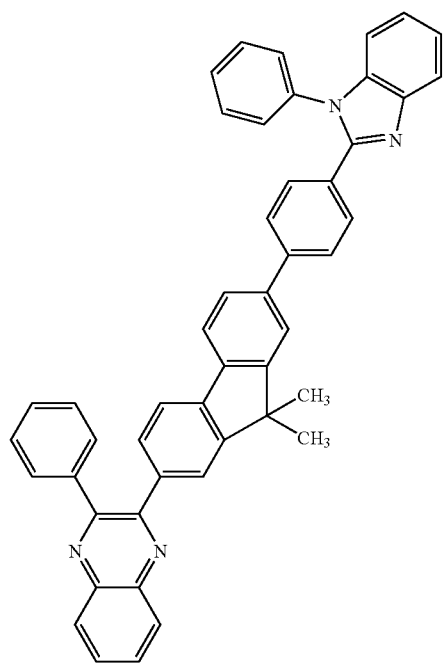
(189)
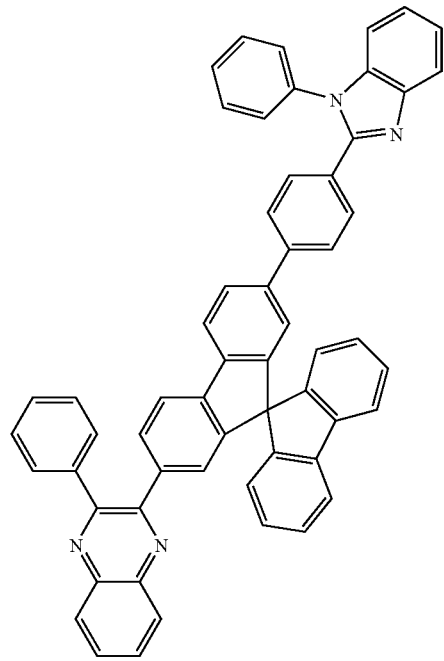
(190)
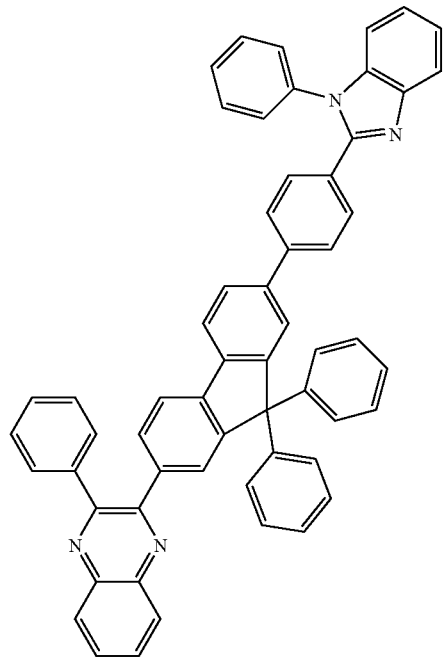

(191)
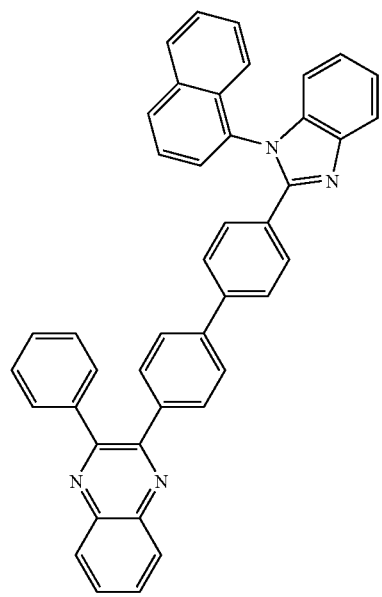
(192)
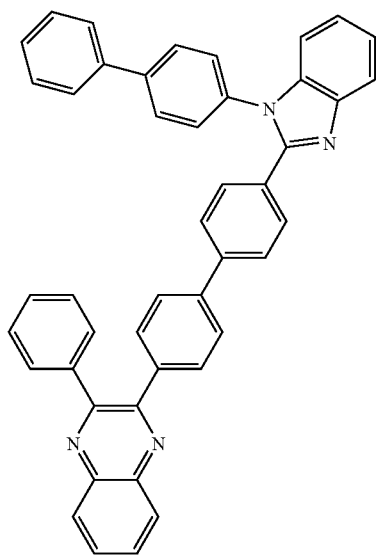
(193)
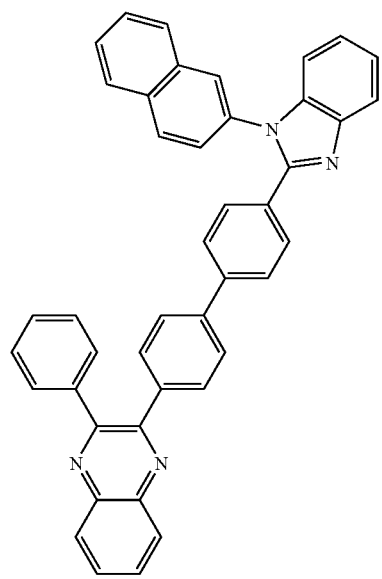
(194)
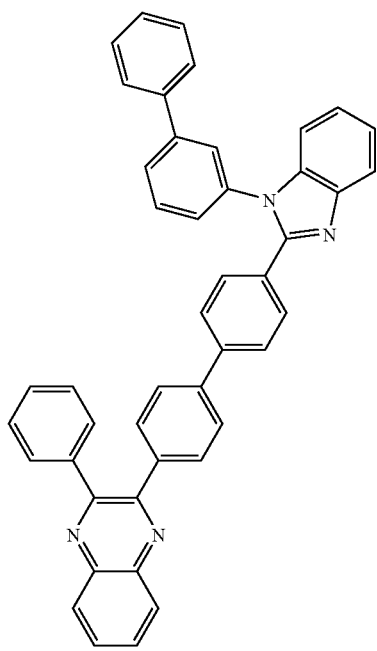

-continued
(195)
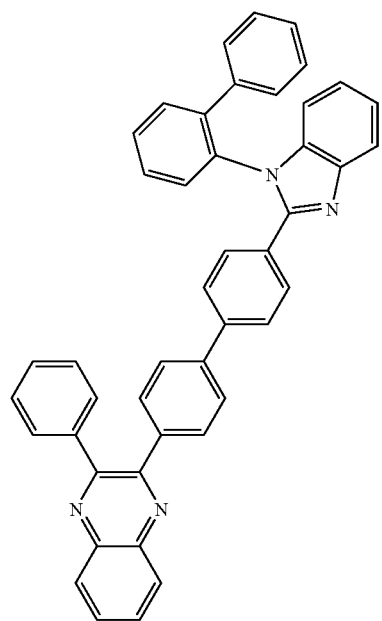
(196)
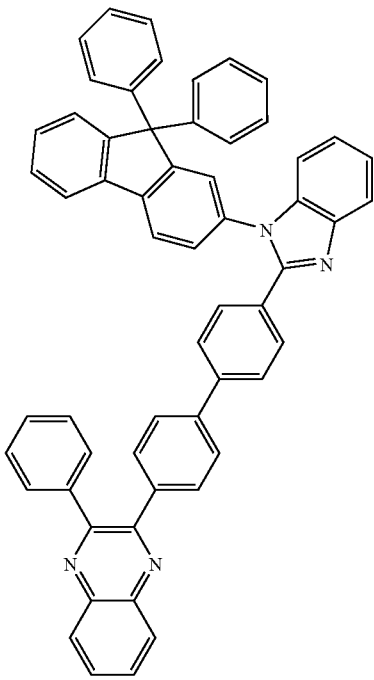
(197)
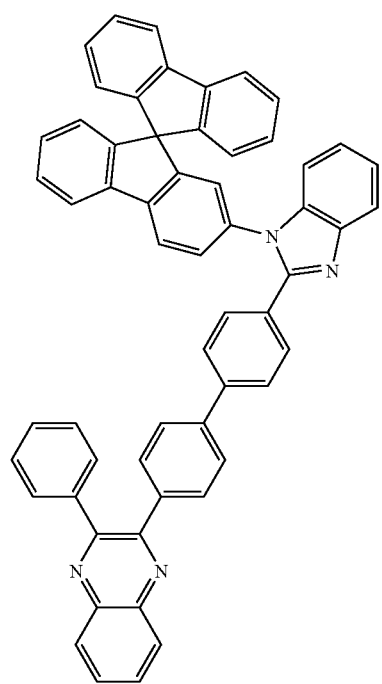
(198)
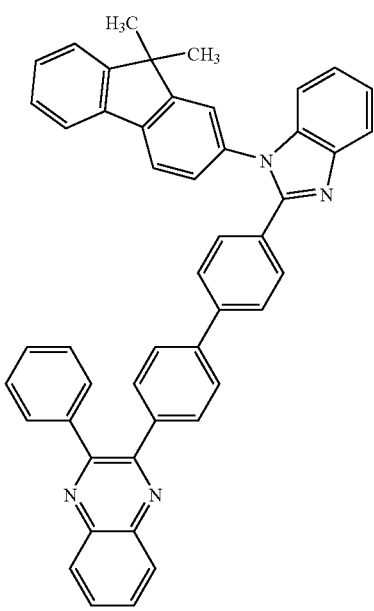

-continued
(199)
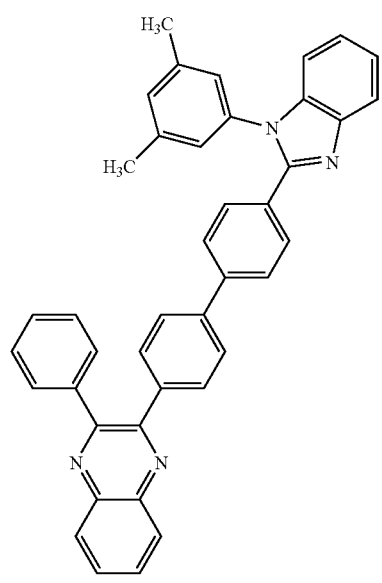
(200)
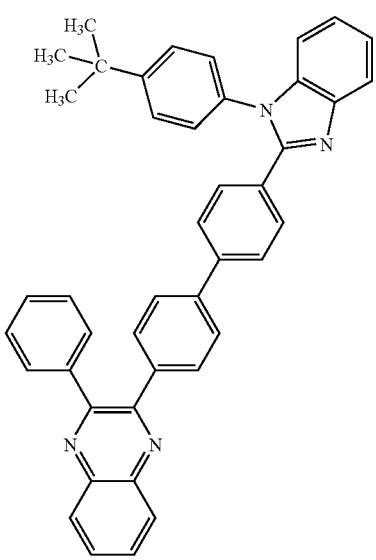
(201)
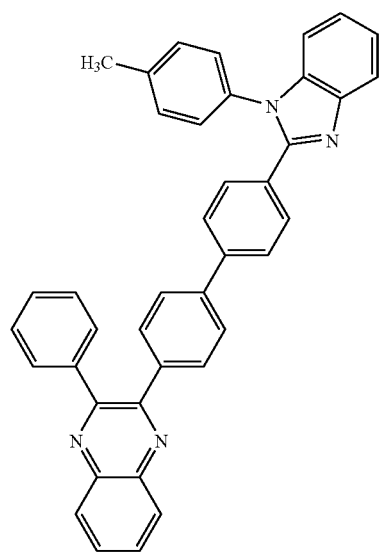
(202)
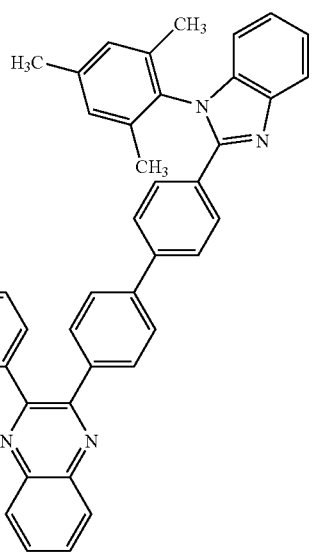
(203)
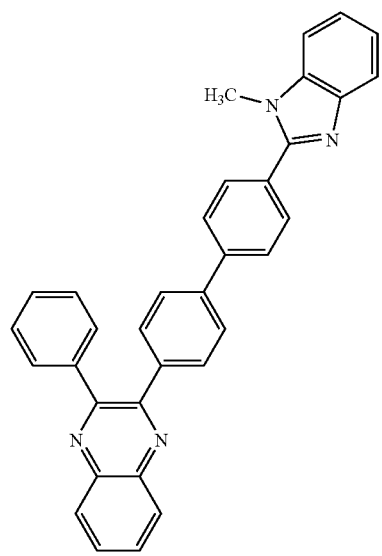
(204)
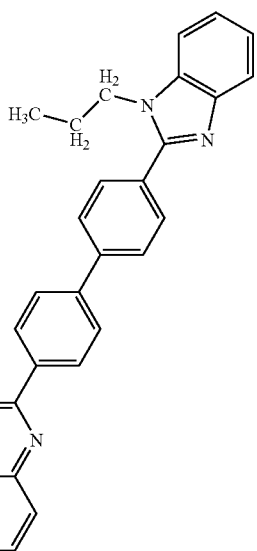

-continued
(205)
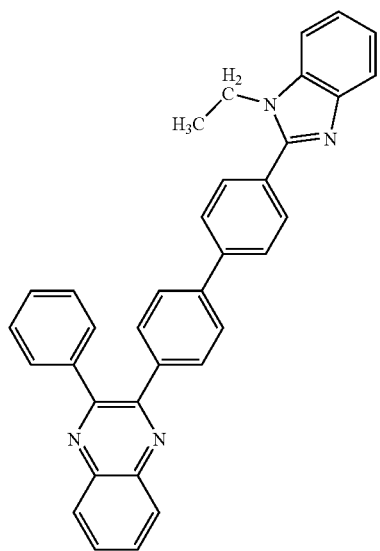
(206)
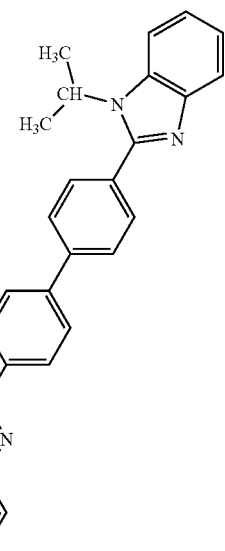
(207)
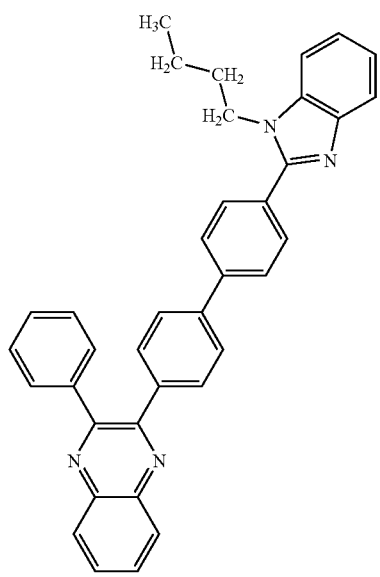
(208)
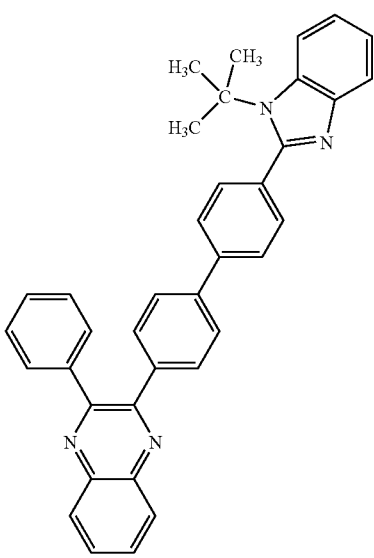
(209)
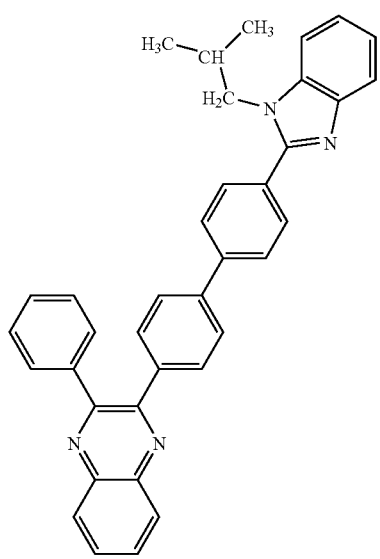
(210)
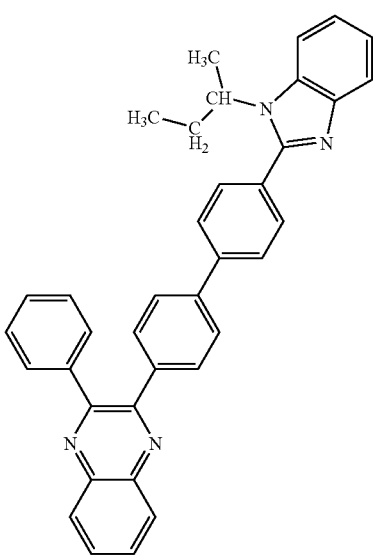

-continued
(300)
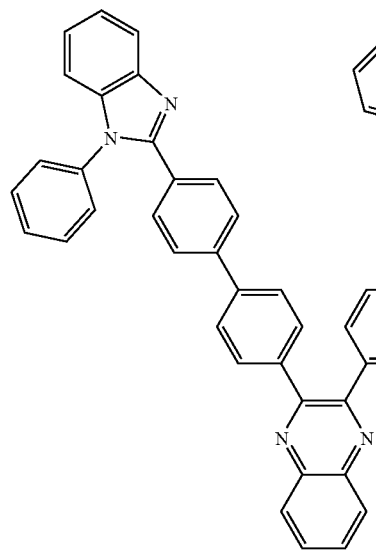
(301)
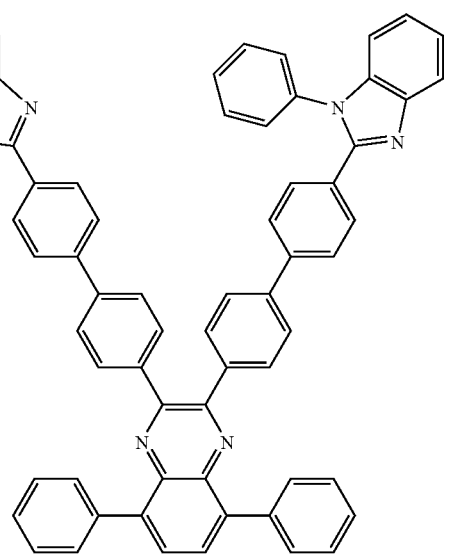
(302)
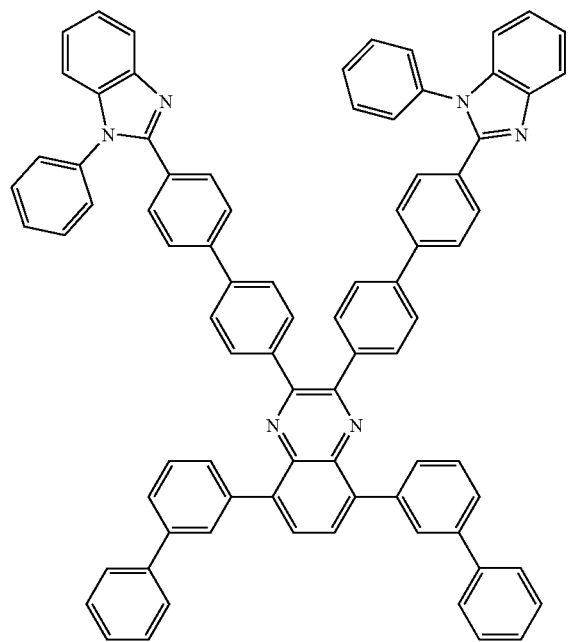
(303)
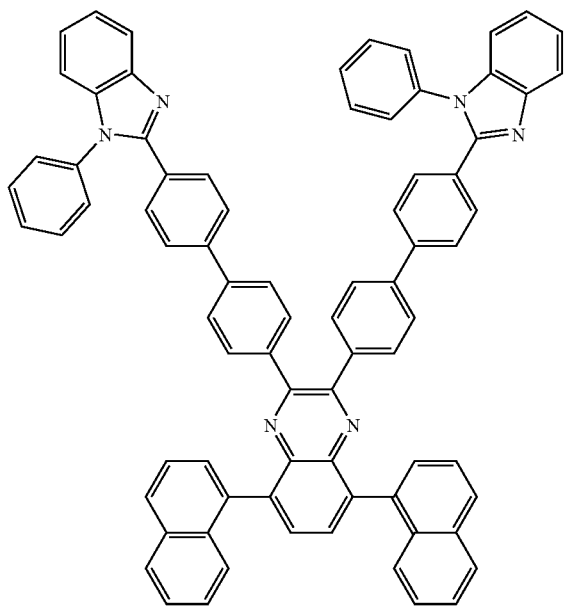

-continued
(304)
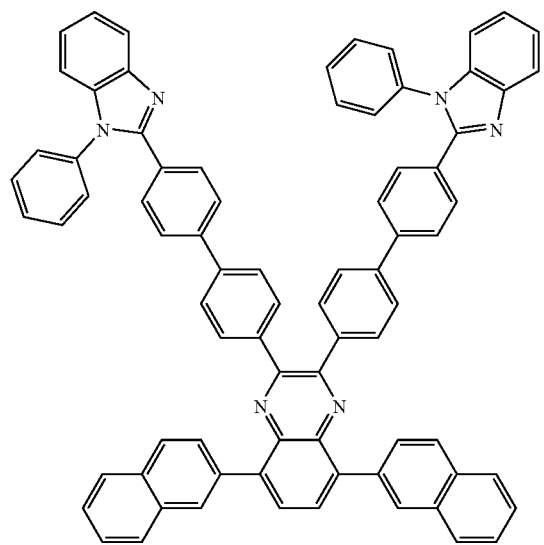
(305)
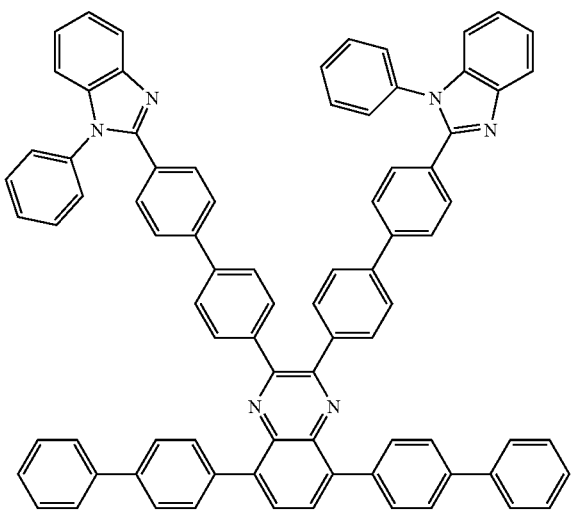
(306)
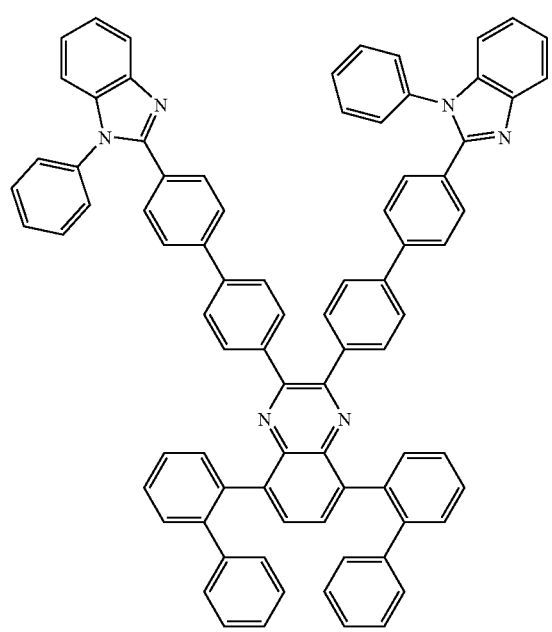
(307)
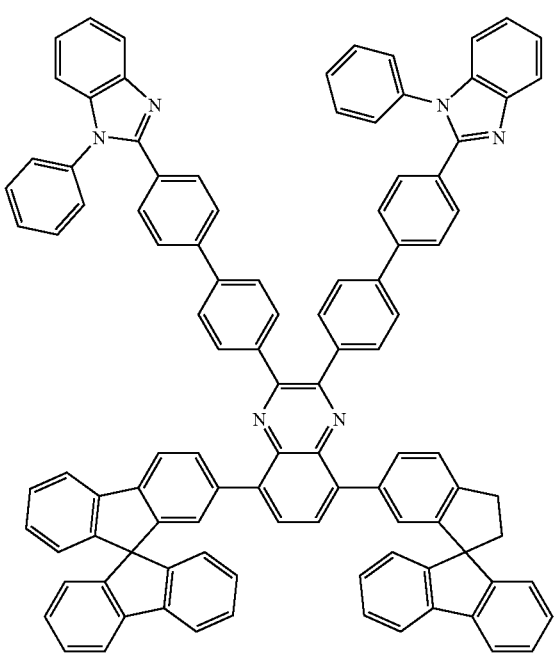

-continued
(308)
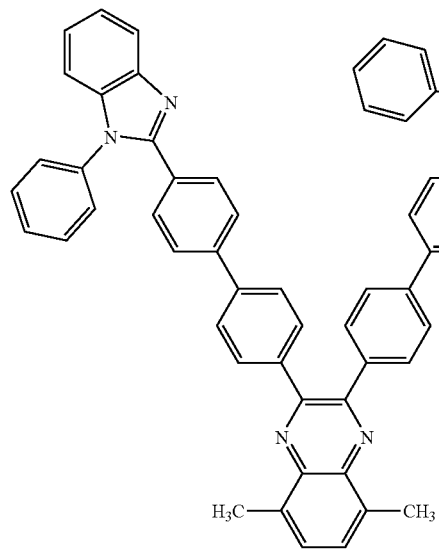
(309)
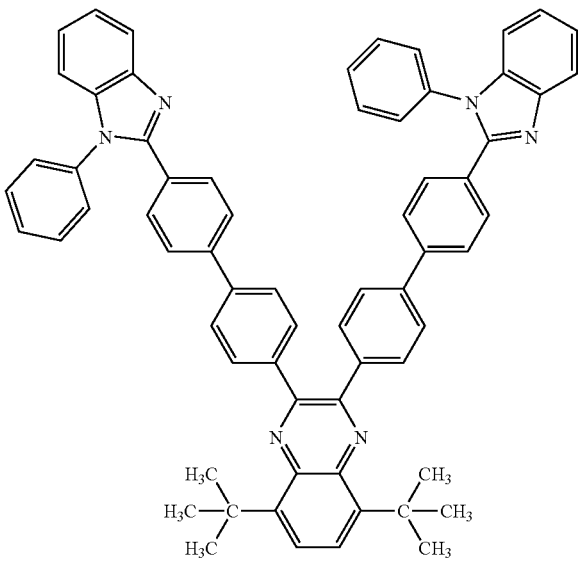
(310)
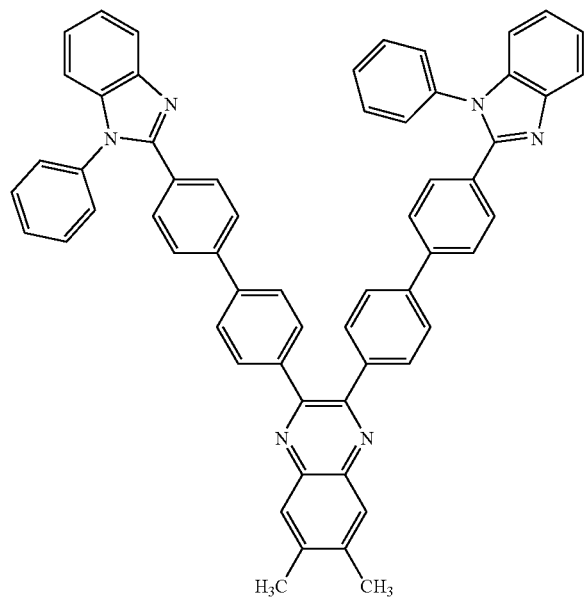
(311)
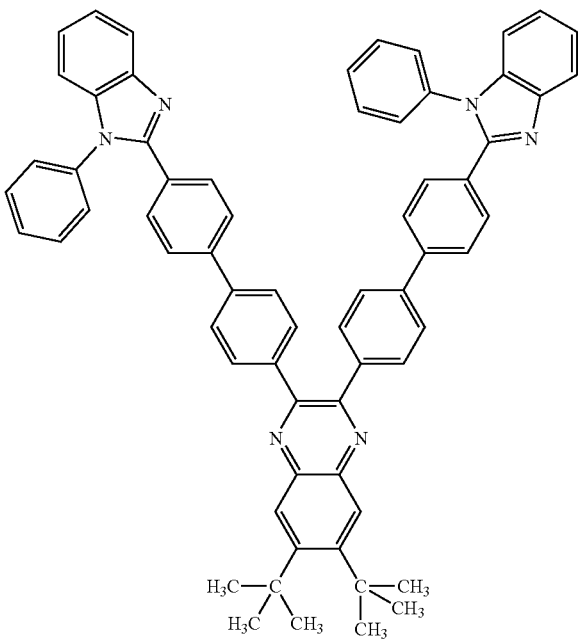

-continued
(312)
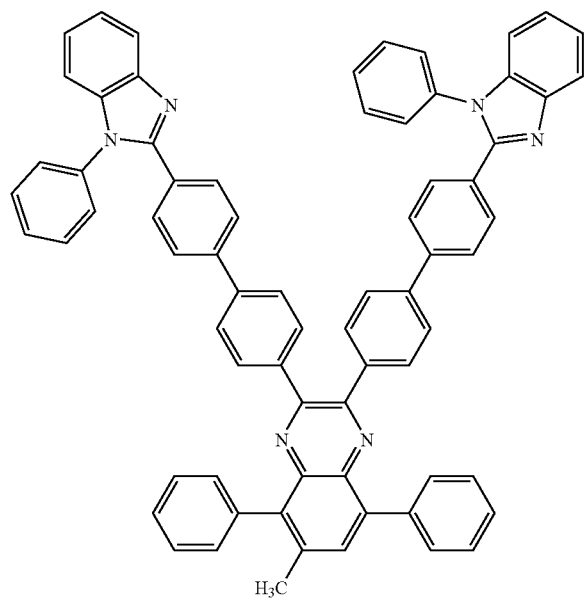
(313)
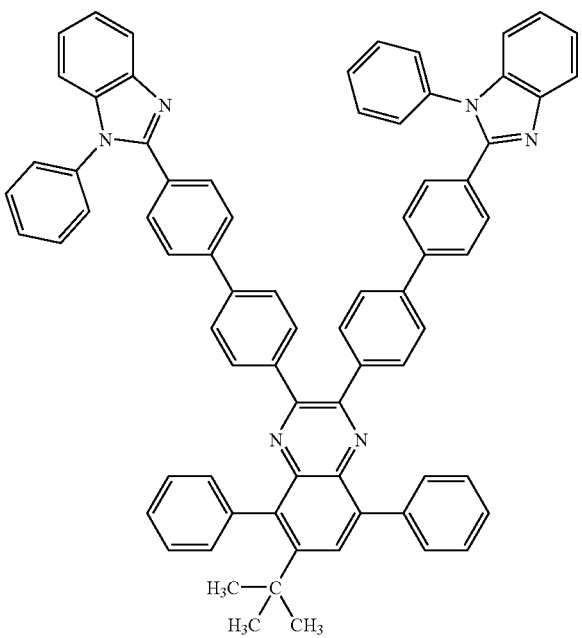
(314)
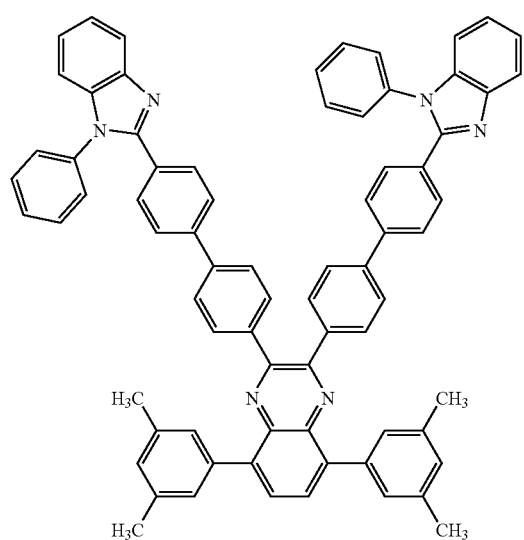
(315)
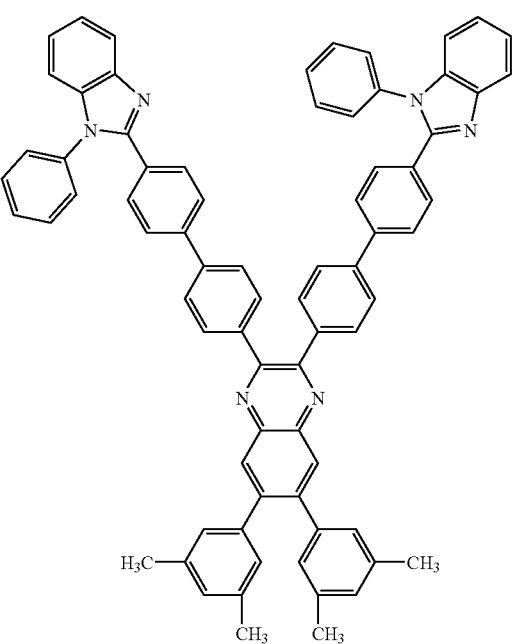

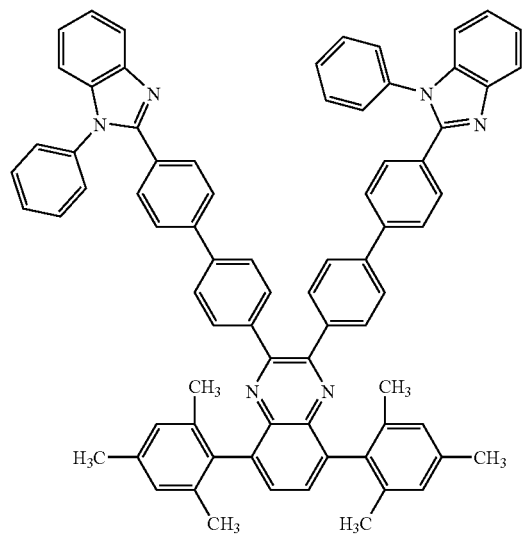
(316)
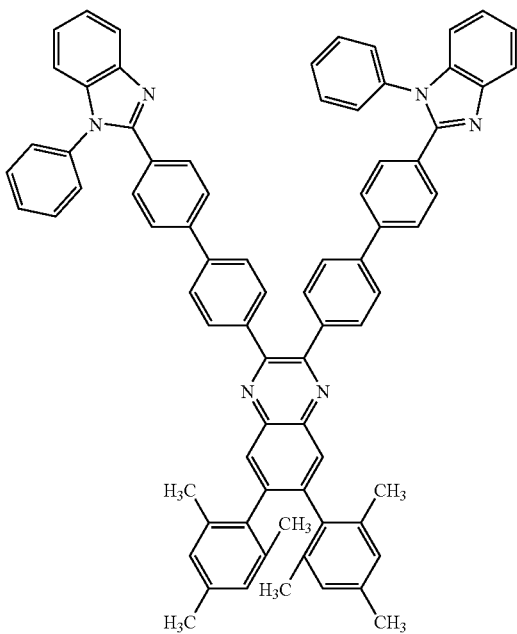
(317)
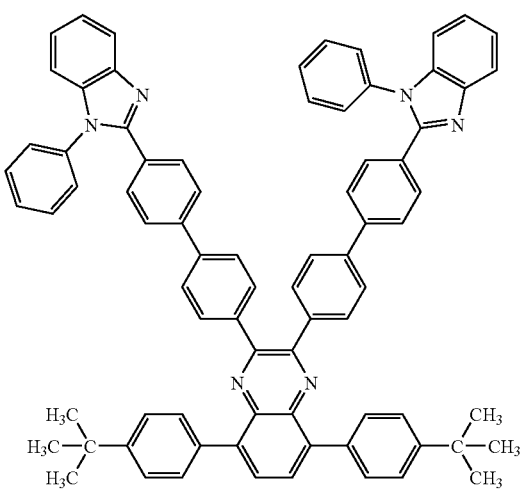
(318)
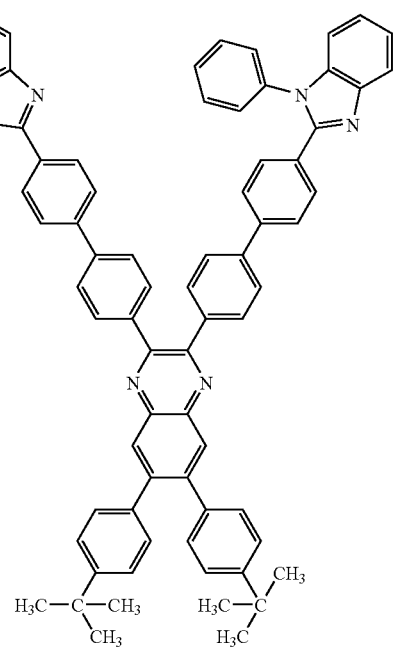
(319)

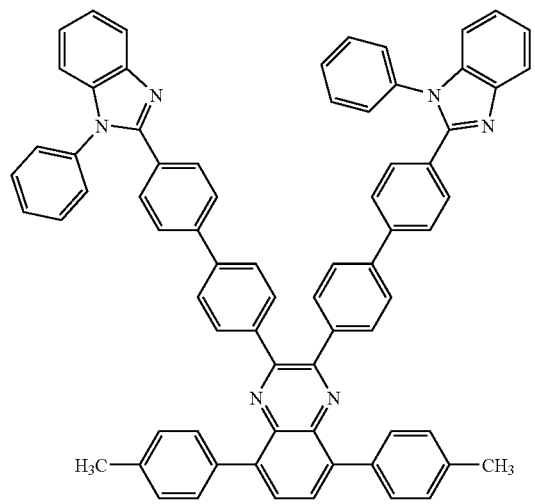
(320)
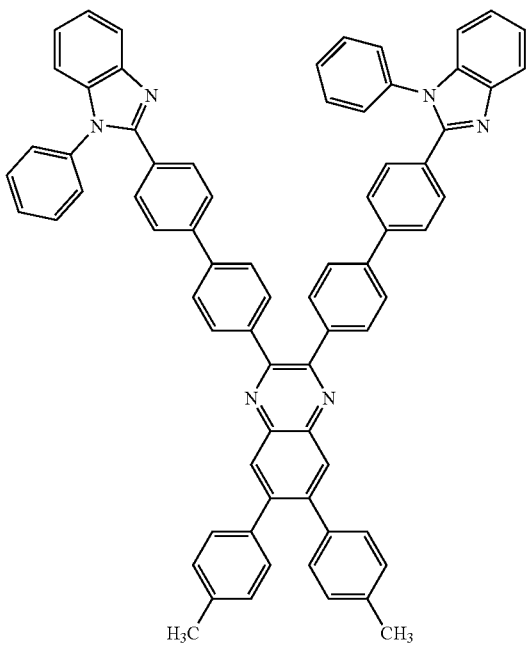
(321)
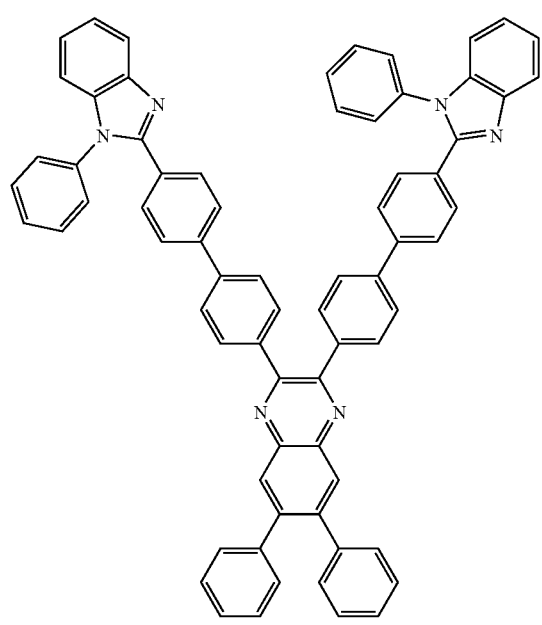
(322)
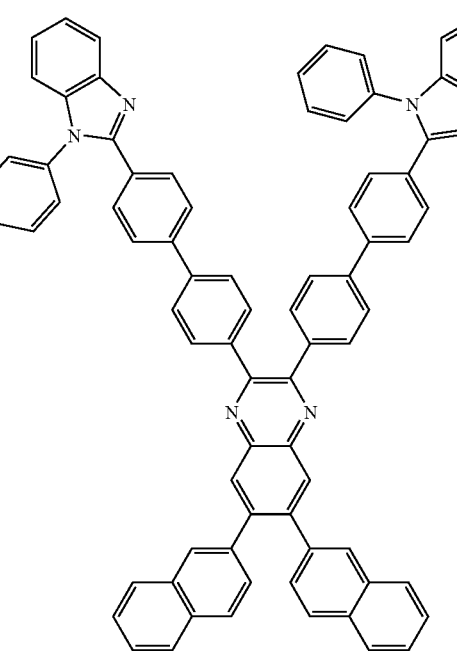
(323)

(324)
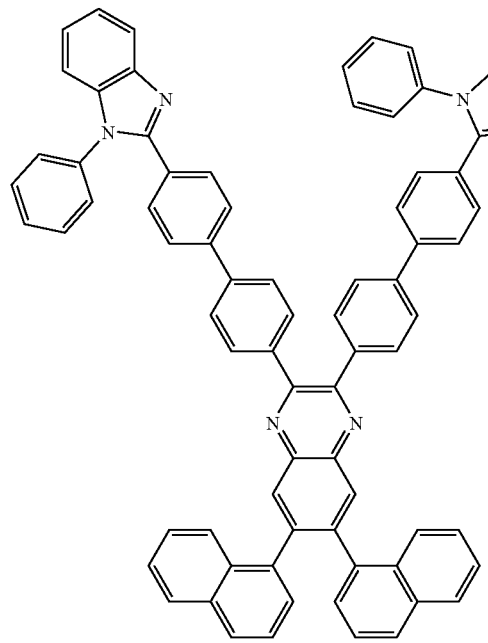
(325)
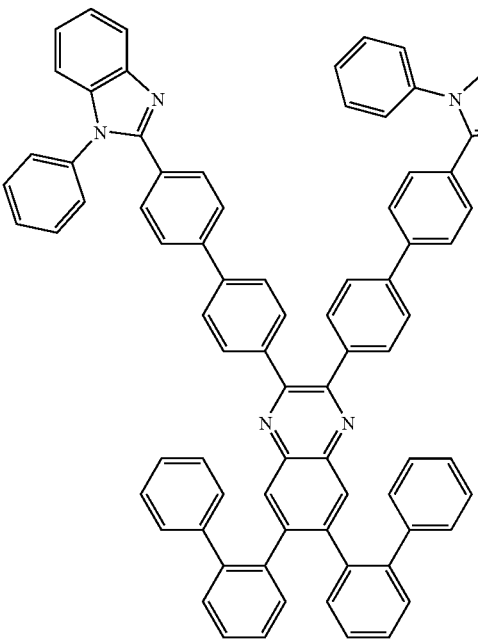
(326)
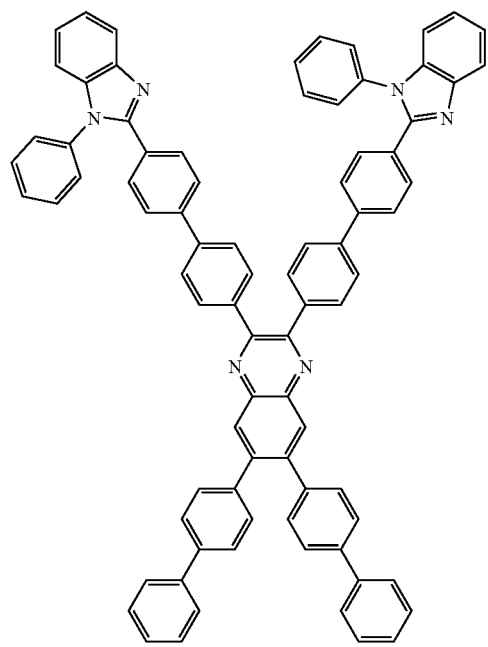
(327)
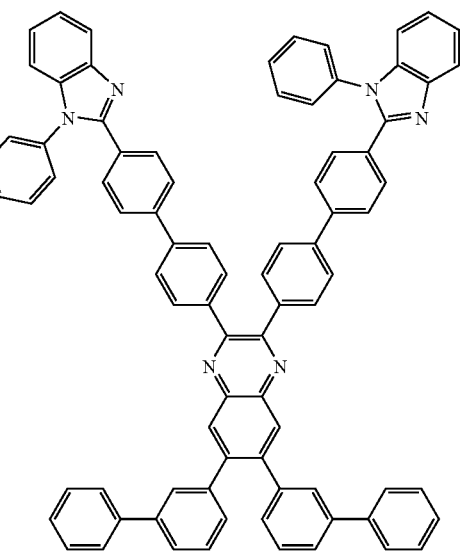

(328)
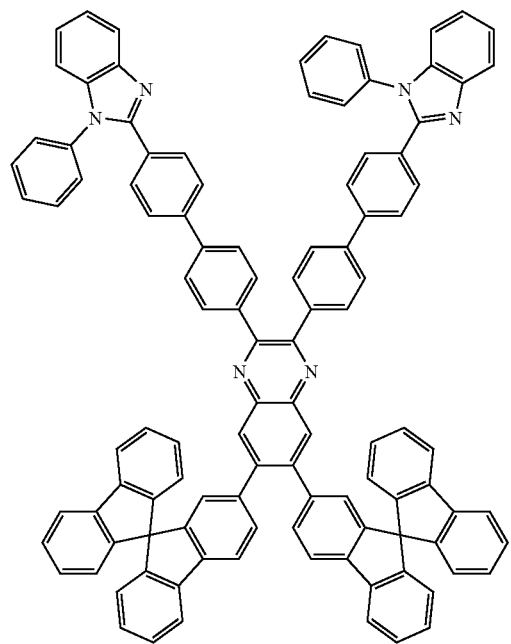
(329)
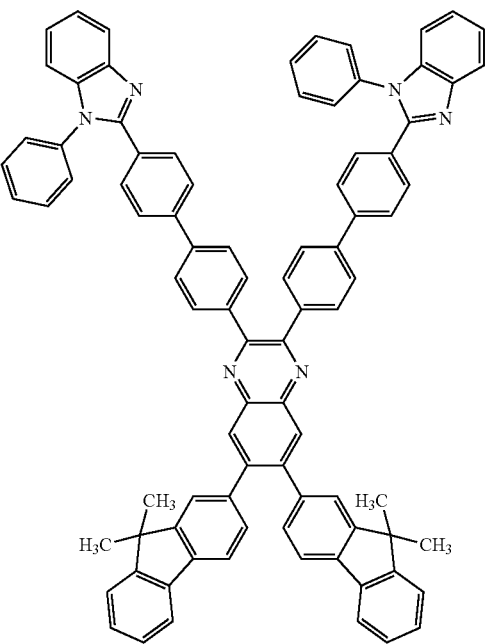
(330)
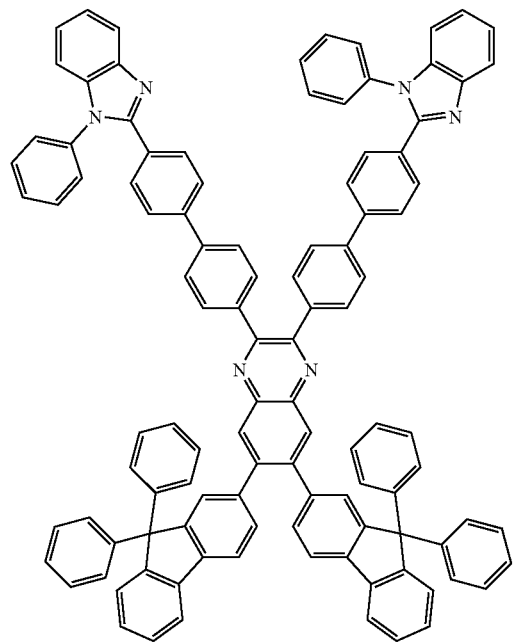
(331)
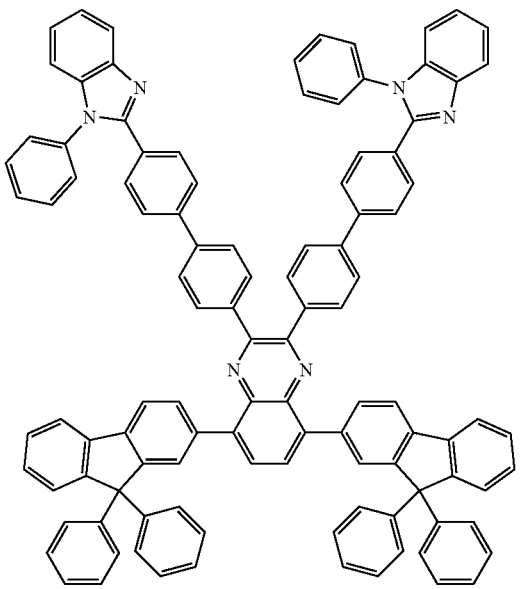

-continued
(332)
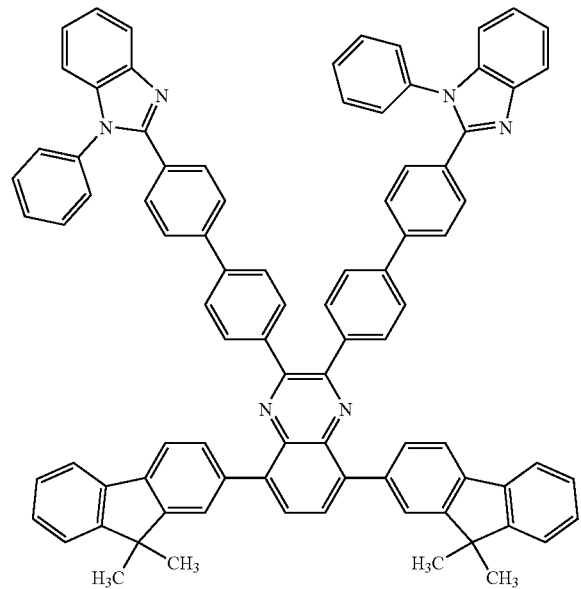
(333)
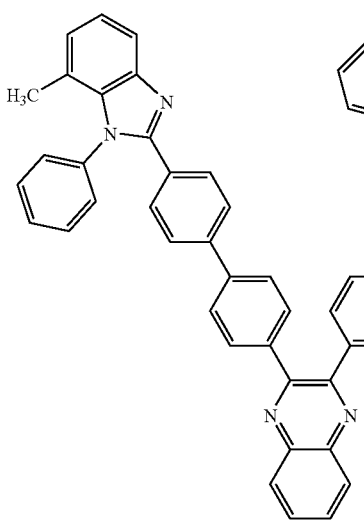
(334)
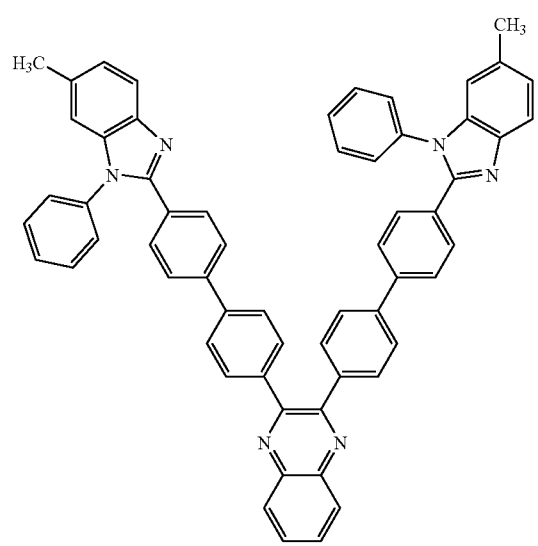
(335)
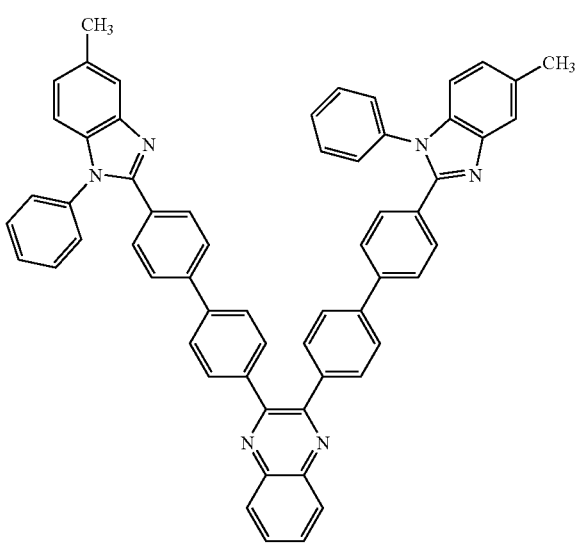
(336)
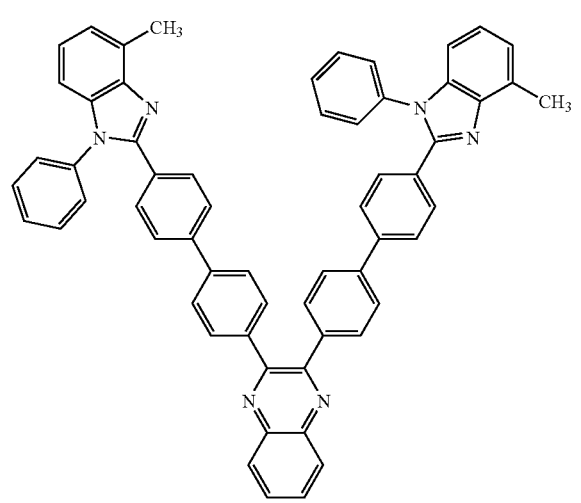
(337)
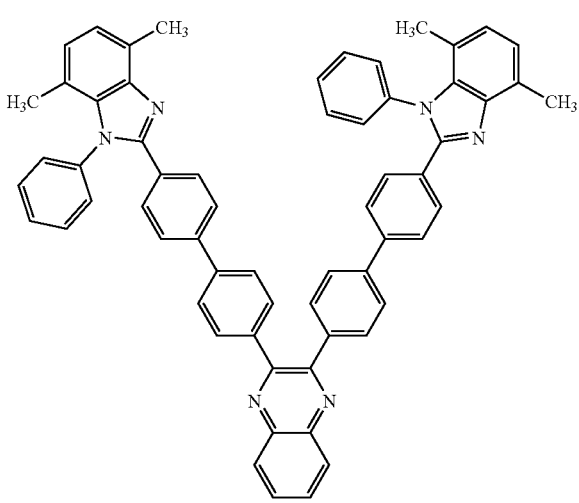

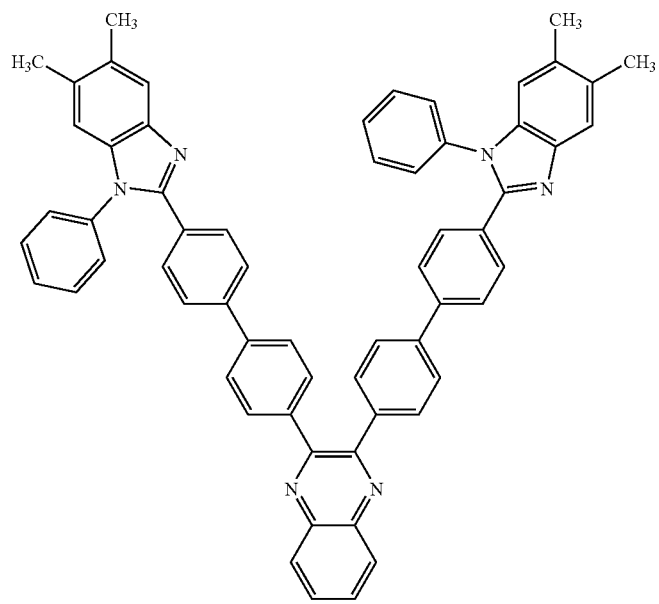
(338)
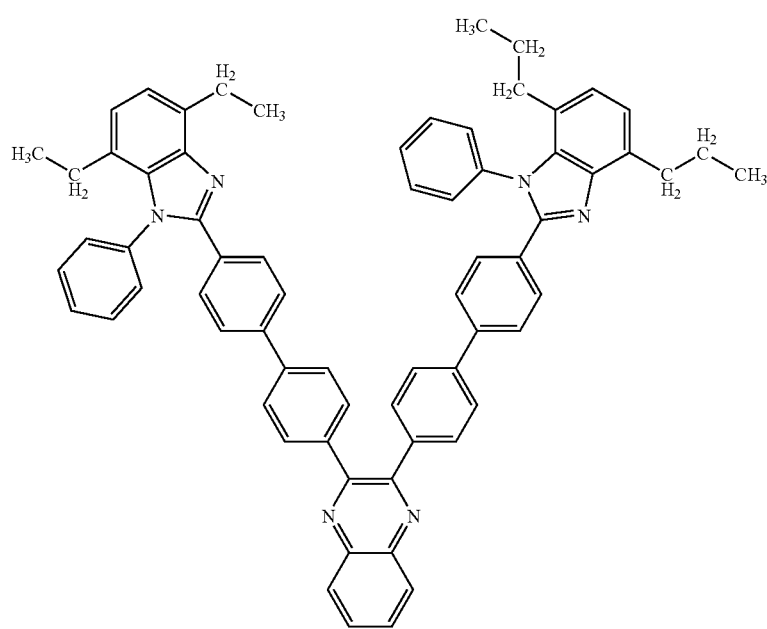
(339)

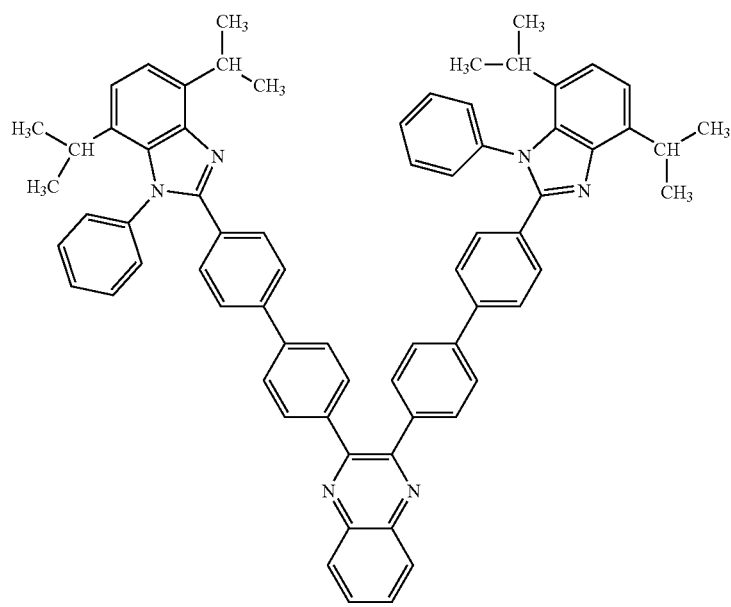
(340)
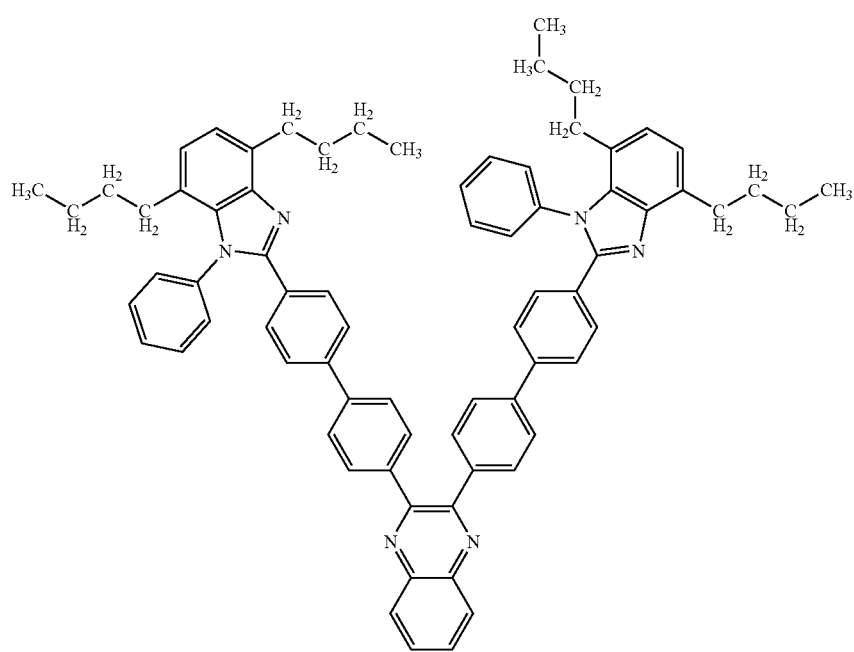
(341)

-continued
(342)
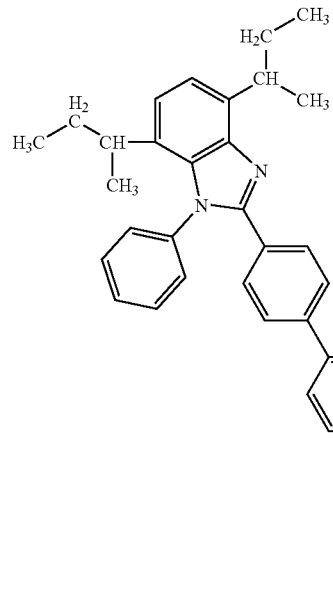 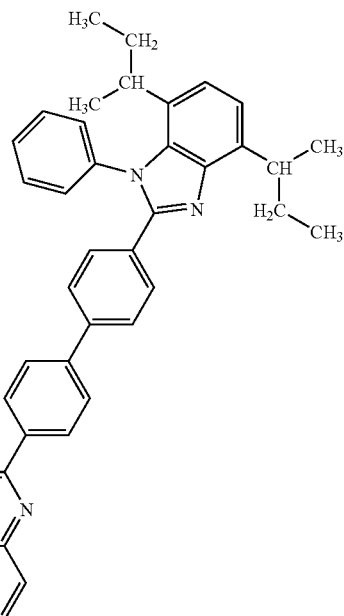
(343)
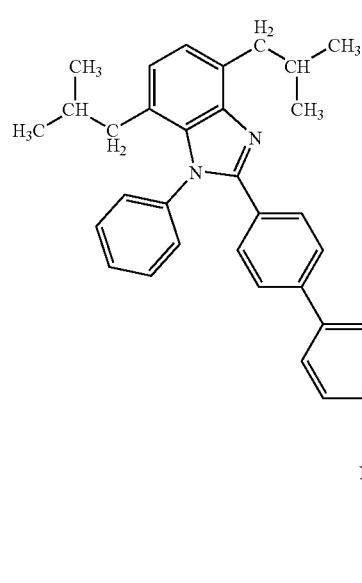 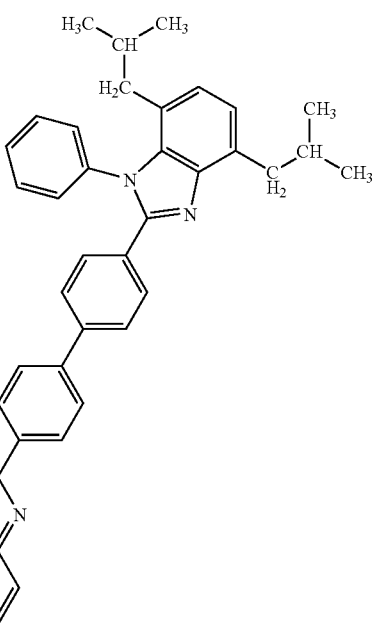

-continued
(344)
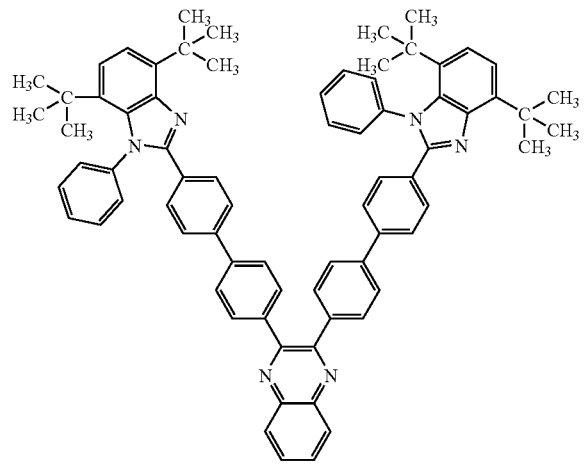
(345)
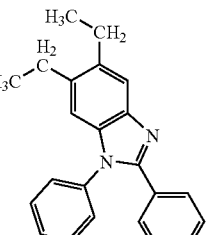
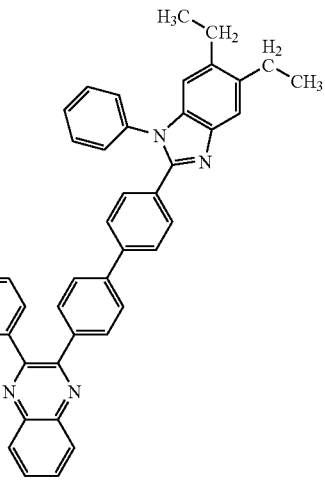
(346)
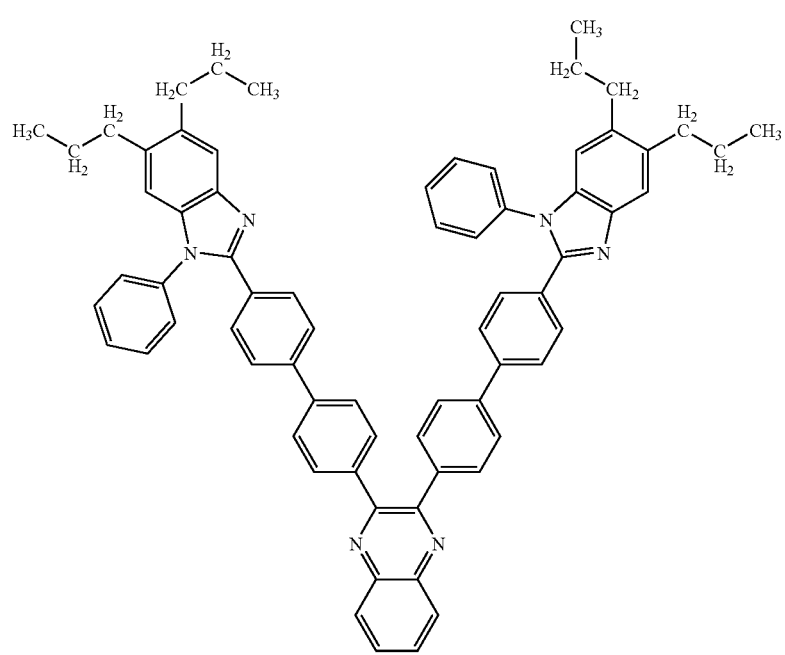

(347)
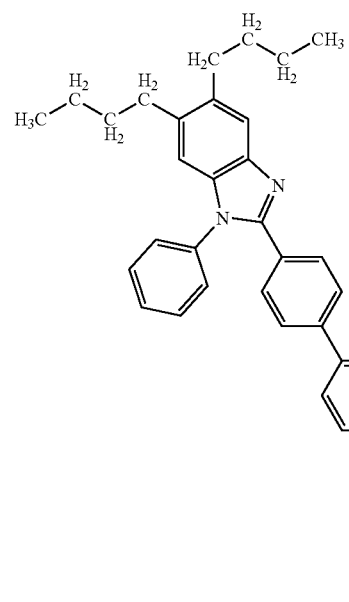 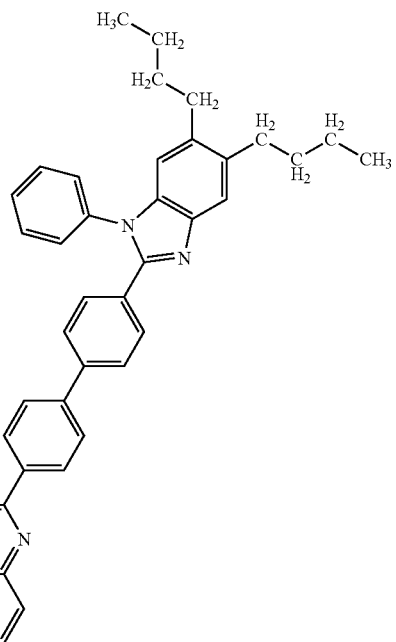
(348)
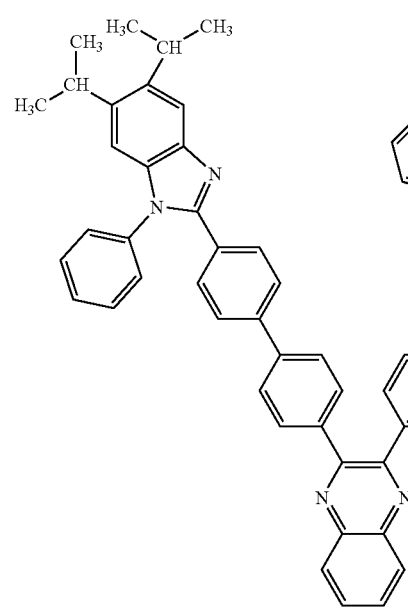 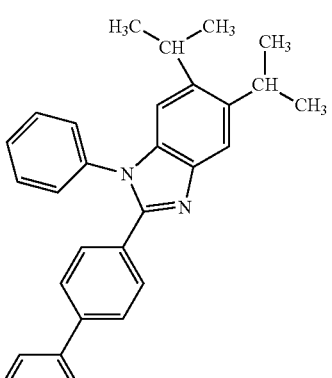

-continued
(349)
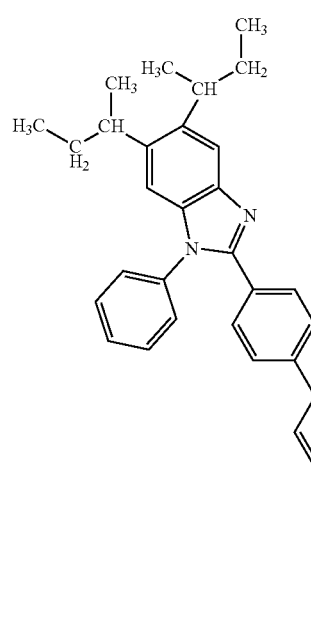
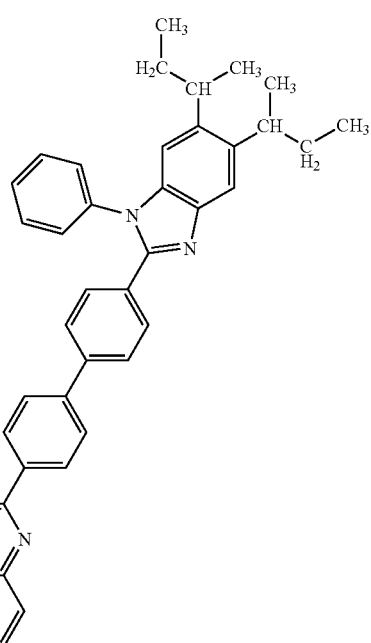
(350)
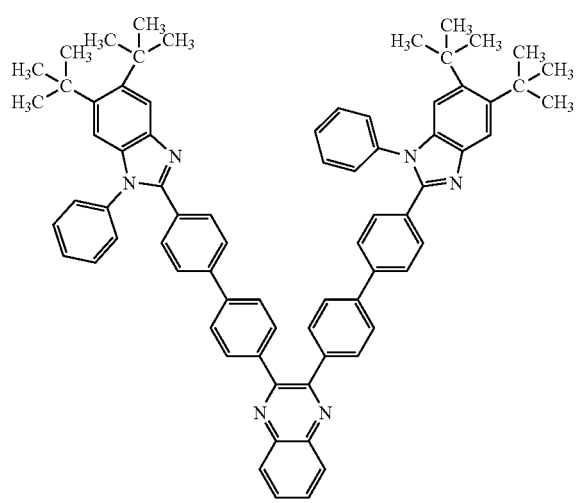
(351)
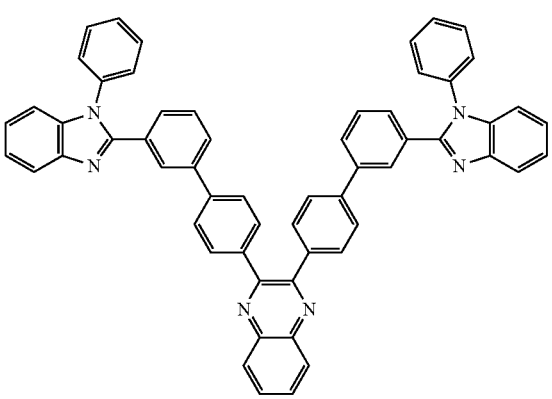
(352)
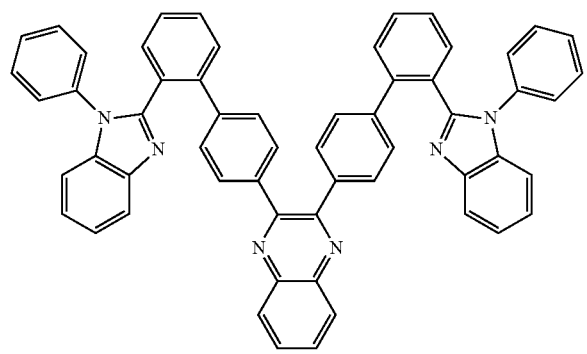
(353)
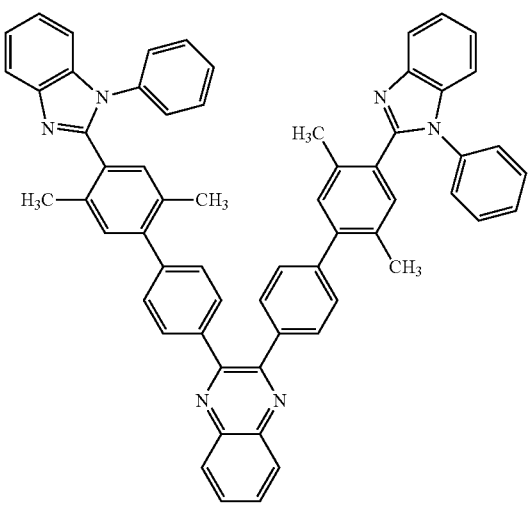

-continued
(354)
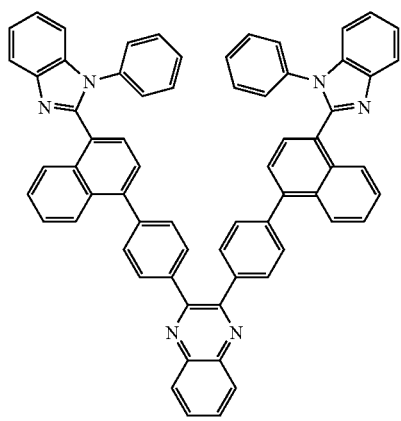
(355)
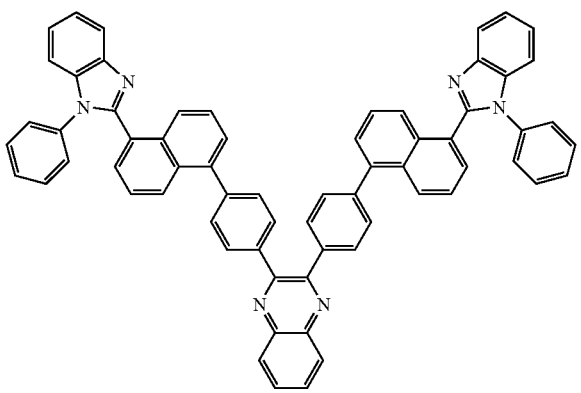
(356)
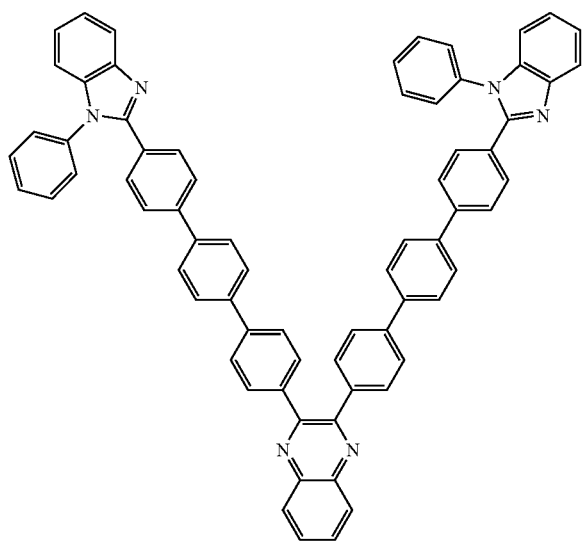
(357)
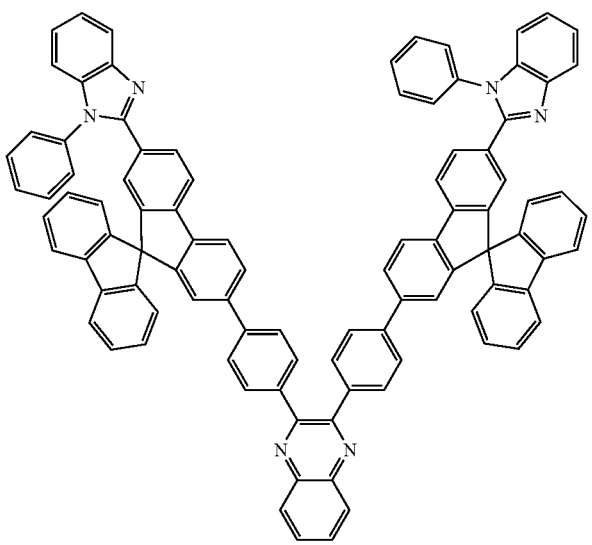
(358)
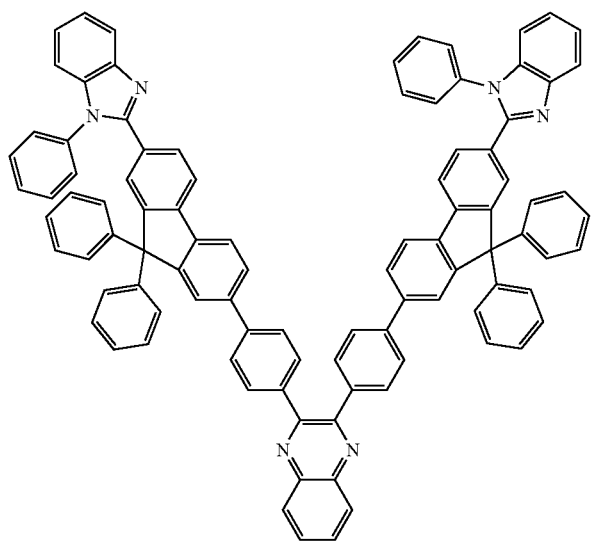
(359)
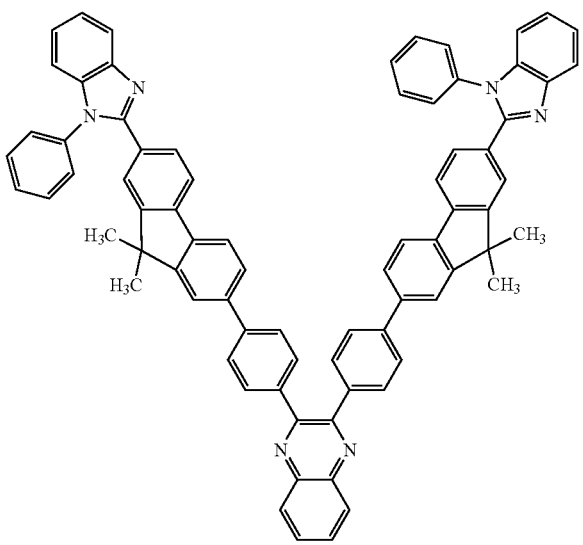

(360)
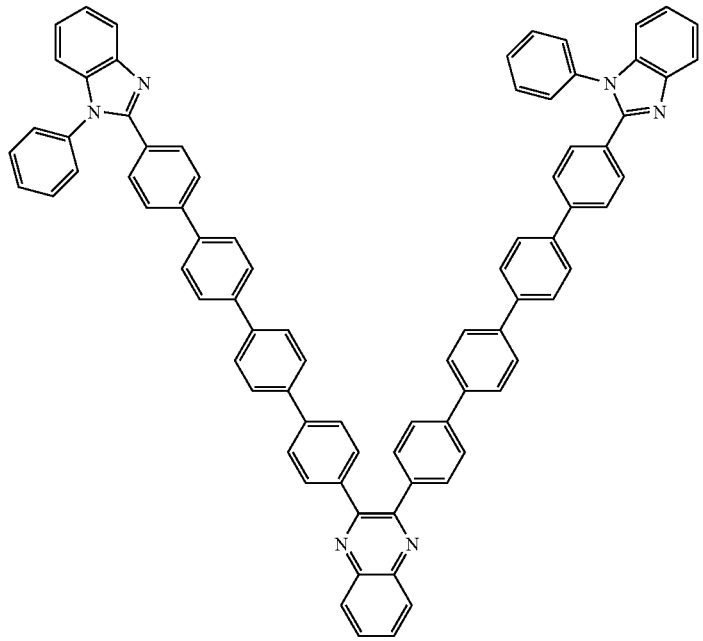
(361)
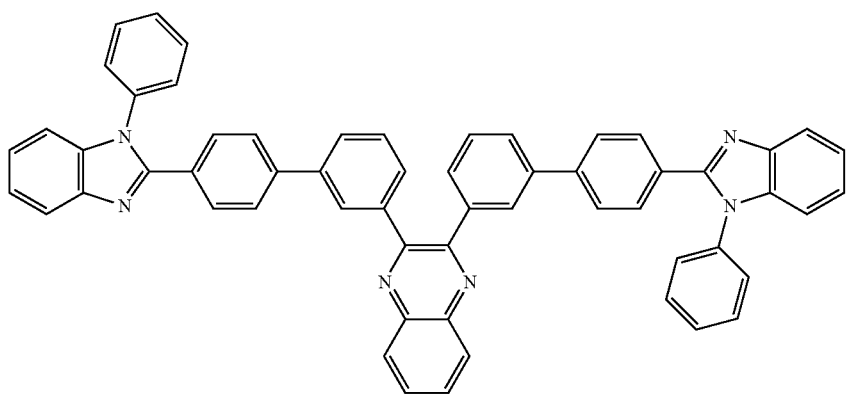
(362)
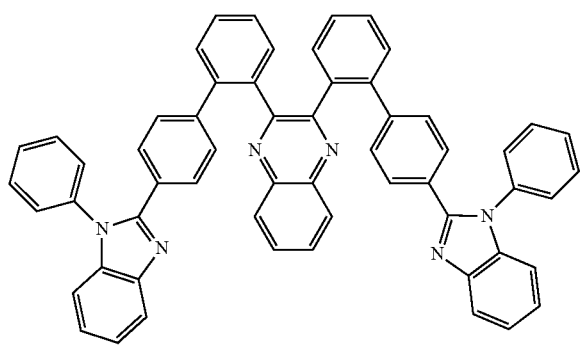
(363)
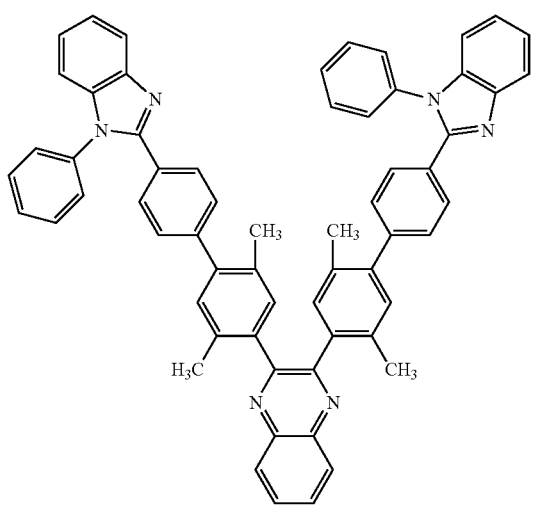

-continued
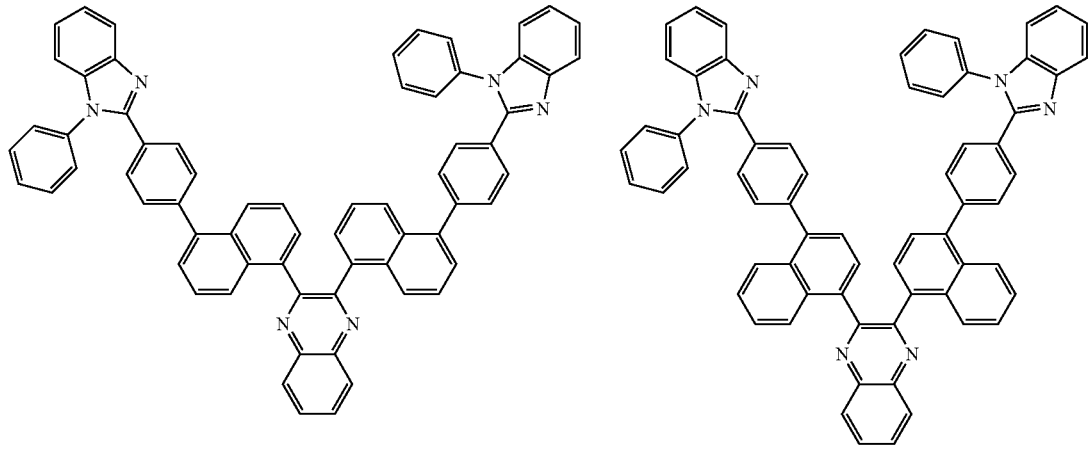
(364)
(365)
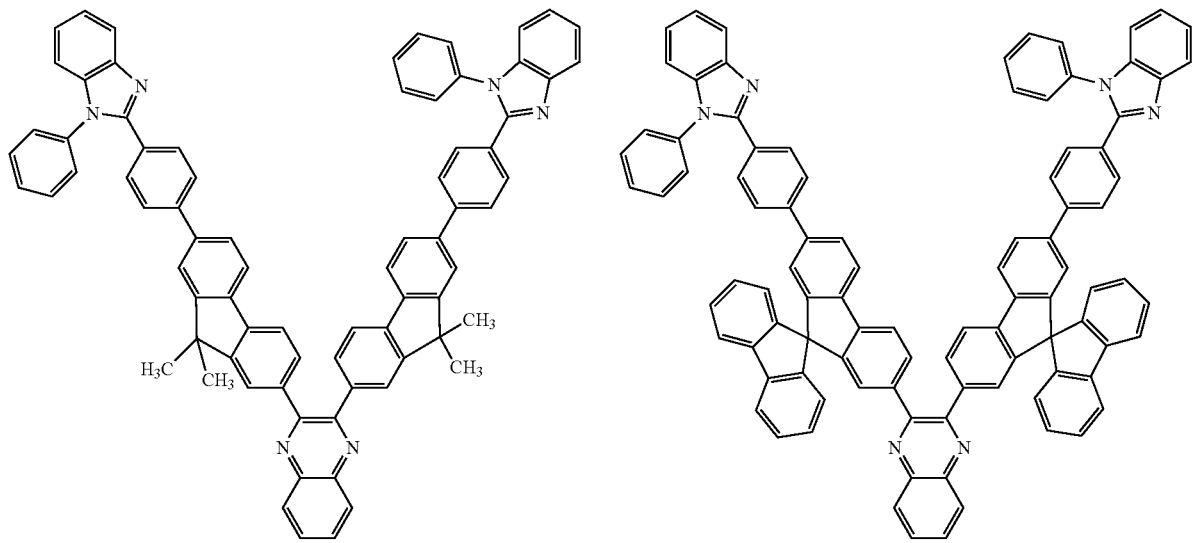
(366)
(367)
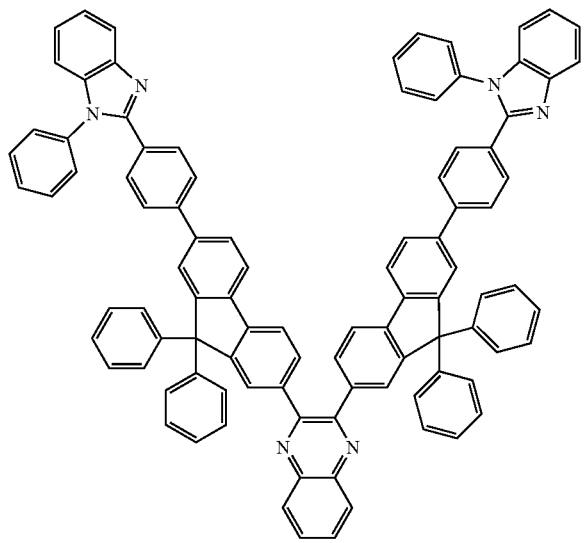
(368)

Various kinds of reactions can be applied to a synthetic method of the quinoxaline derivative of the present invention. For example, the quinoxaline derivative of the present invention can be synthesized by synthesis reactions shown below. Note that the synthetic method of the quinoxaline derivative of the present invention is not limited to the following synthetic methods.

<Synthetic Method of Compound Represented by General Formula (G11)>

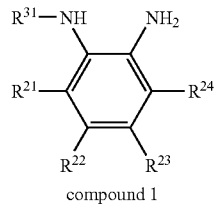

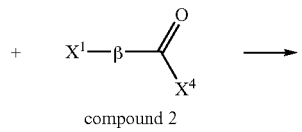

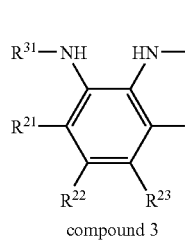

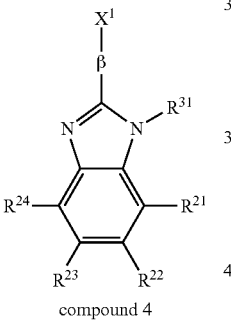

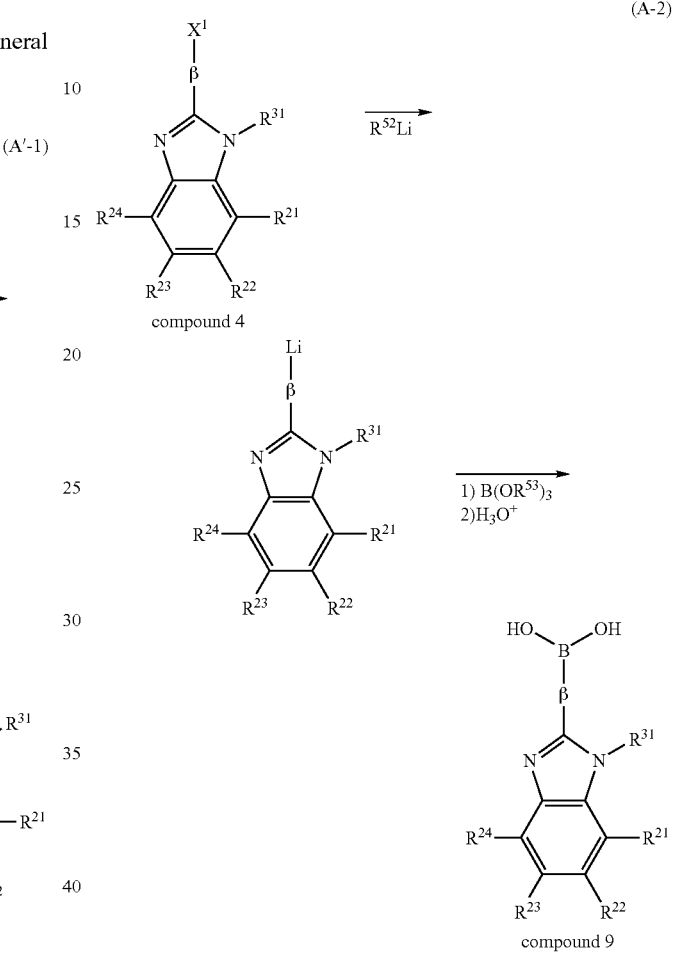

First, as shown in a synthetic scheme (A-1), a benzimidazole derivative (a compound 4) is synthesized according to such a synthetic scheme. In the synthetic scheme (A-1), $R^{21}$ to $R^{24}$ individually represent hydrogen or an alkyl group having 1 to 4 carbon atoms, and $R^{31}$ represents either an alkyl group having 1 to 4 carbon atoms or an aryl group having 6 to 13 carbon atoms. Further, β represents an arylene group having 6 to 13 carbon atoms. Furthermore, $X^1$ represents either a halogen or a triflate group. In the case where $X^1$ is a halogen, chlorine, bromine, or iodine is preferable. Still furthermore, $X^4$ represents a halogen for which chloride is particularly preferable. First, a phenylenediamine (a compound 1) which may include a substituent and an acyl halide (a compound 2) are condensed, whereby an arylenamide derivative (a compound 3) is synthesized. A solvent used in this case can be an ether-based solvent such as diethyl ether or tetrahydrofuran or a halogen-based solvent such as chloroform, dichloromethane, or carbon tetrachloride. Next, the arylenamide derivative (the compound 3) is subjected to cyclodehydration, whereby a benzimidazole ring can be formed. A dehydrating agent used at this time can be inorganic acid such as hydrochloric acid, sulfuric acid, or phosphoric acid or organic acid such as para-toluenesulfonic acid or trifuluoroacetic acid. A solvent used in this case can be a halogen-based solvent such as chloroform, dichloromethane, or carbon tetrachloride or hydrocarbon such as benzene, toluene, or xylene. In such a manner, the benzimidazole derivative (the compound 4) can be obtained.

Next, as shown in a synthetic scheme (A-2), the benzimidazole derivative (the compound 4) is lithiated with use of an alkyl lithium reagent and hydrolyzed with acid or water using a boron reagent, whereby a boronic acid of the benzimidazole derivative (a compound 9) can be obtained. In the synthetic scheme (A-2), $R^{21}$ to $R^{24}$ individually represent hydrogen or an alkyl group having 1 to 4 carbon atoms, $R^{31}$ represents either an alkyl group having 1 to 4 carbon atoms or an aryl group having 6 to 13 carbon atoms, $R^{52}$ represents an alkyl group having 1 to 6 carbon atoms, and $R^{53}$ represents an alkyl group having 1 to 6 carbon atoms. Further, $X^1$ represents a halogen. In the synthetic scheme (A-2), as a solvent that can be used, an ether-based solvent such as diethyl ether, tetrahydrofuran (THF), or cyclopentyl methyl ether can be used. As an alkyl lithium reagent, n-butyllithium, t-butyllithium, methyllithium, or the like can be given when $R^{52}$ is an n-butyl group, a t-butyl group, a methyl group, or the like, respectively. As a boron reagent, trimethyl borate, triisopropyl borate, or the like can be given when $R^{53}$ is a methyl group, an isopropyl group, or the like, respectively. Further, the boronic acid obtained in the synthetic scheme (A-2) may be protected by ethyl alcohol, propyl alcohol, or the like to form an organoboron compound or may be protected by diol like ethylene glycol or pinacol to form an organoboron compound which forms a ring.

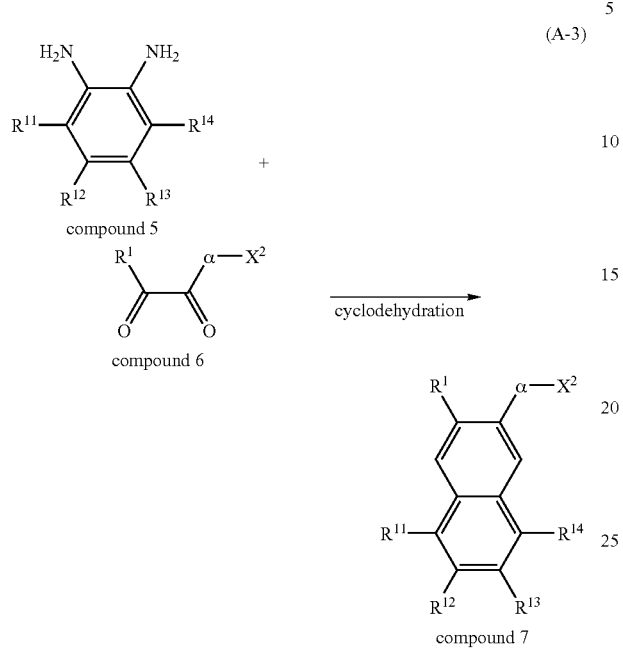

compound 5 compound 6 compound 7

Next, as shown in a synthetic scheme (A-3), a 1,2-phenylenediamine derivative (a compound 5) which may include a substituent and a diketone derivative (a compound 6) are subjected to cyclodehydration, so that a quinoxaline derivative (a compound 7) can be obtained. In the synthetic scheme (A-3), α represents an arylene group having 6 to 13 carbon atoms, $R^{11}$ to $R^{14}$ individually represent any of hydrogen, an alkyl group having 1 to 4 carbon atoms, or an aryl group having 6 to 13 carbon atoms, and $R^1$ represents either an alkyl group having 1 to 4 carbon atoms or an aryl group having 6 to 13 carbon atoms. Further, $X^2$ represents either a halogen or a triflate group. In the case where $X^2$ is a halogen, chlorine, bromine, or iodine is preferable. In the synthetic scheme (A-3), as a solvent that can be used, a halogen-based solvent such as dichloromethane, chloroform, or carbon tetrachloride, alcohol such as ethanol, methanol, or isopropanol, acetic acid, a sodium carbonate aqueous solution, a sodium hydrogen sulfate aqueous solution, a sodium acetate aqueous solution, a mixed solvent of a sodium acetate aqueous solution and acetic acid, or the like can be given. Further, in the case where the halogen-based solvent is used, chloroform or carbon tetrachloride which has higher boiling point is preferably used.

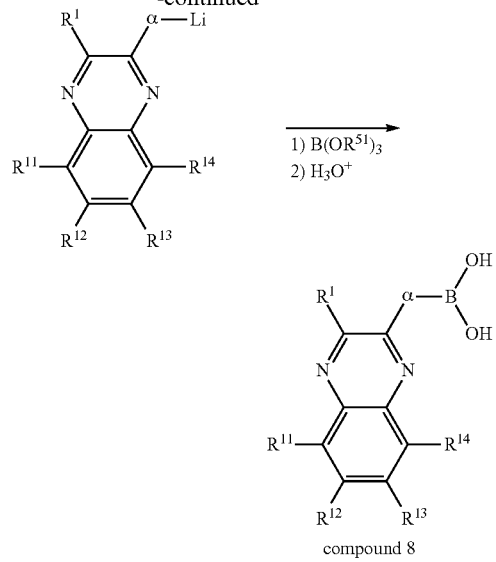

compound 8

Next, as shown in a synthetic scheme (A-4), the quinoxaline derivative (the compound 7) is lithiated with use of an alkyl lithium reagent and hydrolyzed with acid or water using a boron reagent, whereby a boronic acid of the quinoxaline derivative (a compound 8) can be obtained. In the synthetic scheme (A-4), α represents an arylene group having 6 to 13 carbon atoms, $R^1$ represents either an alkyl group having 1 to 4 carbon atoms or an aryl group having 6 to 13 carbon atoms, $R^{11}$ to $R^{14}$ individually represent any of hydrogen, an alkyl group having 1 to 4 carbon atoms, or an aryl group having 6 to 13 carbon atoms, $R^{50}$ represents an alkyl group having 1 to 6 carbon atoms, and $R^{51}$ represents an alkyl group having 1 to 6 carbon atoms. Further, $X^2$ represents a halogen. In the synthetic scheme (A-4), as a solvent that can be used, an ether-based solvent such as diethyl ether, tetrahydrofuran (THF), or cyclopentyl methyl ether can be given. As an alkyl lithium reagent, n-butyllithium, t-butyllithium, methyllithium, or the like can be given when $R^{50}$ is an n-butyl group, a t-butyl group, a methyl group, or the like, respectively. As a boron reagent, trimethyl borate, triisopropyl borate, or the like can be given when $R^{51}$ is a methyl group, an isopropyl group, or the like, respectively. Further, the boronic acid obtained in the synthetic scheme (A-4) may be protected by ethyl alcohol, propyl alcohol, or the like to form an organoboron compound or may be protected by diol like ethylene glycol or pinacol to form an organoboron compound which forms a ring.

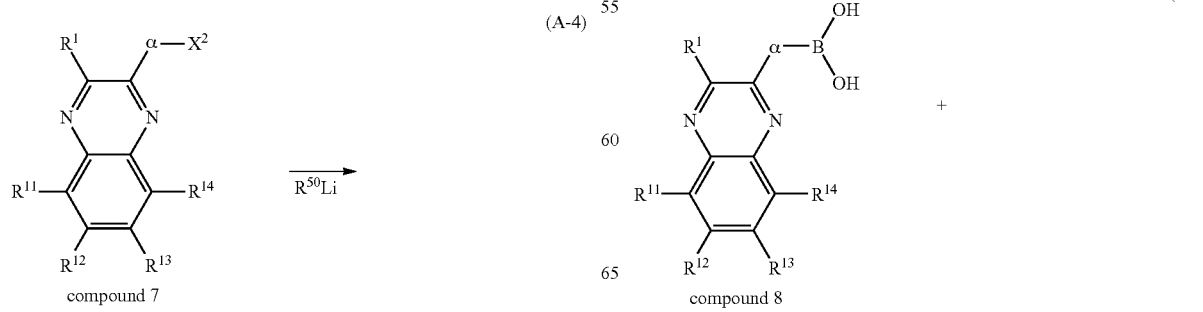

compound 7 compound 8

117

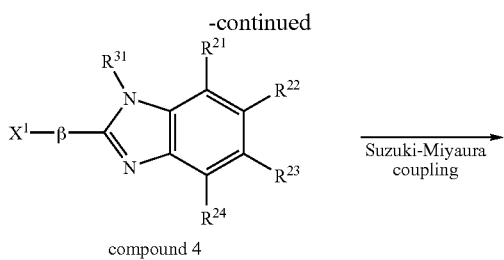

compound 4

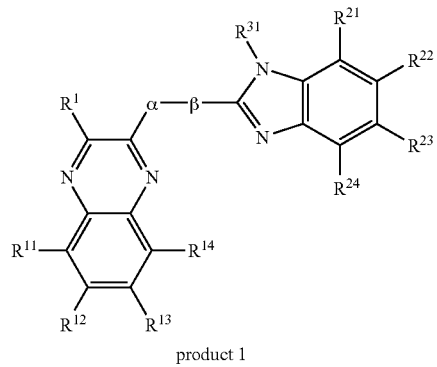

product 1

Next, as shown in a synthetic scheme (A-5), the boronic acid of the quinoxaline derivative (the compound 8) and the benzimidazole derivative (the compound 4) are coupled by a Suzuki-Miyaura reaction, so that a quinoxaline derivative which is a product (a product 1) can be obtained. In the synthetic scheme (A-5), $R^1$ represents either an alkyl group having 1 to 4 carbon atoms or an aryl group having 6 to 13 carbon atoms, $R^{11}$ to $R^{14}$ individually represent any of hydrogen, an alkyl group having 1 to 4 carbon atoms, or an aryl group having 6 to 13 carbon atoms, $R^{21}$ to $R^{24}$ individually represent hydrogen or an alkyl group having 1 to 4 carbon atoms, and $R^{31}$ represents either an alkyl group having 1 to 4 carbon atoms or an aryl group having 6 to 13 carbon atoms. Further, $X^1$ represents either a halogen or a triflate group, α represents an arylene group having 6 to 13 carbon atoms, and β represents an arylene group having 6 to 13 carbon atoms. In the case where $X^1$ is a halogen, chlorine, bromine, or iodine is preferable, and in particular, bromine or iodine is more preferable. In the synthetic scheme (A-5), as the palladium catalyst that can be used, palladium(II) acetate, tetrakis(triphenylphosphine)palladium(0), bis(triphenylphosphine)palladium(II) dichloride, or the like can be given. In the synthetic scheme (A-5), as a ligand of the palladium catalyst that can be used, tri(ortho-tolyl)phosphine, triphenylphosphine, tricyclohexylphosphine, or the like can be given. In the synthetic scheme (A-5), as a base that can be used, an organic base such as sodium t-butoxide, an inorganic base such as potassium carbonate, or the like can be given. In the synthetic scheme (A-5), as a solvent that can be used, the following can be given: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; or the like. Further, a mixed solvent of toluene and water, a mixed solvent of toluene, ethanol, and water, or a mixed solvent of an ether such as ethyleneglycoldimethylether and water is more preferable. An organoboron compound may be used, which is obtained by protecting the boronic acid obtained in the synthetic scheme (A-5) by ethyl alcohol, propyl alcohol, or the like.

118

Alternatively, an organoboron compound which forms a ring may be used, which is obtained by protecting the boronic acid obtained in the synthetic scheme (A-5) by diol like ethylene glycol or pinacol. Further, instead of Suzuki-Miyaura Coupling, Cross Coupling using organoaluminum, organozirconium, organozinc, an organotin compound, or the like may be used.

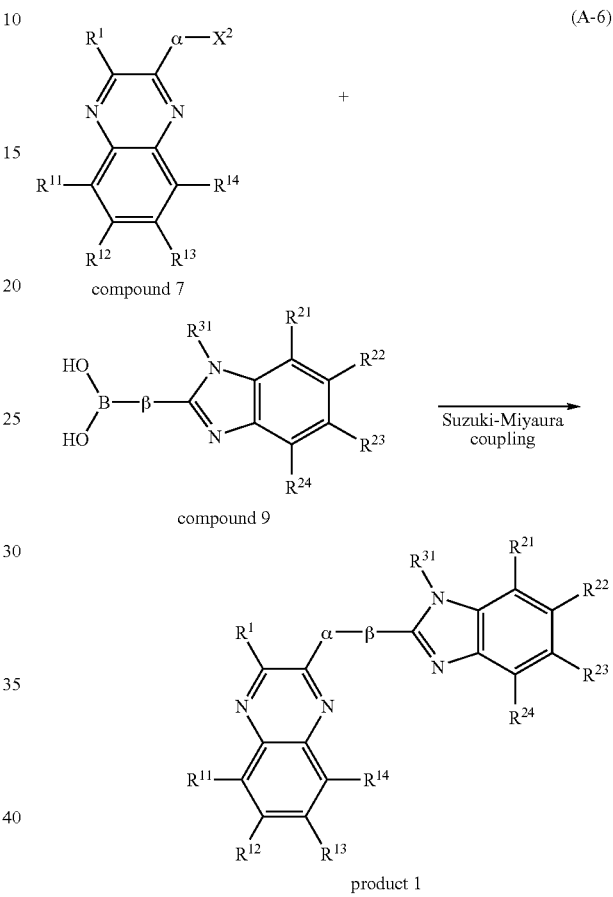

Further, as shown in a synthetic scheme (A-6), the quinoxaline derivative (the compound 7) and the boronic acid of the benzimidazole derivative (the compound 9) are coupled by a Suzuki-Miyaura reaction, whereby the quinoxaline derivative which is a product (the product 1) can also be obtained. In the synthetic scheme (A-6), $R^1$ represents either an alkyl group having 1 to 4 carbon atoms or an aryl group having 6 to 13 carbon atoms, $R^{11}$ to $R^{14}$ individually represent any of hydrogen, an alkyl group having 1 to 4 carbon atoms, or an aryl group having 6 to 13 carbon atoms, $R^{21}$ to $R^{24}$ individually represent hydrogen or an alkyl group having 1 to 4 carbon atoms, and $R^{31}$ represents an alkyl group having 1 to 4 carbon atoms or an aryl group having 6 to 13 carbon atoms. Further, $X^2$ represents either a halogen or a triflate group, α represents an arylene group having 6 to 13 carbon atoms, and β represents an arylene group having 6 to 13 carbon atoms. When $X^2$ is a halogen, chlorine, bromine, or iodine is preferable, and in particular, bromine or iodine is more preferable. In the synthetic scheme (A-6), as the palladium catalyst that can be used, palladium(II) acetate, tetrakis(triphenylphosphine)palladium(0), bis(triphenylphosphine)palladium(II) dichloride, or the like can be given. In the synthetic scheme (A-6), as a ligand of the palladium catalyst that can be used, tri(ortho-tolyl)phosphine, triphenylphosphine, tricyclohexylphosphine, or the like can be given. In the synthetic scheme (A-6), as a base that can be used, an organic base such as sodium t-butoxide, an inorganic base such as potassium carbonate, or the like can be given. In the synthetic scheme (A-6), as a solvent that can be used, the following can be given: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; or the like. Further, a mixed solvent of toluene and water, a mixed solvent of toluene, ethanol, and water, or a mixed solvent of an ether such as ethyleneglycoldimethylether and water is more preferable. An organoboron compound may be used, which is obtained by protecting the boronic acid obtained in the synthetic scheme (A-6) by ethyl alcohol, propyl alcohol, or the like. Alternatively, an organoboron compound which forms a ring may be used, which is obtained by protecting the boronic acid obtained in the synthetic scheme (A-6) by diol like ethylene glycol or pinacol. Further, instead of Suzuki-Miyaura Coupling, Cross Coupling using organoaluminum, organozirconium, organozinc, an organotin compound, or the like may be employed.

<Synthetic Method of Compound Represented by General Formula (G21)>

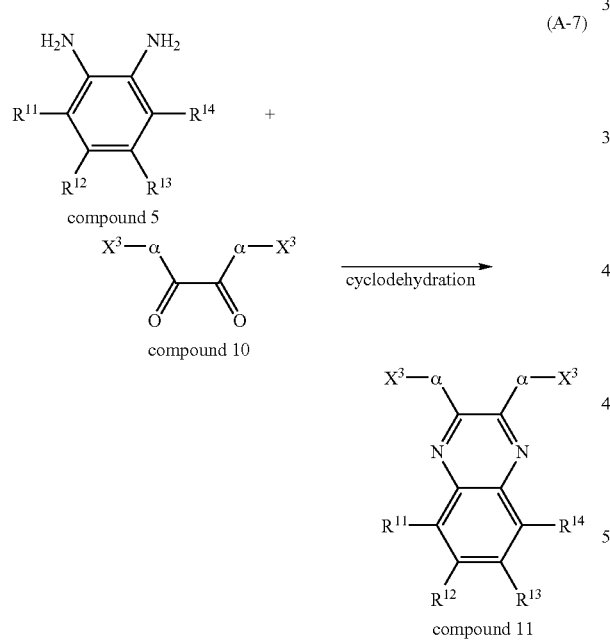

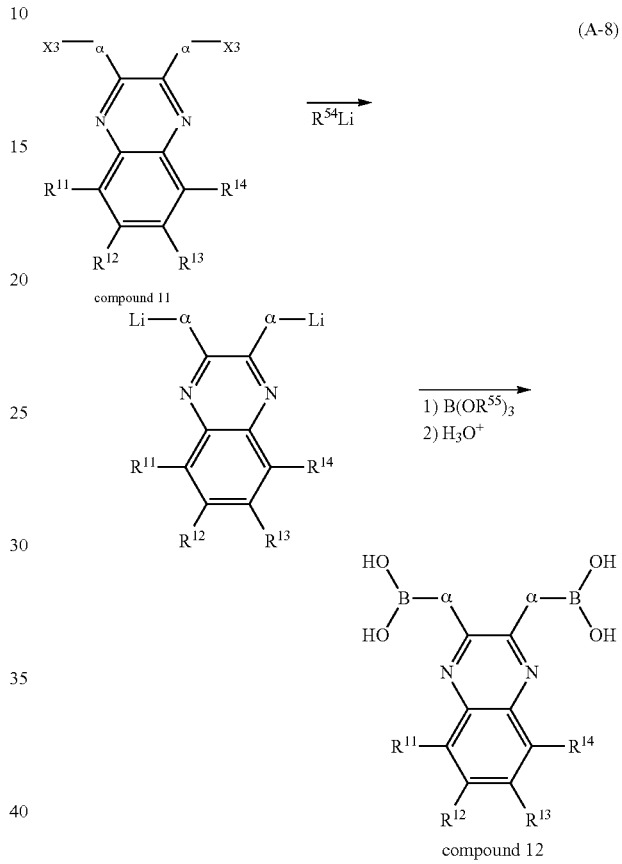

First, as shown in a synthetic scheme (A-7), the 1,2-phenylenediamine derivative (the compound 5) which may include a substituent and a diketone derivative (a compound 10) are subjected to cyclodehydration, whereby a quinoxaline derivative (a compound 11) can be obtained. In the synthetic scheme (A-7), $R^{11}$ to $R^{14}$ individually represent any of hydrogen, an alkyl group having 1 to 4 carbon atoms, or an aryl group having 6 to 13 carbon atoms. Further, $X^3$ represents either a halogen or a triflate group. When $X^3$ is a halogen, chlorine, bromine, or iodine is preferable. In the synthetic scheme (A-7), as a solvent that can be used, a halogen-based solvent such as dichloromethane, chloroform, or carbon tetrachloride, alcohols such as ethanol, methanol, or isopropanol, acetic acid, a sodium carbonate aqueous solution, a sodium hydrogensulfate aqueous solution, a sodium acetate aqueous solution, a mixed solvent of sodium acetate aqueous solution and acetic acid, or the like can be given. Further, in the case where the halogen-based solvent is used, chloroform or carbon tetrachloride which has higher boiling point is preferably used.

Next, as shown in a synthetic scheme (A-8), the quinoxaline derivative (the compound 11) is lithiated with use of an alkyl lithium reagent and hydrolyzed with acid or water using a boron reagent, whereby a boronic acid of the quinoxaline derivative (a compound 12) can be obtained. In the synthetic scheme (A-8), $R^{11}$ to $R^{14}$ individually represent any of hydrogen, an alkyl group having 1 to 4 carbon atoms, or an aryl group having 6 to 13 carbon atoms, $R^{54}$ represents an alkyl group having 1 to 6 carbon atoms, and $R^{55}$ represents an alkyl group having 1 to 6 carbon atoms. Further, $X^3$ represents a halogen. In the synthetic scheme (A-8), as a solvent that can be used, an ether-based solvent such as diethyl ether, tetrahydrofuran (THF), or cyclopentyl methyl ether can be given. As an alkyl lithium reagent, n-butyllithium, t-butyllithium, methyllithium, or the like can be given when $R^{54}$ is an n-butyl group, a t-butyl group, a methyl group, or the like, respectively. As a boron reagent, trimethyl borate, triisopropyl borate, or the like can be given when $R^{55}$ is a methyl group, an isopropyl group, or the like, respectively. Further, the boronic acid obtained in the synthetic scheme (A-8) may be protected by ethyl alcohol, propyl alcohol, or the like to form an organoboron compound or may be protected by diol like ethylene glycol or pinacol to form an organoboron compound which forms a ring.

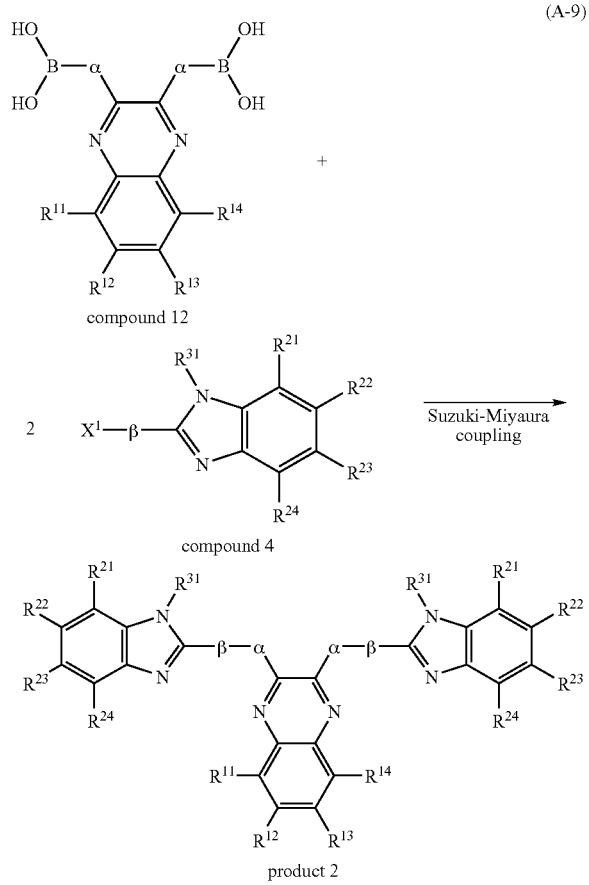

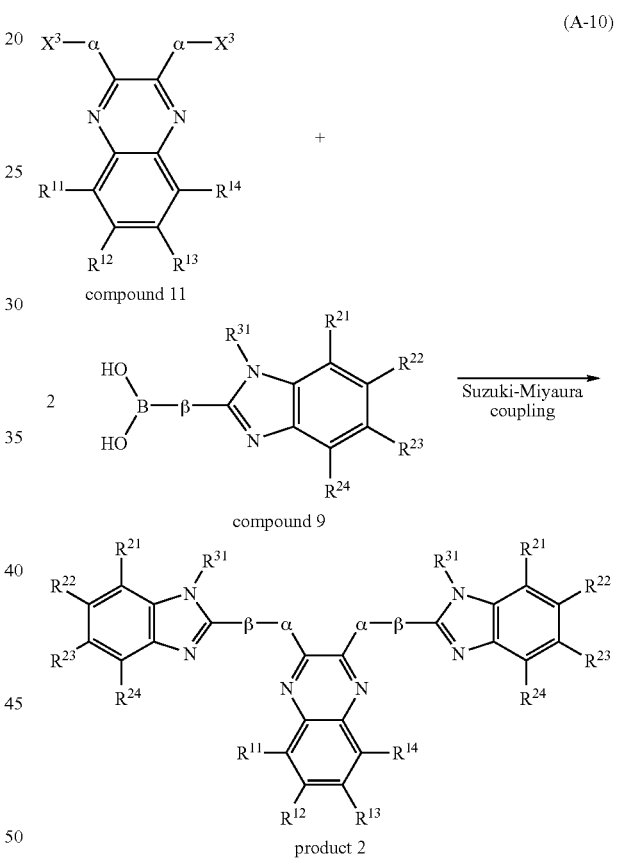

Next, as shown in a synthetic scheme (A-9), the boronic acid of the quinoxaline derivative (the compound 12) and the benzimidazole derivative (the compound 4) are coupled by a Suzuki-Miyaura reaction, whereby a quinoxaline derivative which is a product (a product 2) can be obtained. In the synthetic scheme (A-9), $R^{11}$ to $R^{14}$ individually represent any of hydrogen, an alkyl group having 1 to 4 carbon atoms, or an aryl group having 6 to 13 carbon atoms, $R^{21}$ to $R^{24}$ individually represent hydrogen or an alkyl group having 1 to 4 carbon atoms, and $R^{31}$ represents either an alkyl group having 1 to 4 carbon atoms or an alkyl group having 6 to 13 carbon atoms. Further, $X^1$ represents either a halogen or a triflate group, a represents an arylene group having 6 to 13 carbon atoms, and β represents an arylene group having 6 to 13 carbon atoms. When $X^1$ is a halogen, chlorine, bromine, or iodine is preferable, and in particular, bromine or iodine is more preferable. In the synthetic scheme (A-9), as the palladium catalyst that can be used, palladium(II) acetate, tetrakis(triphenylphosphine)palladium(0), bis(triphenylphosphine)palladium(II) dichloride, and the like can be given. In the synthetic scheme (A-9), as a ligand of the palladium catalyst that can be used, tri(ortho-tolyl)phosphine, triphenylphosphine, tricyclohexylphosphine, or the like can be given. In the synthetic scheme (A-9), as a base that can be used, an organic base such as sodium t-butoxide, an inorganic base such as potassium carbonate, or the like can be given. In the synthetic scheme (A-9), as a solvent that can be used, the following can be given: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; or the like. Further, a mixed solvent of toluene and water, a mixed solvent of toluene, ethanol, and water, or a mixed solvent of an ether such as ethyleneglycoldimethylether and water is more preferable. An organoboron compound may be used, which is obtained by protecting the boronic acid obtained in the synthetic scheme (A-9) by ethyl alcohol, propyl alcohol, or the like. Alternatively, an organoboron compound which forms a ring may be used, which is obtained by protecting the boronic acid obtained in the synthetic scheme (A-9) by diol like ethylene glycol or pinacol. Further, instead of Suzuki-Miyaura Coupling, Cross Coupling using organoaluminum, organozirconium, organozinc, an organotin compound, or the like may be employed.

As shown in a synthetic scheme (A-10), the quinoxaline derivative (the compound 11) and the boronic acid of the benzimidazole derivative (the compound 9) are coupled by a Suzuki-Miyaura reaction, whereby the quinoxaline derivative which is a product (the product 2) can also be obtained. In the synthetic scheme (A-10), $R^{11}$ to $R^{14}$ individually represent any of hydrogen, an alkyl group having 1 to 4 carbon atoms, or an aryl group having 6 to 13 carbon atoms, $R^{21}$ to $R^{24}$ individually represent hydrogen or an alkyl group having 1 to 4 carbon atoms, and $R^{31}$ represents an alkyl group having 1 to 4 carbon atoms or an alkyl group having 6 to 13 carbon atoms. $X^3$ represents either a halogen or a triflate group; a represents an arylene group having 6 to 13 carbon atoms, and β represents an arylene group having 6 to 13 carbon atoms. When $X^3$ is a halogen, chlorine, bromine, or iodine is preferable, and in particular, bromine or iodine is more preferable. In the synthetic scheme (A-10), as the palladium catalyst that can be used, palladium(II) acetate, tetrakis(triphenylphosphine)palladium(0), bis(triphenylphosphine)palladium(II) dichloride, or the like can be given. In the synthetic scheme (A-10), as a ligand of the palladium catalyst that can be used, tri(ortho-tolyl)phosphine, triphenylphosphine, tricyclohexylphosphine, or the like can be given. In the synthetic scheme (A-10), as a base that can be used, an organic base such as sodium t-butoxide, an inorganic base such as potassium carbonate, or the like can be given. In the synthetic scheme (A-10), as a solvent that can be used, the following can be given: a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; or the like. Further, a mixed solvent of toluene and water, a mixed solvent of toluene, ethanol, and water, or a mixed solvent of an ether such as ethyleneglycoldimethylether and water is more preferable. An organoboron compound may be used, which is obtained by protecting the boronic acid obtained in the synthetic scheme (A-10) by ethyl alcohol, propyl alcohol, or the like. Alternatively, an organoboron compound which forms a ring may be used, which is obtained by protecting the boronic acid obtained in the synthetic scheme (A-10) by diol like ethylene glycol or pinacol. Further, instead of Suzuki-Miyaura Coupling, Cross Coupling using organoaluminum, organozirconium, organozinc, an organotin compound, or the like may be employed.

The quinoxaline derivative of the present invention has a structure in which at least one of carbon at a 2-position and carbon at a 3-position of quinoxaline is bonded to carbon at a 2-position of a benzimidazole ring via an arylene group. Since a quinoxaline skeleton has an electron-transporting property and a benzimidazole skeleton also has an electron-transporting property, a quinoxaline derivative having an excellent electron-transporting property can be obtained by binding of at least one of carbon at a 2-position and carbon at a 3-position of quinoxaline to carbon at a 2-position of the benzimidazole ring via an arylene group.

A quinoxaline derivative in which carbon at a 2-position and carbon at a 3-position (that is, both carbon at a 2-position and carbon at a 3-position) of quinoxaline are bonded to carbon at a 2-position of the benzimidazole ring via an arylene group has higher molecular weight and more improved thermophysical property than the quinoxaline derivative in which one of carbon at a 2-position and carbon at a 3-position of quinoxaline is bonded to carbon at a 2-position of the benzimidazole ring via an arylene group. In addition, by the improvement in the thermophysical property, an improvement in the stability of film quality (suppression of crystallization) can be expected.

Further, the quinoxaline derivative of the present invention has an excellent electron-transporting property. Therefore, by using the quinoxaline derivative of the present invention for an electronics device such as a light-emitting element or an organic transistor, favorable electrical characteristics can be obtained.

(Embodiment Mode 2)

In this embodiment mode, one mode of a light-emitting element using the quinoxaline derivative described in Embodiment Mode 1 is described with reference to FIG. 1 and FIG. 2.

The light-emitting element of the present invention has a plurality of layers between a pair of electrodes. The plurality of layers are a combination of layers formed of a material with a high carrier-injecting property and a material with a high carrier-transporting property which are stacked so that a light-emitting region is formed in a region away from the electrodes, that is, recombination of carriers is performed in an area away from the electrodes.

In this embodiment mode, the light-emitting element includes a first electrode 102, a second electrode 104, and an EL layer which is provided between the first electrode 102 and the second electrode 104. Note that description will be made below in this embodiment mode on the assumption that the first electrode 102 functions as an anode and the second electrode 104 functions as a cathode. That is, description will be made below on the assumption that light emission can be obtained when voltage is applied to the first electrode 102 and the second electrode 104 so that the potential of the first electrode 102 is higher than that of the second electrode 104.

A substrate 101 is used as a support of the light-emitting element. For the substrate 101, glass, plastics, metal, or the like can be used, for example. Note that materials other than these can be used as long as they can function as a support of a light-emitting element. In the case where light from the light-emitting element is extracted to the outside through the substrate, the substrate 101 preferably has a light-transmitting property.

Preferably, the first electrode 102 is formed using any of metals, alloys, or conductive compounds, a mixture thereof, or the like with a high work function (specifically, a work function of 4.0 eV or higher is preferable). Specifically, indium tin oxide (ITO), indium tin oxide containing silicon or silicon oxide, indium zinc oxide (IZO), indium oxide containing tungsten oxide and zinc oxide (IWZO), and the like can be used, for example. Such conductive metal oxide films are usually formed by a sputtering method, but may also be formed by an ink-jet method, a spin coating method, or the like by application of a sol-gel method or the like. For example, indium zinc oxide (IZO) can be formed by a sputtering method using indium oxide into which 1 to 20 wt % of zinc oxide is added, as a target. Indium oxide containing tungsten oxide and zinc oxide (IWZO) can be formed by a sputtering method using a target in which 0.5 to 5 wt % of tungsten oxide and 0.1 to 1 wt % of zinc oxide are mixed to indium oxide. Other than these, gold (Au), platinum (Pt), nickel (Ni), tungsten (W), chromium (Cr), molybdenum (Mo), iron (Fe), cobalt (Co), copper (Cu), palladium (Pd), titanium (Ti), a nitride of a metal material (such as titanium nitride), and the like can be given.

In the case where a layer including a composite material described below is used as a layer in contact with the first electrode 102, various metals, alloys, electrically conductive compounds, a mixture thereof, or the like can be used for the first electrode 102 regardless of the levels of their work functions. For example, aluminum (Al), silver (Ag), an aluminum alloy (AlSi), or the like can be used. Further, an element belonging to Group 1 or Group 2 of the periodic table, which is a material with a low function, i.e., an alkali metal such as lithium (Li) or cesium (Cs), an alkaline-earth metal such as magnesium (Mg), calcium (Ca), or strontium (Sr), an alloy containing any of these elements (e.g., MgAg or AlLi), a rare earth metal such as europium (Eu) or ytterbium (Yb), an alloy containing such rare earth metals, or the like can be used. A film made of an alkali metal, an alkaline-earth metal, or an alloy containing any of them can be formed by a vacuum evaporation method. Further, an alloy containing an alkali metal or an alkaline-earth metal can be formed by a sputtering method. Furthermore, silver paste or the like can be formed by an ink-jet method or the like.

An EL layer 103 described in this embodiment mode includes a hole-injecting layer 111, a hole-transporting layer 112, a light-emitting layer 113, an electron-transporting layer 114, and an electron-injecting layer 115. Note that the EL layer 103 is acceptable as long as it has the quinoxaline derivative described in Embodiment Mode 1, and a stacked structure of layers other than the EL layer 103 is not particularly limited. That is, there is no particular limitation on a stack structure of layers of the EL layer 103. The EL layer 103 may be formed by an appropriate combination of a layer containing the quinoxaline derivative described in Embodiment Mode 1 with any of layers which contain a substance having a high electron-transporting property, a substance having a high hole-transporting property, a substance having a high electron-injecting property, a substance having a high hole-injecting property, a bipolar substance (a substance having high electron- and hole-transporting properties), a substance having a high light-emitting property, and the like. For example, the EL layer 103 can be formed by an appropriate combination of a hole-injecting layer, a hole-transporting layer, a light-emitting layer, an electron-transporting layer, an electron-injecting layer, and the like. Specific materials to form each of the layers will be given below.

The hole-injecting layer 111 is a layer containing a substance with a high hole-injecting property. As the substance with a high hole-injecting property, molybdenum oxide, vanadium oxide, ruthenium oxide, tungsten oxide, manganese oxide, or the like can be used. Alternatively, as a low molecular organic compound, the following are given: a phthalocyanine-based compound such as phthalocyanine (abbreviation: H$_2$Pc), copper(II) phthalocyanine (abbreviation: CuPc), or vanadyl(IV) phthalocyanine (abbreviation: VOPc); an aromatic amine compound such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), and 3-[N-(1-naphthyl)-N-(9-phenylcarbazol-3-yl)amino]-9-phenylcarbazole (abbreviation: PCzPCN1); and the like.

As a further alternative, a composite material with a high hole-transporting property which contains an acceptor substance can also be used for the hole-injecting layer 111. Note that, by using the material with a high hole-transporting property which contains an acceptor substance, a material used to form an electrode may be selected regardless of its work function. In other words, besides a material with a high work function, a material with a low work function may also be used as the first electrode 102. Such a composite material can be formed by co-evaporation of a substance with a high hole-transporting property and an acceptor substance.

In this specification, "composition" refers to a state in which electric charges are given and received between materials by the mixture of a plurality of materials, in addition to a state in which two types of materials are simply mixed.

As an organic compound used for the composite material, various compounds can be used, such as an aromatic amine compound, a carbazole derivative, aromatic hydrocarbon, or a high molecular compound (e.g., an oligomer, a dendrimer, a polymer, or the like). Note that the organic compound used for the composite material is preferably an organic compound with a high hole-transporting property. Specifically, a substance having a hole mobility of $10^{-6}$ cm$^2$/Vs or higher is preferably used. However, a material other than the above materials may be used as long as the material has a higher hole-transporting property than an electron-transporting property. Examples of the organic compound which can be used for the composite material are specifically listed below.

As the organic compound that can be used for the composite material, the following materials can be given, for example: aromatic amine compounds such as MTDATA, TDATA, DPAB, DNTPD, DPA3B, PCzPCA1, PCzPCA2, PCzPCN1, 4,4'-bis[N-(1-naphthyl)-N-phenylamino]biphenyl (abbreviation: NPB or α-NPD), and N,N'-bis(3-methylphenyl)-N,N'-diphenyl-[1,1'-biphenyl]-4,4'-diamine (abbreviation: TPD); carbazole derivatives such as 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), and 1,4-bis[4-(N-carbazolyl)phenyl]-2,3,5,6-tetraphenylbenzene; and aromatic hydrocarbon compounds such as 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, pentacene, coronene, 4,4'-bis(2,2-diphenylvinyl)biphenyl (abbreviation: DPVBi), and 9,10-bis[4-(2,2-diphenylvinyl)phenyl]anthracene (abbreviation: DPVPA).

As the acceptor substance, organic compounds such as 7,7,8,8-tetracyano-2,3,5,6-tetrafluoroquinodimethane (abbreviation: F$_4$-TCNQ) and chloranil, and transition metal oxide can be given. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. In particular, use of molybdenum oxide is more preferable because of its stability in the atmosphere, low hygroscopic property, and easiness of handling.

As the hole-injecting layer 111, high molecular compounds (such as oligomer, dendrimer, and polymer) can be used. For example, the following high molecular compound can be given: poly(N-vinylcarbazole) (abbreviation: PVK); poly(4-vinyltriphenylamine) (abbreviation: PVTPA); poly [N-(4-{N'-[4-(4-diphenylamino)phenyl]phenyl-N'-phenylamino}phenyl)methacrylamide] (abbreviation: PTTDMA); and poly[N,N'-bis(4-butylphenyl)-N,N'-bisphenyl)benzidine] (abbreviation: Poly-TPD). Further, high molecular compounds doped with acid such as poly(3,4-ethylenedioxythiophene)/poly(styrenesulfonic acid) (PEDOT/PSS), and polyanline/poly(styrenesulfonic acid) (PAni/PSS) can be used.

Furthermore, the hole-injecting layer 111 can be formed using a composite material of the above-described high molecular compound, such as PVK, PVTPA, PTPDMA, or Poly-TPD, and the above-described acceptor substance.

The hole-transporting layer 112 is a layer containing a substance having a high hole-transporting property. As a low molecular organic compound of a substance having a high hole-transporting property, aromatic amine compounds such as NPB (or α-NPD), TPD, 4,4'-bis[N-(9,9-dimethylfluoren-2-yl)-N-phenylamino]biphenyl (abbreviation; DFLDPBi), and can be used. These substances are mainly substances each having a hole mobility of $10^{-6}$ cm$^2$/Vs or higher. However, materials other than these can also be used as long as the hole-transporting property is higher than the electron-transporting property. The layer including a substance having a high hole-transporting property is not limited to a single layer, but two or more layers including the aforementioned substances may be stacked.

Further, for the hole-transporting layer 112, a composite material in which an acceptor substance is contained in a substance having a high hole-transporting property described above can be used.

For the hole-transporting layer 112, a high molecular compound such as PVK, PVTPA, PTPDMA, or Poly-TPD can be used alternatively.

The light-emitting layer 113 is a layer including a substance with a high light-emitting property, and various materials can be used for the light-emitting layer. For example, as a substance with a high light-emitting property, a fluorescent compound which emits fluorescence or a phosphorescent compound which emits phosphorescence can be used.

As the phosphorescent compound which can be used for the light-emitting layer, the following substances are given. For example, as a light-emitting material that exhibits blue emission, the following can be given: bis[2-(4',6'-difluorophenyl)pyridinato-N,C$^{2'}$]iridium(III) tetrakis(1-pyrazolyl) borate (abbreviation: FIr6); bis[2-(4',6'-dffluorophenyl)pyridinato-N,C$^{2'}$]iridium(III) picolinate (abbreviation: FIrpic); bis[2-(3',5'bistrifluoromethylphenyl)pyridinato-N,C$^{2'}$]iridium(III) picolinate (abbreviation: Ir(CF$_3$ppy)$_2$(pic)); bis[2-(4',6'-difluorophenyl)pyridinato-N,C$^{2'}$]iridium(III) acetylacetonate (abbreviation: FIr(acac)); and the like. As a light-emitting material that exhibits green emission, the following can be given: tris(2-phenylpyridinato-N,C$^{2'}$)iridium(III) (abbreviation: Ir(ppy)$_3$); bis(2-phenylpyridinato-N,C$^{2'}$)iridium(III) acetylacetonate (abbreviation: Ir(ppy)$_2$(acac)); bis(1,2-diphenyl-1H-benzimidazolato)iridium(III) acetylacetonate (abbreviation: Ir(pbi)$_2$(acac)); bis(benzo[h]quinolinato)iridium(III) acetylacetonate (abbreviation: Ir(bzq)$_2$(acac)); and the like. As a light-emitting material that exhibits yellow light emission, the following can be given: bis(2,4-diphenyl-1,3-oxazolato-N,C$^{2'}$)iridium(III) acetylacetonate (abbreviation: Ir(dpo)$_2$(acac)); bis[2-(4'-perfluorophenylphenyl)pyridinato] iridium(III) acetylacetonate (abbreviation: Ir(p-PF-ph)$_2$ (acac)); bis(2-phenylbenzothiazolato-N,C$^{2'}$)iridium(III) acetylacetonate (abbreviation: Ir(bt)$_2$(acac)); and the like. As a light-emitting material that exhibits orange light emission, the following can be given: tris(2-phenylquinolinato-N,C$^{2'}$) iridium(III) (abbreviation: Ir(pq)$_3$); bis(2-phenylquinolinato-N,C$^{2'}$)iridium(III) acetylacetonate (abbreviation: Ir(pq)$_2$ (acac)); and the like. As a light-emitting material that exhibits red light emission, the following can be given: bis[2-(2'-benzo[4,5-α]thienyl)pyridinato-N,C$^{3'}$)iridium(III) acetylacetonate (abbreviation: Ir(btp)$_2$(acac)); bis(1-phenylisoquinolinato-N,C$^{2'}$)iridium(III) acetylacetonate (abbreviation: Ir(piq)$_2$(acac)); (acetylacetonato)bis[2,3-bis(4-fluorophenyl) quinoxalinato]iridium(III) (abbreviation: Ir(Fdpq)$_2$(acac)); 2,3,7,8,12,13,17,18-octaethyl-21H,23H-porphyrinplatinum (II) (abbreviation: PtOEP); and the like. In addition, a rare-earth metal complex such as tris(acetylacetonato) (monophenanthroline)terbium(III) (abbreviation: Tb(acac)$_3$ (Phen)); tris(1,3-diphenyl-1,3-propanedionato) (monophenanthroline)europium(III) (abbreviation: Eu(DBM)$_3$(Phen)); or tris[1-(2-thenoyl)-3,3,3-trifluoroacetonato](monophenanthroline)europium(III) (abbreviation: Eu(TTA)$_3$(Phen)) exhibits light emission (electron transition between different multiplicities) from a rare-earth metal ion; therefore, such a rare-earth metal complex can be used as the phosphorescent compound.

As the fluorescent compound which can be used for the light-emitting layer, for example, as a light-emitting material that exhibits blue light emission, the following can be given: N,N'-bis[4-(9H-carbazol-9-yl)phenyl]-N,N'-diphenylstilbene-4,4'-diamine (abbreviation: YGA2S); 4-(9H-carbazol-9-yl)-4'-(10-phenyl-9-anthryl)triphenylamine (abbreviation: YGAPA); and the like. As a light-emitting material that exhibits green light emission, the following can be given: N-(9,10-diphenyl-2-anthryl)-N,9-diphenyl-9H-carbazol-3-amine (abbreviation: 2PCAPA); N-[9,10-bis(1,1'-biphenyl-2-yl)-2-anthryl]-N,9-diphenyl-9H-carbazol-3-amine (abbreviation: 2PCABPhA); N-(9,10-diphenyl-2-anthryl)-N,N',N'-triphenyl-1,4-phenylenediamine (abbreviation: 2DPAPA); N-[9,10-bis(1,1'-biphenyl-2-yl)-2-anthryl]-N,N',N'-triphenyl-1,4-phenylenediamine (abbreviation: 2DPABPhA); N-[9,10-bis(1,1'-biphenyl-2-yl)-N-[4-(9H-carbazol-9-yl) phenyl]-N-phenylanthracen-2-a mine (abbreviation: 2YGABPhA); N,N,9-triphenylanthracen-9-amine (abbreviation: DPhAPhA); and the like are given. As a light-emitting material that exhibits yellow light emission, the following can be given: rubrene; 5,12-bis(1,1'-biphenyl-4-yl)-6,11-diphenyltetracene (abbreviation: BPT); and the like. As a light-emitting material that exhibits red light emission, the following can be given: N,N,N',N'-tetrakis(4-methylphenyl) tetracene-5,11-diamine (abbreviation: p-mPhTD); 7,13-diphenyl-N,N,N',N'-tetrakis(4-methylphenyl)acenaphtho[1,2-a]fluoranthene-3,10-diamine (abbreviation: p-mPhAFD); and the like.

Note that the light-emitting layer may have a structure in which the above substance with a high light-emitting property (a guest material) is dispersed in another substance (a host material). As a substance in which the substance with a light-emitting property is dispersed, various kinds of substances can be used, and it is preferable to use a substance whose lowest unoccupied molecular orbital (LUMO) level is higher than that of the substance with a light-emitting property and whose highest occupied molecular orbital (HOMO) level is lower than that of the substance with a light-emitting property.

As the substance in which the substance with a high light-emitting property is dispersed, the following can be given: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h] quinolinato)beryllium(II) (abbreviation: BeBq$_2$), or bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato] zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-[(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)-tris(1-phenyl-1H-benzimidazole) (abbreviation: TPBI), bathophenanthroline (abbreviation: BPhen), and bathocuproine (abbreviation: BCP); or condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDBA), 9,9'-bianthryl (BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl) tripyrene (abbreviation: TPB3), 9,10-diphenylanthracene (abbreviation: DPAnth), 6,12-dimethoxy-5,11-diphenylchrysene; aromatic amine compounds such as N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB.

As a substance in which the substance with a light-emitting property is dispersed, plural kinds of substances can be used. For example, in order to suppress crystallization, a substance for suppressing crystallization of rubrene or the like may be further added. In addition, NPB, Alq, or the like may be further added in order to efficiently transfer energy to the substance with a light-emitting property.

When a structure in which the substance with a high light-emitting property is dispersed in another substance is employed, crystallization of the light-emitting layer 113 can be suppressed. Further, concentration quenching due to high concentration of the substance with a high light-emitting property can be suppressed.

As the light-emitting layer 113, high molecular compounds can be used. Specifically, as a light-emitting material that exhibits blue light emission, the following can be given: poly(9,9-dioctylfluorene-2,7-diyl) (abbreviation: PFO), poly[(9,9-dioctylfluorene-2,7-diyl)-co-(2,5-dimethoxybenzene-1,4-diyl)] (abbreviation: PF-DMOP), poly{(9,9-dioctylfluorene-2,7-diyl)-co-[N,N'-di-(p-butylphenyl)-1,4-diaminobenzene]}(abbreviation: TAB-PFH), and the like. As a light-emitting material that exhibits green light emission, the following can be given: poly(p-phenylenvinylene) (abbreviation: PPV), poly[(9,9-dihexylfluorene-2,7-diyl)-alt-co-(benzo[2,1,3]thiadiazole-4,7-diyl)] (abbreviation: PFBT), poly[(9,9-dioctyl-2,7-divinylenfluorenylene)-alt-co-(2-methoxy-5-(2-ethylhexyloxy)-1,4-phenylene)], or the like can be given. As a light-emitting material that exhibits orange light emission to red light emission, the following can be given: poly[2-methoxy-5-(2'-ethylhexoxy)-1,4-phenylenevinylene] (abbreviation: MEH-PPV), poly(3-butylthiophene-2,5-diyl) (abbreviation: R4-PAT), poly{[9,9-dihexyl-2,7-bis(1-cyanovinylene)fluorenylene]-alt-co-[2,5-bis(N,N'-diphenylamino)-1,4-phenylene]}, poly{[2-methoxy-5-(2-ethylhexyloxy)-1,4-bis(1-cyanovinylenephenylene)]-alt-co-[2,5-bis(N,N-diphenylamino)-1,4-phenylene]} (abbreviation: CN-PPV-DPD), and the like.

The electron-transporting layer 114 is a layer containing a substance with a high electron-transporting property. The quinoxaline derivative described in Embodiment Mode 1 is excellent in an electron-transporting property, so the quinoxaline derivative can be suitably used for the electron-transporting layer 114. Note that the electron-transporting layer is not limited to a single layer, and may be a stack of two or more layers.

In the case where the electron-transporting layer is a stack of two or more layers, as other substances with a high electron-transporting property, for example, particularly as a low molecular organic compound, any of the following can be used: metal complexes such as tris(8-quinolinolato)aluminum(III) (abbreviation: Alq), tris(4-methyl-8-quinolinolato) aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato] zinc(II) (abbreviation: ZnBTZ). Further, as well as metal complexes, the following can be given: heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ01), bathophenanthroline (abbreviation: BPhen), and bathocuproine (abbreviation: BCP). The substances described here are mainly substances having an electron mobility of $10^{-6}$ cm$^2$/Vs or higher. If a substance has a higher electron-transporting property than a hole-transporting property, substances other than the above may be used for the electron-transporting layer. Furthermore, the electron-transporting layer is not limited to a single layer but may have a stacked structure of two or more layers made of the above-described substances.

In the case where the electron-transporting layer is a stack of two or more layers, as other substances with an electron-transporting property, high molecular compounds can be used. For example, poly[(9,9-dihexylfluorene-2,7-diyl)-co-(pyridine-3,5-diyl)] (abbreviation: PF-Py), poly[(9,9-dioctylfluorene-2,7-diyl)-co-(2,2'-bipyridine-6,6'-diyl)] (abbreviation: PF-BPy) or the like can be used.

The electron-injecting layer 115 is a layer containing a substance with a high electron-injecting property. As the substance with a high electron-injecting property, alkali metals or alkaline-earth metals such as lithium (Li), cesium (Cs), barium (Ba), magnesium (Mg), calcium (Ca), or compounds thereof such as lithium fluoride (LiF), cesium fluoride (CsF), and calcium fluoride (CaF$_2$) can be used. For example, a layer of a substance with an electron-transporting property which contains an alkali metal, an alkaline-earth metal, or a compound thereof, such as Alq which contains magnesium (Mg), may be used. By using a layer of a substance with an electron-transporting property which contains an alkali metal or an alkaline-earth metal as the electron-injecting layer, electron injection from the second electrode 104 is performed efficiently, which is preferable.

As a substance used for the second electrode 104, a metal, an alloy, an electrically conductive compound, or a mixture thereof, or the like with a low work function (specifically, a work function of 3.8 eV or lower is preferable) can be used. Specific examples of such cathode materials are given below: elements belonging to Group 1 and Group 2 of the periodic table, that is, alkali metals such as lithium (Li) and cesium (Cs) and alkaline-earth metals such as magnesium (Mg), calcium (Ca), and strontium (Sr); alloys thereof (MgAg, AlLi); rare earth metals such as europium (Eu) and ytterbium (Yb); alloys thereof; and the like. A film of an alkali metal, an alkaline-earth metal, or an alloy including any of these can be formed by a vacuum evaporation method. In addition, an alloy including an alkali metal or an alkaline-earth metal can be formed by a sputtering method. Further, silver paste or the like can be formed by an ink-jet method or the like.

When the electron-injecting layer 115 which is a layer having a function of promoting electron injection is provided between the second electrode 104 and the electron-transporting layer 114, the second electrode 104 can be formed using any of various conductive materials such as Al, Ag, ITO, and ITO containing silicon or silicon oxide, regardless of levels of their work functions. These conductive materials can be formed by a sputtering method, an ink-jet method, a spin coating method, or the like.

Various methods can be used for forming the EL layer, regardless of a dry process or a wet process. For example, a vacuum evaporation method, an ink-jet method, a spin coat method, or the like may be used. Moreover, a different forming method may be used for each electrode or each layer.

For example, the EL layer may be formed by a wet process using a high molecular compound selected from the above-described materials. Alternatively, a low molecular organic compound may be selected to form the EL layer by a wet process. Further, it is also possible to form the EL layer by selecting a low molecular organic compound and using a dry process such as a vacuum evaporation method.

The electrode may be formed by a wet process using a sol-gel method, or by a wet process using a paste of a metal material. Alternatively, a dry process such as a sputtering method or a vacuum evaporation method may also be employed.

For example, in the case where the light-emitting element of the present invention is applied to a display device and is manufactured using a large substrate, the light-emitting layer is preferably formed by a wet process. When the light-emitting layer is formed by an ink-jet method, selective deposition of the light-emitting layer for each color can be easily performed even when a large substrate is used.

In the light-emitting element of the present invention having the above structure, a current flows due to a potential difference between the first electrode 102 and the second electrode 104 and holes and electrons are recombined in the EL layer 103 so that light is emitted.

The emitted light is extracted out through one or both of the first electrode 102 and the second electrode 104. Therefore, one or both of the first electrode 102 and the second electrode 104 are light-transmitting electrodes. For example, in the case where only the first electrode 102 has a light-transmitting property, light emission is extracted from a substrate side through the first electrode 102. Meanwhile, in the case where only the second electrode 104 has a light-transmitting property, the emitted light is extracted from the side opposite to the substrate side through the second electrode 104. In the case where each of the first electrode 102 and the second electrode 104 has a light-transmitting property, light emission is extracted from both of the substrate side and the side opposite to the substrate through the first electrode 102 and the second electrode 104.

The structure of the layers provided between the first electrode 102 and the second electrode 104 is not limited to the aforementioned one. Besides the above described structure, any structure can be employed, in which a light-emitting region for recombination of holes and electrons is provided in a portion apart from the first electrode 102 and the second electrode 104 so that quenching caused by adjacency of the light-emitting region and a metal can be prevented and in which the quinoxaline derivative described in Embodiment Mode 1 is included.

That is, there is no particular limitation on the stacked structure of the layers, and the quinoxaline derivative described in Embodiment Mode 1 may be combined, as appropriate, with a layer formed of a substance with a high electron-transporting property, a substance with a high hole-transporting property, a substance with a high electron-injecting property, a substance with a high hole-injecting property, a bipolar substance (a substance with high electron-transporting and hole-transporting properties), or the like.

Figure 2:
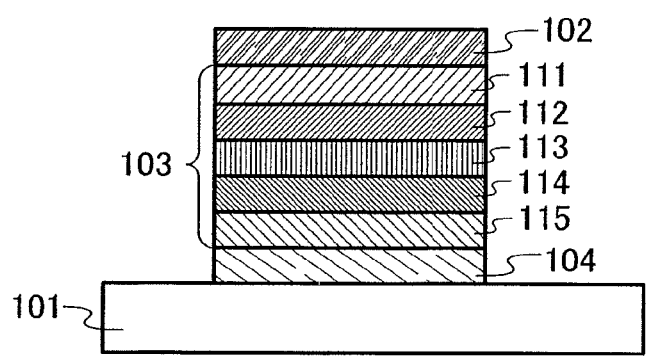
FIG. 2 is a drawing illustrating a light-emitting element according to an aspect of the present invention.

In addition, as illustrated in FIG. 2, a structure may be employed in which, over the substrate 101, the second electrode 104 functioning as a cathode, the EL layer 103, and the first electrode 102 functioning as an anode are stacked in this order. In FIG. 2, a structure is employed in which, over the second electrode 104, the electron-injecting layer 115, the electron-transporting layer 114, the light-emitting layer 113, the hole-transporting layer 112, and the hole-injecting layer 111 are stacked in this order.

In this embodiment mode, the light-emitting element is formed over a substrate made of glass, plastic, or the like. By forming a plurality of such light-emitting elements over a substrate, a passive matrix light-emitting device can be manufactured. Moreover, the light-emitting element may be manufactured over an electrode electrically connected to, for example, a thin film transistor (TFT) formed over a substrate made of glass, plastic, or the like. Thus, an active matrix light-emitting device which controls the driving of a light-emitting element by a TFT can be manufactured. Note that the structure of a TFT is not particularly limited, and either a staggered TFT or an inversed staggered TFT may be used. In addition, a driver circuit formed over a TFT substrate may be formed using both n-channel TFTs and p-channel TFTs, or using either n-channel TFTs or p-channel TFTs. In addition, the crystallinity of a semiconductor film used for the TFT is not particularly limited. Either an amorphous semiconductor film or a crystalline semiconductor film may be used for the TFT. Further, a single crystalline semiconductor film may be used. The single crystal semiconductor film can be formed by a Smart-Cut method or the like.

Because the quinoxaline derivatives described in Embodiment Mode 1 have an excellent electron-transporting property, the quinoxaline derivatives can be suitably used for an electron-transporting layer of the light-emitting element. By using the quinoxaline derivative described in Embodiment Mode 1, a light-emitting element with low driving voltage can be obtained. Further, a light-emitting element consuming low power can be obtained.

Note that this embodiment mode can be combined with any of other embodiment modes as appropriate.

(Embodiment Mode 3)

In this embodiment mode, a structure in which any of the quinoxaline derivatives described in Embodiment Mode 1 is used for a light-emitting layer is described as one mode of a light-emitting element of the present invention.

Because the quinoxaline derivatives described in Embodiment Mode 1 have an excellent electron-transporting property, the quinoxaline derivatives can each be used as a host material in a light-emitting layer having a structure in which a substance with a high light-emitting property (guest material) is dispersed in another substance (host material).

In the case where any of the quinoxaline derivatives described in Embodiment Mode 1 is used as a host material and where a guest material emits fluorescence, it is preferable to use, as a guest material, a substance whose lowest unoccupied molecular orbital (LUMO) level is lower than that of each quinoxaline derivative described in Embodiment Mode 1 and whose highest occupied molecular orbital (HOMO) level is higher than that of each quinoxaline derivative described in Embodiment Mode 1. For example, as a light-emitting material that exhibits blue light emission, the following can be given: N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like. As a light-emitting material that exhibits green light emission, the following can be given: N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), and the like. As a light-emitting material that exhibits yellow light emission, the following can be given: rubrene, 5,12-bis(1,1'-biphenyl-4-yl)-6,11-diphenyltetracene (abbreviation: BPT), and the like. As a light-emitting material that exhibits red light emission, the following can be given: N,N',N'-tetrakis(4-methylphenyl)tetracene-5,11-diamine (abbreviation: p-mPhTD), 7,13-diphenyl-N,N,N',N'-tetrakis(4-methylphenyl)acenaphtho[1,2-α]fluoranthene-3,10-diamine (abbreviation: p-mPhAFD), and the like.

Alternatively, in the case where the quinoxaline derivative shown in Embodiment Mode 1 is used as a host material and where a guest material emits phosphorescence, it is preferable to use, as a guest material, a substance having lower triplet excitation energy than the quinoxaline derivative described in Embodiment Mode 1. Examples include organometallic complexes such as bis[2-(2'-benzo[4,5-α]thienyl)pyridinato-N,C$^{3'}$]iridium(III) acetylacetonate (abbreviation: Ir(btp)$_2$(acac)), bis(1-phenylisoquinolinato-N,C$^2$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), and 2,3,7,8,12,13,17,18-octaethyl-21H,23H-porphyrin platinum(II) (abbreviation: PtOEP).

Because the quinoxaline derivatives described in Embodiment Mode 1 have an excellent electron-transporting property, by using any of the quinoxaline derivatives for a light-emitting layer, the light-emitting layer having a high electron-transporting property can be obtained. Such a light-emitting layer can exhibit light emission with high efficiency when a guest material with a high electron-trapping property is used.

As the substance (host material) into which the substance with a light-emitting property (guest material) is dispersed, a plural kinds of substances can be used. Thus, the light-emitting layer may include a second host material in addition to any of the quinoxaline derivatives described in Embodiment Mode 1. Since the quinoxaline derivatives described in Embodiment Mode 1 have an excellent electron-transporting property, it is preferable to use a material having an excellent hole-transporting property as the second host material. With such a structure, the light-emitting layer has a hole-transporting property and an electron-transporting property, and the recombination probability of holes and electrons in the light-emitting layer is increased, so that light emission with high efficiency can be obtained. Further, a light-emitting element with low driving voltage can be obtained.

Note that this embodiment mode can be combined with any of other embodiment modes as appropriate.

(Embodiment Mode 4)

In this embodiment mode, a structure in which any of the quinoxaline derivatives described in Embodiment Mode 1 is used for an electron-injecting layer is described as one mode of a light-emitting element of the present invention.

Because the quinoxaline derivatives shown in Embodiment Mode 1 also have an excellent electron-injecting property, the quinoxaline derivatives can each be used for an electron-injecting layer of a light-emitting element. In the case where any of the quinoxaline derivatives described in Embodiment Mode 1 is used for an electron-injecting layer, it is preferable for the electron-injecting layer to include an alkali metal, an alkaline-earth metal, or a compound thereof in addition to any of the quinoxaline derivatives described in Embodiment Mode 1. With such a structure, an electron-injecting property from an electrode serving as a cathode is increased, and a light-emitting element with low driving voltage can be obtained.

Note that this embodiment mode can be combined with any of other embodiment modes as appropriate (Embodiment Mode 5)

In this embodiment mode, a mode of a light-emitting element according to the present invention in which a plurality of light-emitting units is stacked (hereinafter this light-emitting element is referred to as a stacked-type element) will be described with reference to FIG. 3. This light-emitting element is a stacked-type light-emitting element including a plurality of light-emitting units between a first electrode and a second electrode. The structure of each light-emitting unit can be similar to the structure described in Embodiment Modes 2 to 4. In other words, the light-emitting element described in Embodiment Mode 2 is a light-emitting element having one light-emitting unit. In this embodiment mode, a light-emitting element having a plurality of light-emitting units will be described.

Figure 3:
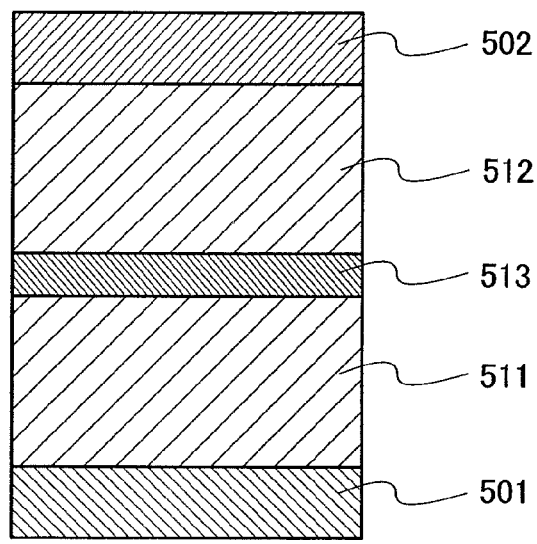
FIG. 3 is a drawing illustrating a light-emitting element according to an aspect of the present invention.

In FIG. 3, a first light-emitting unit 511 and a second light-emitting unit 512 are stacked between a first electrode 501 and a second electrode 502. As the first electrode 501 and the second electrode 502, electrodes similar to the electrodes shown in Embodiment Mode 2 can be employed. Note that the first light-emitting unit 511 and the second light-emitting unit 512 may have the same structure or different structures, and may have a structure similar to the structure shown in Embodiment Mode 2.

A charge-generating layer 513 is a layer which injects electrons into a light-emitting unit on one side and injects holes into a light-emitting unit on the other side when voltage is applied to the first electrode 501 and the second electrode 502, and may be either a single layer or a stacked structure of two or more layers. As a stacked structure of two or more layers, a structure in which a hole-injecting layer and an electron-injecting layer are stacked is preferable.

As the hole-injecting layer, a semiconductor or an insulator, such as molybdenum oxide, vanadium oxide, rhenium oxide, or ruthenium oxide, can be used. Alternatively, the hole-injecting layer may have a structure in which an acceptor substance is added to a substance having a high hole-transporting property. The layer including a substance having a high hole-transporting property and an acceptor substance is formed of the composite material shown in Embodiment Mode 2 and includes, as an acceptor substance, 7,7,8,8-tetracyano-2,3,5,6-tetrafluoroquinodimethane (abbreviation: F$_4$-TCNQ) or metal oxide such as vanadium oxide, molybdenum oxide, or tungsten oxide. As the substance having a high hole-transporting property, various compounds such as an aromatic amine compound, a carbazole derivative, aromatic hydrocarbon, a high molecular compound, an oligomer, a dendrimer, a polymer, or the like can be used. Note that a substance having a hole mobility of $10^{-6}$ cm$^2$/Vs or higher is preferably employed as the substance having a high hole-transporting property. However, other substances may also be used as long as the hole-transporting properties thereof are higher than the electron-transporting properties thereof. Since the composite material of the substance having a high hole-transporting property and the acceptor substance has excellent carrier-injecting and carrier-transporting properties, low-voltage driving and low-current driving can be realized.

As the electron-injecting layer, an insulator or a semiconductor, such as lithium oxide, lithium fluoride, or cesium carbonate, can be used. Alternatively, the electron-injecting layer may have a structure in which a donor substance is added to a substance having a high electron-transporting property. As the donor substance, an alkali metal, an alkaline-earth metal, a rare earth metal, a metal belonging to Group 13 of the periodic table, or an oxide or carbonate of any of these can be used. Specifically, lithium (Li), cesium (Cs), magnesium (Mg), calcium (Ca), ytterbium (Yb), indium (In), lithium oxide, cesium carbonate, or the like is preferably used. Alternatively, an organic compound such as tetrathianaphthacene may be used as the donor substance. As the substance having a high electron-transporting property, the materials shown in Embodiment Mode 2 can be used. Note that a substance having an electron mobility of $10^{-6}$ cm$^2$/Vs or higher is preferably employed as the substance having a high electron-transporting property. However, other substances may also be used as long as the electron-transporting properties thereof are higher than the hole-transporting properties thereof. Since the composite material of the substance having a high electron-transporting property and the donor substance has excellent carrier-injecting and carrier-transporting properties, low-voltage driving and low-current driving can be realized.

Further, the electrode materials described in Embodiment Mode 2 can be used for the charge-generating layer 513. For example, the charge-generating layer 513 may be formed with a combination of a layer including a substance having a hole-transporting property and metal oxide with a transparent conductive film. Note that a layer having a high light-transmitting property is preferably used as the charge-generating layer in terms of light extraction efficiency.

In any case, it is acceptable as long as the charge-generating layer 513 interposed between the first light-emitting unit 511 and the second light-emitting unit 512 injects electrons into a light-emitting unit on one side and injects holes into a light-emitting unit on the other side when voltage is applied to the first electrode 501 and the second electrode 502. For example, any structure is acceptable for the charge-generating layer 513 as long as the charge-generating layer 513 injects electrons into the first light-emitting unit 511 and holes into the second light-emitting unit 512 when voltage is applied so that potential of the first electrode becomes higher than potential of the second electrode.

In this embodiment mode, the light-emitting element having two light-emitting units is described. However, the present invention can similarly be applied to a light-emitting element in which three or more light-emitting units are stacked. When a charge-generating layer is provided between a pair of electrodes so as to partition a plurality of light-emitting units, like the light-emitting element of this embodiment mode, a long-life element in a high luminance range can be realized while current density is kept low. When the light-emitting element is applied to lighting, voltage drop due to resistance of an electrode material can be suppressed, thereby achieving homogeneous light emission in a large area. Moreover, a light-emitting device with low driving voltage which consumes low power can be realized.

When light-emitting units are formed to emit light of different colors from each other, a light-emitting element as a whole can provide light emission of a desired color. For example, in the light-emitting element having two light-emitting units, the emission color of the first light-emitting unit and the emission color of the second light-emitting unit are made to be complementary colors, whereby the light-emitting element can exhibit white light emission as a whole. Note that "complementary colors" refer to colors which can produce an achromatic color when mixed. That is, white light emission can be obtained by mixture of light from substances whose emission colors are complementary colors. The same can be applied to a light-emitting element which has three light-emitting units. For example, the light-emitting element as a whole can provide white light emission when the emission color of the first light-emitting unit is red, the emission color of the second light-emitting unit is green, and the emission color of the third light-emitting unit is blue.

Note that this embodiment mode can be combined with any of other embodiment modes as appropriate.

(Embodiment Mode 6)

In this embodiment mode, a light-emitting device having a light-emitting element of the present invention will be described.

A light-emitting device having a light-emitting element of the present invention in a pixel portion is described in this embodiment mode with reference to FIGS. 4A and 4B. Note that FIG. 4A is a top view illustrating the light-emitting device and FIG. 4B is a cross-sectional view taken along lines A-A' and B-B' of FIG. 4A. This light-emitting device includes a driver circuit portion (source side driver circuit) 601, a pixel portion 602, and a driver circuit portion (gate side driver circuit) 603, which are indicated by dotted lines, in order to control the light emission of the light-emitting element. Further, reference numeral 604 denotes a sealing substrate and reference numeral 605 denotes a sealing material. Reference numeral 607 denotes a space surrounded by the sealing material 605.

Note that a leading wiring 608 is a wiring for transmitting signals that are input to the source side driver circuit 601 and the gate side driver circuit 603. The leading wiring 608 receives video signals, clock signals, start signals, reset signals, and the like from an FPC (flexible printed circuit) 609 that serves as an external input terminal. Although only an FPC is illustrated here, this FPC may be provided with a printed wiring board (PWB). The light-emitting device in this specification includes not only a light-emitting device itself but also a light-emitting device with an FPC or a PWB attached thereto.

Next, a cross-sectional structure is described with reference to FIG. 4B. The driver circuit portion and the pixel portion are provided over an element substrate 610, but only the source side driver circuit 601, which is the driver circuit portion, and one pixel of the pixel portion 602 are illustrated in FIG. 4B.

Note that a CMOS circuit which is a combination of an n-channel TFT 623 and a p-channel TFT 624 is formed in the source side driver circuit 601. The driver circuit may be formed with various CMOS circuits, PMOS circuits, or NMOS circuits. In this embodiment mode, a driver-integrated type in which a driver circuit is formed over the substrate provided with the pixel portion is described; however, the present invention is not limited to this type, and the driver circuit can be formed outside the substrate.

The pixel portion 602 includes a plurality of pixels each having a switching TFT 611, a current controlling TFT 612, and a first electrode 613 that is electrically connected to a drain of the current controlling TFT 612. Note that an insulator 614 is formed to cover the edge portion of the first electrode 613. Here, a positive photosensitive acrylic resin film is used to form the insulator 614.

Further, in order to improve the coverage, the insulator 614 is provided such that either an upper edge portion or a lower edge portion of the insulator 614 has a curved surface with a curvature. For example, when positive photosensitive acrylic is used as a material for the insulator 614, it is preferable that only an upper edge portion of the insulator 614 have a curved surface with a radius of curvature (0.2 µm to 3 µm). The insulator 614 can be formed using either a negative type that becomes insoluble in an etchant by light irradiation or a positive type that becomes soluble in an etchant by light irradiation.

An EL layer 616 and a second electrode 617 are formed over the first electrode 613. Here, various metals, alloys, electrically conductive compounds, or mixtures thereof can be used for a material of the first electrode 613. If the first electrode is used as an anode, it is preferable that the first electrode be formed using a metal, an alloy, an electrically conductive compound, or a mixture thereof with a high work function (preferably, a work function of 4.0 eV or higher) among such materials. For example, the first electrode 613 can be formed using a single-layer film such as an indium tin oxide film containing silicon, an indium zinc oxide film, a titanium nitride film, a chromium film, a tungsten film, a Zn film, a Pt film, or the like; a stacked film of a titanium nitride film and a film containing aluminum as its main component; or a stacked film such as a film having a three-layer structure including a titanium nitride film, a film containing aluminum as its main component, and a titanium nitride film. Note that when a film having a stacked structure is employed, the first electrode 613 has low resistance as a wiring, forms a favorable ohmic contact, and can serve as an anode.

The EL layer 616 is formed by various methods such as an evaporation method using an evaporation mask, an ink-jet method, a spin coating method, and the like. The EL layer 616 includes the quinoxaline derivative described in Embodiment Mode 1. Any of a low molecular compound, a high molecular compound, an oligomer, a dendrimer, or the like may be employed as a material for the EL layer 616. As the material for the EL layer, not only an organic compound but also an inorganic compound may be used.

As the material for the second electrode 617, various types of metals, alloys, electrically conductive compounds, mixtures thereof, and the like can be used. If the second electrode is used as a cathode, it is preferable that the second electrode be formed using a metal, an alloy, an electrically conductive compound, a mixture thereof, or the like with a low work function (preferably, a work function of 3.8 eV or lower) among such materials. Examples include: elements belonging to Group 1 and Group 2 of the periodic table, that is, alkali metals such as lithium (Li) and cesium (Cs) and alkaline-earth metals such as magnesium (Mg), calcium (Ca), and strontium (Sr); alloys including any of these (MgAg, AlLi); and the like. In the case where light generated in the EL layer 616 is made to be transmitted through the second electrode 617, the second electrode 617 may also be formed using a stacked film of a thin metal film with a small film thickness and a transparent conductive film (indium tin oxide (ITO), indium tin oxide containing silicon or silicon oxide, indium zinc oxide (IZO), indium oxide containing tungsten oxide and zinc oxide (IWZO), or the like).

By attaching the sealing substrate 604 and the element substrate 610 to each other with the sealing material 605, a light-emitting element 618 is provided in the space 607 which is surrounded by the element substrate 610, the sealing substrate 604, and the sealing material 605. Note that the space 607 is filled with a filler. There are also cases where the space 607 may be filled with an inert gas (such as nitrogen or argon) as such a filler, or where the space 607 may be filled with the sealing material 605.

As the sealing material 605, an epoxy-based resin is preferably used. In addition, it is desirable that a material thereof allows as little moisture or oxygen as possible to permeate. As the sealing substrate 604, a plastic substrate formed of fiberglass-reinforced plastics (FRP), polyvinyl fluoride (PVF), polyester, acrylic, or the like can be used besides a glass substrate or a quartz substrate.

As described above, the light-emitting device including a light-emitting element of the present invention can be obtained.

A light-emitting device of the present invention includes any of the light-emitting elements described in Embodiment Modes 2 to 5. Driving voltage of each light-emitting element shown in Embodiment Modes 2 to 5 is low; therefore, a light-emitting device which consumes low power can be obtained.

Figure 5A:
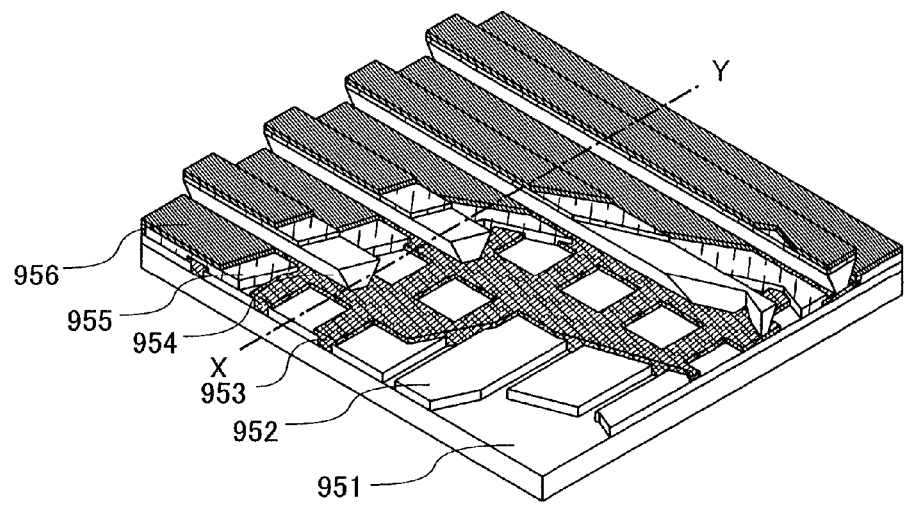
FIGS. 5A and 5B are drawings illustrating a light-emitting device according to an aspect of the present invention.
Figure 5B:
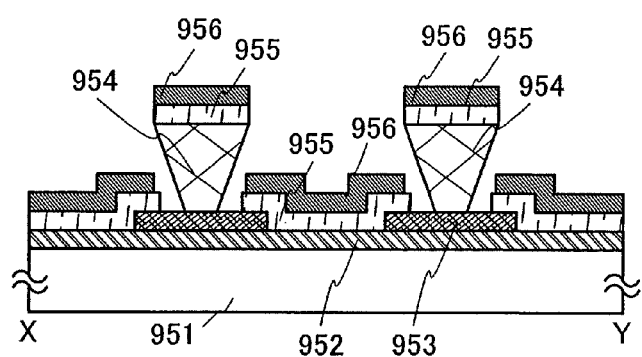

As described above, an active matrix light-emitting device that controls driving of a light-emitting element with a transistor is described in this embodiment mode; however, a passive matrix light-emitting device may be used. FIGS. 5A and 5B illustrate a passive matrix light-emitting device manufactured according to the present invention. Note that FIG. 5A is a perspective view of the light-emitting device and FIG. 5B is a cross-sectional view taken along a line X-Y of FIG. 5A. In FIGS. 5A and 5B, an EL layer 955 is provided between an electrode 952 and an electrode 956 over a substrate 951. The edge portion of the electrode 952 is covered with an insulating layer 953. A partition layer 954 is provided over the insulating layer 953. The sidewalls of the partition layer 954 slope so that the distance between one sidewall and the other sidewall is gradually reduced toward the surface of the substrate. In other words, a cross section taken along the direction of the short side of the partition layer 954 is trapezoidal, and the lower side (a side which is in the same direction as a plane direction of the insulating layer 953 and in contact with the insulating layer 953) is shorter than the upper side (a side which is in the same direction as the plane direction of the insulating layer 953 and not in contact with the insulating layer 953). The cathode can be patterned by providing the partition layer 954 in this manner. In addition, in a passive matrix light-emitting device, a light-emitting device with low power consumption can be obtained by including a light-emitting element with low driving voltage according to the present invention.

Note that this embodiment mode can be combined with any of other embodiment modes as appropriate.

(Embodiment Mode 7)

In this embodiment mode, an electronic appliance of the present invention which includes the light-emitting device shown in Embodiment Mode 6 will be described. An electronic appliance of the present invention includes any of the light-emitting elements described in Embodiment Modes 2 to 5 and a display portion which consumes low power.

Examples of electronic appliances each manufactured using a light-emitting device of the present invention can be given as follows: video cameras, digital cameras, goggle type displays, navigation systems, audio reproducing devices (car audio sets, audio component sets, and the like), computers, game machines, portable information terminals (mobile computers, cellular phones, portable game machines, electronic book readers, and the like), image reproducing devices each provided with a storage medium (specifically, devices each provided with a display device that can reproduce a storage medium such as a digital versatile disc (DVD) and display the image), and the like. Specific examples of these electronic appliances are illustrated in FIGS. 6A to 6D.

Figure 6A:
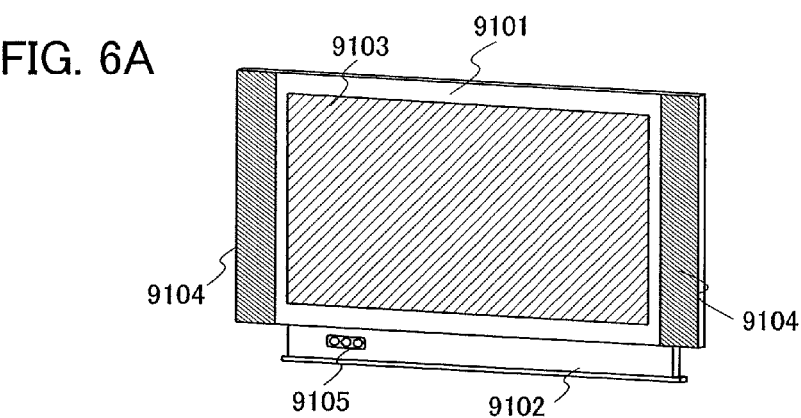
FIGS. 6A to 6D are drawings illustrating electronic appliances according to an aspect of the present invention.

FIG. 6A illustrates a television device of this embodiment mode, which includes a housing 9101, a support 9102, a display portion 9103, speaker portions 9104, a video input terminal 9105, and the like. In the display portion 9103 of this television device, light-emitting elements similar to those described in Embodiment Modes 2 to 5 are arranged in matrix. Features of the light-emitting elements are that driving voltage is low and power consumption is low. The display portion 9103 which includes the light-emitting elements has similar features. Therefore, in this television device, low power consumption is achieved. With such features, a power supply circuit can be significantly reduced or downsized in the television device; therefore, reduction in size and weight of the housing 9101 and the support 9102 can be achieved. In the television device of this embodiment mode, reduction in power consumption, in size, and in weight is achieved; therefore, a product which is suitable for living environment can be provided.

Figure 6B:
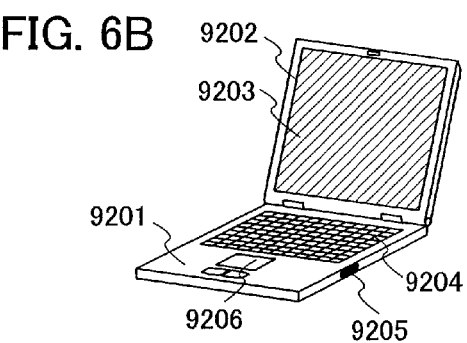

FIG. 6B illustrates a computer of this embodiment mode, which includes a main body 9201, a housing 9202, a display portion 9203, a keyboard 9204, an external connection port 9205, a pointing device 9206, and the like. In the display portion 9203 of this computer, light-emitting elements similar to those described in Embodiment Modes 2 to 5 are arranged in matrix. Features of the light-emitting element are that driving voltage is low and power consumption is low. The display portion 9203 which includes the light-emitting elements has similar features. Therefore, in this computer, lower power consumption is achieved. With such features, a power supply circuit can be significantly reduced or downsized in the computer; therefore, reduction in size and weight of the main body 9201 and the housing 9202 can be achieved. In the computer of this embodiment mode, reduction in power consumption, in size, and in weight is achieved; therefore, a product which is suitable for environment can be provided.

Figure 6C:
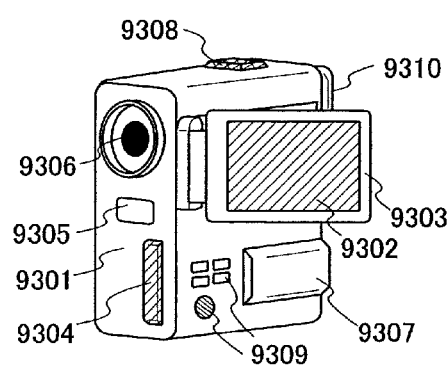

FIG. 6C illustrates a camera that includes a main body 9301, a display portion 9302, a housing 9303, an external connection port 9304, a remote control receiving portion 9305, an image receiving portion 9306, a battery 9307, an audio input portion 9308, operation keys 9309, an eyepiece portion 9310, and the like. In the display portion 9302 of this camera, light-emitting elements similar to those described in Embodiment Modes 2 to 5 are arranged in matrix. Features of the light-emitting elements are that driving voltage is low and power consumption is low. The display portion 9302 which includes the light-emitting elements has similar features. Therefore, in this camera, lower power consumption is achieved. With such features, a power supply circuit can be significantly reduced or downsized in the camera; therefore, reduction in size and weight of the main body 9301 can be achieved. In the camera of this embodiment mode, reduction in power consumption, in size, and in weight is achieved; therefore, a product which is suitable for being carried around can be provided.

Figure 6D:
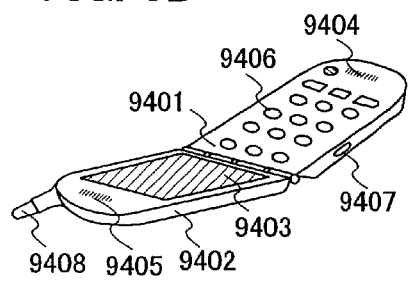

FIG. 6D illustrates a cellular phone of this embodiment mode, which includes a main body 9401, a housing 9402, a display portion 9403, an audio input portion 9404, an audio output portion 9405, operation keys 9406, an external connection port 9407, an antenna 9408, and the like. In the display portion 9403 of this cellular phone, light-emitting elements similar to those described in Embodiment Modes 2 to 5 are arranged in matrix. Features of the light-emitting elements are that driving voltage is low and power consumption is low. The display portion 9403 which includes the light-emitting elements has similar features. Therefore, in this cellular phone, lower power consumption is achieved. With such features, a power supply circuit can be significantly reduced or downsized in the cellular phone; therefore, reduction in size and weight of the main body 9401 and the housing 9402 can be achieved. In the cellular phone of this embodiment mode, reduction in power consumption, in size, and in weight is achieved; therefore, a product which is suitable for being carried around can be provided.

Figure 12A:
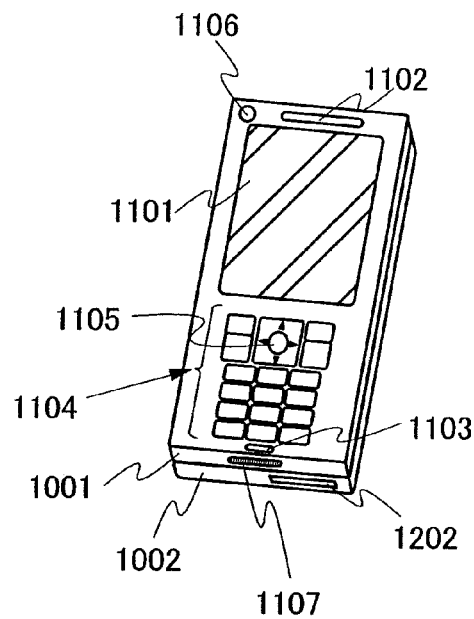
FIGS. 12A to 12C are drawings illustrating an electronic appliance according to an aspect of the present invention.
Figure 12B:
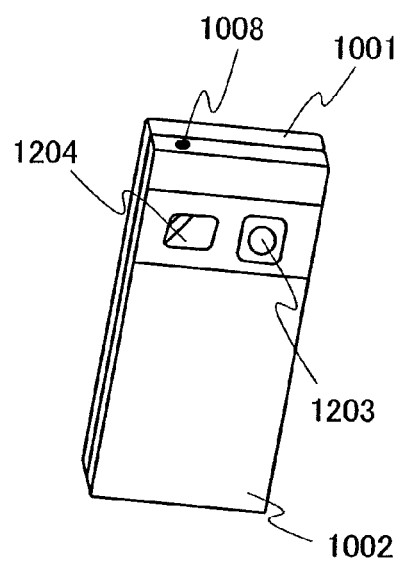
Figure 12C:
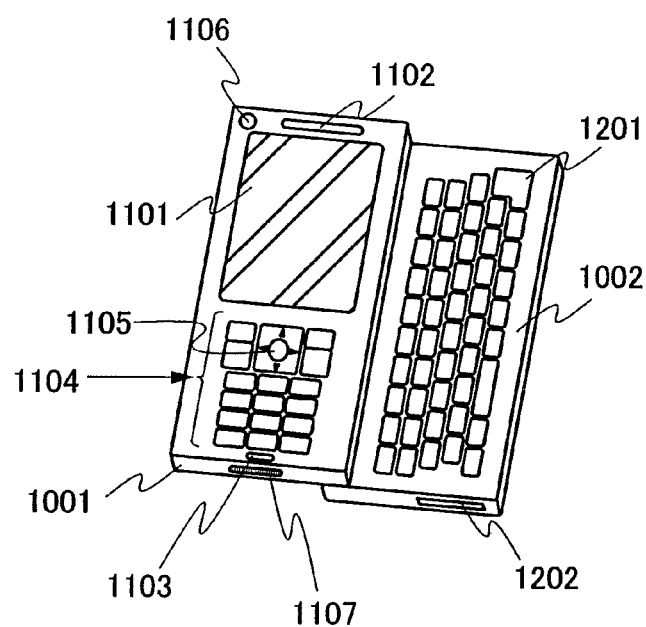

FIGS. 12A to 12C illustrate an example of a cellular phone having a structure different from that of the cellular phone of FIG. 6D. FIG. 12A is a front view, FIG. 12B is a rear view, and FIG. 12C is a development view. The cellular phone in FIGS. 12A to 12C is a so-called smartphone which has both a function as a phone and a function as a portable information terminal, and incorporates a computer to conduct a variety of data processing in addition to voice calls.

The cellular phone illustrated in FIGS. 12A to 12C has two housings 1001 and 1002. The housing 1001 includes a display portion 1101, a speaker 1102, a microphone 1103, operation keys 1104, a pointing device 1105, a camera lens 1106, an external connection terminal 1107, an earphone terminal 1108, and the like, while the housing 1002 includes a keyboard 1201, an external memory slot 1202, a camera lens 1203, a light 1204, and the like. In addition, an antenna is incorporated in the housing 1001.

In addition to the above structure, the cellular phone may incorporate a non-contact IC chip, a small-sized memory device, or the like.

In the display portion 1101, the light-emitting device shown in Embodiment Mode 6 can be incorporated, and a display direction can be appropriately changed depending on the usage mode. The cellular phone is provided with the camera lens 1106 on the same surface as the display portion 1101; therefore, the cellular phone can be used as a videophone. Further, a still image and a moving image can be taken using the camera lens 1203 and the light 1204 with the display portion 1101 used as a viewfinder. The speaker 1102 and the microphone 1103 can be used for video calls, recording, reproducing, and the like without being limited to voice calls. With the use of the operation keys 1104, making and receiving calls, inputting simple information such as e-mail or the like, scrolling the screen, moving the cursor, and the like are possible. Furthermore, the housing 1001 and the housing 1002 (FIG. 12A), which overlap with each other, are developed by sliding as show in FIG. 12C and can be used as a portable information terminal. In this case, smooth operation can be conducted using the keyboard 1201 and the pointing device 1105. The external connection terminal 1107 can be connected to an AC adaptor and various types of cables such as a USB cable, and charging, data communication with a computer, and the like are possible. Furthermore, a large amount of data can be stored and moved by inserting a storage medium into the external memory slot 1202.

In addition to the above functions, the cellular phone may include an infrared communication function, a television receiving function, or the like.

Figure 7:
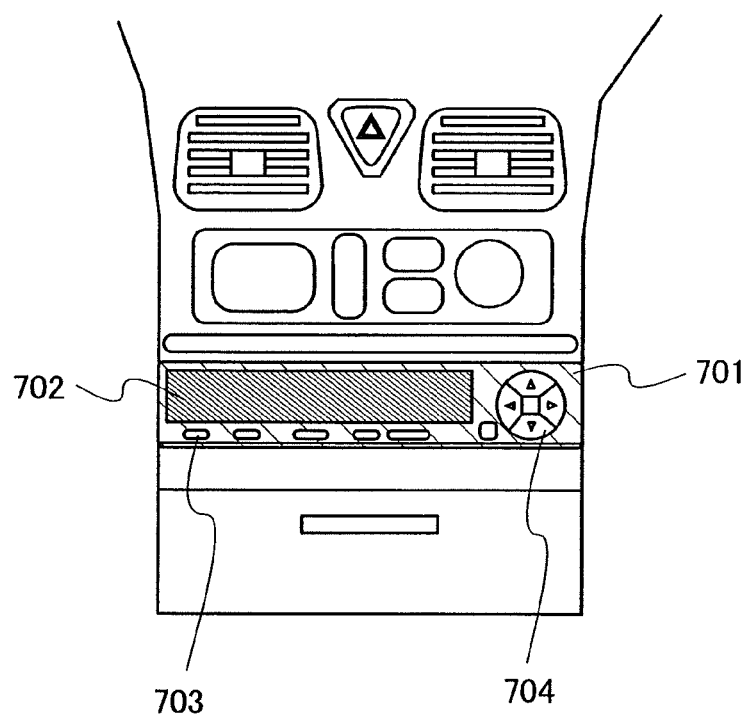
FIG. 7 is a drawing illustrating an electronic appliance according to an aspect of the present invention.

FIG. 7 illustrates an audio reproducing device, specifically, a car audio system, which includes a main body 701, a display portion 702, and operation switches 703 and 704. The display portion 702 can be realized with the light-emitting device (passive matrix type or active matrix type) described in Embodiment Mode 6. Further, the display portion 702 may be formed using a segment type light-emitting device. In any case, the use of a light-emitting element of the present invention makes it possible to form a bright display portion while achieving low power consumption, with the use of a vehicle power source (12 V to 42 V). Furthermore, although this embodiment mode describes an in-car audio system, a light-emitting device of the present invention may also be used in portable audio systems or audio systems for home use.

Figure 8:
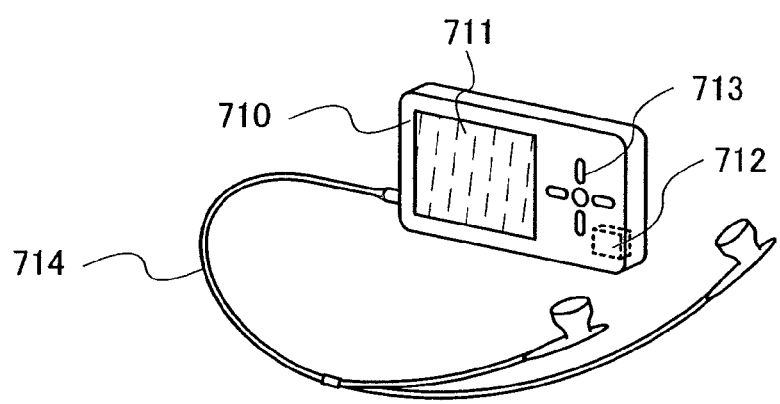
FIG. 8 is a drawing illustrating an electronic appliance according to an aspect of the present invention.

FIG. 8 illustrates a digital player as an example of an audio reproducing device. The digital player illustrated in FIG. 8 includes a main body 710, a display portion 711, a memory portion 712, an operation portion 713, earphones 714, and the like. Note that headphones or wireless earphones can be used instead of the earphones 714. The display portion 711 can be realized with the light-emitting device (passive matrix type or active matrix type) described in Embodiment Mode 6. Further, the display portion 711 may be formed using a segment type light-emitting device. In any case, the use of a light-emitting element of the present invention makes it possible to form a bright display portion which can display images even when using a secondary battery (a nickel-hydrogen battery or the like) while achieving low power consumption. As the memory portion 712, a hard disk or a nonvolatile memory is used. For example, by using a NAND-type nonvolatile memory with a recording capacity of 20 to 200 gigabytes (GB) and by operating the operating portion 713, an image or a sound (music) can be recorded and reproduced. Note that in the display portion 702 and the display portion 711, white characters are displayed against a black background, and thus, power consumption can be reduced. This is particularly effective for portable audio systems.

As described above, the applicable range of the light-emitting device manufactured by applying the present invention is so wide that the light-emitting device is applicable to electronic appliances in various fields. By applying the present invention, an electronic appliance which has a display portion consuming low power can be manufactured.

A light-emitting device to which the present invention is applied has a light-emitting element with high light emission efficiency and can also be used as a lighting apparatus. One mode of using a light-emitting element to which the present invention is applied as a lighting apparatus is described with reference to FIG. 9.

Figure 9:
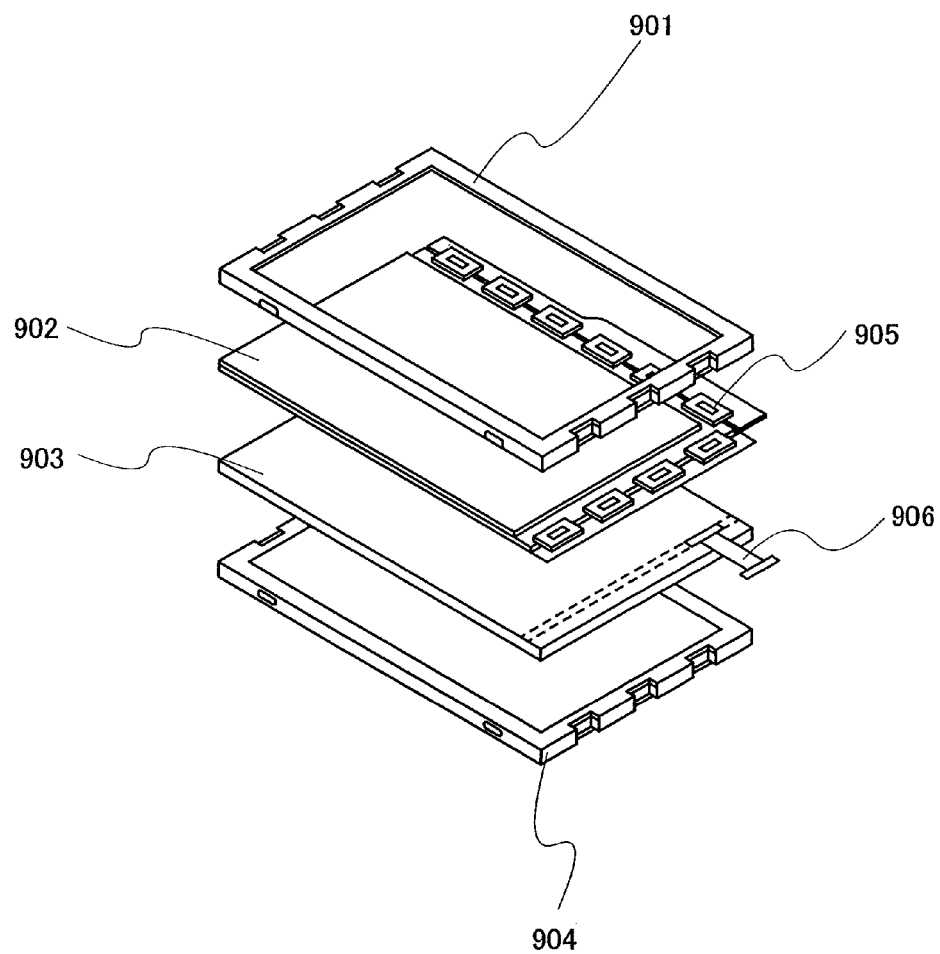
FIG. 9 is a drawing illustrating an electronic appliance according to an aspect of the present invention.

FIG. 9 illustrates a liquid crystal display device using the light-emitting device to which the present invention is applied as a backlight, as an example of the electronic appliance using a light-emitting device according to the present invention as a lighting apparatus. The liquid crystal display device illustrated in FIG. 9 includes a housing 901, a liquid crystal layer 902, a backlight 903, and a housing 904, and the liquid crystal layer 902 is connected to a driver IC 905. The light-emitting device to which the present invention is applied is used as the backlight 903, and current is supplied through a terminal 906.

Because the light-emitting device according to the present invention is thin and consumes less power, reduction in thickness and power consumption of a display device is possible by using a light-emitting device according to the present invention as a backlight of a liquid crystal display device. Moreover, a light-emitting device according to the present invention is a plane emission type lighting apparatus and can have a large area. Thus, the backlight can have a large area, and a liquid crystal display device having a large area can also be obtained.

Figure 10:
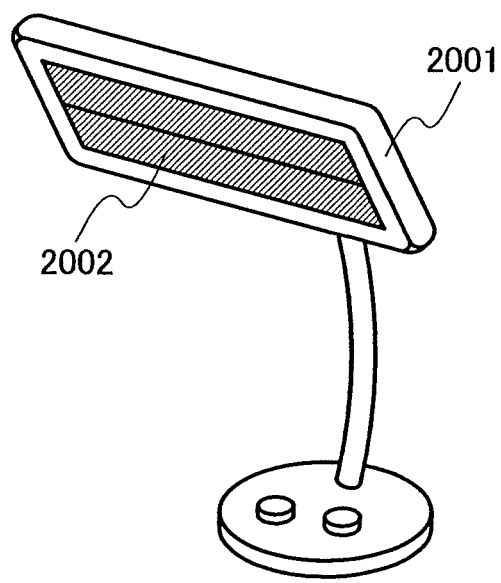
FIG. 10 is a drawing illustrating a lighting apparatus according to an aspect of the present invention.

FIG. 10 illustrates an example in which a light-emitting device according to the present invention is used as a desk lamp, which is one of lighting apparatuses. The desk lamp illustrated in FIG. 10 includes a housing 2001 and a light source 2002, and a light-emitting device according to the present invention is used as the light source 2002. Because a light-emitting device of the present invention consumes less power, the desk lamp also consumes less power.

Figure 11:
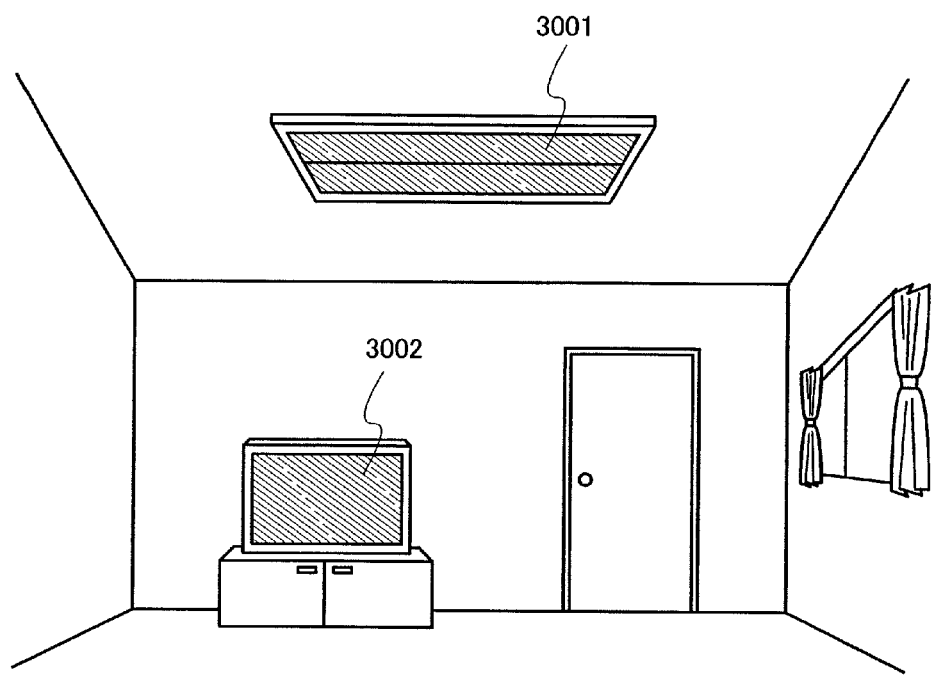
FIG. 11 is a drawing illustrating a lighting apparatus according to an aspect of the present invention.

FIG. 11 illustrates an example in which a light-emitting device to which the present invention is applied is used as an interior lighting apparatus 3001. Because a light-emitting device according to the present invention can have a large area, a light-emitting device according to the present invention can be used as a lighting apparatus having a large area. Moreover, because a light-emitting device according to the present invention consumes less power, a light-emitting device according to the present invention can be used as a lighting apparatus which consumes less power. Thus, a television device 3002 according to the present invention as illustrated in FIG. 6A may be placed in a room where a light-emitting device to which the present invention is applied is used as the interior lighting apparatus 3001, and public broadcasting or movies can be watched there. In such a case, since both devices consume less power, environmental load can be reduced.

Note that this embodiment mode can be combined with any of other embodiment modes as appropriate.

[Embodiment 1]

In this embodiment, a synthetic method of 2-phenyl-3-[4'-(1-phenyl-1H-benzimidazol-2-yl)biphenyl-4-yl]quinoxaline (abbreviation: BIm1PQ) which is represented by a structural formula (100) is described.

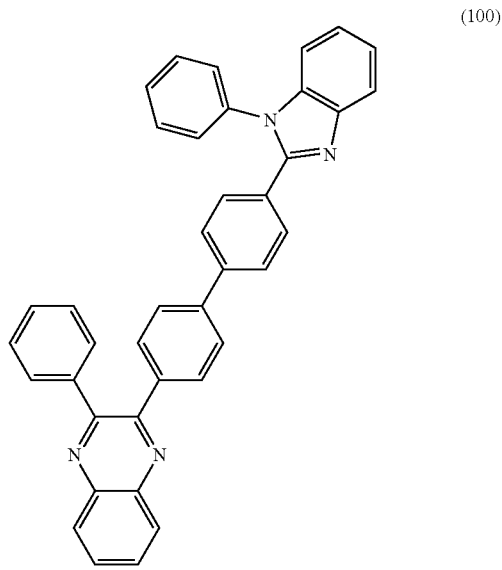 [SMILES: c1ccc(-c2nc3ccccc3nc2-c2ccc(-c3ccc(-c4nc5ccccc5n4-c4ccccc4)cc3)cc2)cc1]

(100)

Step 1 Synthesis of 4-bromo-N-[2-(N'-phenylamino)phenyl]benzamido

A synthetic scheme of 4-bromo-N-[2-(N'-phenylamino)phenyl]benzamido is shown in (B-1).

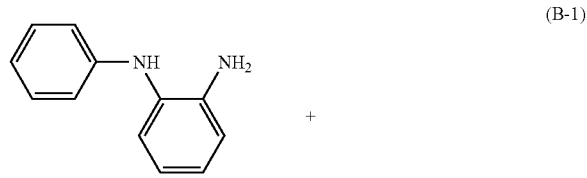

(B-1)

-continued

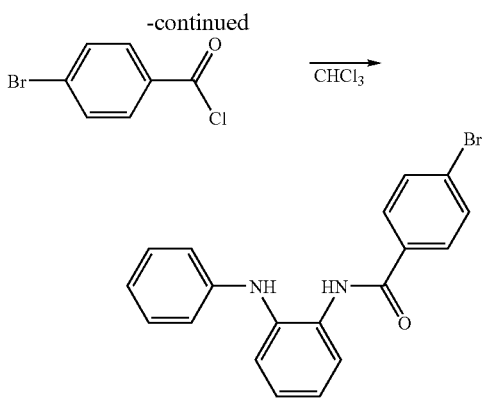

In a 500-mL three-neck flask were placed 8.5 g (46 mmol) of N-phenyl-1,2-phenylenediamine and 120 mL of chloroform, and the mixture was cooled to 0° C. under a nitrogen stream. After the cooling, 50 mL of a chloroform solution containing 10 g (46 mmol) of 4-bromobenzoic acid chloride was dripped into the solution, and the mixture was heated to room temperature and stirred for 20 hours. After a predetermined time, the solution was added to water, and an organic substance was extracted with chloroform from the aqueous phase. The obtained organic phase was washed with brine, and then dried with magnesium sulfate. The mixture was filtered, and the obtained filtrate was concentrated to give a solid. The obtained solid was washed with methanol; thus, 13 g of a white powder which was a product was obtained in the yield of 81%.

Step 2 Synthesis of 2-(4-bromophenyl)-1-phenyl-1H-benzimidazole

A synthetic scheme of 2-(4-bromophenyl)-1-phenyl-1H-benzimidazole is shown in (B-2).

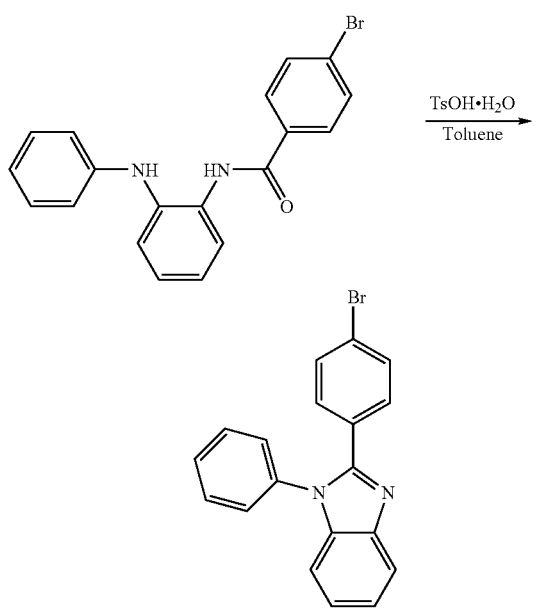

In a 300-mL three-neck flask were placed 13 g (37 mmol) of 4-bromo-N-[2-(N'-phenylamino)phenyl]benzamido, 0.64 g (3.7 mmol) of p-toluenesulphonic acid monohydrate, and 120 mL of toluene. The mixture was refluxed at 120° C. for 8.5 hours. After a predetermined time, the precipitated solid was separated by filtration. The obtained filtrate was washed with water and a saturated sodium hydrogen carbonate aqueous solution in that order, and the organic phase was dried with magnesium sulfate. The obtained mixture was filtered, and the obtained filtrate was concentrated to give a solid. Further, the solid which had been obtained by the above-described separation by filtration was dissolved in chloroform, and the solution was washed with a saturated sodium hydrogen carbonate aqueous solution. The obtained organic phase was dried with magnesium sulfate. The mixture was filtered, and the obtained filtrate was concentrated to give a solid. The obtained solids were combined with each other, and the combined solids were recrystallized with toluene/hexane; thus, 11 g of a white powder which was a product was obtained in the yield of 84%.

Step 3 Synthesis of (4-bromophenyl)phenylacetylene

A synthetic scheme of (4-bromophenyl)phenylacetylene is shown in (B-3).

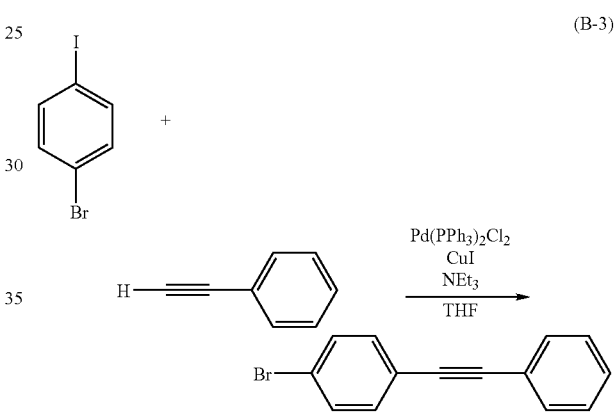

In a 500-mL three-neck flask were placed 14 g (51 mmol) of p-bromoiodobenzene, 5.2 g (52 mmol) of phenylacetylene, and 98 mg (0.50 mmol) of copper(I) iodide. After the atmosphere in the flask was replaced with nitrogen, 200 mL of tetrahydrofuran and 9.0 mL of triethylamine were placed in the flask, and the mixture was degassed by being stirred under reduced pressure. To this mixture was added 0.34 mg (0.50 mmol) of bis(triphenylphosphine)palladium(II) dichloride, and the mixture was stirred under a nitrogen stream at room temperature for 20 hours. After a predetermined time, 3% hydrochloric acid was added to the mixture, and an organic substance was extracted with ethyl acetate from the aqueous phase. The extracted solution combined with the organic phase was washed with brine and dried with magnesium sulfate. The mixture was subjected to suction filtration through Celite (produced by Wako Pure Chemical Industries, Ltd., Catalog No. 531-16855), Florisil (produced by Wako Pure Chemical Industries, Ltd., Catalog No. 540-00135), and alumina, and the filtrate was concentrated to give a solid. The obtained solid was recrystallized with hexane; thus, 7.4 g of a light-brown powder which was a product was obtained in a yield of 55%.

Step 4 Synthesis of 1-(4-bromophenyl)-2-phenylethanedione

A synthetic scheme of 1-(4-bromophenyl)-2-phenylethanedione is shown in (B-4).

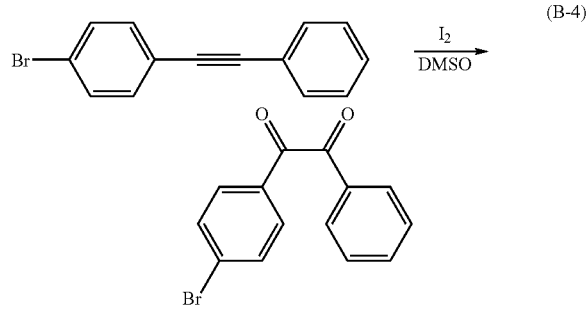

In a 300-mL three-neck flask were placed 7.4 g (28 mmol) of (4-bromophenyl)phenylacetylene, 3.7 g (14 mmol) of iodine, and 70 mL of dimethyl sulfoxide. The solution was stirred under a nitrogen stream at 155° C. for 4 hours. After a predetermined time, the solution was cooled to room temperature and added to an approximately 200 mL of 1 wt % aqueous sodium thiosulfate solution; then, a solid was precipitated. The solid was collected by suction filtration. The obtained solid was dissolved in ethyl acetate, and the solution was subjected to suction filtration through Celite (produced by Wako Pure Chemical Industries, Ltd., Catalog No. 531-16855). The filtrate was concentrated to give a solid. The obtained solid was recrystallized with ethyl acetate/hexane; thus, 4.5 g of a pale-yellow powder which was a product was obtained in a yield of 71%.

Step 5Synthesis of 2-(4-bromophenyl)-3-phenylquinoxaline

A synthetic scheme of 2-(4-bromophenyl)-3-phenylquinoxaline is shown in (B-5).

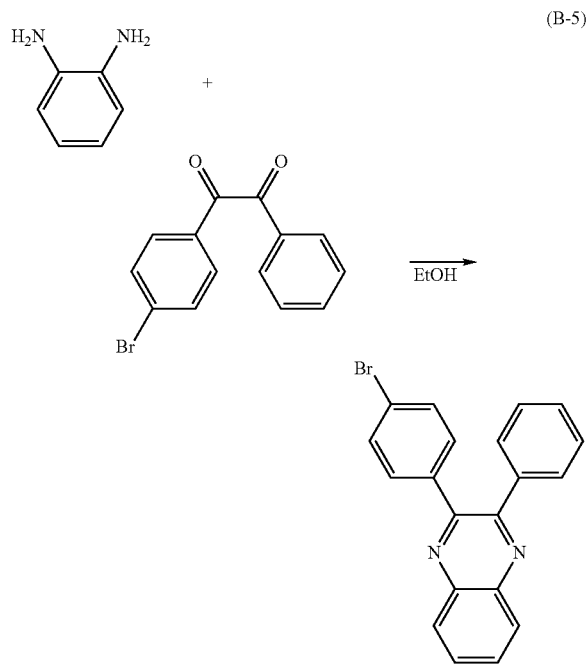

In a 200-mL flask were placed 4.5 g (15 mmol) of 1-(4-bromophenyl)-2-phenylethanedione, 1.8 g (17 mmol) of 1,2-phenylenediamine, and 50 mL of ethanol. This solution was refluxed under a nitrogen stream for 2.5 hours. After a predetermined time, the solution was cooled to room temperature, and the precipitated solid was collected by suction filtration. The collected solid was washed with ethanol; thus, 5.2 g of a white powder which was a product was obtained in a yield of 92%.

Step 6Synthesis of 4-(3-phenylquinoxalin-2-yl)phenylboronic acid

A synthetic scheme of 4-(3-phenylquinoxalin-2-yl)phenylboronic acid is shown in (B-6).

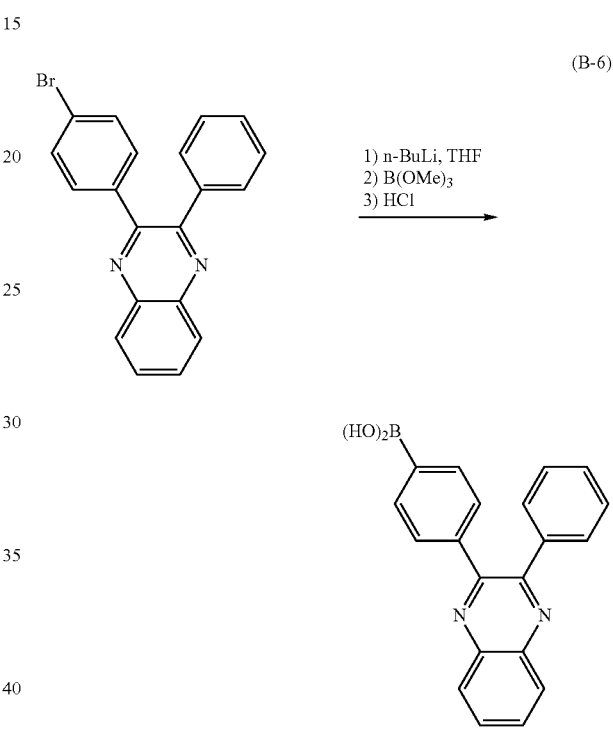

In a 300-mL three-neck flask was placed 5.0 g (13 mmol) of 2-(4-bromophenyl)-3-phenylquinoxaline, and the atmosphere in the flask was replaced with nitrogen. There was added 40 mL of tetrahydrofuran, and the mixture was cooled to −78° C. under a nitrogen stream. After the cooling, 10 mL (16 mmol) of 1.6 M n-butyllithium was dripped thereinto, and the mixture was stirred at the same temperature for 1 hour. After a predetermined time, 3.1 mL (27 mmol) of trimethyl borate was added thereto, and the temperature of the reaction solution was raised to room temperature, and then, the solution was stirred for 10 hours. After a predetermined time, the reaction solution was cooled to 0° C., to which 100 mL of 0.1 M hydrochloric acid was added, and the solution was stirred for 1 hour. After a predetermined time, an organic substance was extracted with ethyl acetate from the aqueous phase. The extracted solution combined with the organic phase was washed with brine, and then dried with magnesium sulfate. The mixture was subjected to suction filtration through Celite (produced by Wako Pure Chemical Industries, Ltd., Catalog No. 531-16855). The obtained filtrate was concentrated to give a solid. The solid was recrystallized with ethyl acetate/hexane; thus, 3.0 g of a pale-yellow powder which was a product was obtained in a yield of 66%.

Step 7 Synthesis of 2-phenyl-3-[4'-(1-phenyl-1H-benzimidazol-2-yl)biphenyl-4-yl]quinoxaline (abbreviation: BIm1PQ)

A synthetic scheme of BIm1PQ is shown in (B-7).

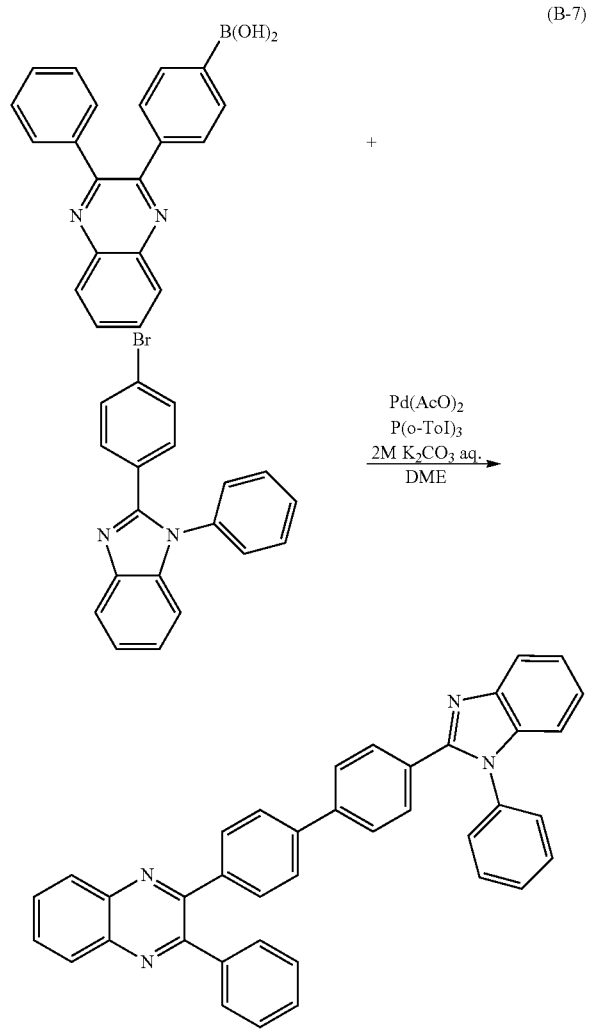

In a 100-mL three-neck flask were placed 0.87 g (2.3 mmol) of 2-(4-bromophenyl)-1-phenyl-1H-benzimidazole, 0.96 g (2.5 mmol) of 4-(3-phenylquinoxalin-2-yl)phenylboronic acid, 0.011 g (0.058 mmol) of palladium(II) acetate, and 0.18 g (0.60 mmol) of tri(ortho-tolyl)phosphine, and the atmosphere in the flask was replaced with nitrogen. To the mixture were added 30 mL of ethylene glycol dimethyl ether (DME) and 2.5 mL (5.0 mmol) of a 2.0 mol/L potassium carbonate aqueous solution. The mixture was degassed by being stirred under reduced pressure, and was refluxed under a nitrogen stream for 6 hours. After a predetermined time, water was added to the mixture, and an organic substance was extracted with ethyl acetate and chloroform from the aqueous phase. The extracted solution combined with the organic phase was washed with brine, and then dried with magnesium sulfate. The mixture was subjected to suction filtration through Celite (produced by Wako Pure Chemical Industries, Ltd., Catalog No. 531-16855), and the obtained filtrate was concentrated to give a solid. The obtained solid was purified by silica gel column chromatography (solvent:chloroform) and further recrystallized with chloroform/hexane; thus, 1.2 g of a pale-yellow crystal which was a product was obtained in a yield of 98%.

Then, 1.0 g of the obtained product was subjected to sublimation purification at 265° C. under an argon stream (flow rate: 3.0 mL/min) and a pressure of 10 Pa for 19 hours; thus, 0.78 g of a compound was obtained at a collection rate of 78%. The compound was measured by nuclear magnetic resonance (NMR) spectrometry and accordingly identified as 2-phenyl-3-[4'-(1-phenyl-1H-benzimidazol-2-yl)biphenyl-4-yl]quinoxaline (abbreviation: BIm1PQ).

$^1$H NMR data is shown below.
$^1$H NMR (300 MHz, CDCl$_3$): δ=7.24-7.37 (m, 7H), 7.49-7.67 (m, 14H), 7.76-7.80 (m, 2H), 7.91 (d, J=7.8 Hz, 1H), 8.17-8.29 (m, 2H).

Figure 13A:
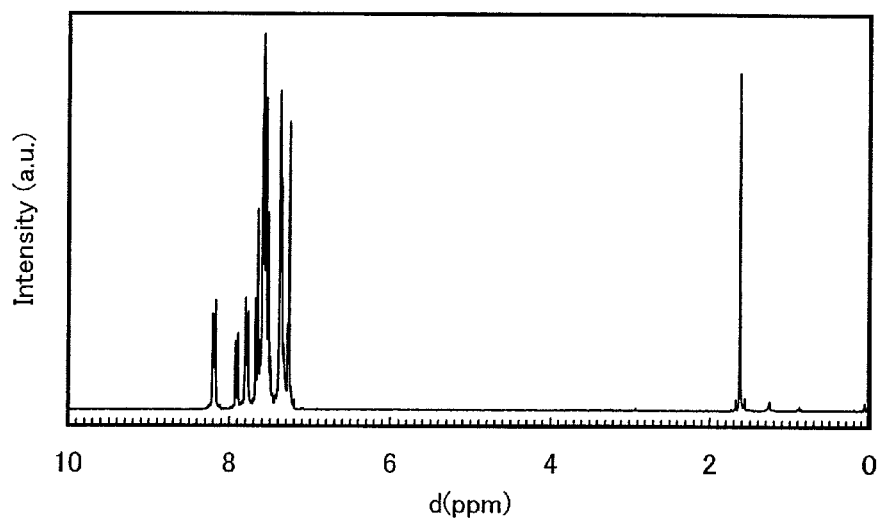
FIGS. 13A and 13B are $^1$H NMR charts of 2-phenyl-3-[4'-(1-phenyl-1H-benzimidazol-2-yl)biphenyl-4-yl]quinoxaline (abbreviation: BIm1PQ).
Figure 13B:
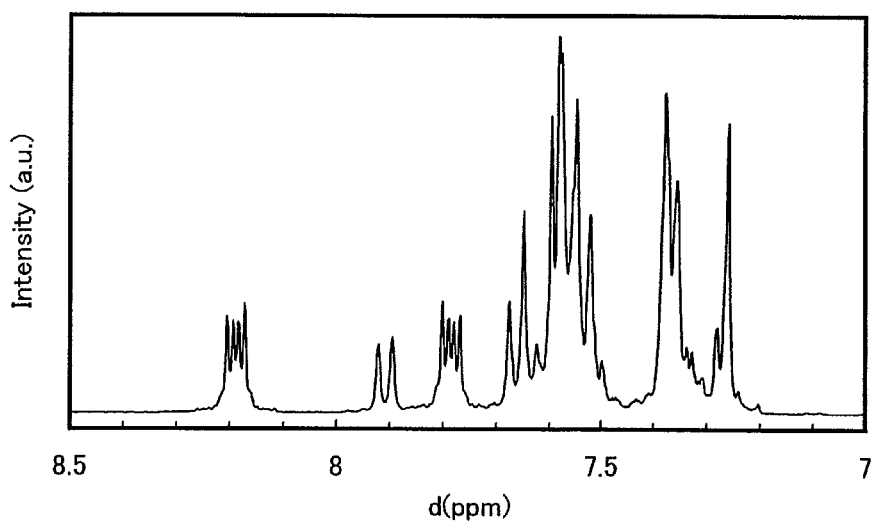

FIGS. 13A and 13B each show a $^1$H NMR chart, and FIG. 13B shows an enlarged chart of FIG. 13A in a range of 7.0 ppm to 8.5 ppm.

The thermogravimetry-differential thermal analysis (TG-DTA) of the obtained BIm1PQ was performed. For the measurement, a high vacuum differential type differential thermal balance (type TG-DTA2410SA, manufactured by Bruker AXS K.K.) was used. The measurement was performed under normal pressure under a nitrogen stream (at a flow rate of 200 mL/min) at a rate of temperature increase of 10° C./min. From the relationship between the weight and the temperature (thermogravimetry), it was seen that a 5% weight loss temperature was 444.4° C.

Figure 14:
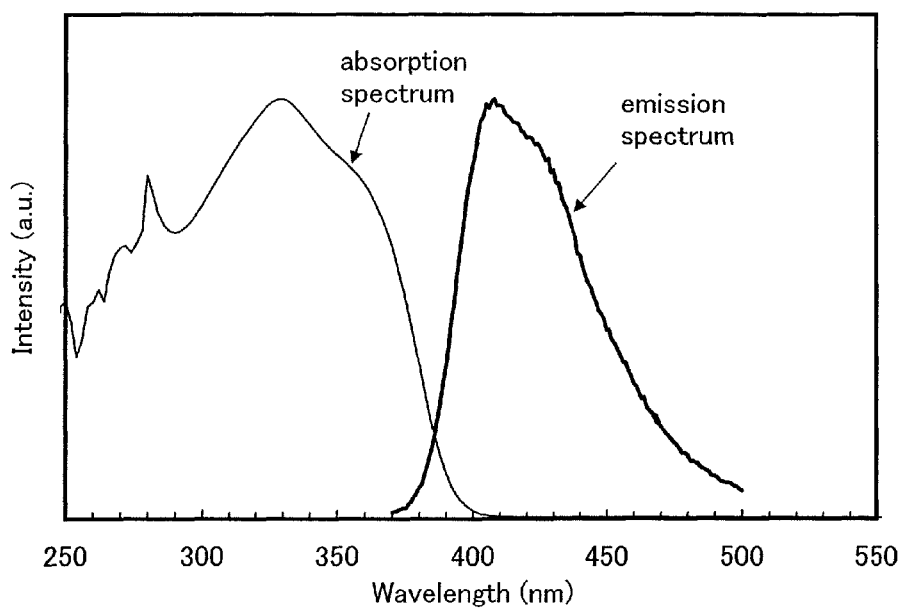
FIG. 14 is a graph showing the absorption spectrum and the emission spectrum of a toluene solution of 2-phenyl-3-[4'-(1-phenyl-1H-benzimidazol-2-yl)biphenyl-4-yl]quinoxaline (abbreviation: BIm1PQ).

FIG. 14 shows the absorption spectrum and the emission spectrum of a toluene solution of BIm1PQ. An ultraviolet-visible spectrophotometer (V-550, manufactured by JASCO Corporation) was used for the measurement. The solution was put in a quartz cell, and the absorption spectrum from which the absorption spectrum of quartz is subtracted was shown in the figure. In FIG. 14, the horizontal axis represents wavelength (nm) and the vertical axis represents intensity (a given unit). In the case of the toluene solution, the absorption was observed at around 330 nm. In addition, the maximum emission wavelength was 408 nm (excitation wavelength: 332 nm) in the case of the toluene solution.

Figure 15:
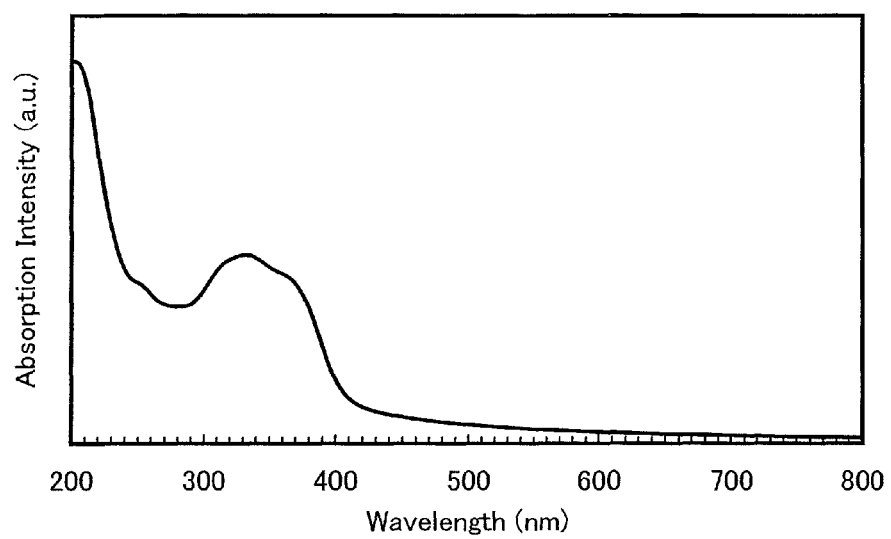
FIG. 15 is a graph showing the absorption spectrum of a thin film of 2-phenyl-3-[4'-(1-phenyl-1H-benzimidazol-2-yl) biphenyl-4-yl]quinoxaline (abbreviation: BIm1PQ).
Figure 16:
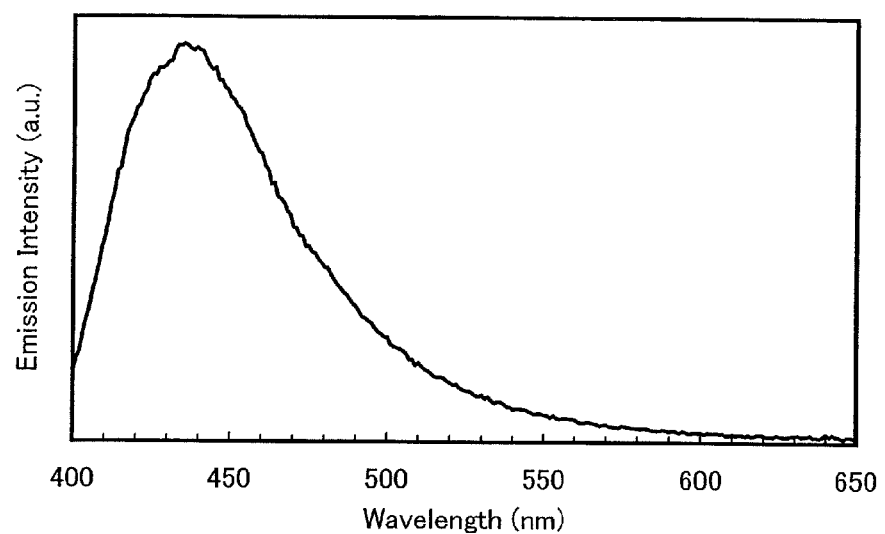
FIG. 16 is a graph showing the emission spectrum of a thin film of 2-phenyl-3-[4'-(1-phenyl-1H-benzimidazol-2-yl)biphenyl-4-yl]quinoxaline (abbreviation: BIm1PQ).

FIG. 15 shows the absorption spectrum of a thin film of BIm1PQ, and FIG. 16 shows the emission spectrum of the thin film of BIm1PQ. An ultraviolet-visible spectrophotometer (V-550, manufactured by JASCO Corporation) was used for the measurement. A sample was manufactured by being deposited on a quartz substrate, and the absorption spectrum from which the absorption spectrum of quartz was subtracted is shown in the figure. In FIG. 15, the horizontal axis represents wavelength (nm) and the vertical axis represents absorption intensity (a given unit). In FIG. 16, the horizontal axis represents wavelength (nm) and the vertical axis represents emission intensity (a given unit). The absorption was observed at around 332 nm in the case of the thin film. In addition, in the case of the thin film, the maximum emission wavelength was 435 nm (excitation wavelength: 332 nm).

The ionizing potential of the thin film of BIm1PQ was measured using a photoelectron spectrometer (AC-2, manufactured by Riken Keiki Co., Ltd) in air and accordingly found to be 5.92 eV. As a result, it was found that the HOMO level was −5.92 eV. The absorption edge was obtained by Tauc plot assuming direct transition with the absorption spectrum data of the thin film of BIm1PQ. When the absorption edge was estimated as an optical energy gap, the energy gap was 3.10 eV. The LUMO level was calculated to be −2.82 eV from the obtained value of the energy gap and the HOMO level.

[Embodiment 2]

Figure 17:
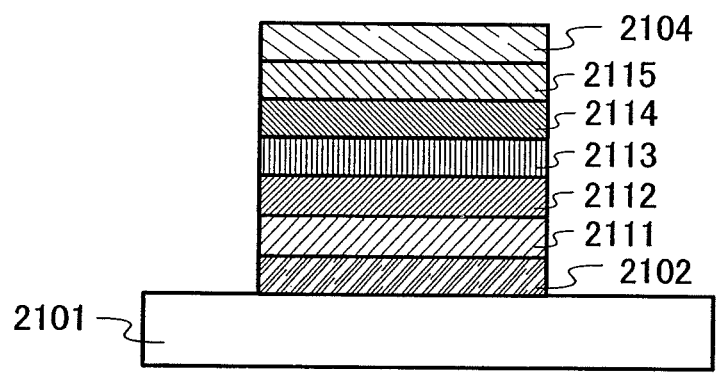
FIG. 17 is a drawing illustrating a light-emitting element of embodiments.

In this embodiment, a light-emitting element of the present invention is described using FIG. 17. Structural formulae of materials used in this embodiment are shown below. Note that the materials of which the structural formulae are shown above are omitted.

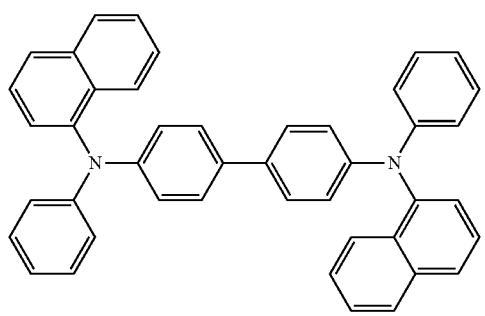

NPB

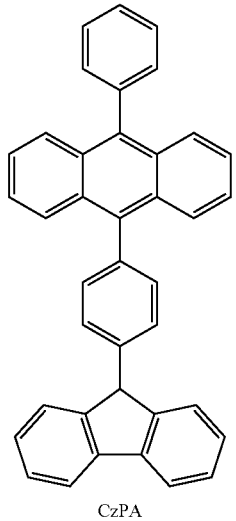

CzPA

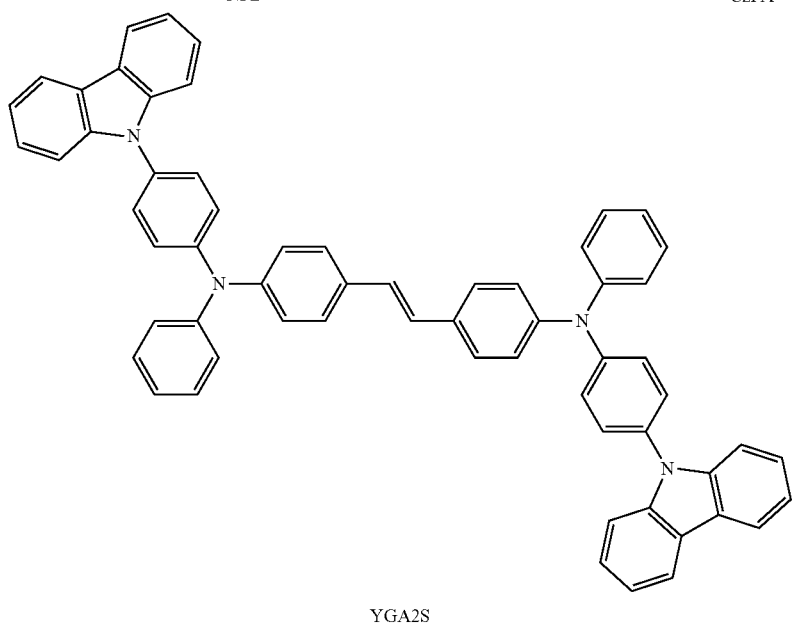

YGA2S

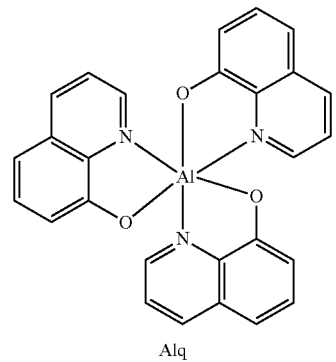

Alq

A method for manufacturing a light-emitting element of this embodiment is described below.

(Light-Emitting Element 1)

First, indium tin oxide containing silicon oxide (ITSO) was deposited by a sputtering method on a glass substrate 2101 to form a first electrode 2102. The thickness of the first electrode 2102 was set to be 110 nm. The area of the electrode was set to be 2 mm×2 mm.

Next, the substrate provided with the first electrode 2102 was fixed to a substrate holder that was provided in a vacuum evaporation apparatus such that the first electrode was underlying the substrate. After the pressure in a deposition chamber was reduced to approximately $10^{-4}$ Pa, 4,4'-bis[N-(1-naphthyl)-N-phenylamino]biphenyl (abbreviation: NPB) and molybdenum(VI) oxide were co-evaporated on the first electrode 2102, whereby a layer 2111, which contains a composite material of an organic compound and an inorganic compound, was formed. The thickness of the layer 2111 was set to be 50 nm and the weight ratio of NPB to molybdenum(VI) oxide was adjusted to be 4:1 (=NPB:molybdenum oxide).

The co-evaporation method is an evaporation method in which evaporation is concurrently conducted from a plurality of evaporation sources in one treatment chamber.

Next, 4,4'-bis[N-(1-naphthyl)-N-phenylamino]biphenyl (abbreviation: NPB) was deposited on the layer 2111 containing the composite material, by an evaporation method using resistance heating to form a hole-transporting layer 2112 having a thickness of 10 nm.

Further, 9-[4-(10-phenyl-9-anthryl)phenyl]-9H-carbazole (abbreviation: CzPA) and N,N'-bis[4-(9H-carbazol-9-yl)phenyl]-N,N'-diphenylstilbene-4,4'-diamine (abbreviation: YGA2S) were co-evaporated, whereby a light-emitting layer 2113 with a thickness of 30 nm was formed on the hole-transporting layer 2112. Here, the weight ratio of CzPA to YGA2S was adjusted to be 1:0.04 (=CzPA:YGA2S).

Then, 2-phenyl-3-[4'-(1-phenyl-1H-benzimidazol-2-yl) biphenyl-4-yl]quinoxaline (abbreviation: BIm1PQ), which was represented by a structural formula (101), was deposited on the light-emitting layer 2113 to a thickness of 30 nm by an evaporation method using resistance heating to form an electron-transporting layer 2114.

Furthermore, lithium fluoride was formed on the electron-transporting layer 2114 to a thickness of 1 nm to form an electron-injecting layer 2115.

Lastly, aluminum was deposited on the electron-injecting layer 2115 to a thickness of 200 nm by an evaporation method using resistance heating to form a second electrode 2104. Thus, a light-emitting element 1 was manufactured.

(Comparative Light-Emitting Element 2)

A comparative light-emitting element 2 was formed like the light-emitting element 1 by using a substrate of the same kind as that of the light-emitting element 1 and using 2,2',2"-(1,3,5-benzenetriyl)-tris(1-phenyl-1H-benzimidazole) (abbreviation: TPBI) instead of BIm1PQ. In other words, 2,2',2"-(1,3,5-benzenetriyl)-tris(1-phenyl-1H-benzimidazole) (abbreviation: TPBI) was deposited to a thickness of 30 nm to form the electron-transporting layer 2114. Except for the electron-transporting layer 2114, the comparative light-emitting element 2 was formed in a manner similar to the light-emitting element 1.

The light-emitting element 1 and the comparative light-emitting element 2 which were obtained in the above-described manner were put in a glove box containing a nitrogen atmosphere, and sealing treatment was conducted so that the light-emitting elements were not exposed to air. Then, operation characteristics of these light-emitting elements were measured. Note that the measurement was carried out at room temperature (in an atmosphere kept at 25° C.).

Figure 18:
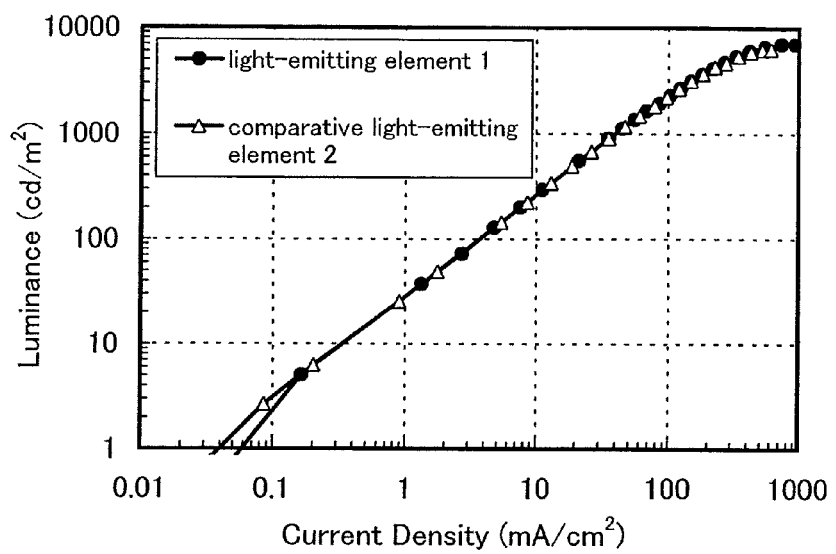
FIG. 18 is a graph showing the current density-luminance characteristics of light-emitting elements manufactured in Embodiment 2.
Figure 19:
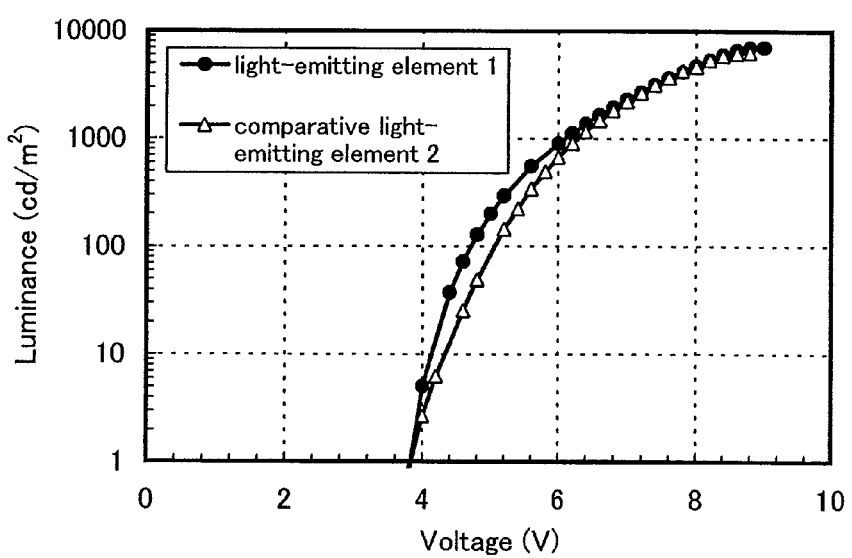
FIG. 19 is a graph showing the voltage-luminance characteristics of light-emitting elements manufactured in Embodiment 2.
Figure 20:
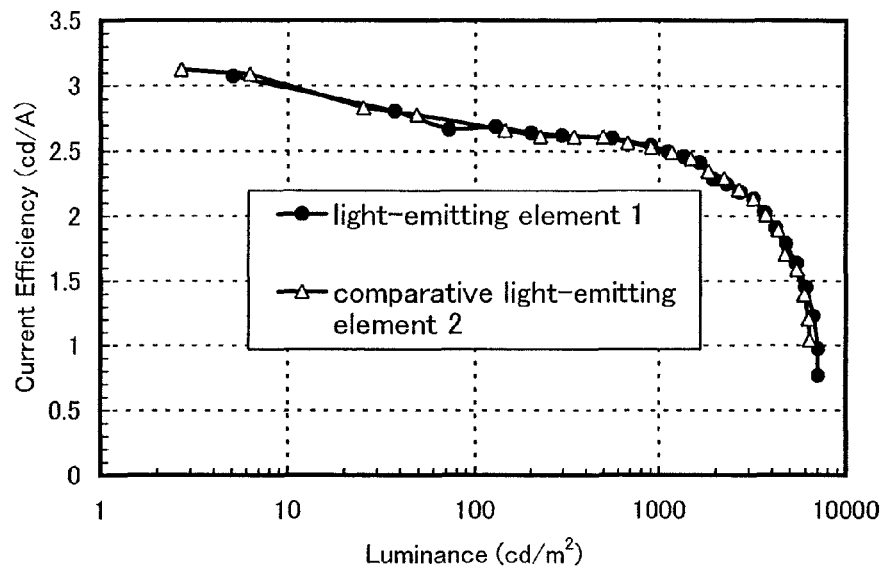
FIG. 20 is a graph showing the luminance-current efficiency characteristics of light-emitting elements manufactured in Embodiment 2.
Figure 21:
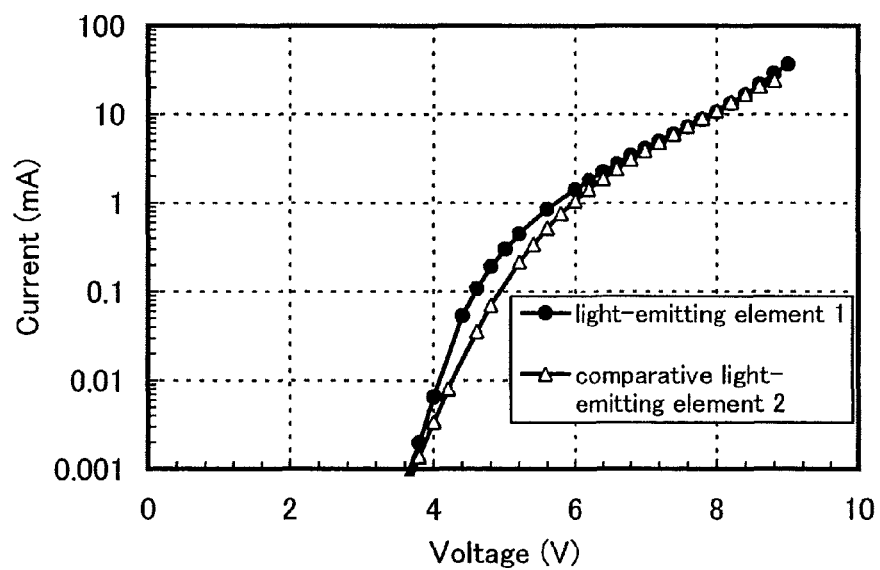
FIG. 21 is a graph showing the voltage-current characteristics of light-emitting elements manufactured in Embodiment 2.
Figure 22:
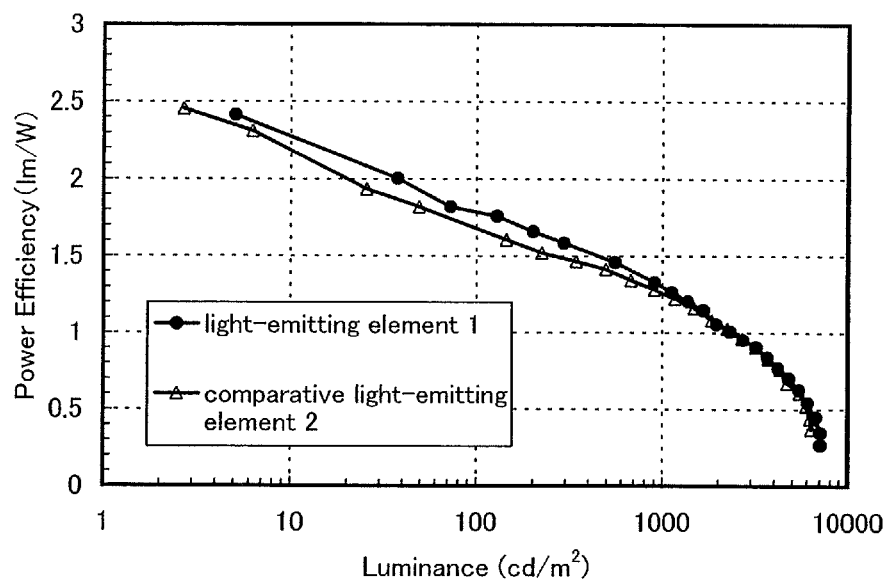
FIG. 22 is a graph showing the power efficiency-luminance characteristics of light-emitting elements manufactured in Embodiment 2.

FIG. 18 shows the current density-luminance characteristics of the light-emitting element 1 and the comparative light-emitting element 2. FIG. 19 shows the voltage-luminance characteristics of the light-emitting element 1 and the comparative light-emitting element 2. FIG. 20 shows the luminance-current efficiency characteristics of the light-emitting element 1 and the comparative light-emitting element 2. FIG. 21 shows the voltage-current characteristics of the light-emitting element 1 and the comparative light-emitting element 2. FIG. 22 shows the luminance-power efficiency characteristics of the light-emitting element 1 and the comparative light-emitting element 2.

Figure 23:
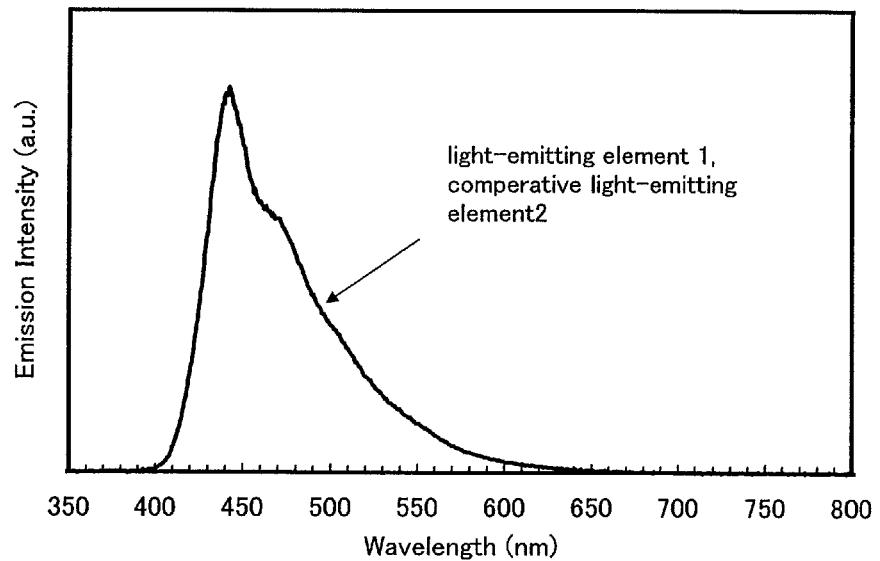
FIG. 23 is a graph showing the emission spectra of light-emitting elements manufactured in Embodiment 2.

FIG. 23 shows the emission spectra of the light-emitting element 1 and the comparative light-emitting element 2 at the time of applying a current of 1 mA. As apparent from FIG. 23, light emission of the light-emitting element 1 and light emission of the comparative light-emitting element 2 were derived from YGA2S, and thus, the obtained emission spectra of the light emission of the light-emitting element 1 and the light emission of the comparative light-emitting element 2 were almost the same.

The comparative light-emitting element 2 exhibited blue light emission where the CIE chromaticity coordinates were (x=0.16, y=0.13) at a luminance of 220 cd/m$^2$. Further, a current efficiency of the comparative light-emitting element 2 at a luminance of 220 cd/m$^2$ was 2.6 cd/A. Furthermore, the voltage, the current density, and the power efficiency of the comparative light-emitting element 2 at the luminance of 220 cd/m$^2$ were 5.4 V, 8.6 mA/cm$^2$, and 1.5 lm/W, respectively.

On the other hand, the light-emitting element 1 exhibited blue light emission where the CIE chromaticity coordinates were (x=0.15, y=0.13) at a luminance of 200 cd/m$^2$. Further, a current efficiency of the light-emitting element 1 at a luminance of 200 cd/m$^2$ was 2.6 cd/A. Furthermore, the voltage, the current density, and the power efficiency of the light-emitting element 1 at a luminance of 200 cd/m$^2$ were 5.0 V, 5.0 mA/cm$^2$, and 1.7 lm/W, respectively.

As apparent from FIG. 21, on the lower voltage side of FIG. 21, the light-emitting element 1 needs lower voltage that allows the same amount of current to flow than the comparative light-emitting element 2. That is, by application of the present invention, current flows more easily when voltage is applied, on the lower voltage side of FIG. 21. Accordingly, the quinoxaline derivative of the present invention has an excellent electron-transporting property.

As apparent from FIG. 20, the light-emitting element 1 and the comparative light-emitting element 2 exhibits almost the same current efficiency. Thus, as shown in FIG. 19, the light-emitting element 1 needs lower voltage that allows the same luminance as the comparative light-emitting element 2 to be provided than the comparative light-emitting element 2, on the lower voltage side of FIG. 19.

Further, as apparent from FIG. 22, the light-emitting element 1 needs lower power to allow the same luminance as the comparative light-emitting element 2 to be exhibited in a practical luminance region (100 cd/m$^2$ to 1000 cd/m$^2$) and accordingly consumes lower power than the comparative light-emitting element 2.

Figure 24:
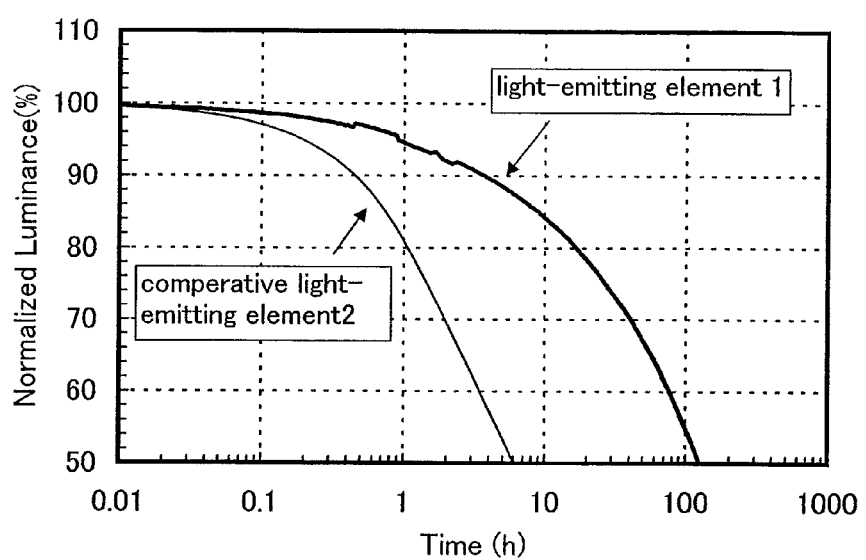
FIG. 24 is a graph showing a change in luminance with respect to driving time of light-emitting elements manufactured in Embodiment 2.

FIG. 24 shows a result of measurement of change in luminance with respect to driving time of the light-emitting element 1 and the comparative light-emitting element. A graph in FIG. 24 shows change in luminance at the time of setting initial luminance to 1000 cd/m$^2$ and driving the light-emitting element 1 and the comparative light-emitting element 2 under a condition of constant current density. In FIG. 24, the horizontal axis represents driving time (h), and the vertical axis represents luminance (normalized luminance (%)) on the assumption that 1000 cd/m$^2$ is 100%. From the result, it took about 130 hours until the luminance of the light-emitting element 1 was reduced to half, while it took about 6 hours until the luminance of the comparative light-emitting element 2 is reduced to half. Accordingly, it can be seen that the light-emitting element 1 has about 20 times as long luminance half life as the comparative light-emitting element 2, and that the light-emitting element of the present invention has a preferable element life.

[Embodiment 3]

In this embodiment, a light-emitting element of the present invention is described using FIG. 17. Structural formulae of materials used in this embodiment are shown below. Note that the materials of which the structural formulae are shown above are omitted.

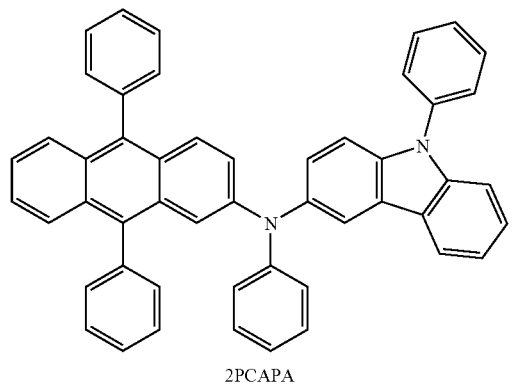 [SMILES: c1ccc(-c2c3ccccc3c(-c3ccccc3)c3cc(N(c4ccccc4)c4ccc5c(c4)c4ccccc4n5-c4ccccc4)ccc23)cc1]

2PCAPA

A method for manufacturing the light-emitting element of this embodiment is described below.

(Light-Emitting Element 3)

First, indium tin oxide containing silicon oxide (ITSO) was deposited by a sputtering method on a glass substrate 2101 to form a first electrode 2102. The thickness of the first electrode 2102 was set to be 110 nm. The area of the first electrode was set to be 2 mm×2 mm.

Next, the substrate provided with the first electrode 2102 was fixed to a substrate holder that was provided in a vacuum evaporation apparatus such that the first electrode was underlying the substrate. After the pressure in a deposition chamber was reduced to approximately $10^{-4}$ Pa, 4,4'-bis[N-(1-naphthyl)-N-phenylamino]biphenyl (abbreviation: NPB) and molybdenum(VI) oxide were co-evaporated on the first electrode 2102, whereby a layer 2111, which contains a composite material of an organic compound and an inorganic compound, was formed. The thickness of the layer 2111 was set to be 50 nm and the weight ratio of NPB to molybdenum(VI) oxide was adjusted to be 4:1 (=NPB:molybdenum oxide). The co-evaporation method is an evaporation method in which evaporation is concurrently conducted from a plurality of evaporation sources in one treatment chamber.

Next, 4,4'-bis[N-(1-naphthyl)-N-phenylamino]biphenyl (abbreviation: NPB) was deposited on the layer 2111 containing the composite material, by an evaporation method using resistance heating to form a hole-transporting layer 2112 having a thickness of 10 nm.

Further, 9-[4-10-phenyl-9-anthryl]phenyl]-9H-carbazole (abbreviation: CzPA) and N-(9,10-diphenyl-2-anthryl)-N,9-diphenyl-9H-carbazol-3-amine (abbreviation: 2PCAPA) were co-evaporated, whereby the light-emitting layer 2113 with a thickness of 40 nm was formed on the hole-transporting layer 2112. Here, the weight ratio between CzPA and 2PCAPA was adjusted to be 1:0.05 (=CzPA:2PCAPA).

Then, 2-phenyl-3-[4'-(1-phenyl-1H-benzimidazol-2-yl)biphenyl-4-yl]quinoxaline (abbreviation: BIm1PQ), which was represented by the structural formula (101), was deposited on the light-emitting layer 2113 to a thickness of 30 nm by an evaporation method using resistance heating to form an electron-transporting layer 2114.

Furthermore, lithium fluoride was formed on the electron-transporting layer 2114 to a thickness of 1 nm to form an electron-injecting layer 2115.

Lastly, aluminum was deposited on the electron-injecting layer 2115 to a thickness of 200 nm by an evaporation method using resistance heating to form a second electrode 2104. Thus, a light-emitting element 3 was manufactured.

(Comparative Light-Emitting Element 4)

A comparative light-emitting element 4 was formed like the light-emitting element 3 by using a substrate of the same kind as that of the light-emitting element 3 and using 2,2',2"-(1,3,5-benzenetriyl)-tris(1-phenyl-1H-benzimidazole) (abbreviation: TPBI) instead of BIm1PQ. In other words, 2,2',2"-(1,3,5-benzenetriyl)-tris(1-phenyl-1H-benzimidazole) (abbreviation: TPBI) was deposited to a thickness of 30 nm to form the electron-transporting layer 2114. Except for the electron-transporting layer 2114, the comparative light-emitting element 4 was formed in a manner similar to the light-emitting element 3.

The light-emitting element 3 and the comparative light-emitting element 4 which were obtained in the above-described manner were put in a glove box containing a nitrogen atmosphere, and sealing treatment was conducted so that the light-emitting elements were not exposed to air. Then, operation characteristics of these light-emitting elements were measured. Note that the measurement was carried out at room temperature (in an atmosphere kept at 25° C.).

Figure 25:
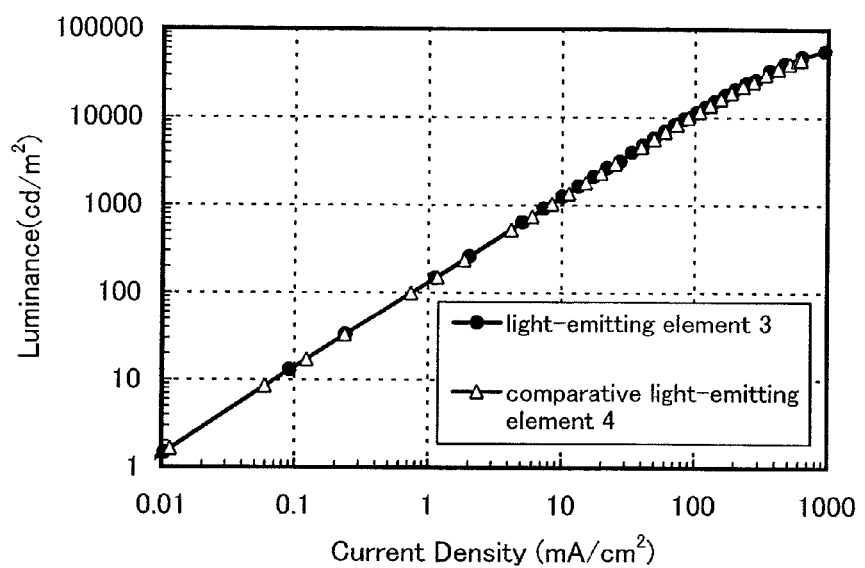
FIG. 25 is a graph showing the current density-luminance characteristics of light-emitting elements manufactured in Embodiment 3.
Figure 26:
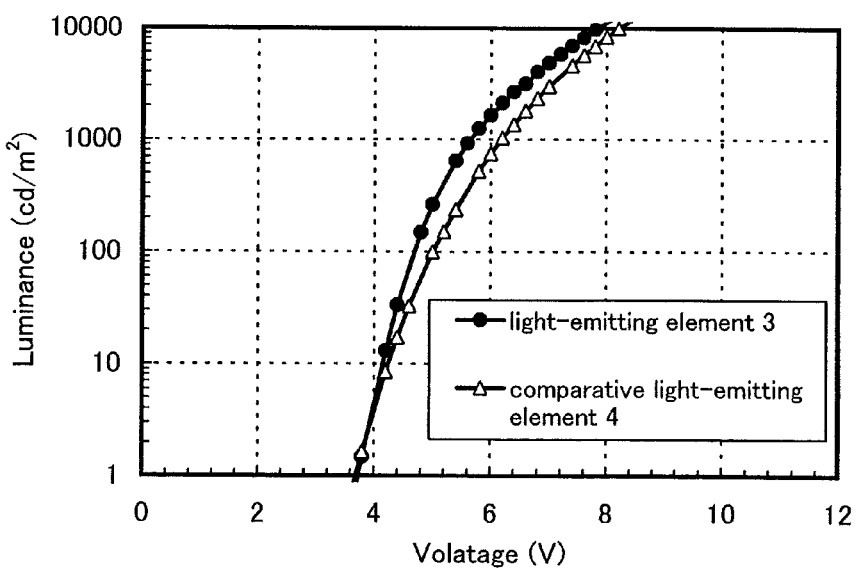
FIG. 26 is a graph showing the voltage-luminance characteristics of light-emitting elements manufactured in Embodiment 3.
Figure 27:
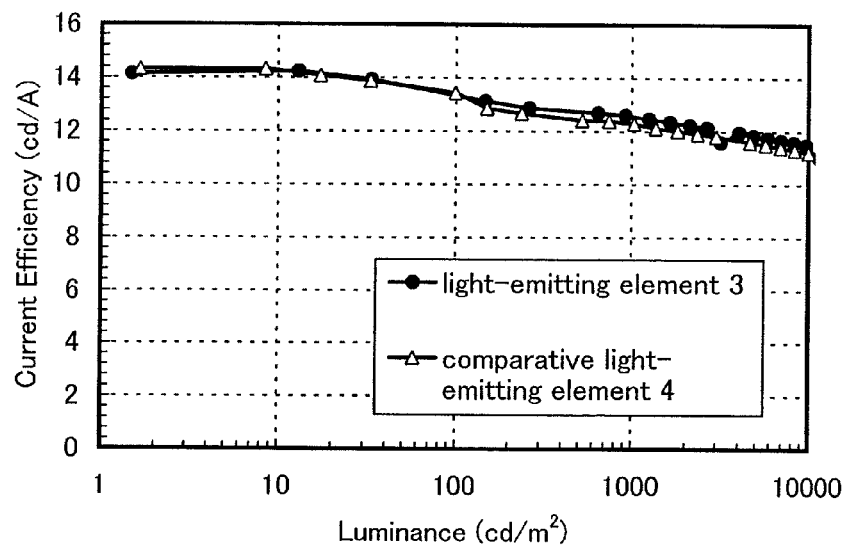
FIG. 27 is a graph showing the luminance-current efficiency characteristics of light-emitting elements manufactured in Embodiment 3.
Figure 28:
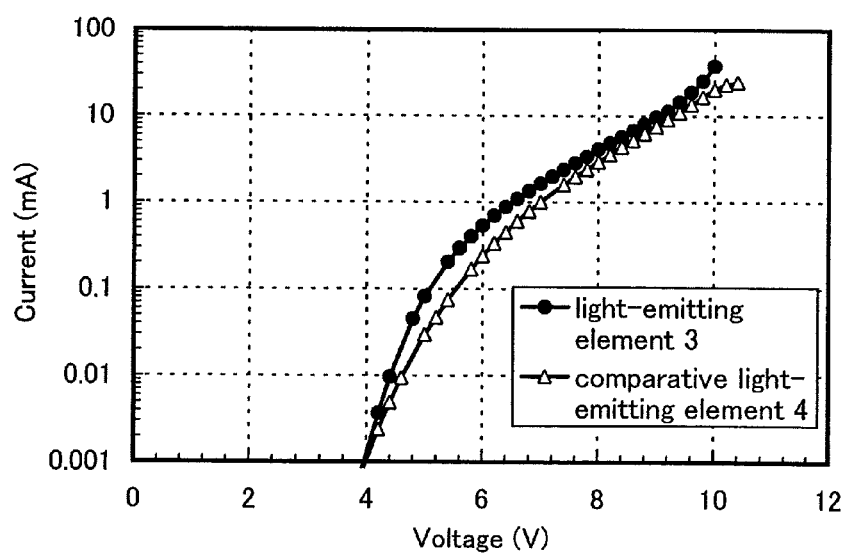
FIG. 28 is a graph showing the voltage-current characteristics of light-emitting elements manufactured in Embodiment 3.
Figure 29:
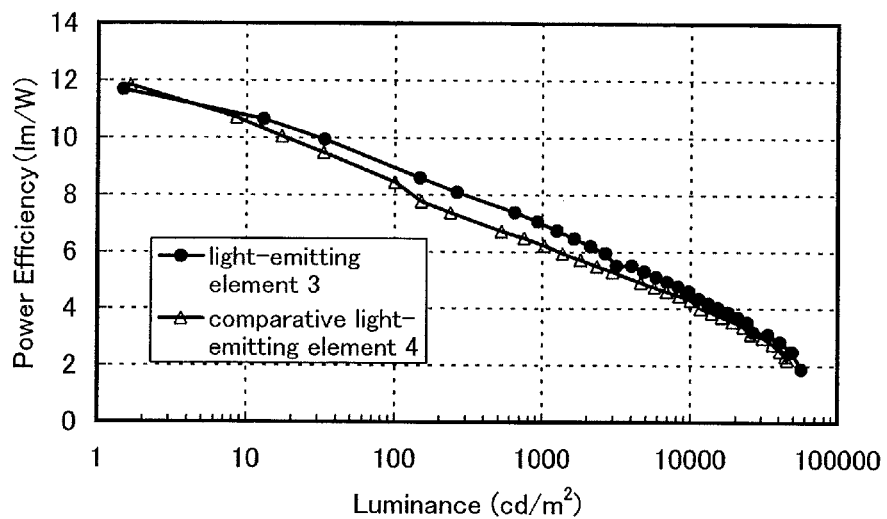
FIG. 29 is a graph showing the power efficiency-luminance characteristics of light-emitting elements manufactured in Embodiment 3.

FIG. 25 shows the current density-luminance characteristics of the light-emitting element 3 and the comparative light-emitting element 4. FIG. 26 shows the voltage-luminance characteristics of the light-emitting element 3 and the comparative light-emitting element 4. FIG. 27 shows the luminance-current efficiency characteristics of the light-emitting element 3 and the comparative light-emitting element 4. FIG. 28 shows the voltage-current characteristics of the light-emitting element 3 and the comparative light-emitting element 4. FIG. 29 shows the luminance-power efficiency characteristics of the light-emitting element 3 and the comparative light-emitting element 4.

Figure 30:
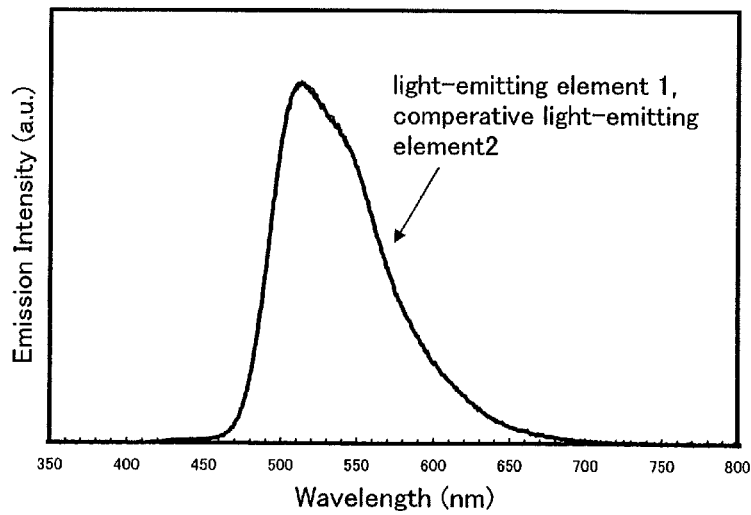
FIG. 30 is a graph showing the emission spectra of light-emitting elements manufactured in Embodiment 3.

FIG. 30 shows the emission spectra of the light-emitting element 3 and the comparative light-emitting element 4 at the time of applying a current of 1 mA. As apparent from FIG. 30, light emission of the light-emitting element 3 and the comparative light-emitting element 4 is light emission derived from 2PCAPA.

The comparative light-emitting element 4 exhibited green light emission where the CIE chromaticity coordinates were (x=0.29, y=0.61) at a luminance of 1030 cd/m$^2$. Note that the CIE chromaticity coordinates are values actually measured using a luminance meter (a color luminance meter BM-5A manufactured by Topcon Technohouse Corporation) with the light-emitting element made to emit light. The same can be said for the same kind of description below. Further, the current efficiency of the comparative light-emitting element 4 at a luminance of 1030 cd/m$^2$ was 12.3 cd/A. Furthermore, the voltage, the current density, and the power efficiency of the comparative light-emitting element 4 at the luminance of 1030 cd/m$^2$ were 6.2 V, 8.4 mA/cm$^2$, and 6.2 lm/W, respectively.

On the other hand, the light-emitting element 3 exhibited green light emission where the CIE chromaticity coordinates were (x=0.29, y=0.61) at a luminance of 920 cd/m$^2$. Further, the current efficiency of the light-emitting element 3 at a luminance of 920 cd/m$^2$ was 12.6 cd/A. Furthermore, the voltage, the current density, and the power efficiency of the light-emitting element 3 at a luminance of 920 cd/m$^2$ were 5.6 V, 7.3 mA/cm$^2$, and 7.1 lm/W, respectively.

As apparent from FIG. 27, the light-emitting element 3 needs lower voltage that allows the same amount of electric current to flow than the comparative light-emitting element 4. That is, by application of the present invention, electric current flows more easily when voltage is applied. Accordingly, the quinoxaline derivative of the present invention has an excellent electron-transporting property.

As apparent from FIG. 26, the light-emitting element 3 and the comparative light-emitting element 4 exhibits almost the same current efficiency. Thus, as shown in FIG. 25, the light-emitting element 3 needs lower voltage that allows the same luminance as the comparative light-emitting element 4 to be exhibited than the comparative light-emitting element 4.

Further, as apparent from FIG. 29, the light-emitting element 3 needs lower power to allow the same luminance as the comparative light-emitting element 4 to be provided and accordingly consumes lower power than the comparative light-emitting element 4.

Thus, by application of the present invention, a light-emitting element which drives at a lower voltage can be obtained. Further, a light-emitting element which consumes low power can be obtained.

[Embodiment 4]

In this embodiment, a synthetic method for 2,3-bis[4'-(1-phenyl-1H-benzimidazol-2-yl)-biphenyl-4-yl]quinoxaline (abbreviation: BIm2PQ) represented by the structural formula (300) is described.

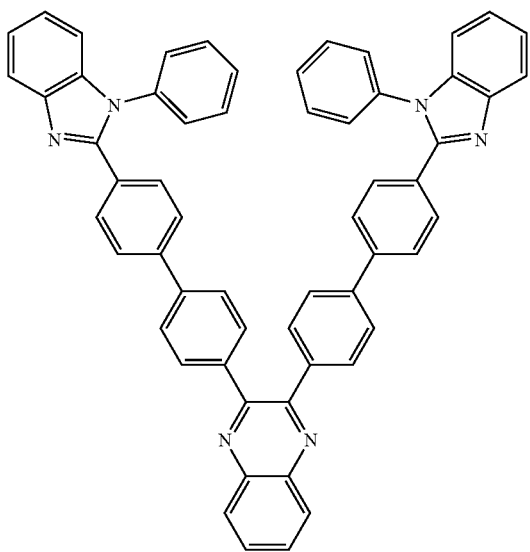

(300)

Step 1 Synthesis of 2,3-bis(4-bromophenyl)quinoxaline

A synthetic scheme of 2,3-bis(4-bromophenyl)quinoxaline is shown in (C-1).

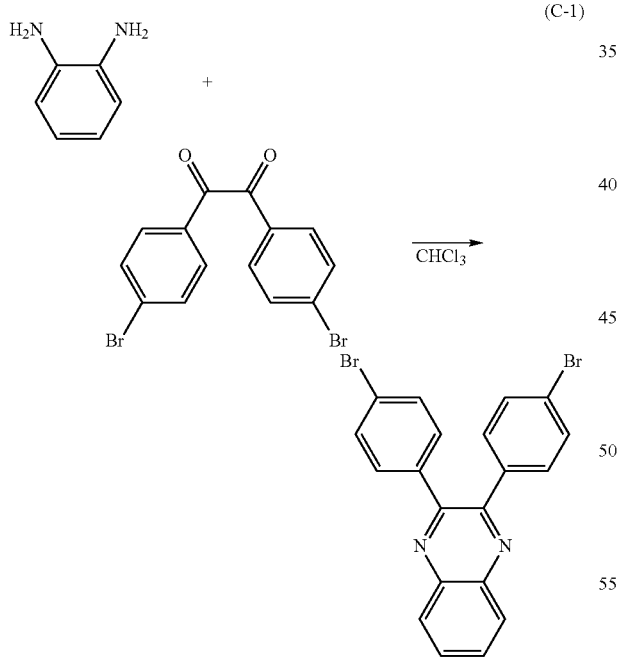

(C-1)

In a 500-mL three-neck flask were placed 30 g (82 mmol) of 4,4'-dibromobenzil, 9.3 g (86 mmol) of 1,2-phenylenediamine, and 300 mL of chloroform. This solution was refluxed at 80° C. for 5 hours under a nitrogen stream. After a predetermined time, the solution was cooled to room temperature, and then, water was added thereto. The aqueous phase was extracted with chloroform, and the extracted solution combined with the organic phase was dried with magnesium sulfate. After the drying, the mixture was subjected to suction filtration and the filtrate was concentrated to give a solid. The obtained solid was dissolved in toluene, and this solution was subjected to suction filtration through Florisil (produced by Wako Pure Chemical Industries, Ltd., Catalog No. 540-00135), Celite (produced by Wako Pure Chemical Industries, Ltd., Catalog No. 531-16855) and alumina. The filtrate was concentrated; thus, 30 g of a white powder of 2,3-bis(4-bromophenyl)quinoxaline, which was a product, was obtained in a yield of 99%.

Step 2 Synthesis of 4,4'-(quinoxaline-2,3-diyl)diphenylboronic Acid

A synthetic scheme of 4,4'-(quinoxaline-2,3-diyl)diphenylboronic acid is shown in (C-2).

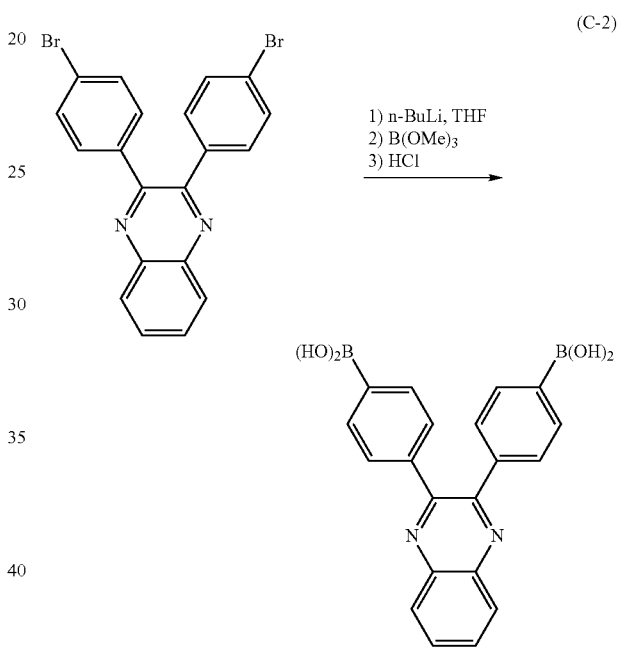

(C-2)

In a 500-mL three-neck flask was placed 10 g (22 mmol) of 2,3-bis(4-bromophenyl)quinoxaline, and the atmosphere in the flask was replaced with nitrogen. There was added 100 mL of tetrahydrofuran, and the mixture was cooled to −78° C. under a nitrogen stream. After the cooling, 31 mL (49 mmol) of 1.6 M n-butyllithium was dripped into the solution, and the solution was stirred at the same temperature for 1 hour. After a predetermined time, 10 mL (90 mmol) of trimethyl borate was added thereto. The solution was heated to room temperature, and stirred for 10 hours. After a predetermined time, the solution was cooled to 0° C., and 100 mL of 0.1 M hydrochloric acid was added thereto. The solution was stirred for 1 hour. The aqueous phase of the obtained mixture was extracted with ethyl acetate. This extracted solution combined with the organic phase was washed with brine, and then the organic phase was dried with magnesium sulfate. This mixture was subjected to suction filtration through Celite (produced by Wako Pure Chemical Industries, Ltd., Catalog No. 531-16855), and the obtained filtrate was concentrated to give a solid. The obtained solid was recrystallized with ethyl acetate; thus, 7.2 g of an yellow powder which was a product was obtained in a yield of 85%.

Step 3 Synthesis of 2,3-bis[4'-(1-phenyl-1H-benzimidazol-2-yl)-biphenyl-4-yl]quinoxaline (Abbreviation: BIm2PQ)

A synthetic scheme of BIm2PQ is shown in (C-3).

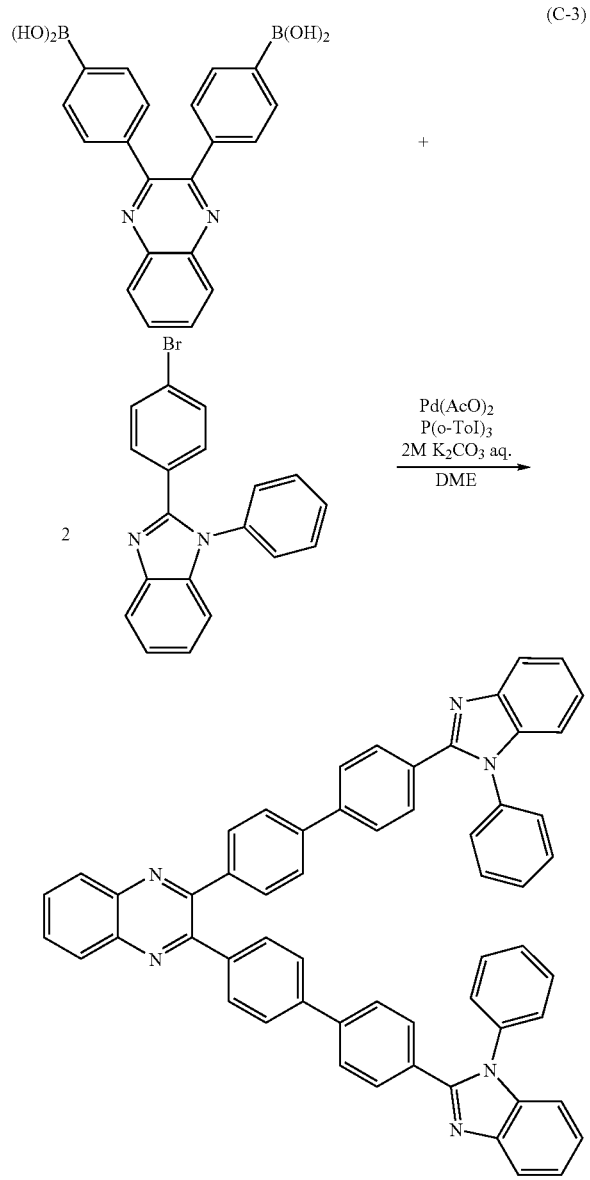

In a 50-mL three-neck flask were placed 0.37 g (1.0 mmol) of 4,4'-(quinoxaline-2,3-diyl)diphenylboronic acid, 0.69 g (2.0 mmol) of 2-(4-bromophenyl)-N-phenyl-1H-benzimidazole, 0.080 g (0.26 mmol) of tri(ortho-tolyl)phosphine, 2.0 mL (4.0 mmol) of a 2 M potassium carbonate aqueous solution, and 15 mL of ethylene glycol dimethyl ether (abbreviation: DME). The mixture was degassed by being stirred under reduced pressure, and the atmosphere in the flask was replaced with nitrogen. To the mixture was added 16 mg (0.072 mmol) of palladium(II) acetate, and the resulting mixture was stirred under a nitrogen stream at 80° C. for 10 hours. After a predetermined time, water was added to the mixture, and an aqueous phase was extracted with chloroform. The obtained extracted solution combined with the organic phase was washed with a saturated sodium hydrogen carbonate aqueous solution and brine in that order, and the organic phase was dried with magnesium sulfate. The mixture was filtered, and the obtained filtrate was concentrated to give an oily substance. The obtained oily substance was purified by silica gel column chromatography (chloroform:ethyl acetate=7:1) and further recrystallized with chloroform/hexane; thus, 0.49 g of an yellow powder which was a product was obtained in a yield of 59%.

Then, 0.45 g of the obtained product was subjected to sublimation purification at 370° C. under an argon stream (flow rate: 3.0 mL/min) and a pressure of 10 Pa for 18 hours; thus, 0.30 g of a compound was obtained at a collection rate of 66%. The compound was measured by nuclear magnetic resonance (NMR) spectrometry and accordingly identified as 2,3-bis[4'-(1-phenyl-1H-benzimidazol-2-yl)-biphenyl-4-yl]quinoxaline (abbreviation: BIm2PQ).

$^1$H NMR data is shown below.

$^1$H NMR (300 MHz, CDCl$_3$): δ (ppm)=7.27-7.38 (m, 8H), 7.46-7.70 (m, 24H), 7.76-7.81 (m, 2H), 7.90 (d, J=7.8 Hz, 2H), 8.17-8.20 (m, 2H).

Figure 31A:
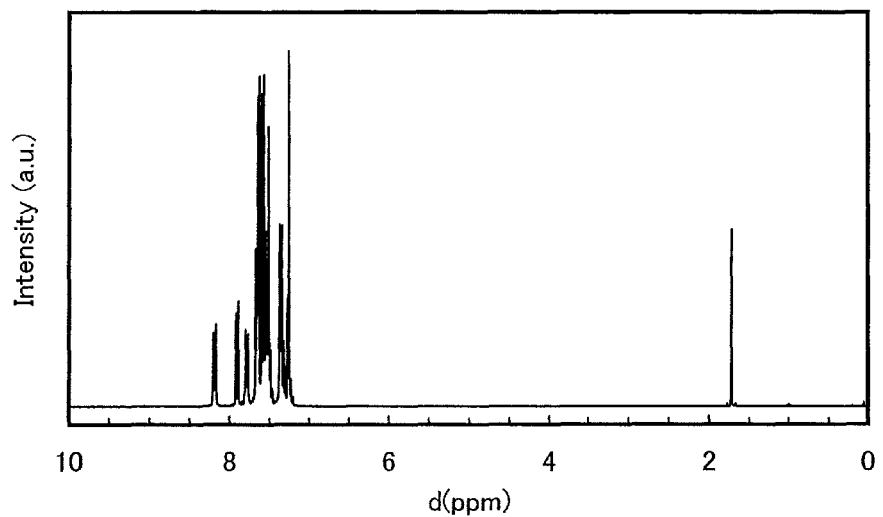
FIGS. 31A and 31B are $^1$H NMR charts of 2,3-bis[4'-(1-phenyl-1H-benzimidazol-2-yl)-biphenyl-4-yl]quinoxaline (abbreviation: BIm2PQ).
Figure 31B:
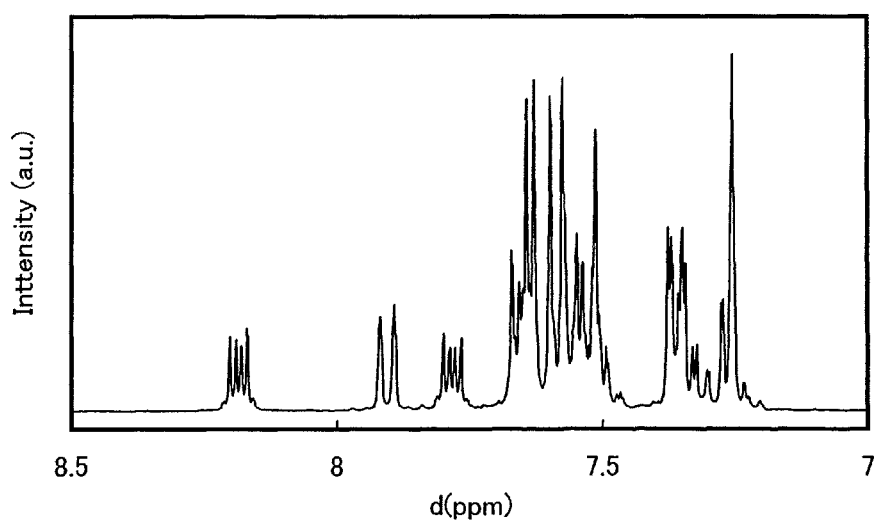

FIGS. 31A and 31B each show a $^1$H NMR chart, and FIG. 31B shows an enlarged chart of FIG. 31A in a range of 7.0 ppm to 8.5 ppm.

Figure 32:
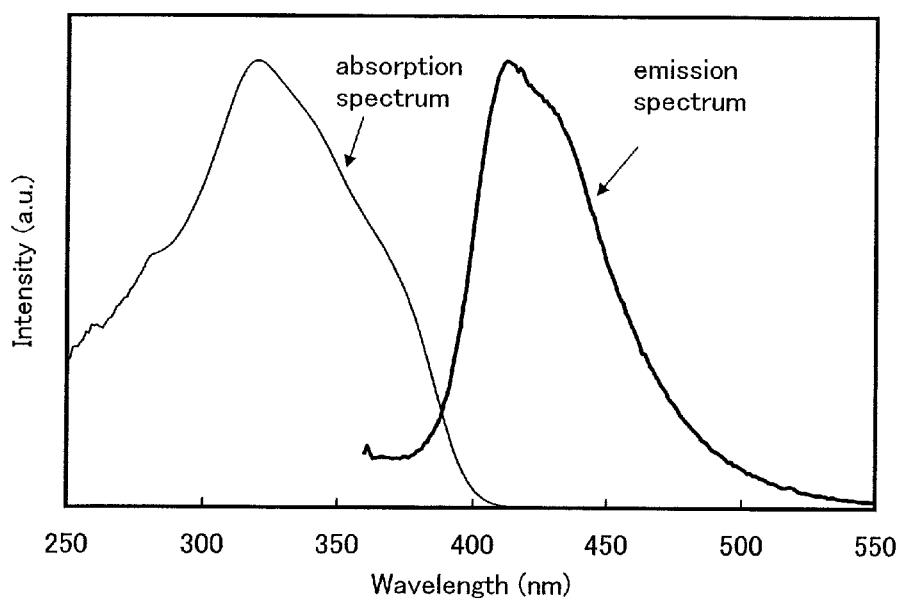
FIG. 32 is a graph showing the absorption spectrum and the emission spectrum of a toluene solution of 2,3-bis[4'-(1-phenyl-1H-benzimidazol-2-yl)-biphenyl-4-yl]quinoxaline (abbreviation: BIm2PQ).

FIG. 32 shows the absorption spectrum and the emission spectrum of a toluene solution of BIm2PQ. An ultraviolet-visible spectrophotometer (V-550, manufactured by JASCO Corporation) was used for the measurement. The solution was put in a quartz cell. The absorption spectrum from which the absorption spectrum of quartz is subtracted is shown in the figure. In FIG. 32, the horizontal axis represents wavelength (nm) and the vertical axis represents intensity (a given unit). In the case of the toluene solution, the absorption was observed at around 320 nm. In addition, in the case of the toluene solution, the maximum emission wavelength was 413 nm (excitation wavelength: 324 nm).

Figure 33:
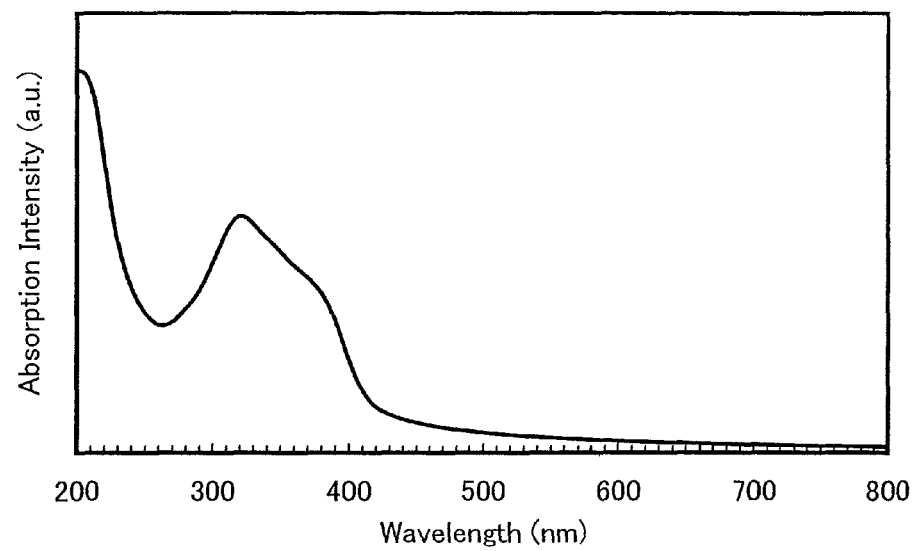
FIG. 33 is a graph showing the absorption spectrum of a thin film of 2,3-bis[4'-(1-phenyl-1H-benzimidazol-2-yl)-biphenyl-4-yl]quinoxaline (abbreviation: BIm2PQ).
Figure 34:
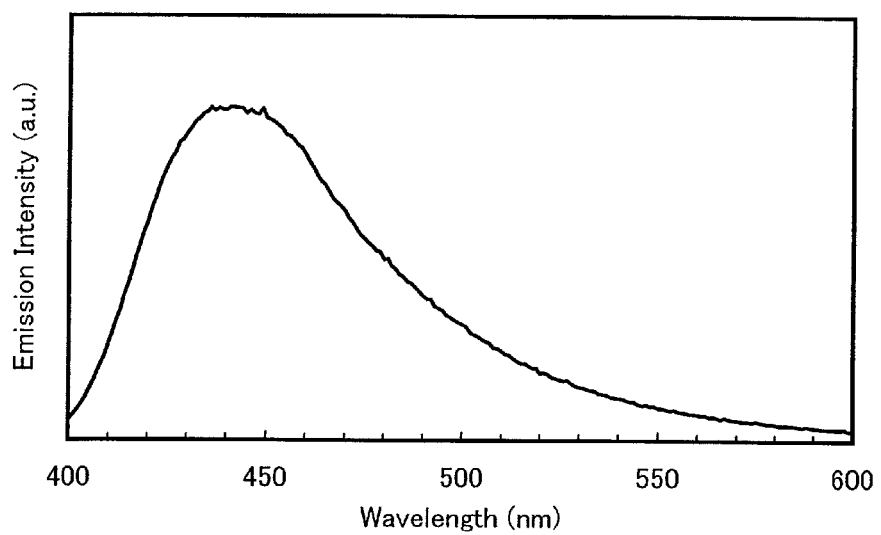
FIG. 34 is a graph showing the emission spectrum of a thin film of 2,3-bis[4'-(1-phenyl-1H-benzimidazol-2-yl)-biphenyl-4-yl]quinoxaline (abbreviation: BIm2PQ).

FIG. 33 shows the absorption spectrum of a thin film of BIm2PQ, and FIG. 34 shows the emission spectrum of the thin film of BIm2PQ. An ultraviolet-visible spectrophotometer (V-550, manufactured by JASCO Corporation) was used for the measurement. A sample was manufactured by being deposited on a quartz substrate, and the absorption spectrum from which the absorption spectrum of quartz was subtracted is shown in the figure. In FIG. 33, the horizontal axis represents wavelength (nm) and the vertical axis represents absorption intensity (a given unit). In FIG. 34, the horizontal axis represents wavelength (nm) and the vertical axis represents emission intensity (a given unit). The absorption was observed at around 321 nm and around 377 nm in the case of the thin film. In addition, in the case of a thin film, the maximum emission wavelength was 442 nm (excitation wavelength: 366 nm).

The ionizing potential of the thin film of BIm2PQ was measured using a photoelectron spectrometer (AC-2, manufactured by Riken Keiki Co., Ltd) in air and accordingly found to be 5.87 eV. As a result, it was found that the HOMO level was −5.87 eV. The absorption edge was obtained by Tauc plot assuming direct transition with the absorption spectrum data of the thin film of BIm2PQ. When the absorption edge was estimated as an optical energy gap, the energy gap was 3.04 eV. The LUMO level was calculated to be 2.83 eV from the obtained value of the energy gap and the HOMO level.

Further, the oxidation-reduction profiles of BIm2PQ were measured. The oxidation-reduction profiles were measured by cyclic voltammetry (CV). Note that an electrochemical analyzer (manufactured by BAS Inc., ALS model 600A) was used for the measurement.

The solution for the CV measurement was prepared as described below. Tetra-n-butylammonium perchlorate (n-Bu$_4$NClO$_4$) (produced by Tokyo Chemical Industry Co., Ltd., Catalog No. T0836) used as a supporting electrolyte was dissolved at a concentration of 100 mmol/L in dehydrated dimethylformamide (DMF) (produced by Sigma-Aldrich Corp., 99.8%, Catalog No. 22705-6) used as a solvent. Further, BIm2PQ which was the measurement object was further dissolved at a concentration of 2 mmol/L therein. A platinum electrode (manufactured by BAS Inc., PTE platinum electrode) was used as a working electrode, a platinum electrode (manufactured by BAS Inc., Pt counter electrode for VC-3, (5 cm)) was used as an auxiliary electrode, and an Ag/Ag$^+$ electrode (manufactured by BAS Inc., RE-7 reference electrode for nonaqueous solvent) was used as a reference electrode. The measurement was conducted at room temperature.

The oxidation profile of BIm2PQ was measured as follows. A scan, in which a potential of the working electrode with respect to the reference electrode was varied from 1.50 V to 0.24 V after being varied from 0.24 V to 1.50 V, was regarded as one cycle, and measurement was performed for 100 cycles. The reduction profile of BIm2PQ was measured as follows. A scan, in which a potential of the working electrode with respect to the reference electrode was varied from −2.10 V to −1.37 V after being varied from −1.37 V to −2.10 V, was regarded as one cycle, and measurement was performed for 100 cycles. Note that the scanning rate of the CV measurement was set to be 0.1 V/s.

Figure 35:
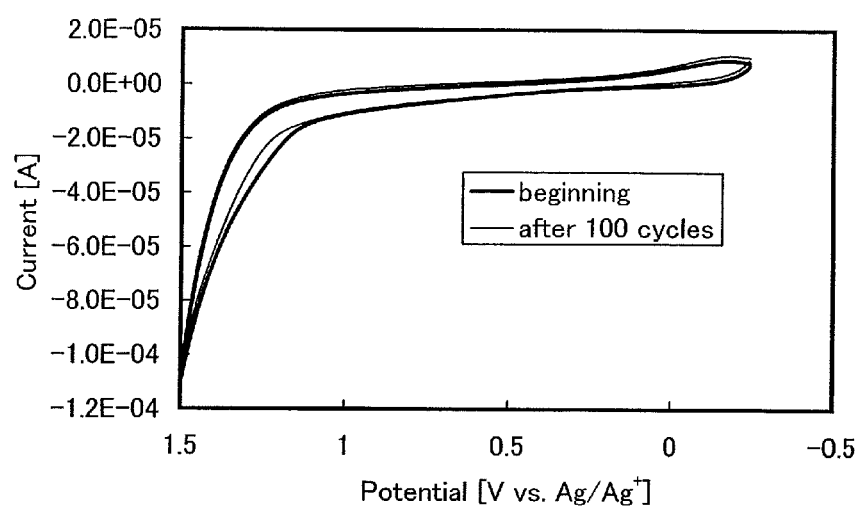
FIG. 35 is a graph showing a result of CV measurement of 2,3-bis[4'-(1-phenyl-1H-benzimidazol-2-yl)-biphenyl-4-yl]quinoxaline (abbreviation: BIm2PQ).
Figure 36:
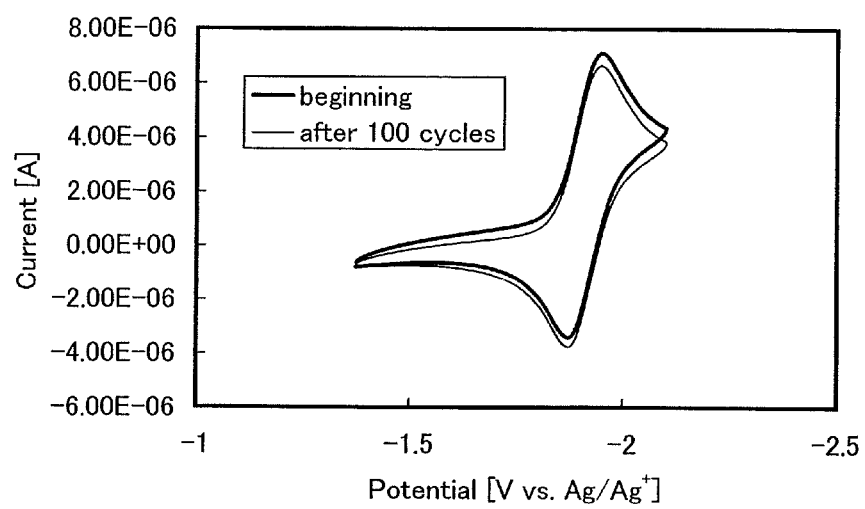
FIG. 36 is a graph showing a result of CV measurement of 2,3-bis[4'-(1-phenyl-1H-benzimidazol-2-yl)-biphenyl-4-yl]quinoxaline (abbreviation: BIm2PQ).

FIG. 35 shows a result of CV measurement of BIm2PQ in an oxidation region, and FIG. 36 shows a result of CV measurement of BIm2PQ in a reduction region. In each of FIGS. 35 and 36, the horizontal axis represents a potential (V) of the working electrode with respect to the reference electrode, and the vertical axis represents a current (A) flowing between the working electrode and the auxiliary electrode. A current for oxidation was not observed in FIG. 35, but a current for reduction was observed at around −1.95 V (vs. Ag/Ag$^+$ electrode) in FIG. 36.

Although the scan was repeated for 100 cycles, changes in the peak position and peak intensity of the CV curves were scarcely observed in the reduction. Accordingly, it is found that BIm2PQ which is the quinoxaline derivative of the present invention is significantly stable to repetitive reduction.

This application is based on Japanese Patent Application serial no. 2007-330084 filed with Japan Patent Office on Dec. 21, 2007, the entire contents of which are hereby incorporated by reference.

What is claimed is:

1. A quinoxaline derivative represented by a general formula (G11):

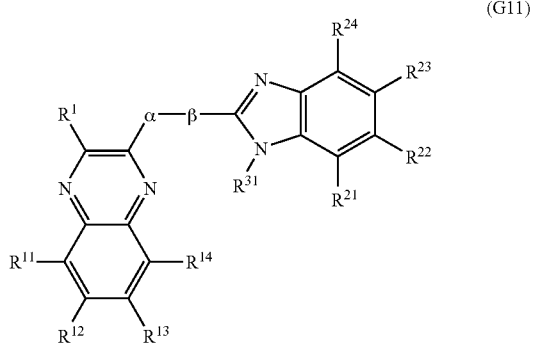

(G11)

wherein α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, $R^1$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, and an aryl group having 6 to 13 carbon atoms.

2. The quinoxaline derivative according to claim 1, wherein β is a phenylene group.

3. The quinoxaline derivative according to claim 1,
wherein α is a phenylene group,
wherein β is a phenylene group, and
wherein each of $R^{11}$ to $R^{14}$ is a hydrogen.

4. The quinoxaline derivative according to claim 1,
wherein each of α and β is a para-phenylene group, and
wherein each of $R^{11}$ to $R^{14}$ is hydrogen.

5. The quinoxaline derivative according to claim 1, wherein $R^1$ is a phenyl group or a biphenyl group.

6. A quinoxaline derivative represented by a general formula (G21):

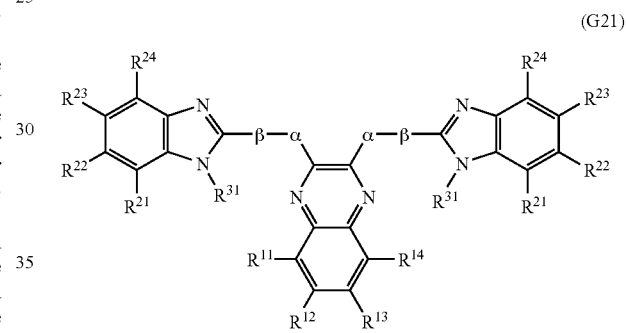

(G21)

wherein α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, and an aryl group having 6 to 13 carbon atoms.

7. The quinoxaline derivative according to claim 6, wherein β is a phenylene group.

8. The quinoxaline derivative according to claim 6,
wherein α is a phenylene group,
wherein β is a phenylene group, and
wherein each of $R^{11}$ to $R^{14}$ is a hydrogen.

9. The quinoxaline derivative according to claim 6,
wherein each of α and β is a para-phenylene group, and
wherein each of $R^{11}$ to $R^{14}$ is hydrogen.

10. A light-emitting element comprising:
a first electrode;
an EL layer over the first electrode, wherein the EL layer includes a quinoxaline derivative; and
a second electrode over the EL layer,
wherein the quinoxaline derivative is represented by a general formula (G11), and

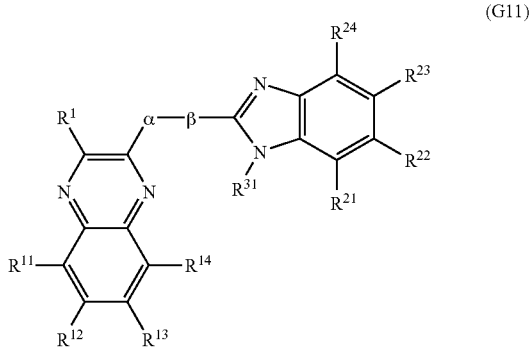

(G11)

wherein α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, $R^1$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, and an aryl group having 6 to 13 carbon atoms.

11. The light-emitting element according to claim 10, wherein β is a phenylene group.

12. The light-emitting element according to claim 10, wherein α is a phenylene group, wherein β is a phenylene group, and wherein each of $R^{11}$ to $R^{14}$ is a hydrogen.

13. The light-emitting element according to claim 10, wherein each of α and β is a para-phenylene group, and wherein each of $R^{11}$ to $R^{14}$ is hydrogen.

14. The light-emitting element according to claim 10, wherein $R^1$ is a phenyl group or a biphenyl group.

15. A light-emitting element comprising:
a first electrode;
an EL layer over the first electrode, wherein the EL layer includes a quinoxaline derivative; and
a second electrode over the EL layer,
wherein the quinoxaline derivative is represented by a general formula (G21), and

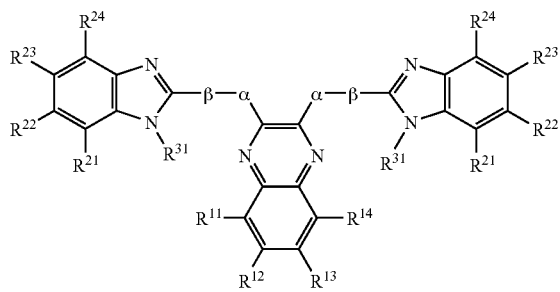

(G21)

wherein α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, and an aryl group having 6 to 13 carbon atoms.

16. The light-emitting element according to claim 15, wherein β is a phenylene group.

17. The light-emitting element according to claim 15, wherein α is a phenylene group, wherein β is a phenylene group, and wherein each of $R^{11}$ to $R^{14}$ is hydrogen.

18. The light-emitting element according to claim 15, wherein each of α and β is a para-phenylene group, and wherein each of $R^{11}$ to $R^{14}$ is a hydrogen.

19. An electronic appliance comprising a quinoxaline derivative represented by a general formula (G11):

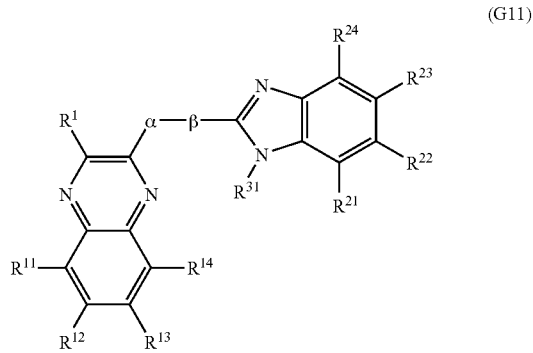

(G11)

wherein α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, $R^1$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, and an aryl group having 6 to 13 carbon atoms.

20. An electronic appliance comprising a quinoxaline derivative represented by a general formula (G21):

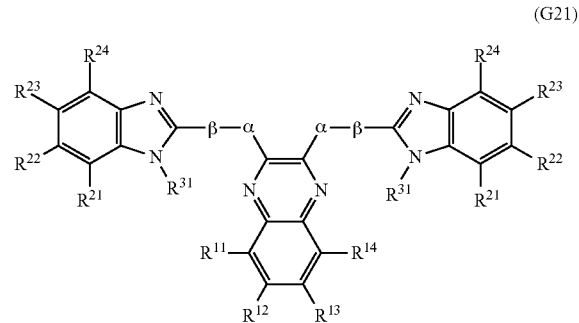

(G21)

wherein α represents a substituted or unsubstituted arylene group having 6 to 13 carbon atoms, β represents a substituted or unsubstituted arylene group having 6 to 13 carbon atoms, $R^{21}$ to $R^{24}$ individually represent hydrogen or an alkyl group having 1 to 4 carbon atoms, $R^{31}$ represents either an alkyl group having 1 to 4 carbon atoms or a substituted or unsubstituted aryl group having 6 to 13 carbon atoms, and $R^{11}$ to $R^{14}$ individually represent any of hydrogen, an alkyl group having 1 to 4 carbon atoms, and an aryl group having 6 to 13 carbon atoms.

* * * * *

UNITED STATES PATENT AND TRADEMARK OFFICE
CERTIFICATE OF CORRECTION

PATENT NO. : 8,815,412 B2
APPLICATION NO. : 12/337297
DATED : August 26, 2014
INVENTOR(S) : Hiroshi Kadoma et al.

It is certified that error appears in the above-identified patent and that said Letters Patent is hereby corrected as shown below:

In the Specification:

Column 2, Line 30; Change "a represents" to --α represents--.

Column 29, Chemical Structure (106);

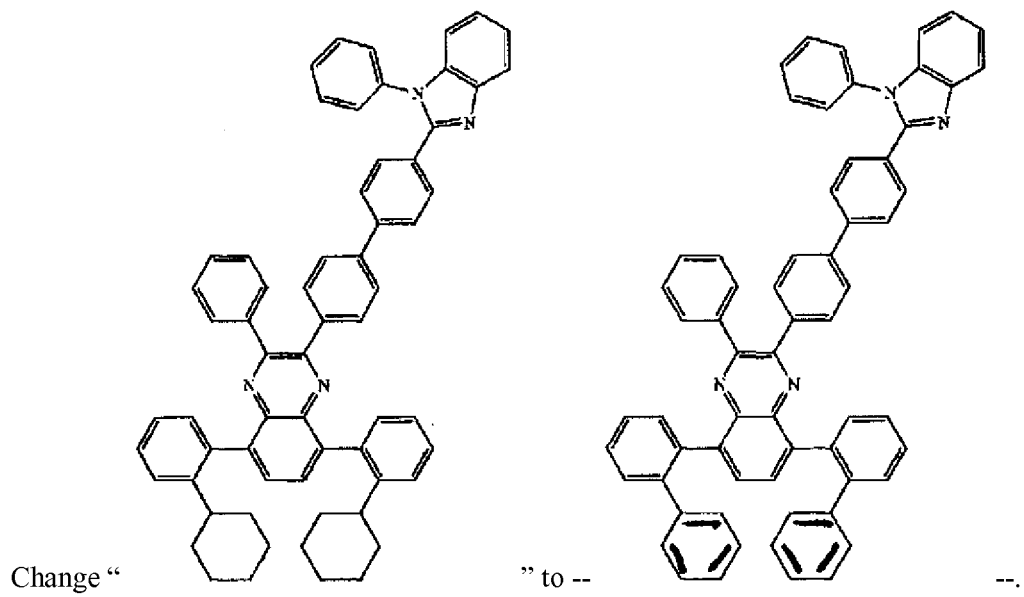

Change " " to -- --.

Column 113, Line 13; Change "(A'-1)" to --(A-1)--.

Column 117, Lines 39 to 40; Change "group, a represents" to --group, α represents--.

Column 118, Line 58; Change "a represents" to --α represents--.

Column 121, Lines 48 to 49; Change "group, a represents" to --group, α represents--.

Column 122, Lines 64 to 65; Change "group; a represents" to --group, α represents--.

Column 125, Lines 40 to 41; Change "{4-[N-(3-methylphenyl)-N-phenylamino]" to
--{4-[N'-(3-methylphenyl)-N'-phenylamino]--.

Signed and Sealed this
Seventh Day of July, 2015

Michelle K. Lee
*Director of the United States Patent and Trademark Office*

CERTIFICATE OF CORRECTION (continued)

Column 126, Line 62; Change "PTTDMA);" to --PTPDMA);--.

Column 126, Lines 62 to 63; Change "N'-bisphenyl)" to --N'-bis(phenyl)--.

Column 127, Line 11; Change "and can be used." to

--and 4,4'-bis[N-(spiro-9,9'-bifluoren-2-yl)-N-phenylamino]biphenyl(abbreviation: BSPB) can be used.--.

Column 127, Line 37; Change "(4',6'-dffluorophenyl)" to --(4',6'-difluorophenyl)--.

Column 128, Line 29; Change "2-a mine" to --2-amine--.

Column 128, Line 64; Change "[5-[(p" to --[5-(p--.

Column 129, Line 61; Change "(N,N-diphenylamino)" to --(N,N'-diphenylamino)--.

Column 133, Line 22; Change "given: N,N',N'-tetrakis" to --given: N,N,N',N'-tetrakis--.

Column 133, Line 35; Change "N,C$^2$)" to --N,C$^{2'}$)--.

Column 147, Chemical Structure (B-7);

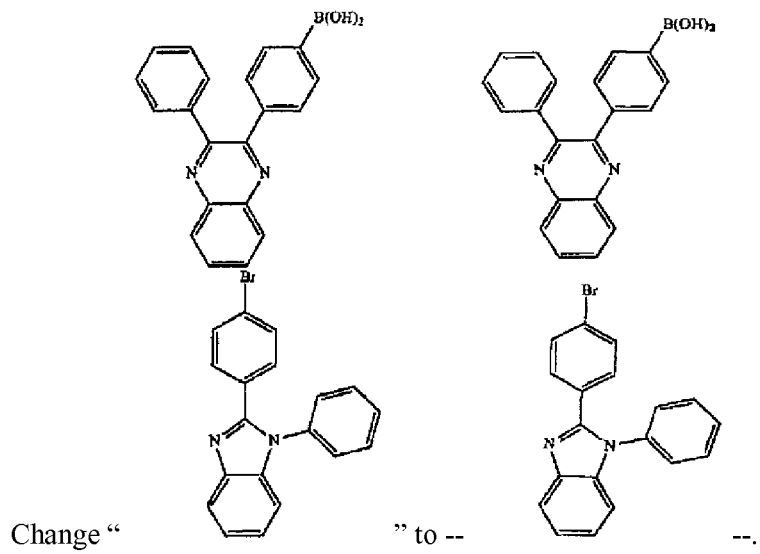

Change " " to -- --.

Column 150, Chemical Formula CzPA;

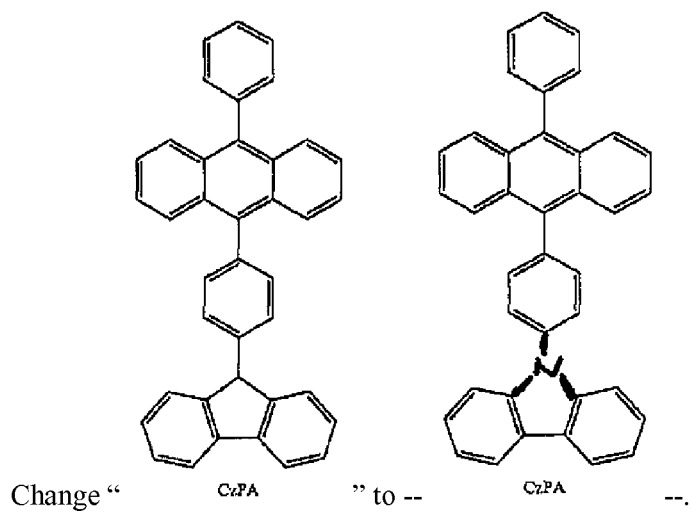

Change " CzPA " to -- CzPA --.

CERTIFICATE OF CORRECTION (continued)
U.S. Pat. No. 8,815,412 B2

In the Claims:

Column 160, Line 16, Claim 3; Change "is a hydrogen." to --is hydrogen.--.

Column 161, Line 35, Claim 12; Change "is a hydrogen." to --is hydrogen.--.

Column 162, Line 17, Claim 18; Change "is a hydrogen." to --is hydrogen.--.